US007897582B2

(12) United States Patent
Bennett et al.

(10) Patent No.: US 7,897,582 B2
(45) Date of Patent: Mar. 1, 2011

(54) OLIGONUCLEOTIDE COMPOSITIONS AND METHODS FOR THE MODULATION OF THE EXPRESSION OF B7 PROTEIN

(75) Inventors: C. Frank Bennett, Carlsbad, CA (US); Susan M Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/748,422

(22) Filed: May 14, 2007

(65) Prior Publication Data

US 2008/0027019 A1 Jan. 31, 2008

Related U.S. Application Data

(63) Continuation of application No. 10/641,962, filed on Aug. 15, 2003, now Pat. No. 7,235,653.

(60) Provisional application No. 60/651,504, filed on May 23, 2003.

(51) Int. Cl.
*A61K 31/70* (2006.01)
*C07H 21/02* (2006.01)
*C07H 21/04* (2006.01)
*C12Q 1/68* (2006.01)

(52) U.S. Cl. ............ 514/44 A; 435/6; 435/375; 435/377; 536/23.1; 536/24.1; 536/24.5

(58) Field of Classification Search ........................ None
See application file for complete search history.

(56) References Cited

U.S. PATENT DOCUMENTS

| | | | |
|---|---|---|---|
| 4,689,320 A | 8/1987 | Kaji | |
| 4,806,463 A | 2/1989 | Goodchild et al. | |
| 5,004,810 A | 4/1991 | Draper | |
| 5,034,506 A | 7/1991 | Summerton et al. | |
| 5,087,617 A | 2/1992 | Smith | |
| 5,098,890 A | 3/1992 | Gewirtz et al. | |
| 5,135,917 A | 8/1992 | Burch | |
| 5,138,045 A | 8/1992 | Cook et al. | |
| 5,166,195 A | 11/1992 | Ecker | |
| 5,194,428 A | 3/1993 | Agrawal et al. | |
| 5,218,105 A | 6/1993 | Cook et al. | |
| 5,242,906 A | 9/1993 | Pagano et al. | |
| 5,264,423 A | 11/1993 | Cohen et al. | |
| 5,276,019 A | 1/1994 | Cohen et al. | |
| 5,286,717 A | 2/1994 | Cohen et al. | |
| 5,434,131 A | 7/1995 | Linsley et al. | |
| 5,459,255 A | 10/1995 | Cook et al. | |
| 5,512,438 A | 4/1996 | Ecker | |
| 5,514,788 A | 5/1996 | Bennett et al. | |
| 5,539,082 A | 7/1996 | Nielsen et al. | |
| 5,667,998 A | 9/1997 | Dougherty et al. | |
| 5,801,154 A | 9/1998 | Baracchini et al. | |
| 5,877,021 A | 3/1999 | Stinchcomb et al. | |
| 5,883,082 A | 3/1999 | Bennett et al. | |
| 5,942,607 A | 8/1999 | Freeman et al. | |
| 5,998,148 A * | 12/1999 | Bennett et al. ............... 435/6 |
| 6,077,833 A | 6/2000 | Bennett et al. | |
| 6,319,906 B1 | 11/2001 | Bennett et al. | |
| 6,582,908 B2 | 6/2003 | Fodor et al. | |
| 7,115,580 B1 | 10/2006 | Bennett et al. | |
| 2001/0053519 A1 | 12/2001 | Fodor et al. | |
| 2003/0228597 A1 | 12/2003 | Cowsert et al. | |

FOREIGN PATENT DOCUMENTS

| | | |
|---|---|---|
| EP | 0600591 | 10/1993 |
| EP | 0643077 | 9/1994 |
| WO | WO 92/20823 | 11/1992 |
| WO | WO 93/24134 | 12/1993 |
| WO | WO 94/17773 | 8/1994 |
| WO | WO 95/03408 | 2/1995 |
| WO | WO 95/05464 | 2/1995 |
| WO | WO 95/06738 | 3/1995 |
| WO | WO 95/07358 | 3/1995 |
| WO | WO 95/22619 | 8/1995 |
| WO | WO 95/32734 | 12/1995 |
| WO | WO 95/34320 | 12/1995 |
| WO | WO 96/11279 | 4/1996 |
| WO | WO 96/15780 | 5/1996 |
| WO | WO 96/18736 | 6/1996 |
| WO | WO 99/01579 | 1/1999 |
| WO | WO 00/74687 | 12/2000 |
| WO | WO 03/083089 | 10/2003 |

OTHER PUBLICATIONS

Bennett et al Biochimica et Biophysica ACAT vol. 1489:19-30, 1999.*
Alberts et al., "Molecular Biology of the Cell" Garland Publishing Inc. (1983) New York, 411-415.
Allison et al., "The Yin and Yang of T Cell Costimulation" Science (1995) 270:932-933.
Allison, "CD28-B7 interactions in T-cell activation" Curr. Opin. Immunol. (1994) 6:414.
Azuma et al., "B70 antigen is a second ligand for CTLA-4 and CD28" Nature (1993) 366:76-79.
Berkow et al., "The Merck Manual of Diagnosis and Therapy" 15th ed. (1987) Rahway, NJ, 302-336 and 2516-2522.
Borriello et al., "Characterization of the Murine B7-1 Genomic Locus Reveals an Additional Exon Encoding an Alternative Cytoplasmic Domain and a Chromosomal Location of Chromosome 16, Band 15" J. Immunol. (1994) 153:5038. Borriello et al., "Differential Expression of Alternate mB7-2 Transcripts" J. Immunol. (1995) 155:5490-5497.
Brand et al., "Transdermal delivery of antisense compounds" Advanced Drug Delivery Review (2000) 44:51-57.
Brigstock et al., "Species-Specific High Molecular Weight Forms of Basic Fibroblast Growth Factors" Growth Factors (1990) 4:45-52.
Charachon et al., "Phosphorothioate Analogues of (2'-5') (A)4: Agonist and Antagonist Activities in Intact Cells" Biochemistry (1990) 29:2550-2555.
Chen et al., "Monoclonal Antibody 2D10 Recognizes a Novel T Cell Costimulatory Molecule on Activated Murine B Lymphocytes" J. Immunol. (1994) 152:2105-2114.
Chen et al., "Molecular Cloning and Expression of Early T Cell Costimulatory Molecule-1 and its Characterization as a B7-2 Molecule" J. Immunol. (1994) 152:4929-4936.

(Continued)

*Primary Examiner* — Sean R McGarry
(74) *Attorney, Agent, or Firm* — Knobbe Martens Olson & Bear

(57) ABSTRACT

Compositions and methods for the treatment of asthma with oligonucleotides which specifically hybridize with nucleic acids encoding B7 proteins.

26 Claims, 25 Drawing Sheets

OTHER PUBLICATIONS

Cook, "Medicinal Chemistry Strategies for Antisense Research" Antisense Research Applications (1993) CRC Press, Boca Raton, 171-172.

Crooke et al., "Antisense Research and Applications" CRC Press, Boca Raton (1993) 171-172.

Crooke et al., "Pharmokinetic Properties of Several Novel Oligonucleotide Analogs in mice" J. Pharmacol. Exp. Ther. (1996) 227:923-937.

Database WPI, Section Ch, Week 199804, XP002230059, Derwent Publications Ltd. (1997).

De Virgilio et al., "Cloning and Disruption of a Gene Required for Growth on Acetate but not on Ethanol: the Acetyl-Coenzyme a Synthetase Gene of *Saccharomyces cerevisiae*" Yeast (1992) 8:1043-1051.

Dulbecco et al., "Plaque Production by the Polyoma Virus" Virol. (1959) 8:396-397.

European Search Report for Application # 97953268.6 dated Dec. 10, 2001.

European Search Report for Application # 00939350.5 dated Mar. 13, 2003.

European Search Report for Application # 04752823.7 dated Apr. 17, 2008.

Freeman et al., "Structure, Expression, and T Cell Costimulatory Activity of the Murine Homologue of the Human B Lymphocyte Activation Antigen B7" J. Exp. Med. (1991) 174:625-631.

Freeman et al., "B7, A New Member of the Ig Superfamily with Unique Expression on Activated and Neoplastic B Cells" J. Immunol. (1989) 143:2714-2722.

Freeman et al., "Cloning of B7-2: A CTLA-4 Counter Receptor That Costimulates Human % Cell Proliferation" Science (1993) 262:909-911.

French et al., "Expression of Two Related Nonstructural Proteins of Bluetongue Virust (BTV) Type 10 in Insect Cells by a Recombinant Baculovirus: Production of Polyclonal Ascitic Fluid and Characterization of the Gene Product in BTV-Infected BHK Cells" J. Virol. (1989) 63:3270-3278.

Gao et al., "Cloning and Characterization of a Mouse Gene with Homology to the Human von Hippel-Lindau Disease Tumor Suppressor Gene: Implications for the Potential Organization of the Human von Hippel-Lindau Disease Gene" Cancer Res. (1995) 55:743-747.

Gebeyehu et al., "Novel biotinylated nucleotide—analogs for labeling and colorimetric detection of DNA" Nucleic Acids Res. (1987) 15:4513-4534.

Gelbert et al., "Analysis of GPT Activity in Mammalian Cells with a Chromosomally Integrated Shuttle Vector Containing Altered gpt Genes" Somat. Cell. Mol. Genet. (1990) 16:173-184.

Gold et al., "*Escherichia coli* and *Salmonella typhimurium*: Cellular and Molecular Biology" vol. 2, 1987.

Hakim et al., "Acute Graft-Versus-Host Reaction Can be Aborted by Blockade of Costimulatory Molecules" J. Immun. (1995) 155:1760-1766.

Harlan et al., "Mice expressing both B7-1 and viral glycoprotein on pancreatic beta cells along with glycoprotein-specific transgenic T Cells develop diabetes due to a breakdown of T-lymphocyte unresponsiveness" PNAS (1994) 91:3137-3141.

Hathcock et al., "Identification of an Alternative CTLA-4 Ligand Costimulatory for T Cell Activation" Science (1993) 262:905-907.

Inobe et al., "The Role of the B7-1a Molecule, an Alternatively Spliced Form of Murine B7-1 (CD80), on T Cell activation" J. Immun. (1996) 157:582-588.

International Search Report for Application # PCT/US97/23270 dated Mar. 26, 1998.

International Search Report for Application # PCT/US00/14471 dated Aug. 14, 2000.

International Search Report for Application # PCT/US2004/015880 dated Nov. 22, 2005.

Jellis et al., "Genomic Organization of the gene coding for the costimulatory human B-lymphocyte antigen (CD86)" Immunogenet. (1995) 42:85.

June et al., "The B7 and CD28 receptor families" Immunol. Today (1994) 15:321-331.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.

Kanagasundaram et al., "Isolation and characterization of the gene encoding gluconolactonase from *Zymomonas mobilis*" Biochim. Biophys. Acta. (1992) 1171: 198-200.

Kornberg, "DNA Replication" W.H. Freeman & Co., San Francisco (1974) 75-77.

Lenschow et al., "Long-Term Survival of Xenogenic Pancreatic Islet Grafts Induced by CTLA4Ig" Science (1992) 257:789-792.

Lenschow et al., "T cell co-stimulation and in vivo tolerance" Curr. Opin. Immunol. (1993) 5:747-752.

Lenschow et al., "Expression and functional significance of an additional ligand for CTLA-4" PNAS (1993) 90:11054-11058.

Lenschow et al., "CD28/B7 System of T-Cell Costimulation" Annual Review of Immunology (1996) 14:233-258.

Letsinger et al., "Cholesteryl-conjugated oligonucleotides: Synthesis, properties, and activity as inhibitors or replication of human immunodeficiency virus in cell culture" PNAS (1989) 86:6553-6556.

Levine et al., "Antiviral Effect and Ex Vivo CD4+T Cell Proliferation in HIV-Positive Patients as a Result of CD28 Costimulation" Science (1996) 272:1939:1942.

Liang et al., "Phenotype and allostimulatory function of dendritic cells treated with antisense oligodeoxyribonucleotides targeting CD80 or CD86 mRNA" Transplantation Proceedings (2001) 33:235.

Lin et al., "Long-Term Acceptance of Major Histocompatibility Complex Mismatched Cardiac Allografts Induced by CTLA4Ig Plus Donor-specific Transfusion" J. Exp. Med. (1993) 178:1801-1806.

Linsley et al., "The Role of the CD28 Receptor During T Cell Response to Antigen" Annu. Rev. Immunol. (1993) 11:191-212.

Linsley et al., "CTLA-4 is a Second Receptor for the B Cell activation Antigen B7" J. Exp. Med. (1991) 174:561-569.

Linsley et al., "Immunosuppression in Vivo by a Soluble Form of the CTLA-4 T Cell Activation Molecule" Science (1992) 257:792-795.

Liu et al., "Costimulation of T-cell growth" Curr. Opin. Immunol. (1992) 4:265-270.

Ly et al., "Expression of insulin-like growth factor-I in rat glioma cells is associated with change in both immunogenicity and apoptosis" Neuroscience Letters (2000) 281:13-16.

Manoharan et al., "Chemical Modifications to Improve Uptake and Bioavailability of Antisense Oligonucleotides" Ann. N.Y. Acad. Sci. (1992) 660:306-309.

Manoharan et al., "Introduction of a Lipophilic Thioether Tether in the Minor Groove of Nucleic Acids for Antisense Applications" Bioorg. Med. Chem. Let. (1993) 3: 2765-2770.

Manoharan et al., "Cholic Acid-Oligonucleotide Conjugates for Antisense Applications" Bioorg. Med. Chem. Let. (1994) 4:1053-1060.

Manoharan et al., "Oligonucleotide Conjugates: Alteration of the Pharmacokinetic Properties of Antisense Agents" Nucleosides & Nucleotides (1995) 14:969-973.

Manoharan et al., "Lipidic Nucleic Acids" Tetrahedron Lett. (1995) 36:3651-3654.

Markussen et al., "Translational control of oskar generates short OSK, the isoform that induces pole lasma assembly" Development (1995) 121:3723-3732.

Martin et al., "Ein neuer Zugang zu 2'O-Alkyribonucleosiden und Eigenschaften deren Oligonucleotide" Helv. Chim. Acta. (1995) 78:486-504.

McDermott et al., "Structure and lens expression of the gene encoding chicken BA3/A1-crystallin" Gene (1992) 117:193.

Mishra et al., "Improved leishmanicidal effect of Phosphorotioate antisense oligonucleotides by LDL-mediated delivery" Biochim. Biophys. Acta (1995) 1264:229-237.

Monaco et al., "Structure of Two Rat Genes Coding for Closely Related Rolipram-sensitive cAMP Phosphorodiesterases" J. Biol. Chem. (1994) 269:347-357.

Moore et al., "Cell Line Derived from Patient with Myeloma" N.Y.J. Med. (1968) 68:2054-2060.

Nabavi et al., "Signalling through the MHC class II cytoplasmic domain is requires for antigen presentation and induces B7 expression" Nature (1992) 360:266-268.

Nielsen et al., "Sequence-Selective Recognition of DNA by Strand Displacement with a Thymine-Substituted Polyamide" Science (1991) 254:1497-1500.

Oberhauser et al., "Effective incorporation of 2'-O-methyl-oligoribonucleotides into liposomes and enhanced cell association through modifications with thiocholesterol" Nucl. Acids. Res. (1992) 20:533-538.

Olsen et al., "Inhibition of Protein Kinase-A by Overexpression of the Cloned Human Protein Kinase Inhibitor" Mol. Endocrinol. (1991) 5:1246-1256.

Perri et al., "Interactions of Plasmid-encoded Replication Initiation Proteins with the Origin of DNA Replication of the Broad Host Range Plasmid RK2" J. Biol. Chem. (1991) 266:12536-12543.

Pushpa-Rekha et al., "Rat Phospholipid-hydroperoxide Glutathione Peroxidase" J. Biol. Chem. (1995) 270:26993.

Reiser et al., "Murine B7 antigen provides an efficient costimulatory signal for activation of murine T Lymphocytes via the T-cell" PNAS (1992) 89:271-275.

Revision History for GenBank Accession No. M27533.

Revision History for GenBank Accession No. L25259.

Rogers et al., "Alternative splicing dictates translational start in Epstein-Barr virus transcripts" EMBO J. (1990) 9:2273-2277.

Romani et al., "Proliferating Dendritic Cell Progenitors in Human Blood" J. Exp. Med. (1994) 180:83-93.

Saison-Behmoaras et al., "Short modified antisense oligonucleotides directed against Ha-ras point mutation induce selective cleavage of the mRNA and inhibit T24 cells proliferation" EMBO J. (1991) 10:1111-1118.

Sambrook et al., Molecular Cloning. A Laboratory Manual, Cold Spring Harbor Laboratory Press (1989) 2:10.59-10.61.

Sambrook et al., Molecular Cloning. A Laboratory Manual, Cold Spring Harbor Laboratory Press (1989) 2:11.31-11.32.

Saul et al., "ce1B, a Gene Coding for Bifunctional Cellulase from the Extreme Thermophile, *Caldocellum saccharolyticum*" Appl. Environ. Microbiol. (1990) 56: 3117-3124.

Sawai et al., "Synthesis and Properties of Some New 2-5A Analogues" Chemica Scripta (1986) 21:169-172.

Shea et al., "Synthesis, hybridization properties and antiviral activity of lipid-oligodeoxynucleotide conjugates" Nucl. Acids Res. (1990) 18:3777-3783.

Smith et al., "The Nucleic Acid of Polyoma Virus" Virol. (1960) 12:185-196.

Stepkowski et al., "Blocking of Heart Allograft Rejection by Intercellular Adhesion Molecule-1 Antisense Oligonucleotides Alone or in Combination with Other Immunosuppressive Modalities" J. Immunol. (1994) 153: 5336-5346.

Svinarchuk et al., "Inhibition of HIV proliferation in MT04 cells by antisense oligonucleotide conjugated to lipophilic groups" Biochimie (1993) 75:49-54.

Wu et al., "A Major Costimulatory Molecule on Antigen-presenting Cells, CTLA4 Ligand A, in Distinct from B7" J. Exp. Med. (1993) 178:1789-1793.

Yang et al., "CD40 Ligand-Dependent T Cell Activation: Requirement of B7-CD-28 Signaling Through CD40" Science (1996) 273:1862-1864.

Yaoita et al., "*Xenopus laevis* a and b thyroid hormone receptors" PNAS (1990) 87:7090-7094.

Liang et al., "Administration of dendritic cells transduced with antisense oligodeoxyribonucleotides targeting CD80 or CD86 prolongs allograft survival." Transplantation (2003) 76:721-729.

Qian et al., "Administration of antisense oligodeoxynucleotides against mRNA of CD80 or CD86 prolongs survival of cardiac allografts by inhibition of CTL activity" Transplantation Proceedings (2001) 33:235.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Gewirtz et al., "Facilitating oligonucleotide delivery: Helping antisense deliver on its promise" Proc. Natl. Acad. Sci. USA (1996) 3161:3163.

Monia et al., "Antitumor activity of a phosphoroth oate antisense oligodeoxyribonucleotide targeted against c-rafkinase" Nature Medicine (1996) 2:668-675.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Vester et al., "LNA (Locked Nucleic Acid): High-Affinity Targeting of Complementary RNA and DNA" Biochemistry (2004) 43(42):13233-13241.

* cited by examiner

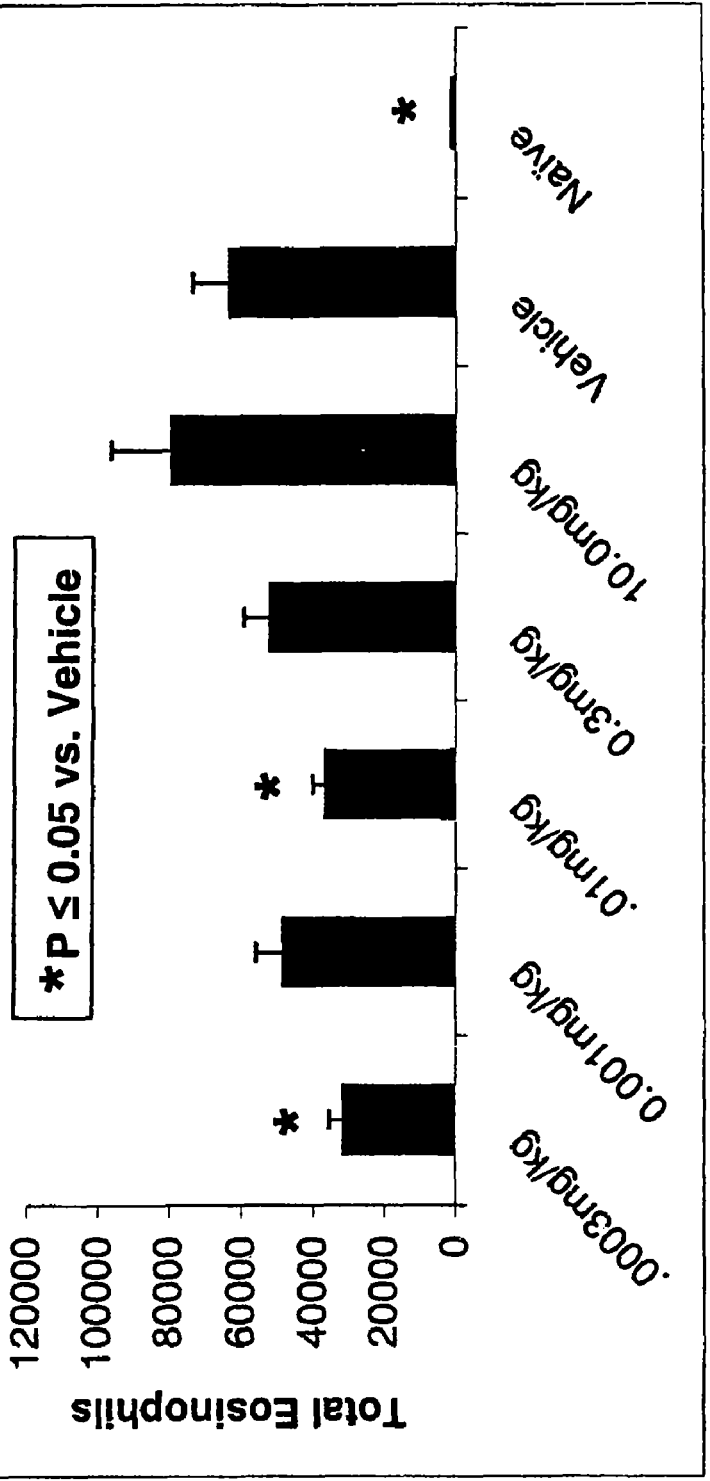

SEQUENCE LISTING

<160> NUMBER OF SEQ ID NOS: 447

<210> SEQ ID NO 1
<211> LENGTH: 32
<212> TYPE: DNA
<213> ORGANISM: Artificial Sequence
<220> FEATURE:
<223> OTHER INFORMATION: Synthetic primer

<400> SEQUENCE: 1
gatcagggta ccaggagcct taggaggtac gg                           32

<210> SEQ ID NO 2
<211> LENGTH: 33
<212> TYPE: DNA
<213> ORGANISM: Artificial Sequence
<220> FEATURE:
<223> OTHER INFORMATION: Synthetic primer

<400> SEQUENCE: 2
gatagcctcg agttatttcc aggtcatgag cca                          33

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ttccaggtca tgagccatta                                          20

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
cataaggtgt gctctgaagt g                                        21

<210> SEQ ID NO 5
<211> LENGTH: 20

```
<212> TYPE: DNA
<213> ORGANISM: Artificial Sequence
<220> FEATURE:
<223> OTHER INFORMATION: Synthetic primer

<400> SEQUENCE: 5
ttactcatgg taatgtcttt                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
attaaaaaca tgtatcactt                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
ggaacacaga agcaaggtgg t                                             21

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ccgtacctcc taaggctcct                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
cccatagtgc tgtcacaaat                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gcacagcagc attcccaagg                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
ttgcaaattg gcatggcagg                                               20
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tggtatgggc tttactcttt                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
aaaaggttgc ccaggaacgg                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
gggagtcctg gagcccctt                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ccattaagct gggcttggcc                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
tgcgagctcc ccgtacctcc                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer
<300> PUBLICATION INFORMATION:
<310> PATENT DOCUMENT NUMBER: US 5514788
<311> PATENT FILING DATE: 1993-05-17
<312> PUBLICATION DATE: 1996-05-07

<400> SEQUENCE: 17
gcccaagctg gcatccgtca                                                   20

<210> SEQ ID NO 18
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 18
ggattgccaa gcccatggtg                                                     20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
ctaagtagtg ctagccggga                                                     20

<210> SEQ ID NO 20
<211> LENGTH: 38
<212> TYPE: DNA
<213> ORGANISM: Artificial Sequence
<220> FEATURE:
<223> OTHER INFORMATION: Synthetic primer

<400> SEQUENCE: 20
gatcagggta ccccaaagaa aaagtgattt gtcattgc                                 38

<210> SEQ ID NO 21
<211> LENGTH: 35
<212> TYPE: DNA
<213> ORGANISM: Artificial Sequence
<220> FEATURE:
<223> OTHER INFORMATION: Synthetic primer

<400> SEQUENCE: 21
gatagcctcg aggataatga attggctgac aagac                                    35

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
gggtaagact ccacttctga                                                     20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
gggtctccaa aggttgtgga                                                     20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
gttcctgggt ctccaaaggt                                                     20
```

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
acacacagag attggagggt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
gctcacgtag aagaccctcc                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
ggcagggctg atgacaatcc                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
tgcaaaacag gcagggctga                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
agaccagggc acttcccagg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
cctgcctccg tgtgtggccc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 31
gaccagccag caccaagagc                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
ccacaggaca gcgttgccac                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
ccggttcttg tactcgggcc                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
ccaaccagga gaggtgaggc                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
ggcaaagcag taggtcaggc                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
gcctcatgat ccccacgatc                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
agtcctacta ccagccgcct                                          20

<210> SEQ ID NO 38
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 38
tcagggtaag actccacttc                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
agggtgttcc tgggtctcca                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
ctccgtgtgt ggcccatggc                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
ggatggtgat gttccctgcc                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic primer

<400> SEQUENCE: 42
tgagaaagac cagccagcac                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
gggcgcagag ccaggatcac                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
ggcccaggat gggagcaggt                                               20
```

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
agggcgtaca ctttcccttc                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
cagccccttg cttctgcgga                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
aaggagaggg atgccagcca                                              20

<210> SEQ ID NO 48
<211> LENGTH: 22
<212> TYPE: DNA
<213> ORGANISM: Artificial Sequence
<220> FEATURE:
<223> OTHER INFORMATION: Synthetic primer

<400> SEQUENCE: 48
ctgttacttt acagagggtt tg                                           22

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
cttctgttac tttacagagg gtttg                                        25

<210> SEQ ID NO 50
<211> LENGTH: 21
<212> TYPE: DNA
<213> ORGANISM: Artificial Sequence
<220> FEATURE:
<223> OTHER INFORMATION: Synthetic primer

<400> SEQUENCE: 50
ctgttacttt acagagggtt t                                            21

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 51
gccctcgtca gatgggcgca                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
agtcctacta ccagccgcct                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic primer

<400> SEQUENCE: 53
agtaagagtc tattgaggta                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic primer

<400> SEQUENCE: 54
ggttgagttt cacaacctga                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
gtccacagaa tggaacagag                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
ggcatccacc cggcagatgc                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic primer

<400> SEQUENCE: 57
tggatggcat ccacccggca                                              20

<210> SEQ ID NO 58
<211> LENGTH: 20
```

<212> TYPE: DNA
<213> ORGANISM: Artificial Sequence
<220> FEATURE:
<223> OTHER INFORMATION: Synthetic primer

<400> SEQUENCE: 58
aggcacctcc taggctcaca                                                    20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
gccaatggag cttaggcacc                                                    20

<210> SEQ ID NO 60
<211> LENGTH: 20
<212> TYPE: DNA
<213> ORGANISM: Artificial Sequence
<220> FEATURE:
<223> OTHER INFORMATION: Synthetic primer

<400> SEQUENCE: 60
catgatgggg aaagccagga                                                    20

<210> SEQ ID NO 61
<211> LENGTH: 20
<212> TYPE: DNA
<213> ORGANISM: Artificial Sequence
<220> FEATURE:
<223> OTHER INFORMATION: Synthetic primer

<400> SEQUENCE: 61
aattgcaagc catagcttca                                                    20

<210> SEQ ID NO 62
<211> LENGTH: 20
<212> TYPE: DNA
<213> ORGANISM: Artificial Sequence
<220> FEATURE:
<223> OTHER INFORMATION: Synthetic primer

<400> SEQUENCE: 62
cggcaaggca gcaatacctt                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic primer

<400> SEQUENCE: 63
cccagcaatg acagacagca                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
ggtctgaaag gaccaggccc                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
tgggaaaccc ccggaagcaa                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic primer

<400> SEQUENCE: 66
ggctttggga aaccccgga                                               20

<210> SEQ ID NO 67
<211> LENGTH: 19
<212> TYPE: DNA
<213> ORGANISM: Artificial Sequence
<220> FEATURE:
<223> OTHER INFORMATION: Synthetic primer

<400> SEQUENCE: 67
tcagattcag gatctggga                                               19

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
cccaggtgaa gtcctctgac                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
ctgcgccgaa tcctgcccca                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic primer

<400> SEQUENCE: 70
caggcccgaa ggtaaggctg                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic primer -continued

<400> SEQUENCE: 71
tcagctagca cggtgctgaa                                        20

<210> SEQ ID NO 72
<211> LENGTH: 20
<212> TYPE: DNA
<213> ORGANISM: Artificial Sequence
<220> FEATURE:
<223> OTHER INFORMATION: Synthetic primer

<400> SEQUENCE: 72
ggcccagcaa acttgcccgt                                        20

<210> SEQ ID NO 73
<211> LENGTH: 20
<212> TYPE: DNA
<213> ORGANISM: Artificial Sequence
<220> FEATURE:
<223> OTHER INFORMATION: Synthetic primer

<400> SEQUENCE: 73
ccaccacagt gggctcagcc                                        20

<210> SEQ ID NO 74
<211> LENGTH: 19
<212> TYPE: DNA
<213> ORGANISM: Artificial Sequence
<220> FEATURE:
<223> OTHER INFORMATION: Synthetic primer

<400> SEQUENCE: 74
ggccatgagg gcaatctaa                                         19

<210> SEQ ID NO 75
<211> LENGTH: 21
<212> TYPE: DNA
<213> ORGANISM: Artificial Sequence
<220> FEATURE:
<223> OTHER INFORMATION: Synthetic primer

<400> SEQUENCE: 75
gtggccatga gggcaatcta a                                      21

<210> SEQ ID NO 76
<211> LENGTH: 20
<212> TYPE: DNA
<213> ORGANISM: Artificial Sequence
<220> FEATURE:
<223> OTHER INFORMATION: Synthetic primer

<400> SEQUENCE: 76
gatttaacat ttggcgccca                                        20

<210> SEQ ID NO 77
<211> LENGTH: 20
<212> TYPE: DNA
<213> ORGANISM: Artificial Sequence
<220> FEATURE:
<223> OTHER INFORMATION: Synthetic primer

<400> SEQUENCE: 77
aaagttacaa cattatatct                                        20

<210> SEQ ID NO 78
<211> LENGTH: 20

```
<212> TYPE: DNA
<213> ORGANISM: Artificial Sequence
<220> FEATURE:
<223> OTHER INFORMATION: Synthetic primer

<400> SEQUENCE: 78
agtgcgattc tcaaacctac                                                    20

<210> SEQ ID NO 79
<211> LENGTH: 16
<212> TYPE: DNA
<213> ORGANISM: Artificial Sequence
<220> FEATURE:
<223> OTHER INFORMATION: Synthetic primer

<400> SEQUENCE: 79
tatttgcgag ctcccc                                                        16

<210> SEQ ID NO 80
<211> LENGTH: 15
<212> TYPE: DNA
<213> ORGANISM: Artificial Sequence
<220> FEATURE:
<223> OTHER INFORMATION: Synthetic primer

<400> SEQUENCE: 80
tatttgcgag ctccc                                                         15

<210> SEQ ID NO 81
<211> LENGTH: 14
<212> TYPE: DNA
<213> ORGANISM: Artificial Sequence
<220> FEATURE:
<223> OTHER INFORMATION: Synthetic primer

<400> SEQUENCE: 81
tatttgcgag ctcc                                                          14

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
cgacagctcc tgcgctcctc                                                    20

<210> SEQ ID NO 83
<211> LENGTH: 16
<212> TYPE: DNA
<213> ORGANISM: Artificial Sequence
<220> FEATURE:
<223> OTHER INFORMATION: Synthetic primer

<400> SEQUENCE: 83
agctccccgt acctcc                                                        16

<210> SEQ ID NO 84
<211> LENGTH: 16
<212> TYPE: DNA
<213> ORGANISM: Artificial Sequence
<220> FEATURE:
<223> OTHER INFORMATION: Synthetic primer

<400> SEQUENCE: 84
tgcgagctcc ccgtac                                                        16
```

<210> SEQ ID NO 85
<211> LENGTH: 10
<212> TYPE: DNA
<213> ORGANISM: Artificial Sequence
<220> FEATURE:
<223> OTHER INFORMATION: Synthetic primer

<400> SEQUENCE: 85
ctccccgtac                                                                    10

<210> SEQ ID NO 86
<211> LENGTH: 11
<212> TYPE: DNA
<213> ORGANISM: Artificial Sequence
<220> FEATURE:
<223> OTHER INFORMATION: Synthetic primer

<400> SEQUENCE: 86
gctccccgta c                                                                  11

<210> SEQ ID NO 87
<211> LENGTH: 12
<212> TYPE: DNA
<213> ORGANISM: Artificial Sequence
<220> FEATURE:
<223> OTHER INFORMATION: Synthetic primer

<400> SEQUENCE: 87
agctccccgt ac                                                                 12

<210> SEQ ID NO 88
<211> LENGTH: 13
<212> TYPE: DNA
<213> ORGANISM: Artificial Sequence
<220> FEATURE:
<223> OTHER INFORMATION: Synthetic primer

<400> SEQUENCE: 88
gagctccccg tac                                                                13

<210> SEQ ID NO 89
<211> LENGTH: 14
<212> TYPE: DNA
<213> ORGANISM: Artificial Sequence
<220> FEATURE:
<223> OTHER INFORMATION: Synthetic primer

<400> SEQUENCE: 89
cgagctcccc gtac                                                               14

<210> SEQ ID NO 90
<211> LENGTH: 15
<212> TYPE: DNA
<213> ORGANISM: Artificial Sequence
<220> FEATURE:
<223> OTHER INFORMATION: Synthetic primer

<400> SEQUENCE: 90
gcgagctccc cgtac                                                              15

<210> SEQ ID NO 91
<211> LENGTH: 13
<212> TYPE: DNA
<213> ORGANISM: Artificial Sequence
<220> FEATURE:
<223> OTHER INFORMATION: Synthetic primer

```
<400> SEQUENCE: 91
gcgagctccc cgt                                              13

<210> SEQ ID NO 92
<211> LENGTH: 15
<212> TYPE: DNA
<213> ORGANISM: Artificial Sequence
<220> FEATURE:
<223> OTHER INFORMATION: Synthetic primer

<400> SEQUENCE: 92
gccgccgcca agtct                                            15

<210> SEQ ID NO 93
<211> LENGTH: 24
<212> TYPE: DNA
<213> ORGANISM: Artificial Sequence
<220> FEATURE:
<223> OTHER INFORMATION: Synthetic primer

<400> SEQUENCE: 93
gagaagcaaa gctttcaccc tgtg                                  24

<210> SEQ ID NO 94
<211> LENGTH: 22
<212> TYPE: DNA
<213> ORGANISM: Artificial Sequence
<220> FEATURE:
<223> OTHER INFORMATION: Synthetic primer

<400> SEQUENCE: 94
gaagcaaagc tttcaccctg tg                                    22

<210> SEQ ID NO 95
<211> LENGTH: 19
<212> TYPE: DNA
<213> ORGANISM: Artificial Sequence
<220> FEATURE:
<223> OTHER INFORMATION: Synthetic primer

<400> SEQUENCE: 95
gcaaagcttt caccctgtg                                        19

<210> SEQ ID NO 96
<211> LENGTH: 24
<212> TYPE: DNA
<213> ORGANISM: Artificial Sequence
<220> FEATURE:
<223> OTHER INFORMATION: Synthetic primer

<400> SEQUENCE: 96
ctccccgtac ctcctaaggc tcct                                  24

<210> SEQ ID NO 97
<211> LENGTH: 22
<212> TYPE: DNA
<213> ORGANISM: Artificial Sequence
<220> FEATURE:
<223> OTHER INFORMATION: Synthetic primer

<400> SEQUENCE: 97
ccccgtacct cctaaggctc ct                                    22

<210> SEQ ID NO 98
<211> LENGTH: 19
```

```
<212> TYPE: DNA
<213> ORGANISM: Artificial Sequence
<220> FEATURE:
<223> OTHER INFORMATION: Synthetic primer

<400> SEQUENCE: 98
ccgtacctcc taaggctcc                                                  19

<210> SEQ ID NO 99
<211> LENGTH: 32
<212> TYPE: DNA
<213> ORGANISM: Artificial Sequence
<220> FEATURE:
<223> OTHER INFORMATION: Synthetic primer

<400> SEQUENCE: 99
gatcagggta ccaagagtgg ctcctgtagg ca                                   32

<210> SEQ ID NO 100
<211> LENGTH: 32
<212> TYPE: DNA
<213> ORGANISM: Artificial Sequence
<220> FEATURE:
<223> OTHER INFORMATION: Synthetic primer

<400> SEQUENCE: 100
gatagcctcg aggtagaatt ccaatcagct ga                                   32

<210> SEQ ID NO 101
<211> LENGTH: 20
<212> TYPE: DNA
<213> ORGANISM: Artificial Sequence
<220> FEATURE:
<223> OTHER INFORMATION: Synthetic primer
<300> PUBLICATION INFORMATION:
<302> TITLE: Blocking of Heart Allograft Rejection by Intercellular
      Adhesion Molecule 1 Synthetic primer Alone or
      in Combination with Other Immunosupprssive Modalities
<303> JOURNAL: J. Immunol.
<304> VOLUME: 153
<306> PAGES: 5336 5346
<307> DATE: 1994-12-01

<400> SEQUENCE: 101
tgcatccccc aggccaccat                                                 20

<210> SEQ ID NO 102
<211> LENGTH: 21
<212> TYPE: DNA
<213> ORGANISM: Artificial Sequence
<220> FEATURE:
<223> OTHER INFORMATION: Synthetic primer
<300> PUBLICATION INFORMATION:
<302> TITLE: Blocking of Heart Allograft Rejection by Intercellular
      Adhesion Molecule 1 Synthetic primer Alone or
      in Combination with Other Immunosupprssive Modalities
<303> JOURNAL: J. Immunol.
<304> VOLUME: 153
<306> PAGES: 5336 5346
<307> DATE: 1994-12-01

<400> SEQUENCE: 102
gccgaggtcc atgtcgtacg c                                               21

<210> SEQ ID NO 103
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 103
acacgtctac aggagtctgg                                            20

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
caagcccatg gtgcatctgg                                            20

<210> SEQ ID NO 105
<211> LENGTH: 20
<212> TYPE: DNA
<213> ORGANISM: Artificial Sequence
<220> FEATURE:
<223> OTHER INFORMATION: Synthetic primer

<400> SEQUENCE: 105
ctggggtcca tcgtgggtgc                                            20

<210> SEQ ID NO 106
<211> LENGTH: 20
<212> TYPE: DNA
<213> ORGANISM: Artificial Sequence
<220> FEATURE:
<223> OTHER INFORMATION: Synthetic primer

<400> SEQUENCE: 106
ccgtgctgcc tacaggagcc                                            20

<210> SEQ ID NO 107
<211> LENGTH: 20
<212> TYPE: DNA
<213> ORGANISM: Artificial Sequence
<220> FEATURE:
<223> OTHER INFORMATION: Synthetic primer

<400> SEQUENCE: 107
ggtgcttccg taagttctgg                                            20

<210> SEQ ID NO 108
<211> LENGTH: 20
<212> TYPE: DNA
<213> ORGANISM: Artificial Sequence
<220> FEATURE:
<223> OTHER INFORMATION: Synthetic primer

<400> SEQUENCE: 108
ggattgccaa gcccatggtg                                            20

<210> SEQ ID NO 109
<211> LENGTH: 20
<212> TYPE: DNA
<213> ORGANISM: Artificial Sequence
<220> FEATURE:
<223> OTHER INFORMATION: Synthetic primer

<400> SEQUENCE: 109
ctaagtagtg ctagccggga                                            20

<210> SEQ ID NO 110
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 110
tgcgtctcca cggaaacagc                                               20

<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111
gtgcggccca ggtacttggc                                               20

<210> SEQ ID NO 112
<211> LENGTH: 20
<212> TYPE: DNA
<213> ORGANISM: Artificial Sequence
<220> FEATURE:
<223> OTHER INFORMATION: Synthetic primer

<400> SEQUENCE: 112
acaaggagga gggccacagt                                               20

<210> SEQ ID NO 113
<211> LENGTH: 20
<212> TYPE: DNA
<213> ORGANISM: Artificial Sequence
<220> FEATURE:
<223> OTHER INFORMATION: Synthetic primer

<400> SEQUENCE: 113
tgagaggttt ggaggaaatc                                               20

<210> SEQ ID NO 114
<211> LENGTH: 20
<212> TYPE: DNA
<213> ORGANISM: Artificial Sequence
<220> FEATURE:
<223> OTHER INFORMATION: Synthetic primer

<400> SEQUENCE: 114
gatagtctct ctgtcagcgt                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic primer

<400> SEQUENCE: 115
gttgctgggc ctgctaggct                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic primer

<400> SEQUENCE: 116
ctaggtctcg tcgtcggtgg                                               20
```

<210> SEQ ID NO 117
<211> LENGTH: 20
<212> TYPE: DNA
<213> ORGANISM: Artificial Sequence
<220> FEATURE:
<223> OTHER INFORMATION: Synthetic primer

<400> SEQUENCE: 117
tctcactgcc ttcactctgc                                              20

<210> SEQ ID NO 118
<211> LENGTH: 21
<212> TYPE: DNA
<213> ORGANISM: Artificial Sequence
<220> FEATURE:
<223> OTHER INFORMATION: Synthetic primer

<400> SEQUENCE: 118
gtaccagatg aaggttatca a                                            21

<210> SEQ ID NO 119
<211> LENGTH: 20
<212> TYPE: DNA
<213> ORGANISM: Artificial Sequence
<220> FEATURE:
<223> OTHER INFORMATION: Synthetic primer

<400> SEQUENCE: 119
ctttggagat tattcgagtt                                              20

<210> SEQ ID NO 120
<211> LENGTH: 20
<212> TYPE: DNA
<213> ORGANISM: Artificial Sequence
<220> FEATURE:
<223> OTHER INFORMATION: Synthetic primer

<400> SEQUENCE: 120
gcaagtgtaa agccctgagt                                              20

<210> SEQ ID NO 121
<211> LENGTH: 20
<212> TYPE: DNA
<213> ORGANISM: Artificial Sequence
<220> FEATURE:
<223> OTHER INFORMATION: Synthetic primer

<400> SEQUENCE: 121
agaattccaa tcagctgaga                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic primer

<400> SEQUENCE: 122
tctgagaaac tctgcacttc                                              20

<210> SEQ ID NO 123
<211> LENGTH: 20
<212> TYPE: DNA
<213> ORGANISM: Artificial Sequence
<220> FEATURE:
<223> OTHER INFORMATION: Synthetic primer

<400> SEQUENCE: 123
tcctcaggct ctcactgcct                                                   20

<210> SEQ ID NO 124
<211> LENGTH: 20
<212> TYPE: DNA
<213> ORGANISM: Artificial Sequence
<220> FEATURE:
<223> OTHER INFORMATION: Synthetic primer

<400> SEQUENCE: 124
ggttgttcaa gtccgtgctg                                                   20

<210> SEQ ID NO 125
<211> LENGTH: 21
<212> TYPE: DNA
<213> ORGANISM: Artificial Sequence
<220> FEATURE:
<223> OTHER INFORMATION: Synthetic primer

<400> SEQUENCE: 125
gccgaggtcc atgtcgtagc c                                                 21

<210> SEQ ID NO 126
<211> LENGTH: 20
<212> TYPE: DNA
<213> ORGANISM: Artificial Sequence
<220> FEATURE:
<223> OTHER INFORMATION: Synthetic primer

<400> SEQUENCE: 126
agactccact tctgagatgt                                                   20

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
tgaagaaaaa ttccactttt                                                   20

<210> SEQ ID NO 128
<211> LENGTH: 20
<212> TYPE: DNA
<213> ORGANISM: Artificial Sequence
<220> FEATURE:
<223> OTHER INFORMATION: Synthetic primer

<400> SEQUENCE: 128
tttagtttca cagcttgctg                                                   20

<210> SEQ ID NO 129
<211> LENGTH: 20
<212> TYPE: DNA
<213> ORGANISM: Artificial Sequence
<220> FEATURE:
<223> OTHER INFORMATION: Synthetic primer

<400> SEQUENCE: 129
tcccaggtgc aaaacaggca                                                   20

<210> SEQ ID NO 130
<211> LENGTH: 20

```
<212> TYPE: DNA
<213> ORGANISM: Artificial Sequence
<220> FEATURE:
<223> OTHER INFORMATION: Synthetic primer

<400> SEQUENCE: 130
gtgaaagcca acaatttgga                                               20

<210> SEQ ID NO 131
<211> LENGTH: 20
<212> TYPE: DNA
<213> ORGANISM: Artificial Sequence
<220> FEATURE:
<223> OTHER INFORMATION: Synthetic primer

<400> SEQUENCE: 131
catggcttca gatgcttagg                                               20

<210> SEQ ID NO 132
<211> LENGTH: 20
<212> TYPE: DNA
<213> ORGANISM: Artificial Sequence
<220> FEATURE:
<223> OTHER INFORMATION: Synthetic primer

<400> SEQUENCE: 132
ttgaggtatg gacacttgga                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic primer

<400> SEQUENCE: 133
gcgttgccac ttctttcact                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
ttttgccagt agatgcgagt                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic primer

<400> SEQUENCE: 135
ggccatatat tcatgtcccc                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
gccaggatca caatggagag                                               20
```

```
<210> SEQ ID NO 137
<211> LENGTH: 20
<212> TYPE: DNA
<213> ORGANISM: Artificial Sequence
<220> FEATURE:
<223> OTHER INFORMATION: Synthetic primer

<400> SEQUENCE: 137
gtatgtgccc tcgtcagatg                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic primer

<400> SEQUENCE: 138
ttcagccagg tgttcccgct                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic primer

<400> SEQUENCE: 139
ggaagtcagc tttgactgat                                               20

<210> SEQ ID NO 140
<211> LENGTH: 20
<212> TYPE: DNA
<213> ORGANISM: Artificial Sequence
<220> FEATURE:
<223> OTHER INFORMATION: Synthetic primer

<400> SEQUENCE: 140
cctccagagg ttgagcaaat                                               20

<210> SEQ ID NO 141
<211> LENGTH: 20
<212> TYPE: DNA
<213> ORGANISM: Artificial Sequence
<220> FEATURE:
<223> OTHER INFORMATION: Synthetic primer

<400> SEQUENCE: 141
ccaaccagga gaggtgaggc                                               20

<210> SEQ ID NO 142
<211> LENGTH: 20
<212> TYPE: DNA
<213> ORGANISM: Artificial Sequence
<220> FEATURE:
<223> OTHER INFORMATION: Synthetic primer

<400> SEQUENCE: 142
gaagctgtgg ttggttgtca                                               20

<210> SEQ ID NO 143
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 143
ttgaaggtct gattcactct                                                    20

<210> SEQ ID NO 144
<211> LENGTH: 20
<212> TYPE: DNA
<213> ORGANISM: Artificial Sequence
<220> FEATURE:
<223> OTHER INFORMATION: Synthetic primer

<400> SEQUENCE: 144
aaggtaatgg cccaggatgg                                                    20

<210> SEQ ID NO 145
<211> LENGTH: 20
<212> TYPE: DNA
<213> ORGANISM: Artificial Sequence
<220> FEATURE:
<223> OTHER INFORMATION: Synthetic primer

<400> SEQUENCE: 145
aagcagtagg tcaggcagca                                                    20

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146
ccttgcttct gcggacactg                                                    20

<210> SEQ ID NO 147
<211> LENGTH: 20
<212> TYPE: DNA
<213> ORGANISM: Artificial Sequence
<220> FEATURE:
<223> OTHER INFORMATION: Synthetic primer

<400> SEQUENCE: 147
agccccttgc ttctgcggac                                                    20

<210> SEQ ID NO 148
<211> LENGTH: 20
<212> TYPE: DNA
<213> ORGANISM: Artificial Sequence
<220> FEATURE:
<223> OTHER INFORMATION: Synthetic primer

<400> SEQUENCE: 148
tgacggaggc taccttcaga                                                    20

<210> SEQ ID NO 149
<211> LENGTH: 20
<212> TYPE: DNA
<213> ORGANISM: Artificial Sequence
<220> FEATURE:
<223> OTHER INFORMATION: Synthetic primer

<400> SEQUENCE: 149
gtaaaacagc ttaaatttgt                                                    20

<210> SEQ ID NO 150
<211> LENGTH: 20

```
<212> TYPE: DNA
<213> ORGANISM: Artificial Sequence
<220> FEATURE:
<223> OTHER INFORMATION: Synthetic primer

<400> SEQUENCE: 150
agaagaggtt acattaagca                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic primer

<400> SEQUENCE: 151
agataatgaa ttggctgaca                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic primer

<400> SEQUENCE: 152
gcgtcatcat ccgcaccatc                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic primer

<400> SEQUENCE: 153
cgttgcttgt gccgacagtg                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic primer

<400> SEQUENCE: 154
gctcacgaag aacaccttcc                                               20

<210> SEQ ID NO 155
<211> LENGTH: 20
<212> TYPE: DNA
<213> ORGANISM: Artificial Sequence
<220> FEATURE:
<223> OTHER INFORMATION: Synthetic primer

<400> SEQUENCE: 155
agagaaacta gtaagagtct                                               20

<210> SEQ ID NO 156
<211> LENGTH: 20
<212> TYPE: DNA
<213> ORGANISM: Artificial Sequence
<220> FEATURE:
<223> OTHER INFORMATION: Synthetic primer

<400> SEQUENCE: 156
tggcatccac ccggcagatg                                               20
```

<210> SEQ ID NO 157
<211> LENGTH: 20
<212> TYPE: DNA
<213> ORGANISM: Artificial Sequence
<220> FEATURE:
<223> OTHER INFORMATION: Synthetic primer

<400> SEQUENCE: 157
tcgagaaaca gagatgtaga                                          20

<210> SEQ ID NO 158
<211> LENGTH: 20
<212> TYPE: DNA
<213> ORGANISM: Artificial Sequence
<220> FEATURE:
<223> OTHER INFORMATION: Synthetic primer

<400> SEQUENCE: 158
tggagcttag gcacctccta                                          20

<210> SEQ ID NO 159
<211> LENGTH: 20
<212> TYPE: DNA
<213> ORGANISM: Artificial Sequence
<220> FEATURE:
<223> OTHER INFORMATION: Synthetic primer

<400> SEQUENCE: 159
tggggaaagc caggaatcta                                          20

<210> SEQ ID NO 160
<211> LENGTH: 20
<212> TYPE: DNA
<213> ORGANISM: Artificial Sequence
<220> FEATURE:
<223> OTHER INFORMATION: Synthetic primer

<400> SEQUENCE: 160
cagcacaaag agaagaatga                                          20

<210> SEQ ID NO 161
<211> LENGTH: 20
<212> TYPE: DNA
<213> ORGANISM: Artificial Sequence
<220> FEATURE:
<223> OTHER INFORMATION: Synthetic primer

<400> SEQUENCE: 161
atgaggagag ttgtaacggc                                          20

<210> SEQ ID NO 162
<211> LENGTH: 20
<212> TYPE: DNA
<213> ORGANISM: Artificial Sequence
<220> FEATURE:
<223> OTHER INFORMATION: Synthetic primer

<400> SEQUENCE: 162
aagtccggtt cttatactcg                                          20

<210> SEQ ID NO 163
<211> LENGTH: 20
<212> TYPE: DNA
<213> ORGANISM: Artificial Sequence
<220> FEATURE:
<223> OTHER INFORMATION: Synthetic primer

<400> SEQUENCE: 163
gcaggtaatc cttttagtgt                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic primer

<400> SEQUENCE: 164
gtgaagtcct ctgacacgtg                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic primer

<400> SEQUENCE: 165
cgaatcctgc cccaaagagc                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic primer

<400> SEQUENCE: 166
actgcgccga atcctgcccc                                               20

<210> SEQ ID NO 167
<211> LENGTH: 20
<212> TYPE: DNA
<213> ORGANISM: Artificial Sequence
<220> FEATURE:
<223> OTHER INFORMATION: Synthetic primer

<400> SEQUENCE: 167
ttgatgatga caacgatgac                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic primer

<400> SEQUENCE: 168
ctgttgtttg tttctctgct                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic primer

<400> SEQUENCE: 169
tgttcagcta atgcttcttc                                               20

<210> SEQ ID NO 170
<211> LENGTH: 20

```
<212> TYPE: DNA
<213> ORGANISM: Artificial Sequence
<220> FEATURE:
<223> OTHER INFORMATION: Synthetic primer

<400> SEQUENCE: 170
gttaactcta tcttgtgtca                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic primer

<400> SEQUENCE: 171
tccacttcag tcatcaagca                                              20

<210> SEQ ID NO 172
<211> LENGTH: 20
<212> TYPE: DNA
<213> ORGANISM: Artificial Sequence
<220> FEATURE:
<223> OTHER INFORMATION: Synthetic primer

<400> SEQUENCE: 172
tgctcaatac tctctttta                                               20

<210> SEQ ID NO 173
<211> LENGTH: 20
<212> TYPE: DNA
<213> ORGANISM: Artificial Sequence
<220> FEATURE:
<223> OTHER INFORMATION: Synthetic primer

<400> SEQUENCE: 173
aggcccagca aacttgcccg                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic primer

<400> SEQUENCE: 174
aacggcaagg cagcaatacc                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic primer

<400> SEQUENCE: 175
cagaagcaag gtggtaagaa                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic primer

<400> SEQUENCE: 176
gcctgtccac tgtagctcca                                              20
```

<210> SEQ ID NO 177
<211> LENGTH: 20
<212> TYPE: DNA
<213> ORGANISM: Artificial Sequence
<220> FEATURE:
<223> OTHER INFORMATION: Synthetic primer

<400> SEQUENCE: 177
agaatgttac tcagtcccat                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic primer

<400> SEQUENCE: 178
tcagaggagc agcaccagag                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic primer

<400> SEQUENCE: 179
tggcatggca ggtctgcagt                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic primer

<400> SEQUENCE: 180
agctcactca ggctttggtt                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic primer

<400> SEQUENCE: 181
tgcctaagta tacctcattc                                              20

<210> SEQ ID NO 182
<211> LENGTH: 20
<212> TYPE: DNA
<213> ORGANISM: Artificial Sequence
<220> FEATURE:
<223> OTHER INFORMATION: Synthetic primer

<400> SEQUENCE: 182
ctgtcaaatt tctctttgcc                                              20

<210> SEQ ID NO 183
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 183
catatacttg gaatgaacac                                                     20

<210> SEQ ID NO 184
<211> LENGTH: 20
<212> TYPE: DNA
<213> ORGANISM: Artificial Sequence
<220> FEATURE:
<223> OTHER INFORMATION: Synthetic primer

<400> SEQUENCE: 184
ggtccaactg tccgaatcaa                                                     20

<210> SEQ ID NO 185
<211> LENGTH: 20
<212> TYPE: DNA
<213> ORGANISM: Artificial Sequence
<220> FEATURE:
<223> OTHER INFORMATION: Synthetic primer

<400> SEQUENCE: 185
tgatctgaag attgtgaagt                                                     20

<210> SEQ ID NO 186
<211> LENGTH: 20
<212> TYPE: DNA
<213> ORGANISM: Artificial Sequence
<220> FEATURE:
<223> OTHER INFORMATION: Synthetic primer

<400> SEQUENCE: 186
aagcccttgt ccttgatctg                                                     20

<210> SEQ ID NO 187
<211> LENGTH: 20
<212> TYPE: DNA
<213> ORGANISM: Artificial Sequence
<220> FEATURE:
<223> OTHER INFORMATION: Synthetic primer

<400> SEQUENCE: 187
tgtgatggat gatacattga                                                     20

<210> SEQ ID NO 188
<211> LENGTH: 20
<212> TYPE: DNA
<213> ORGANISM: Artificial Sequence
<220> FEATURE:
<223> OTHER INFORMATION: Synthetic primer

<400> SEQUENCE: 188
tcaggttgac tgaagttagc                                                     20

<210> SEQ ID NO 189
<211> LENGTH: 20
<212> TYPE: DNA
<213> ORGANISM: Artificial Sequence
<220> FEATURE:
<223> OTHER INFORMATION: Synthetic primer

<400> SEQUENCE: 189
gtgtatagat gagcaggtca                                                     20

<210> SEQ ID NO 190
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 190
tctgtgacat tatcttgaga                                              20

<210> SEQ ID NO 191
<211> LENGTH: 20
<212> TYPE: DNA
<213> ORGANISM: Artificial Sequence
<220> FEATURE:
<223> OTHER INFORMATION: Synthetic primer

<400> SEQUENCE: 191
aagataaaag ccgcgtcttg                                              20

<210> SEQ ID NO 192
<211> LENGTH: 20
<212> TYPE: DNA
<213> ORGANISM: Artificial Sequence
<220> FEATURE:
<223> OTHER INFORMATION: Synthetic primer

<400> SEQUENCE: 192
agaaaaccat cacacatata                                              20

<210> SEQ ID NO 193
<211> LENGTH: 20
<212> TYPE: DNA
<213> ORGANISM: Artificial Sequence
<220> FEATURE:
<223> OTHER INFORMATION: Synthetic primer

<400> SEQUENCE: 193
agagttgcga ggccgcttct                                              20

<210> SEQ ID NO 194
<211> LENGTH: 20
<212> TYPE: DNA
<213> ORGANISM: Artificial Sequence
<220> FEATURE:
<223> OTHER INFORMATION: Synthetic primer

<400> SEQUENCE: 194
tccctctcca ttgtgttggt                                              20

<210> SEQ ID NO 195
<211> LENGTH: 20
<212> TYPE: DNA
<213> ORGANISM: Artificial Sequence
<220> FEATURE:
<223> OTHER INFORMATION: Synthetic primer

<400> SEQUENCE: 195
catcagatct ttcaggtata                                              20

<210> SEQ ID NO 196
<211> LENGTH: 20
<212> TYPE: DNA
<213> ORGANISM: Artificial Sequence
<220> FEATURE:
<223> OTHER INFORMATION: Synthetic primer

<400> SEQUENCE: 196
ggctttactc tttaattaaa                                              20
```

<210> SEQ ID NO 197
<211> LENGTH: 20
<212> TYPE: DNA
<213> ORGANISM: Artificial Sequence
<220> FEATURE:
<223> OTHER INFORMATION: Synthetic primer

<400> SEQUENCE: 197
gaaatcaaaa aggttgccca                                               20

<210> SEQ ID NO 198
<211> LENGTH: 20
<212> TYPE: DNA
<213> ORGANISM: Artificial Sequence
<220> FEATURE:
<223> OTHER INFORMATION: Synthetic primer

<400> SEQUENCE: 198
ggagtcctgg agccccctta                                               20

<210> SEQ ID NO 199
<211> LENGTH: 20
<212> TYPE: DNA
<213> ORGANISM: Artificial Sequence
<220> FEATURE:
<223> OTHER INFORMATION: Synthetic primer

<400> SEQUENCE: 199
ttggcatacg gagcagagct                                               20

<210> SEQ ID NO 200
<211> LENGTH: 20
<212> TYPE: DNA
<213> ORGANISM: Artificial Sequence
<220> FEATURE:
<223> OTHER INFORMATION: Synthetic primer

<400> SEQUENCE: 200
tgtgctctga agtgaaaaga                                               20

<210> SEQ ID NO 201
<211> LENGTH: 20
<212> TYPE: DNA
<213> ORGANISM: Artificial Sequence
<220> FEATURE:
<223> OTHER INFORMATION: Synthetic primer

<400> SEQUENCE: 201
ggcttggccc ataagtgtgc                                               20

<210> SEQ ID NO 202
<211> LENGTH: 20
<212> TYPE: DNA
<213> ORGANISM: Artificial Sequence
<220> FEATURE:
<223> OTHER INFORMATION: Synthetic primer

<400> SEQUENCE: 202
cctaaatttt atttccaggt                                               20

<210> SEQ ID NO 203
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 203
gctccaagtg tcccaatgaa                                               20

<210> SEQ ID NO 204
<211> LENGTH: 20
<212> TYPE: DNA
<213> ORGANISM: Artificial Sequence
<220> FEATURE:
<223> OTHER INFORMATION: Synthetic primer

<400> SEQUENCE: 204
agtatgtttc tcactccgat                                               20

<210> SEQ ID NO 205
<211> LENGTH: 20
<212> TYPE: DNA
<213> ORGANISM: Artificial Sequence
<220> FEATURE:
<223> OTHER INFORMATION: control oligonucleotide

<400> SEQUENCE: 205
tgccagcacc cggtacgtcc                                               20

<210> SEQ ID NO 206
<211> LENGTH: 20
<212> TYPE: DNA
<213> ORGANISM: Artificial Sequence
<220> FEATURE:
<223> OTHER INFORMATION: Synthetic primer

<400> SEQUENCE: 206
gctgcctaca ggagccactc                                               20

<210> SEQ ID NO 207
<211> LENGTH: 20
<212> TYPE: DNA
<213> ORGANISM: Artificial Sequence
<220> FEATURE:
<223> OTHER INFORMATION: Synthetic primer

<400> SEQUENCE: 207
tcaagtccgt gctgcctaca                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic primer

<400> SEQUENCE: 208
gtctacagga gtctggttgt                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic primer

<400> SEQUENCE: 209
agcttgcgtc tccacggaaa                                               20

<210> SEQ ID NO 210
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 210
tcacactatc aagtttctct                                           20

<210> SEQ ID NO 211
<211> LENGTH: 20
<212> TYPE: DNA
<213> ORGANISM: Artificial Sequence
<220> FEATURE:
<223> OTHER INFORMATION: Synthetic primer

<400> SEQUENCE: 211
gtcaaagctc gtgcggccca                                           20

<210> SEQ ID NO 212
<211> LENGTH: 20
<212> TYPE: DNA
<213> ORGANISM: Artificial Sequence
<220> FEATURE:
<223> OTHER INFORMATION: Synthetic primer

<400> SEQUENCE: 212
gtgaagtcgt agagtccagt                                           20

<210> SEQ ID NO 213
<211> LENGTH: 20
<212> TYPE: DNA
<213> ORGANISM: Artificial Sequence
<220> FEATURE:
<223> OTHER INFORMATION: Synthetic primer

<400> SEQUENCE: 213
gtgaccttgc ttagacgtgc                                           20

<210> SEQ ID NO 214
<211> LENGTH: 20
<212> TYPE: DNA
<213> ORGANISM: Artificial Sequence
<220> FEATURE:
<223> OTHER INFORMATION: Synthetic primer

<400> SEQUENCE: 214
catcttctta ggtttcgggt                                           20

<210> SEQ ID NO 215
<211> LENGTH: 20
<212> TYPE: DNA
<213> ORGANISM: Artificial Sequence
<220> FEATURE:
<223> OTHER INFORMATION: Synthetic primer

<400> SEQUENCE: 215
ggctgttgga gatactgaac                                           20

<210> SEQ ID NO 216
<211> LENGTH: 20
<212> TYPE: DNA
<213> ORGANISM: Artificial Sequence
<220> FEATURE:
<223> OTHER INFORMATION: Synthetic primer

<400> SEQUENCE: 216
gggaatgaaa gagagaggct                                           20
```

<210> SEQ ID NO 217
<211> LENGTH: 20
<212> TYPE: DNA
<213> ORGANISM: Artificial Sequence
<220> FEATURE:
<223> OTHER INFORMATION: Synthetic primer

<400> SEQUENCE: 217
acatacaatg atgagcagca                                              20

<210> SEQ ID NO 218
<211> LENGTH: 20
<212> TYPE: DNA
<213> ORGANISM: Artificial Sequence
<220> FEATURE:
<223> OTHER INFORMATION: Synthetic primer

<400> SEQUENCE: 218
gtctctctgt cagcgttact                                              20

<210> SEQ ID NO 219
<211> LENGTH: 20
<212> TYPE: DNA
<213> ORGANISM: Artificial Sequence
<220> FEATURE:
<223> OTHER INFORMATION: Synthetic primer

<400> SEQUENCE: 219
tgccaagccc atggtgcatc                                              20

<210> SEQ ID NO 220
<211> LENGTH: 20
<212> TYPE: DNA
<213> ORGANISM: Artificial Sequence
<220> FEATURE:
<223> OTHER INFORMATION: Synthetic primer

<400> SEQUENCE: 220
gcaatttggg gttcaagttc                                              20

<210> SEQ ID NO 221
<211> LENGTH: 20
<212> TYPE: DNA
<213> ORGANISM: Artificial Sequence
<220> FEATURE:
<223> OTHER INFORMATION: Synthetic primer

<400> SEQUENCE: 221
caatcagctg agaacatttt                                              20

<210> SEQ ID NO 222
<211> LENGTH: 20
<212> TYPE: DNA
<213> ORGANISM: Artificial Sequence
<220> FEATURE:
<223> OTHER INFORMATION: Synthetic primer

<400> SEQUENCE: 222
ttttgtataa aacaatcata                                              20

<210> SEQ ID NO 223
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 223
ccttcactct gcatttggtt                                              20

<210> SEQ ID NO 224
<211> LENGTH: 20
<212> TYPE: DNA
<213> ORGANISM: Artificial Sequence
<220> FEATURE:
<223> OTHER INFORMATION: Synthetic primer

<400> SEQUENCE: 224
tgcatgttat caccatactc                                              20

<210> SEQ ID NO 225
<211> LENGTH: 20
<212> TYPE: DNA
<213> ORGANISM: Artificial Sequence
<220> FEATURE:
<223> OTHER INFORMATION: Synthetic primer

<400> SEQUENCE: 225
ccctccagtg atgtttacaa                                              20

<210> SEQ ID NO 226
<211> LENGTH: 20
<212> TYPE: DNA
<213> ORGANISM: Artificial Sequence
<220> FEATURE:
<223> OTHER INFORMATION: Synthetic primer

<400> SEQUENCE: 226
gaagaccctc cagtgatgtt                                              20

<210> SEQ ID NO 227
<211> LENGTH: 20
<212> TYPE: DNA
<213> ORGANISM: Artificial Sequence
<220> FEATURE:
<223> OTHER INFORMATION: Synthetic primer

<400> SEQUENCE: 227
cgtagaagac cctccagtga                                              20

<210> SEQ ID NO 228
<211> LENGTH: 20
<212> TYPE: DNA
<213> ORGANISM: Artificial Sequence
<220> FEATURE:
<223> OTHER INFORMATION: Synthetic primer

<400> SEQUENCE: 228
ttcccaggtg caaaacaggc                                              20

<210> SEQ ID NO 229
<211> LENGTH: 20
<212> TYPE: DNA
<213> ORGANISM: Artificial Sequence
<220> FEATURE:
<223> OTHER INFORMATION: Synthetic primer

<400> SEQUENCE: 229
tggcttcaga tgcttagggt                                              20

<210> SEQ ID NO 230
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 230
cctccgtgtg tggcccatgg                                              20

<210> SEQ ID NO 231
<211> LENGTH: 20
<212> TYPE: DNA
<213> ORGANISM: Artificial Sequence
<220> FEATURE:
<223> OTHER INFORMATION: Synthetic primer

<400> SEQUENCE: 231
ggtgatgttc cctgcctccg                                              20

<210> SEQ ID NO 232
<211> LENGTH: 20
<212> TYPE: DNA
<213> ORGANISM: Artificial Sequence
<220> FEATURE:
<223> OTHER INFORMATION: Synthetic primer

<400> SEQUENCE: 232
gatggtgatg ttccctgcct                                              20

<210> SEQ ID NO 233
<211> LENGTH: 20
<212> TYPE: DNA
<213> ORGANISM: Artificial Sequence
<220> FEATURE:
<223> OTHER INFORMATION: Synthetic primer

<400> SEQUENCE: 233
aggtatggac acttggatgg                                              20

<210> SEQ ID NO 234
<211> LENGTH: 20
<212> TYPE: DNA
<213> ORGANISM: Artificial Sequence
<220> FEATURE:
<223> OTHER INFORMATION: Synthetic primer

<400> SEQUENCE: 234
gaaagaccag ccagcaccaa                                              20

<210> SEQ ID NO 235
<211> LENGTH: 20
<212> TYPE: DNA
<213> ORGANISM: Artificial Sequence
<220> FEATURE:
<223> OTHER INFORMATION: Synthetic primer

<400> SEQUENCE: 235
cagcgttgcc acttctttca                                              20

<210> SEQ ID NO 236
<211> LENGTH: 20
<212> TYPE: DNA
<213> ORGANISM: Artificial Sequence
<220> FEATURE:
<223> OTHER INFORMATION: Synthetic primer

<400> SEQUENCE: 236
gtgaccacag gacagcgttg                                              20
```

<210> SEQ ID NO 237
<211> LENGTH: 20
<212> TYPE: DNA
<213> ORGANISM: Artificial Sequence
<220> FEATURE:
<223> OTHER INFORMATION: Synthetic primer

<400> SEQUENCE: 237
agatgcgagt ttgtgccagc                                              20

<210> SEQ ID NO 238
<211> LENGTH: 20
<212> TYPE: DNA
<213> ORGANISM: Artificial Sequence
<220> FEATURE:
<223> OTHER INFORMATION: Synthetic primer

<400> SEQUENCE: 238 cctttttgcca gtagatgcga                                             20

<210> SEQ ID NO 239
<211> LENGTH: 20
<212> TYPE: DNA
<213> ORGANISM: Artificial Sequence
<220> FEATURE:
<223> OTHER INFORMATION: Synthetic primer

<400> SEQUENCE: 239
cggttcttgt actcgggcca                                              20

<210> SEQ ID NO 240
<211> LENGTH: 20
<212> TYPE: DNA
<213> ORGANISM: Artificial Sequence
<220> FEATURE:
<223> OTHER INFORMATION: Synthetic primer

<400> SEQUENCE: 240
cgcagagcca ggatcacaat                                              20

<210> SEQ ID NO 241
<211> LENGTH: 20
<212> TYPE: DNA
<213> ORGANISM: Artificial Sequence
<220> FEATURE:
<223> OTHER INFORMATION: Synthetic primer

<400> SEQUENCE: 241
cttcagccag gtgttcccgc                                              20

<210> SEQ ID NO 242
<211> LENGTH: 20
<212> TYPE: DNA
<213> ORGANISM: Artificial Sequence
<220> FEATURE:
<223> OTHER INFORMATION: Synthetic primer

<400> SEQUENCE: 242
taacgtcact tcagccaggt                                              20

<210> SEQ ID NO 243
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 243
ttctccattt tccaaccagg                                              20

<210> SEQ ID NO 244
<211> LENGTH: 20
<212> TYPE: DNA
<213> ORGANISM: Artificial Sequence
<220> FEATURE:
<223> OTHER INFORMATION: Synthetic primer

<400> SEQUENCE: 244
ctgttgtgtt gatggcattt                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic primer

<400> SEQUENCE: 245
catgaagctg tggttggttg                                              20

<210> SEQ ID NO 246
<211> LENGTH: 20
<212> TYPE: DNA
<213> ORGANISM: Artificial Sequence
<220> FEATURE:
<223> OTHER INFORMATION: Synthetic primer

<400> SEQUENCE: 246
aggaaaatgc tcttgcttgg                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic primer

<400> SEQUENCE: 247
tgggagcagg ttatcaggaa                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic primer

<400> SEQUENCE: 248
taaggtaatg gcccaggatg                                              20

<210> SEQ ID NO 249
<211> LENGTH: 20
<212> TYPE: DNA
<213> ORGANISM: Artificial Sequence
<220> FEATURE:
<223> OTHER INFORMATION: Synthetic primer

<400> SEQUENCE: 249
ggtcaggcag catatcacaa                                              20

<210> SEQ ID NO 250
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 250
gccccttgct tgtgcggaca                                               20

<210> SEQ ID NO 251
<211> LENGTH: 20
<212> TYPE: DNA
<213> ORGANISM: Artificial Sequence
<220> FEATURE:
<223> OTHER INFORMATION: Synthetic primer

<400> SEQUENCE: 251
agatcttttc agccccttgc                                               20

<210> SEQ ID NO 252
<211> LENGTH: 20
<212> TYPE: DNA
<213> ORGANISM: Artificial Sequence
<220> FEATURE:
<223> OTHER INFORMATION: Synthetic primer

<400> SEQUENCE: 252
tttgttaagg gaagaatgcc                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic primer

<400> SEQUENCE: 253
aaaggagagg gatgccagcc                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic primer

<400> SEQUENCE: 254
caagacaatt caagatggca                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic primer

<400> SEQUENCE: 255
cgtgtgtctg tgctagtccc                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic primer

<400> SEQUENCE: 256
gctgcttctg ctgtgaccta                                               20
```

<210> SEQ ID NO 257
<211> LENGTH: 20
<212> TYPE: DNA
<213> ORGANISM: Artificial Sequence
<220> FEATURE:
<223> OTHER INFORMATION: Synthetic primer

<400> SEQUENCE: 257
tatttgcgag ctccccgtac                                              20

<210> SEQ ID NO 258
<211> LENGTH: 20
<212> TYPE: DNA
<213> ORGANISM: Artificial Sequence
<220> FEATURE:
<223> OTHER INFORMATION: Synthetic primer

<400> SEQUENCE: 258
gcataagcac agcagcattc                                              20

<210> SEQ ID NO 259
<211> LENGTH: 20
<212> TYPE: DNA
<213> ORGANISM: Artificial Sequence
<220> FEATURE:
<223> OTHER INFORMATION: Synthetic primer

<400> SEQUENCE: 259
tccaaaaaga gaccagatgc                                              20

<210> SEQ ID NO 260
<211> LENGTH: 20
<212> TYPE: DNA
<213> ORGANISM: Artificial Sequence
<220> FEATURE:
<223> OTHER INFORMATION: Synthetic primer

<400> SEQUENCE: 260
aaatgcctgt ccactgtagc                                              20

<210> SEQ ID NO 261
<211> LENGTH: 20
<212> TYPE: DNA
<213> ORGANISM: Artificial Sequence
<220> FEATURE:
<223> OTHER INFORMATION: Synthetic primer

<400> SEQUENCE: 261
cttcagagga gcagcaccag                                              20

<210> SEQ ID NO 262
<211> LENGTH: 20
<212> TYPE: DNA
<213> ORGANISM: Artificial Sequence
<220> FEATURE:
<223> OTHER INFORMATION: Synthetic primer

<400> SEQUENCE: 262
gaatcttcag aggagcagca                                              20

<210> SEQ ID NO 263
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 263
caaattggca tggcaggtct                                              20

<210> SEQ ID NO 264
<211> LENGTH: 20
<212> TYPE: DNA
<213> ORGANISM: Artificial Sequence
<220> FEATURE:
<223> OTHER INFORMATION: Synthetic primer

<400> SEQUENCE: 264
gctttggttt tgagagtttg                                              20

<210> SEQ ID NO 265
<211> LENGTH: 20
<212> TYPE: DNA
<213> ORGANISM: Artificial Sequence
<220> FEATURE:
<223> OTHER INFORMATION: Synthetic primer

<400> SEQUENCE: 265
aggctttggt tttgagagtt                                              20

<210> SEQ ID NO 266
<211> LENGTH: 20
<212> TYPE: DNA
<213> ORGANISM: Artificial Sequence
<220> FEATURE:
<223> OTHER INFORMATION: Synthetic primer

<400> SEQUENCE: 266
gctcactcag gctttggttt                                              20

<210> SEQ ID NO 267
<211> LENGTH: 20
<212> TYPE: DNA
<213> ORGANISM: Artificial Sequence
<220> FEATURE:
<223> OTHER INFORMATION: Synthetic primer

<400> SEQUENCE: 267
ggtcctgcca aaatactact                                              20

<210> SEQ ID NO 268
<211> LENGTH: 20
<212> TYPE: DNA
<213> ORGANISM: Artificial Sequence
<220> FEATURE:
<223> OTHER INFORMATION: Synthetic primer

<400> SEQUENCE: 268
agcccttgtc cttgatctga                                              20

<210> SEQ ID NO 269
<211> LENGTH: 20
<212> TYPE: DNA
<213> ORGANISM: Artificial Sequence
<220> FEATURE:
<223> OTHER INFORMATION: Synthetic primer

<400> SEQUENCE: 269
tgtgggcttt ttgtgatgga                                              20

<210> SEQ ID NO 270
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 270
aatcattcct gtgggctttt                                               20

<210> SEQ ID NO 271
<211> LENGTH: 20
<212> TYPE: DNA
<213> ORGANISM: Artificial Sequence
<220> FEATURE:
<223> OTHER INFORMATION: Synthetic primer

<400> SEQUENCE: 271
ccgtgtatag atgagcaggt                                               20

<210> SEQ ID NO 272
<211> LENGTH: 20
<212> TYPE: DNA
<213> ORGANISM: Artificial Sequence
<220> FEATURE:
<223> OTHER INFORMATION: Synthetic primer

<400> SEQUENCE: 272
accgtgtata gatgagcagg                                               20

<210> SEQ ID NO 273
<211> LENGTH: 20
<212> TYPE: DNA
<213> ORGANISM: Artificial Sequence
<220> FEATURE:
<223> OTHER INFORMATION: Synthetic primer

<400> SEQUENCE: 273
tcatcttctt aggttctggg                                               20

<210> SEQ ID NO 274
<211> LENGTH: 20
<212> TYPE: DNA
<213> ORGANISM: Artificial Sequence
<220> FEATURE:
<223> OTHER INFORMATION: Synthetic primer

<400> SEQUENCE: 274
acaagctgat ggaaacgtcg                                               20

<210> SEQ ID NO 275
<211> LENGTH: 20
<212> TYPE: DNA
<213> ORGANISM: Artificial Sequence
<220> FEATURE:
<223> OTHER INFORMATION: Synthetic primer

<400> SEQUENCE: 275
tgctcgtaac atcagggaat                                               20

<210> SEQ ID NO 276
<211> LENGTH: 20
<212> TYPE: DNA
<213> ORGANISM: Artificial Sequence
<220> FEATURE:
<223> OTHER INFORMATION: Synthetic primer

<400> SEQUENCE: 276
aagatggtca tattgctcgt                                               20
```

<210> SEQ ID NO 277
<211> LENGTH: 20
<212> TYPE: DNA
<213> ORGANISM: Artificial Sequence
<220> FEATURE:
<223> OTHER INFORMATION: Synthetic primer

<400> SEQUENCE: 277
cgcgtcttgt cagtttccag                                               20

<210> SEQ ID NO 278
<211> LENGTH: 20
<212> TYPE: DNA
<213> ORGANISM: Artificial Sequence
<220> FEATURE:
<223> OTHER INFORMATION: Synthetic primer

<400> SEQUENCE: 278
cagctgtaat ccaaggaatg                                               20

<210> SEQ ID NO 279
<211> LENGTH: 20
<212> TYPE: DNA
<213> ORGANISM: Artificial Sequence
<220> FEATURE:
<223> OTHER INFORMATION: Synthetic primer

<400> SEQUENCE: 279
gggcttcatc agatctttca                                               20

<210> SEQ ID NO 280
<211> LENGTH: 20
<212> TYPE: DNA
<213> ORGANISM: Artificial Sequence
<220> FEATURE:
<223> OTHER INFORMATION: Synthetic primer

<400> SEQUENCE: 280
catgtatcac ttttgtcgca                                               20

<210> SEQ ID NO 281
<211> LENGTH: 20
<212> TYPE: DNA
<213> ORGANISM: Artificial Sequence
<220> FEATURE:
<223> OTHER INFORMATION: Synthetic primer

<400> SEQUENCE: 281
agccccctta ttactcatgg                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic primer

<400> SEQUENCE: 282
ggagttacag ccaggctatt                                               20

<210> SEQ ID NO 283
<211> LENGTH: 20
<212> TYPE: DNA
<213> ORGANISM: Artificial Sequence
<220> FEATURE:
<223> OTHER INFORMATION: Synthetic primer

<400> SEQUENCE: 283
agtctcctct tggcatacgg                                         20

<210> SEQ ID NO 284
<211> LENGTH: 20
<212> TYPE: DNA
<213> ORGANISM: Artificial Sequence
<220> FEATURE:
<223> OTHER INFORMATION: Synthetic primer

<400> SEQUENCE: 284
cccataagtg tgctctgaag                                         20

<210> SEQ ID NO 285
<211> LENGTH: 20
<212> TYPE: DNA
<213> ORGANISM: Artificial Sequence
<220> FEATURE:
<223> OTHER INFORMATION: Synthetic primer

<400> SEQUENCE: 285
tccgtcatcg ctcctcaggg                                         20

<210> SEQ ID NO 286
<211> LENGTH: 20
<212> TYPE: DNA
<213> ORGANISM: Artificial Sequence
<220> FEATURE:
<223> OTHER INFORMATION: Synthetic primer

<400> SEQUENCE: 286
gctcagcctt tccacttcag                                         20

<210> SEQ ID NO 287
<211> LENGTH: 20
<212> TYPE: DNA
<213> ORGANISM: Artificial Sequence
<220> FEATURE:
<223> OTHER INFORMATION: Synthetic primer

<400> SEQUENCE: 287 gctcagcctttccacttcag                                          20

<210> SEQ ID NO 288
<211> LENGTH: 19
<212> TYPE: DNA
<213> ORGANISM: Artificial Sequence
<220> FEATURE:
<223> OTHER INFORMATION: Synthetic primer

<400> SEQUENCE: 288
ggccctcctc cttgtgatg                                          19

<210> SEQ ID NO 289
<211> LENGTH: 29
<212> TYPE: DNA
<213> ORGANISM: Artificial Sequence
<220> FEATURE:
<223> OTHER INFORMATION: Synthetic primer

<400> SEQUENCE: 289
tgctcatcat tgtatgtcac aagaagccg                               29

<210> SEQ ID NO 290
<211> LENGTH: 19

```
<212> TYPE: DNA
<213> ORGANISM: Artificial Sequence
<220> FEATURE:
<223> OTHER INFORMATION: Synthetic primer

<400> SEQUENCE: 290
ctgggcctgc taggctgat                                              19

<210> SEQ ID NO 291
<211> LENGTH: 20
<212> TYPE: DNA
<213> ORGANISM: Artificial Sequence
<220> FEATURE:
<223> OTHER INFORMATION: Synthetic primer

<400> SEQUENCE: 291
caggaagcta cgggcaagtt                                             20

<210> SEQ ID NO 292
<211> LENGTH: 27
<212> TYPE: DNA
<213> ORGANISM: Artificial Sequence
<220> FEATURE:
<223> OTHER INFORMATION: Synthetic primer

<400> SEQUENCE: 292
tgggcctttg attgcttgat gactgaa                                     27

<210> SEQ ID NO 293
<211> LENGTH: 18
<212> TYPE: DNA
<213> ORGANISM: Artificial Sequence
<220> FEATURE:
<223> OTHER INFORMATION: Synthetic primer

<400> SEQUENCE: 293
gtgggctcag cctttcca                                               18

<210> SEQ ID NO 294
<211> LENGTH: 20
<212> TYPE: DNA
<213> ORGANISM: Artificial Sequence
<220> FEATURE:
<223> OTHER INFORMATION: Synthetic primer

<400> SEQUENCE: 294
tcaagtcctt ccacacccaa                                             20

<210> SEQ ID NO 295
<211> LENGTH: 1424
<212> TYPE: DNA
<213> ORGANISM: Homo sapiens
<220> FEATURE:
<221> NAME/KEY: CDS
<222> LOCATION: (148)...(1119)

<400> SEQUENCE: 295
aggagcctta ggaggtacgg ggagctcgca aatactcctt ttggtttatt cttaccacct    60
tgcttctgtg ttccttggga atgctgctgt gcttatgcat ctggtctctt tttggagcta   120
cagtggacag gcatttgtga cagcact atg gga ctg agt aac att ctc ttt gtg   174
                              Met Gly Leu Ser Asn Ile Leu Phe Val
                                1               5 atg gcc ttc ctg ctc tct ggt gct gct cct ctg aag att caa gct tat   222
Met Ala Phe Leu Leu Ser Gly Ala Ala Pro Leu Lys Ile Gln Ala Tyr
 10                  15                  20                  25
```

```
ttc aat gag act gca gac ctg cca tgc caa ttt gca aac tct caa aac    270
Phe Asn Glu Thr Ala Asp Leu Pro Cys Gln Phe Ala Asn Ser Gln Asn
             30              35              40 caa agc ctg agt gag cta gta gta ttt tgg cag gac cag gaa aac ttg    318
Gln Ser Leu Ser Glu Leu Val Val Phe Trp Gln Asp Gln Glu Asn Leu
         45              50              55 gtt ctg aat gag gta tac tta ggc aaa gag aaa ttt gac agt gtt cat    366
Val Leu Asn Glu Val Tyr Leu Gly Lys Glu Lys Phe Asp Ser Val His
         60              65              70 tcc aag tat atg ggc cgc aca agt ttt gat tcg gac agt tgg acc ctg    414
Ser Lys Tyr Met Gly Arg Thr Ser Phe Asp Ser Asp Ser Trp Thr Leu
     75              80              85 aga ctt cac aat ctt cag atc aag gac aag ggc ttg tat caa tgt atc    462
Arg Leu His Asn Leu Gln Ile Lys Asp Lys Gly Leu Tyr Gln Cys Ile
 90              95             100             105 atc cat cac aaa aag ccc aca gga atg att cgc atc cac cag atg aat    510
Ile His His Lys Lys Pro Thr Gly Met Ile Arg Ile His Gln Met Asn
                 110             115             120 tct gaa ctg tca gtg ctt gct aac ttc agt caa cct gaa ata gta cca    558
Ser Glu Leu Ser Val Leu Ala Asn Phe Ser Gln Pro Glu Ile Val Pro
             125             130             135 att tct aat ata aca gaa aat gtg tac ata aat ttg acc tgc tca tct    606
Ile Ser Asn Ile Thr Glu Asn Val Tyr Ile Asn Leu Thr Cys Ser Ser
         140             145             150 ata cac ggt tac cca gaa cct aag aag atg agt gtt ttg cta aga acc    654
Ile His Gly Tyr Pro Glu Pro Lys Lys Met Ser Val Leu Leu Arg Thr
     155             160             165 aag aat tca act atc gag tat gat ggt att atg cag aaa tct caa gat    702
Lys Asn Ser Thr Ile Glu Tyr Asp Gly Ile Met Gln Lys Ser Gln Asp
170             175             180             185 aat gtc aca gaa ctg tac gac gtt tcc atc agc ttg tct gtt tca ttc    750
Asn Val Thr Glu Leu Tyr Asp Val Ser Ile Ser Leu Ser Val Ser Phe
             190             195             200 cct gat gtt acg agc aat atg acc atc ttc tgt att ctg gaa act gac    798
Pro Asp Val Thr Ser Asn Met Thr Ile Phe Cys Ile Leu Glu Thr Asp
         205             210             215 aag acg cgg ctt tta tct tca cct ttc tct ata gag ctt gag gac cct    846
Lys Thr Arg Leu Leu Ser Ser Pro Phe Ser Ile Glu Leu Glu Asp Pro
     220             225             230 cag cct ccc cca gac cac att cct tgg att aca gct gta ctt cca aca    894
Gln Pro Pro Pro Asp His Ile Pro Trp Ile Thr Ala Val Leu Pro Thr
235             240             245 gtt att ata tgt gtg atg gtt ttc tgt cta att cta tgg aaa tgg aag    942
Val Ile Ile Cys Val Met Val Phe Cys Leu Ile Leu Trp Lys Trp Lys
250             255             260             265 aag aag aag cgg cct cgc aac tct tat aaa tgt gga acc aac aca atg    990
Lys Lys Lys Arg Pro Arg Asn Ser Tyr Lys Cys Gly Thr Asn Thr Met
             270             275             280 gag agg gaa gag agt gaa cag acc aag aaa aga gaa aaa atc cat ata   1038
Glu Arg Glu Glu Ser Glu Gln Thr Lys Lys Arg Glu Lys Ile His Ile
         285             290             295 cct gaa aga tct gat gaa gcc cag cgt gtt ttt aaa agt tcg aag aca   1086
Pro Glu Arg Ser Asp Glu Ala Gln Arg Val Phe Lys Ser Ser Lys Thr
     300             305             310 tct tca tgc gac aaa agt gat aca tgt ttt taa ttaaagagta aagcccatac  1139
Ser Ser Cys Asp Lys Ser Asp Thr Cys Phe *
315             320 aagtattcat tttttctacc ctttcctttg taagttcctg ggcaaccttt ttgatttctt  1199
ccagaaggca aaaagacatt accatgagta ataaggdggc tccaggactc cctctaagtg  1259
```

```
gaatagcctc cctgtaactc cagctctgct ccgtatgcca agaggagact ttaattctct   1319
tactgcttct tttcacttca gagcacactt atgggccaag cccagcttaa tggctcatga   1379
cctggaaata aaatttagga ccaataaaaa aaaaaaaaaa aaaaa                    1424
```

<210> SEQ ID NO 296
<211> LENGTH: 2781
<212> TYPE: DNA
<213> ORGANISM: Homo sapiens
<220> FEATURE:
<221> NAME/KEY: CDS
<222> LOCATION: (117)...(1106)

<400> SEQUENCE: 296

```
ggaaggcttg cacagggtga aagctttgct tctctgctgc tgtaacaggg actagcacag    60
acacacggat gagtggggtc atttccagat attaggtcac agcagaagca gccaaa atg   119
                                                               Met
                                                                 1 gat ccc cag tgc act atg gga ctg agt aac att ctc ttt gtg atg gcc    167
Asp Pro Gln Cys Thr Met Gly Leu Ser Asn Ile Leu Phe Val Met Ala
              5                  10                  15 ttc ctg ctc tct ggt gct gct cct ctg aag att caa gct tat ttc aat    215
Phe Leu Leu Ser Gly Ala Ala Pro Leu Lys Ile Gln Ala Tyr Phe Asn
         20                  25                  30 gag act gca gac ctg cca tgc caa ttt gca aac tct caa aac caa agc    263
Glu Thr Ala Asp Leu Pro Cys Gln Phe Ala Asn Ser Gln Asn Gln Ser
 35                  40                  45 ctg agt gag cta gta gta ttt tgg cag gac cag gaa aac ttg gtt ctg    311
Leu Ser Glu Leu Val Val Phe Trp Gln Asp Gln Glu Asn Leu Val Leu
 50                  55                  60                  65 aat gag gta tac tta ggc aaa gag aaa ttt gac agt gtt cat tcc aag    359
Asn Glu Val Tyr Leu Gly Lys Glu Lys Phe Asp Ser Val His Ser Lys
                 70                  75                  80 tat atg ggc cgc aca agt ttt gat tcg gac agt tgg acc ctg aga ctt    407
Tyr Met Gly Arg Thr Ser Phe Asp Ser Asp Ser Trp Thr Leu Arg Leu
             85                  90                  95 cac aat ctt cag atc aag gac aag ggc ttg tat caa tgt atc atc cat    455
His Asn Leu Gln Ile Lys Asp Lys Gly Leu Tyr Gln Cys Ile Ile His
        100                 105                 110 cac aaa aag ccc aca gga atg att cgc atc cac cag atg aat tct gaa    503
His Lys Lys Pro Thr Gly Met Ile Arg Ile His Gln Met Asn Ser Glu
    115                 120                 125 ctg tca gtg ctt gct aac ttc agt caa cct gaa ata gta cca att tct    551
Leu Ser Val Leu Ala Asn Phe Ser Gln Pro Glu Ile Val Pro Ile Ser
130                 135                 140                 145 aat ata aca gaa aat gtg tac ata aat ttg acc tgc tca tct ata cac    599
Asn Ile Thr Glu Asn Val Tyr Ile Asn Leu Thr Cys Ser Ser Ile His
                150                 155                 160 ggt tac cca gaa cct aag aag atg agt gtt ttg cta aga acc aag aat    647
Gly Tyr Pro Glu Pro Lys Lys Met Ser Val Leu Leu Arg Thr Lys Asn
            165                 170                 175 tca act atc gag tat gat ggt att atg cag aaa tct caa gat aat gtc    695
Ser Thr Ile Glu Tyr Asp Gly Ile Met Gln Lys Ser Gln Asp Asn Val
        180                 185                 190 aca gaa ctg tac gac gtt tcc atc agc ttg tct gtt tca ttc cct gat    743
Thr Glu Leu Tyr Asp Val Ser Ile Ser Leu Ser Val Ser Phe Pro Asp
    195                 200                 205 gtt acg agc aat atg acc atc ttc tgt att ctg gaa act gac aag acg    791
Val Thr Ser Asn Met Thr Ile Phe Cys Ile Leu Glu Thr Asp Lys Thr
210                 215                 220                 225 cgg ctt tta tct tca cct ttc tct ata gag ctt gag gac cct cag cct    839
```

```
                 Arg Leu Leu Ser Ser Pro Phe Ser Ile Glu Leu Glu Asp Pro Gln Pro
                                 230                 235                 240 ccc cca gac cac att cct tgg att aca gct gta ctt cca aca gtt att      887
Pro Pro Asp His Ile Pro Trp Ile Thr Ala Val Leu Pro Thr Val Ile
                245                 250                 255 ata tgt gtg atg gtt ttc tgt cta att cta tgg aaa tgg aag aag aag      935
Ile Cys Val Met Val Phe Cys Leu Ile Leu Trp Lys Trp Lys Lys Lys
                260                 265                 270 aag cgg cct cgc aac tct tat aaa tgt gga acc aac aca atg gag agg      983
Lys Arg Pro Arg Asn Ser Tyr Lys Cys Gly Thr Asn Thr Met Glu Arg
        275                 280                 285 gaa gag agt gaa cag acc aag aaa aga gaa aaa atc cat ata cct gaa     1031
Glu Glu Ser Glu Gln Thr Lys Lys Arg Glu Lys Ile His Ile Pro Glu
290                 295                 300                 305 aga tct gat gaa acc cag cgt gtt ttt aaa agt tcg aag aca tct tca     1079
Arg Ser Asp Glu Thr Gln Arg Val Phe Lys Ser Ser Lys Thr Ser Ser
                    310                 315                 320 tgc gac aaa agt gat aca tgt ttt taa ttaaagagta aagcccatac           1126
Cys Asp Lys Ser Asp Thr Cys Phe  *
                325 aagtattcat ttttctacc ctttcctttg taagttcctg ggcaaccttt ttgatttctt    1186 ccagaaggca aaaagacatt accatgagta ataaggggc tccaggactc cctctaagtg    1246 gaatagcctc cctgtaactc cagctctgct ccgtatgcca agaggagact ttaattctct   1306 tactgcttct tttcacttca gagcacactt atgggccaag cccagcttaa tggctcatga   1366 cctggaaata aaatttagga ccaataccte ctccagatca gattcttctc ttaatttcat   1426 agattgtgtt tttttttaaa tagacctctc aatttctgga aaactgcctt ttatctgccc   1486 agaattctaa gctggtgccc cactgaatct tgtgtacctg tgactaaaca actacctcct   1546 cagtctgggt gggacttatg tatttatgac cttatagtgt taatatcttg aaacatagag   1606 atctatgtac tgtaatagtg tgattactat gctctagaga aaagtctacc cctgctaagg   1666 agttctcatc cctctgtcag ggtcagtaag gaaaacggtg gcctagggta caggcaacaa   1726 tgagcagacc aacctaaatt tggggaaatt aggagaggca gagatagaac ctggagccac   1786 ttctatctgg gctgttgcta atattgagga ggcttgcccc acccaacaag ccatagtgga   1846 gagaactgaa taaacaggaa aatgccgag cttgtgaacc ctgtttctct tgaagaactg    1906 actagtgaga tggcctgggg aagctgtgaa agaaccaaaa gagatcacaa tactcaaaag   1966 agagagagag agaaaaaaga gagatcttga tccacagaaa tacatgaaat gtctggtctg   2026 tccaccccat caacaagtct tgaaacaagc aacagatgga tagtctgtcc aaatggacat   2086 aagacagaca gcagtttccc tggtggtcag ggaggggttt tggtgatacc caagttattg   2146 ggatgtcatc ttcctggaag cagagctggg gagggagagc catcaccttg ataatgggat   2206 gaatggaagg aggcttagga cttcccactc ctggctgaga gaggaagagc tgcaacggaa   2266 ttaggaagac caagacacag atcacccggg gcttacttag cctacagatg tcctacggga   2326 acgtgggctg gcccagcata gggctagcaa atttgagttg gatgattgtt tttgctcaag   2386 gcaaccagag gaaacttgca tacagagaca gatatactgg gagaaatgac tttgaaaacc   2446 tggctctaag gtgggatcac taagggatgg ggcagtctct gcccaaacat aaagagaact   2506 ctggggagcc tgagccacaa aaatgttcct ttattttatg taaaccctca agggttatag   2566 actgccatgc tagacaagct tgtccatgta atattcccat gttttaccc tgcccctgcc    2626 ttgattagac tcctagcacc tggctagttt ctaacatgtt ttgtgcagca cagttttaa    2686 taaatgcttg ttacattcaa aaaaaaaaa aaaaaaaaa aaaaaaaaa aaaaaaaaa       2746
```

```
aaaaaaaaaa aaaaaaaaaa aaaaaaaaaa aaaaa                              2781

<210> SEQ ID NO 297
<211> LENGTH: 68001
<212> TYPE: DNA
<213> ORGANISM: Homo sapiens

<400> SEQUENCE: 297
gctgtcttgg tggtggtatt tctgttgcag ttgttgtttt cttgcctgct tggtgacata    60
tttctattga cttgacactt aactggcatc ttatctaggt agataatgct aattcaaaat   120
tctgcagata ttgttctgtt gttttttgcc atttaggggt gagtaagatg ccaagttgtt   180
ttttgtttct ctgtagtcat tctgttttca ttttgttttt agctttgcct ttggaattta   240
aaatgttcaa aatgatttgt ctggatgaga atcgattttc ataacttttg ctttgataca   300
ctaaacagtt tgagtttcta gatgatgccc atttttaattc atacgaggaa atatcttcta   360
gtatagtttc tgcttgatta attctatgtt tgtctcttag ggacatctat taatttata   420 atgctgcctt ttttcagac ttctgtttca gaatattcgc tttcatcaat gtaatccttg   480
gctatagtag gaatgaaata ataaaagcag tagcttctgt ctgccctcct tggttatgca   540
gtccttacag aacatctccc catctcccat cccccaccc cagctcagtg aaactctcca   600
cactttggtt gtggaaattg gcagggttag gtggctactc actcccaatc cacatccaca   660
ataaatcact ttttattatc ttatcaaaat ctgtagaatg cctctttatt ctattttgtt   720
gctgcggagg tttgttttct ctttctaatt atttttatttt ctaggttttt tgagggaatt   780
tcaagagggg agattttta ttcaggctca tcttaacgtc atgtctggaa ctcaagctac   840
tgaattatat attctttaat acatatagac ctacgtcaat gagtttaaac tgcaaggaaa   900
gggttaaatt tcttcctcaa gtgtggtcaa aatctgtaga gaaagagga acagcttctc   960 ttaaagaaag ttagctgggt aggtatacag tcattgccga ggaaggcttg cacagggtga  1020
aagctttgct tctctgctgc tgtaacaggg actagcacag acacacggat gagtggggtc  1080
atttccagat attaggtcac agcagaagca gccaaaatgg atccccagtg gtgagtaata  1140
attcttattc tttgcagaga agttatgagt tgtgactgca gtgaaaggct gaggttgaag  1200
atggtgcttt gatgtgtgtc cttcacttag ttcctaagtg gagaagcttt ctttttctac  1260
aaaagatctt tggcacataa aggcaagaat tatttgcaat gcccaaagca gttcattggt  1320
ggtagttata tatattttta ggtgcctaat tttggttttg taaatctgtt attcaaatac  1380
tgaatgttac agtcattgat tttagtgaag aatcaggaat ttttaaaata tctgcataag  1440
aatgacaaat aacagggaat atgtttttg tctaccaggg tcagtttggt ctgagggtgg  1500
aggaatgaga tagagaaggt agagggagag agatcaagaa aaagaaagag aaaaaagagg  1560
tataaggaga aaatgcaaaa ctcagttaat atgtcataat caggccatgg gagattctgg  1620
gcagggttgg gtagtggaag gaggtagagt gattaaatta gttaccatgt attgaacatg  1680
catgatgtgc tgggtacttt actagtgcta tttcattgaa ttttattctt cacaatgact  1740
tttggaaaga catcatcatt cttttttgaca gatggggtaa ctgtggctta aaaaacttgc  1800
ccaagttcac actattcata aggggtagag ctaaaatctt tcctgcccgc ttcgtggtgc  1860
gccagaaggt ttctccatgc tgtggagact tcctggaagg agtcacaccc gcccttctct  1920
tgggtggtgg cagctggcgc cagtcactat gtatttattt atttttaatt atttattttt  1980
gaaacagagt ctcgctctgt cgccaagctg gagtgcagtg gcgcaatctc agctcactgc  2040
aacctccgcc tctcggattc aaacgattct ccttcctcag tctcctgagt agctgggact  2100
```

```
acaggcgccc accaccacgc ccggctaatt tttgtatttt tggtagagac ggggtccacc    2160
atgttggcca ggatggtctc gatctcttga ccttgtgatc tggccacctc ggcctcccaa    2220
agtgctggga ttacaggcgt gagccaccgc gcacccggcc gtcactatgt atttataatt    2280
actgttcttt gaaaatcgaa gtaactttca tctacccagt gcttactggt ttgagaaaaa    2340
gctttgttgc ttttatttca gaagattaaa atttaatttt ccagtaaaga ttccttttgc    2400
tccagtggaa ttttgaagcg ttatacttgt atgaagaaaa aaagaatttc aaaatttata    2460
atttttgtgg taccatagag gggatactac ttaattatgc tagcactgtc tgcagaggtc    2520
taaaaaacca taggctgctg tctatattga acttgttaag attccttttg tttcacagtg    2580
cctgaagatt ggtcatgaac cagtaatagc cattaaacaa tgtctgttct cataagagat    2640
gaaataaata caaattaaaa caacagtgaa gtatcatttt ttctctatca aagagataaa    2700
tattaagttt taaaaagcaa gcaatcaaga accctctatc ttgctaagaa gggaggatta    2760
tttgtaccct agttgcgcac tagtggtgat atcatctttc tggacaataa tctagtgata    2820
catatcaaaa gcctttaaaa tgtatatgcc ctttaaccaa gcaattcacc ttttaggaat    2880
ttattctaag atataataat acatgtttgt aaagttttag tgatggatat ttttcttgct    2940
attgtttcta ataaggaaaa tcttagaaac aatttacgtg tttaaaaaca agtgattgga    3000
tgattatgga acatccataa tggaatacca tgtaattatt taaaattcca ctgtagaaca    3060
attcataatg tgtttagtta aaggggaaaa atgcagaacg aacagtgcta tcacttttat    3120
acatgataca tgtatacaaa caatattaat cagaaatata ggtagtttgt attttctact    3180
gtgtgctttt caatttgaat cccatctgta ggcagaaaaa taaagttaaa tatttaagat    3240
ttaaaaaaaa caatagctgg ttttttttcag agaagtaacc atctagtgat gtgtgataat    3300
ttataagttg tgagattcca tagttagggc tttagccctt tgcatttatc tttcttcatc    3360
tcttgaatcc tcttcaaaat acacccactc tacccataac tcattagatc ttgaaaggca    3420
tgttctgata gaatttttata tttagaacag gctgcagcac tcttccctta ttttacagaa    3480
gtgattgcat ggctctctag ggtgagttgc atattgagag ggaggacagt gcagtggcta    3540
agtggccgca cattgaagcc aggctgctgg ggtttgaata ccagttcccc aacttcctag    3600
ctatgtgatt ttgacaagt tgcttaacca ttgtaattcc cagtttcttg tctgtaaaat    3660
gggagtatgg taatatgtcg taaagtagtt gtgagatttt aatgagataa tccatatcct    3720
gctaagtact caggaattgt tagtagtttt tattactatt actgtttgga ttaagaaaca    3780
gaggaaaagt gatttgtcca agattataca accacttaat ggcattacta agaacagaat    3840
ggaggaaggt tttttccagc agaaatgttc agtatcctct gtgcctggca ggacaacccc    3900
aagttgtgct tttgggatgg aggagctgat ctaaaacaag cagtacccag gacaaggcca    3960
gcctccaggg agtgactgat gacagtggga agccaaatgg tagaaaggca ggtgaagtta    4020
aggaaactga gagtcaactt aggagcagga atgaagcctg gagcaaagag ctagtgcaag    4080
agagagcaga tgactcagag ctactggggc ttttgtaggc caccagctat gggcttcacg    4140
ggaggttaat gtggtttaaa gtctcaagac ctgggtaatt aaatagacaa atggggtcta    4200
ggtgcatggg ggaattttaa gtatagcttt gagaagatgc ctaatgggga gtaataatag    4260
agaaagaagc tgggtggggc cagaacaagg agcccacagt ccaggcatcc agctatgatc    4320
atcctaaagg aacagcctaa gtttgaagaa tcataaacaa atagagacat gataaaattt    4380
actttaaaaa aaatcccttg gcagaagaat gaaaactgat ttggagtgac aaggagatca    4440
tttaggagac tattggagta agccaaggag aaatggcgag ggcatgaaac cagggcagtt    4500
```

```
atggtgggat cagactggag aggatgcatt taagagatat tttagcacca gaattgacag   4560
aatttggttt ttgacagatg tagacactgg gagaggagga gagatctaag tgcatagtgg   4620
catccttcac aaaatggaag gtataggaag cagagtgggt ttgcgccagg cagagagaaa   4680
agacagatgg tgaattcctt ctctaacatg ttgagtttga ggtgcctgtg gagcagctgg   4740
atagagatgt ccaagcagac aagtagatat ttaggtgcaa gttcaaaaaa gagggatggc   4800
ctggaatgca catgaagagt cttctgcata agtatggttg acagttgaaa ttctcattgt   4860
gggtcaattc agtagcagag aggttggagg attgagagga agccaaggac agaacctgga   4920
aaaccttgac atctaaggag ggagatgagg aagaagaatc tacaatagat actaaggagg   4980
ggctagagag actggagcag cccaggagaa aagtggtgtc atagaaatca agtgggcctg   5040
tagtcccagc tacttgggag actgaggcac gagaatagct tgaacccagg aggcagaggt   5100
tgcagtgagc tgagatagca ccacggcact ccagcctggg tgacagagtg agactccgtc   5160 tcaaaaaaa aaaaaaaga aagaaatcaa gtggggagat ggatgcaaga aagaggagaa   5220
tgcattcatg gaaagagcat atttaccaag cttccatgt tgaacacatg agatgtgaca   5280
tgaaaggtaa ctgtagtgac tacatgttaa gcgttgaatt gtggctccct taaaattcat   5340
atgttgaaat cctaactccc agggcttcag gatttgatca tatttggaga tagggtcttt   5400
acagagataa taaaatttaa atgaggtcat tagggtgggt cctaatccaa gacaattgtt   5460
gtgcttattg taaggaaggg aaacacacag cggaaaagcg gtgtgaagac acagggcgaa   5520
gacggccatc cacatacaag ccagagagaa aggctcgcaa cagattcttt cctcacaacc   5580
ttcagaaaga accaaccctg tggaaaccct aagtttggac tcctggcttc cagaaaaaaa   5640
ataaattttt tttgtttaag ccaccccagt ttgtggtact tgttaccac agccccagca   5700 aactaataca cttggtgaga gtgcatacag ccagagaaag aagctgtgaa taagtgcatc   5760
agggaggagg gaaagaaacc aaaacaggat tacatcactt aaattaagag tagaaacatt   5820
tcacaaagca gagtgtagtc acaggtcaaa ttctgcagaa aggcgaagta ggagaatgac   5880
tgaaaatgtc agtccagagg ccctcagtga ccttgacctt tgcagaacac tcccagttga   5940
gtggaggcag tagactttgg agagcttgga aaatggaggc agcacagatg gtctcctgca   6000
gaaagtctgg tgataaaatg agacctcctc actggagtaa actcacctct gctgtcggtg   6060
gaaataatct ggagtcaggc cagccagacc cagagttctt ccttcctcca ttttaaaggt   6120
taaacagagc tgaggtcaat ggctcatgcc tgtaatccca gtgactcagg aggcggaggt   6180
gggaggatgg cttgaggcga ggagttccgt tcaagaccag tctgagcaac atagcgagac   6240
tcccattcct aaaaaaattt taatttaaat taaaaaaaaa ggctaaccaa aaataaaatc   6300 caatactta ttttttcccac ccaaaactag tttgggaagg atttctggaa gaaaataatt   6360
tttgcagtca ttttacatgt tggatttttga gtgcacataa catacagatt ctattctgta   6420
ttatcagttc agaggcaagt tgagatttga ggcttcgcag aggtaaagcc tctggtgaat   6480
ctggtgagat aaagaagaaa acaagcccaa gaggaatttc agggatcatt tataatttac   6540
atcaataaac agaatgggaa aaaaaaccca ttagagtttg gaatagagaa gtattaaaac   6600
actttcttag aaagctttga gtcaaaatta atctttctgt agtggcagga atatgataag   6660
ccaaacaacc ctaatgtcac agctctatat tattaggtgt cgaatcagat ttgcactaaa   6720
acatcaagta aaaataaaag gaatgaacat ttggttaagt gaaccaatta gtcaatacac   6780
gccagaaaat ggtaaaactg gataaaccta aatactcaa ctaccctagat taatcaaggc   6840 caacctagat tatcaccca atattacaac tattttcaac caactaaaca ataaatcttt   6900
```

```
atcaagagcc tgatagttta aggtactgtg atgaatacaa atgaaattgc tgatactttt    6960
tttcaagtct atttagaaat agaaacccac aattatgaaa tgacaaaaac aattaatgca    7020
gttaataatt cagtaacttt taaaaagaaa taaacatgac aaaaagttca ttctcaccaa    7080
atactaaaga aatgccaatt caaacaccaa tgagatattt tcctgtatca gattagacag    7140
taaaacaaac aatccaatca gaaaatgggc aaaagatat aaaaagacat tcccccaaag    7200
aaaatataca gatggtgaac aaccatataa gagagtcaac atcatttgcc tttatgaaaa    7260
aattaaacca ctacctacct ataaaaatgg ttaaaataat aaaagataat gacaacacca    7320
aatgatggca ggatgcggag aaactggatc atgcatacat tgcttgttgg gaatgtacaa    7380
tggtcaagcc actctagaaa acagtttggc agtttcttat aaaaccaaac atgcatttag    7440
tatatgaccc agcaactgca ttcttgggtt ttgatcccag agaaataaaa gcctatgctc    7500
ctgcaaaaat cagtatatga atatttatac cagctttatt cataatagta aaaaactggg    7560
gaaaaaagtc cctcagtggg tgaatcgtaa cacaaactgt gtgtgcaaga tgttaccact    7620
gaaggaagct gggtgaaggt acacaggact tccctgtaca ttttttcaac ttcttttgaa    7680
tcaataatta tttaaaaatg aaaagtttaa aaagtaaaaa aaaaaacaa aaactaaaaa    7740
tgttcatctt cactaaatat taaaaaaaat gccaattcaa acacaagata ttctccttt    7800
acaaattaac aatttatatg gattttggga gggttgggag taatcatgct aataagtatg    7860
caataagagg atactttcgt atactactga ttgtgggaat atgaatgggg agaacatttc    7920
tggaaagcaa tatgtcaaca atatcaagag tcttaaaaat ggttgtacaa gcagacaccc    7980
attctgggca ctgccaattt ctccatgtcc ttagtacatt tttttcagt tcattcagca    8040
tctttgttcc aggcactgtg ctaaacatta aaaatacacc aaagatgagt atgagtaaac    8100
atgatttctg ttctcaagaa tttcagtttt gtggtaaata tcaaaggt gattttttat    8160
aagagttttt tataacaggg tgtgacgttt cataggagca tgaaggtagc tgtttcctat    8220
ttgtctgtag gcagtatgat gtcttagata aatgccaggg ttttgagcta gtttggttgg    8280
tatcaaataa taagtagtta ataaatcatc ttctatttat tagtggtatc actttgggaa    8340
gcctattagc ttcctgaact tcagtgtcct ctgtaagatg aggctactaa gcacttgcca    8400
atgccatgag gaataataca atttataatg gacaggaagt cctatggata taagatattt    8460
taggactcac attctttgct ttaaaatcta ttatttccta tattttaat tgtcagagtt    8520
ctttagctct gccttttctg attgatttcc agcagatgga ctcttaccta aacctagaa    8580
gttgctatag tagacctcct aactatagat aagagaaggg catgccaaat gcagttgaat    8640
caggtgaaag tcaagcaaca aagctgccta aaataaattt tatgtaaggt agggtgccaa    8700
aatcattaaa ataaaattct attctataac tgtaatcacg taagtgcttt catgaagttg    8760
tctatgaaaa ctttcttttt cgctttctgg acttcaaata ttttaagttt gcttttcatt    8820
tacaaagatt ttttgctca ttagtaatca tgaactgtat tcaaacttac acttctaatt    8880
ctagaagata tataaactac catttttaa ttataaaaat gtttatatat cttgctttaa    8940
taatttcacc tctagggatc tagctagtta ataacaaga gctacggaaa catatttgtg    9000
caccaaaatg tttattacat tatttaatgt aatgaaaaat aagaatcaac ctaaataagt    9060
agaagaatag gtaagtaagt taaaatgaa gttaataatg actccttaat gagagaagac    9120
aacataaggc tacatacaga attgtaaaga aaataatcca cagaatgtgt gttttatttt    9180
ggtaaatggt tcctaaaact aagtaagtac atagaaagat ttttttttt ttttttttaa    9240
agacagagtc tcactcacgt tgtcacctag gctggagtgc agtagtgcaa tctcagttca    9300
```

```
ctgcagcctt cacctcccgg gttcaggaca cgccaccaca cccagctaat tttcttgtat   9360
ttttagtaga gacacagttt catcatgggg ctggtctcaa actcctgacc tcaagtgatc   9420
tgcccacctt ggccttctaa agtgctgtat tataggtgtg acccaccgca cctggcctag   9480
gaagaatttt agaaagaaag ctccatatca ggaattgaga agccggtgtt ttaattgaga   9540
atatatttgc acagaaaaat cttggcataa atattggttt acaaaacaaa caaacaaagt   9600
aatgtccttt aatcttggat caggagctgc ccaacaactc caaaaagtca gctcatgcaa   9660
aaccatccaa ggacagatga atcagccaaa caagagagaa aggggaaggg aaagtgtctt   9720
ttcacaggca gcttttgagg cagtgcataa accatgcctc tgcaccatcc agaccagaca   9780
gttgtgacac agggttgaca aagcaggaca acgaagggta gctgctccta aggtggggat   9840
gatgctggag caaggggag caccaagagg aaaaaaaaaa agcataaaaa taagatagca   9900
tagtaaaaaa taagatagtc atagtagtta cctcttgatt gatgggatta tggaaatagg   9960
gttatttctt tgactaaaat tgccagatct tcagtacaat tacattgctc tgctgagcag   10020
gatgaaatca agttgaaaag taatctagta gtgaggtaca gcccgtatgc tgcaaatggc   10080
caacatagat cctcagatga cagaagtgag tgatgcaggc ctgtggttta cgtacagctc   10140
catgacgtat gaatggcaga agctgtgtat gtccacaggc gagccccatt tcaagaagtg   10200
cttctggtca ccactctgtt gtcctgtgta taaggatgtg gttcagaaca gccaagtctt   10260
atatttcaag aggagccaga aagacaaact taccagtgaa atcctaatat ttatataata   10320
gctcaatatc tggaggggct ggtttggtat aaatcaccag ttttacctct gacctctgtt   10380
aatgcatcag aggttcagga gagagtgaga aaattgtaaa tggaatattt taggactatt   10440
atattgggc ccaggcttta gtgagtcaga gcgagaaagt aggggctga aactatttga    10500
ctattaattt attcaataaa gttttattta atgttggaaa gatgaagatg aatcagatag   10560
aaatcctgtt tagaagcttc tatgggaaga gatatcacca tagctaatat gtcttagcct   10620
ctaaaaggaa ttatggcaaa ctatattgta tcatatatga tctcatttaa tcatcataac   10680
tgcaggaggt aagtagtatt atccctgatt ttccataagt gaaaactgag tctctcttag   10740
ttacatagct gacaacacaa ccaggattcc aaatgccagt ctgatcccag agccaagcta   10800
tgaacaacca tgctatatat tatggcagat cagggaagga agacattact tctagcagca   10860
agaaacattt gtggatgaaa agatttgagc ttggagagag ctgtgttgag ccatgtccaa   10920
aacaattttt ggcaaccata cgataaaggt aaaagccaga gattgaaaag taaaagctgg   10980
tggactaaaa atggtccata gacagagagt catcaaaaca acaaaacaaa acaaaaacct   11040
taatcataat taattgccaa tatttcaaaa gtctggagaa ttcacataag tttagatttc   11100
cagctcttct ggagaattag aatatctagt aacagtgtgc taataatccc acatggtaac   11160
aactggtgaa tctggcagag gctgcccagc ttccaatggt gtataagctc tcctcttcct   11220
atgcaacctg cctgcctcat ttatatgagc tgcttggatg ctgcagatgc ttgaatctaa   11280
gagctttggt ctggaaagtg aggccctaac aaggaagaag gaataaccta tggatcaagg   11340
agaactggga gtccagaaat gaaggttatt tgtaagtctg acccagcca ttccaactcc    11400
tttgaggaaa taagattcta aggaaaaggc cgtttgcatt ctgctctcca agatctctgg   11460
gtgttggaag aaactgaatt gggggagagg gggaaacttg actgggggct caatacagac   11520
atgtaaattt gaaggaaaca gagagtttag atgacaggca gtagaaaagt taatgtgtcc   11580
attctatggc tgacccaaga ttctgttccc agaagacctc tctggcttgt taagtgttca   11640
tggttgcagg ggaaaagtta gaaaaaaaga aaaacaagcc aaaacccagc tccttaaatg   11700
```

```
tttctaattt tattttcaaa caatcaggca gagtaatccc tttacacact cttcaggcat    11760
tggctgaggg tcccagtcaa gaaccattca gttttggggg ccttaagaaa aatatttcct    11820
atgattaaag gaactttgga caggttatta ccttctttga gcctcagttt ctttgtcact    11880
tagaaggttg aatggtttcc acattctgag ggtaaggaat acgagagtga atgaagaaat    11940
atcaagtgca tagctcagag taggaagaaa gaagtgacca gggacaaggc taagaactta    12000
ctcaaaaggt gcccagctgc tcagcattct gtccaaaaaa gggacactga catctctcca    12060
gcattctaac agcagtcaca tagcattatc agctagaaat gaaaacagat tcaattctat    12120
atcctgctaa aagcttgagg gtcacactag ctgtgtgatc tttggcagct ggccaaaacc    12180
ctctgaaagg cagtttcctc acctataaat tttttaaaaa atatttattg tgaagattaa    12240
atgaagtaat gcatttaaaa tacttagggt gccttagagt tccagcacag ttcgtagctc    12300
atagtaatca gttaatagat attgacttta ataaatagat acttaactga gcctccaccc    12360
tgggcctgtt actatgctaa gtaccaggag tgcaaaggga aatgaaacac gttccccaaa    12420
cttgtggaac tcagagcagg ccaactatat gagtagtaga ttttaacac gatgaggaaa    12480 ctgttataat ggaaaaataa atagtgtgaa gagggactaa ggaagataaa gatatggtga    12540 aaaaagagg gttcaggctc caactgtggc atgatctaga tctgcaagga agagtagaga    12600
attgcagtag agaaagcagg gaagacattc caggcagaaa aaacagcttc cacagaggta    12660
aagaaggcaa aacgttttca aaggttctag gggtggggga tggtgggaa gatggtcacg    12720 gaatagtgaa tggttcaagt gaaactgttg tatgggttgt gagggcagtt ttatgggttg    12780
ggtgataaaa tcagaagaga aaaattgaat tcacgctttg aaaggccttg tgtgtcttgc    12840
tgagaagcgt gaacactaac tcatgaggag taaggcgcgg gtctttaaag gaaggaagtt    12900
tcataatcaa attgttttcc atgaaagata atgaagggag ccagccacaa ggctgttgca    12960
atcaatcgtc caaacaagag gtgacaaaga ctctaaaact ggccaccaat gaattgaaag    13020
tggatggtga ggaagaaaga atacagggtg acataaacac aatatgtaaa atccaaggta    13080
tgaaaatggc ctggtccctt cgtccttacc acagtcatcc caagagacca aaacaaaaac    13140
acagaaaatc tcttttaaaa ataatctctt ttgtttgtat gcaaataggc catccacagt    13200
gaaaatgcaa ctcaaatgca atattttatc tgcagtccac caaatgcaaa gatcaaattg    13260
gtttacaaat gctgtccttc ttaaaaattc caactcctca cattaaaact gtagccagct    13320
agtgcaagtt aagattgttt gcaatcttaa ataagatttg agtaaagctg aaattgagac    13380
acttttcaaa agaggccatc ccttactcac attgctgaag agtagaaaga ttgacacctt    13440
cttttatcag aaaatttctt tcagggagta atgcctcttg tgtggtggca gacccttcaa    13500
gtcttccaga taaagcatgt gatggaagta gcagggagct gcaaaaattg caactctatg    13560
attctgcatc accgacttga aaactacaag cccaggttga caaatgtaca ttttaagtgt    13620
tcagagaagt cttaagtgcc ttgctttggt cacaaagttg ccacagggaa gtaagttttt    13680
gaatgtgcag tgccccgtcc ccagctctgt tgtgaaatgg aaactttaaa aaaaaaatca    13740
ctgatttaaa aaaccactgg ttttgttttt taacaagttt agtcatattg cctgtgttct    13800 atataccccca atctatttta tttttacttttg tagtgtacat ttaatttata ctcaaataaa    13860
tattttacat aaggtgcttt cacggacctt catgcttccc taaatattaa atatgctgcc    13920
catttgttaa aatgtgttag ttttgttatg tattatatcc cttcccctgc acacatagaa    13980
aaaaaaaata tgaacttaac cttcaagcaa gttttacgtt tagaatatta cctcatttta    14040
tttcttctaa ctgaggttat aaagaaaatg gcaaatgtca tgtgctttgt aaagaaatga    14100
```

```
cagtttctca gaatacgtaa atgcacaccc ttagacaaat aggccactta aattcagaat   14160
cacagtcttt tgaatattgg tttaatattc tcagataaag attgaaagga taacaagttt   14220
tggaatcagg tgtttacttt gagttctgaa aggtgacatc acaggtgttg gtagtttatt   14280
gatatttaat ttttaaatgt gctgctgtat atatttcatt tgattagaaa tatgttacat   14340
agttatgtta tttgttaaat aatagaccat cttttgtata acctatcaga agaagttctg   14400
agattgtaag attagattgt aaatcctatt gcataactag aatacagaat tattaaattg   14460
gaaaggaagt taaatcactt agaccgtcct tcccccagga agtcctctct acagtgttat   14520
ccatgacaaa tgtttatgca ggaccctaa ccatttaaaa tacgaagaga aggagaagag   14580
atatatcgag aaaactattc ctgagacaag agaccagggg aaaacttttc ttagttgtaa   14640
cctacacaac tagctagaat ctacctcatg ctcttaagat ggtgtttaat catgaggata   14700
tcatacataa ctgaaattgt ataatgttga acatcttttg gtggcaagta ccttgacttt   14760
attaaatcag tgtaggtctc ctgcattcaa ctatggtctc taggagggca gggaccacac   14820
ttcttagctc acccttggatc tcaagaccag tccaaggcct tcattcagtc agagctagtt   14880
aagcatttgt taattgaatg aaggaaatta aaaaaaaaaa aactagaaat tccaaattgt   14940
gcaattacat ctgtgaattt taaggtgtta ttggaaaatg ggaaaaatta ctgagattcg   15000
aagatggata ggaacaaagg taaagcatga aaatgtgcat atttgtgtgt tgctagagtc   15060
aatagtgatt gccagttcct atgcagccct ggcaccacct ctgaaacctt ggccaacccc   15120
tgccattagg tgttgagata cacgacaggc aggtgaggaa ggaggggtgc tctggatgta   15180
gtcttgccgc tagactgtgg tctttagtgt ccatgtccat ggggtgagtt gtgagcccat   15240
cagtttccca cactacagtc cttctctggc ttagccttcc ttccctgtcc tgtggtccag   15300
gttacccctg gccctgtgg ccttcctcca gagatggacc ttcctccaca cacttctcag   15360
gagctcctga ttctaggcat gccccagaac accgcaactc cactctgccc tgtctccatc   15420
agaccagaga cctcacttag accctgggta tggggttgtt ggttctccac ttgctgcggt   15480
tgtcactagc ctgagctcta tcctgagctc tgtccatcct tctcatcttc ctcattgccc   15540
tttctgctaa agcaactgca catctgaagg ctatacttat ccctagtaca atggtacttt   15600
ttctaaaatg catacaccct aatgcttacc cttttgacaa ttttttcctg aacctacctt   15660
ttaatataag caaattcagt cttcaattca aataagtgta ttttgctgct gaagccacca   15720 tgtgatttg agagatagtg aagacagaca gtcttctgca ttcacttgta gaatcctgaa   15780
aatacctctt ggtgtcccctt gccttctga cttcttgctt gaagacatct agacaaaaat   15840
gtgtccctgg gtcctagttt ctgggttcag aaattgatcg aatgcaagaa acaatacac   15900 attgcctctt ccttagcatg catgaatggt aggtgtgaat ttgcatcatg agaaagtaaa   15960
taaaagaaga ttccccaggg cagctaggga ggcagaaaaa gccagcctag gatgggagtg   16020
gaggacatgt tagaggttat gagagtgagg gtccatccta ccccacctcg gtaactcact   16080
ggtatggtat aaatgcaaaa ttttggctca cacaaagaaa aatactcaac ttctaatgct   16140
taactatgta aaatttgctt ttaaagtaca agttaaaatt gtatcgcccc tcaaagaaac   16200
aagaaactca ttcatttct aagaatgttc cttcagaaac atggaactga aagctatttt   16260
taaaaattga tctggccctt agaaaactgg ggcctttttct ttaatttacc taaggaattg   16320
acataaaagt ctagggttct gcaccagaaa aatgcagaaa gtgtcaaaat aaaaggcaga   16380
aatacaaaag gagacttttt gcagcaacgt tctatgtata gcattgattc caagggtgca   16440
acatagggaa gtgaacatgt ggactgtgaa attgatgcta attttctttc ccactagtct   16500
```

```
agcagccctc taaaatgtca cattattaat ttagttactt taccagaaat ccgtgtatgt   16560
ggttagcatg tgtgtttttt tttaattaac agactttact tattttttaga acagttttag   16620
attttcaaaa aattgagcac atagtacgag aattcccatc tactccctttt gtggaacaca   16680
atttcccta ttttttaccat cttgcattag tgtgatgtat ttcttacgat caagccattg   16740
ttgcttcatt attattatta tttaaagccc ataatttaca ttaagtttct ctctttgggt   16800
tgtacagttc tatggatttt gacaaataca caatgtcatg tatccaccat tatagtatca   16860
tacagaatag cttcactgcc ctaagaatcc cctgtgctct gcctgttgac ccttcccacc   16920
cctccccaac ccctggaaac cactgatctt tttactgtct ccacagtttt gccttttcca   16980
gaatgttcta tctttggaat catacagtat gtaccctttt cagattgact tctttcatta   17040
agcaatatga atttaagttt tctccatgtc ttttcacatc ttgatggctc atttctatttt   17100
attaccacat aatattccat tgtctggata taccacagct ttaccaactg aggggcatct   17160
tagttgctaa ttatgaataa agtggctata catattcacg tgtaggtttt gtgtggacat   17220
aagtcttcaa ttcaattgag taaatatacc tagaagtgtg actgctggat catatggtaa   17280
gagtatattt acttttttaa gaaactgcta aactatatcc caaagtagtt ttaccatttt   17340
gcattctttt ctttattttt tttttattat actttaagtt ttagggtatg tgtgcacaat   17400
gtgcaggtta gttacatatg tatacatgtg ccatgttggt gtgctgcacc cattaactca   17460
tcatttagca ttaggaggta aatctcctaa tgctatccct ccccctccc cccacccac   17520
aacagtcccc agagtgtgat gttccccttc ctgtgtccat gtgttctcat tgttcaactc   17580
ctatctatga gtgagaacat gcggtgtttg gttttttgtc cttgcggtag tttactgaga   17640
atgatgattt ccaatttcat ccatgtccct acaaaggaca tgaactcatc atttttatg   17700
gctgcatagt attccatggt gtatatgtgc catattttct taatccagtc tatcattgtt   17760
ggacatttgg gttggttcca agtctttgct attgtgaata gtgccacaat aaacatacgt   17820
gtgcatgtgt ctttatagca gcatgattta tagtcctttg ggtatatacc cagtaatggg   17880
atggctgggt caaatggtat ttctagttct agatccctga ggaatcgcca cactgacttc   17940
cacaatggtt gaactagttt acagtcccac caacagtgta aaagtgttcc tatttctcca   18000
cattctctcc agcacctgtt gtttcctgac tttttaatga ttgccattct aactggtgtg   18060
agatggtatc tcattgtggt tttgatttgc atttgtctga tggccagtga tggtgagcat   18120
tttttcatgt gtcttttggc tgcataaatg tcttcttttg agaagtgtct gttcatatcc   18180
cttgcccact ttttgatggg gttgtttgtt tttttcttgt aaatttgttt gagttcattg   18240
tagattctgg atattagccc tttgtcagat gagtaggttg caaaaatttt ttcccatttt   18300
gtaggttgcc tgttcactct gatggtattt tcttttgctg tgcagaagct ctttagttta   18360
attagatccc atttgtcaat tttggctttg gttgccattg cttttggtgt tttagacatg   18420
aagtccttgc ccatgcctat gtcctgaatg gtaatgtcta ggttttcttc tagggttttt   18480
atggttttag gtctaatgtt taagtctttta atccatcttg aattgatttt tgtataaggt   18540
gtaaggaagg gatccagttt cagctttctg catatggcta gccagttttc ccagcaccat   18600
ttattaaaca gggaatcctt tccccattgc ttgtttttct caggtttgtc aaagatcaga   18660
tagttgtaga tatgcggcct tatttctgag ggctctgtca ctatacatct actagaatgg   18720
gtaaaatcca aaaatctgac aataccaaat gctgctgagg atgtggagca acaggaagcc   18780
tcattgctcc acatcctcag cagcatttgg tattgtcaga tttttggatt ttagccattc   18840
tactagatgt gtagtggtat cttactgttt taatttgcaa ttctctaatg aggtatgatg   18900
```

```
ctgaccacct tttcatatgc ttatttgctg tccgtgtacc ttctttggtg aggtatatgt   18960
tcagatcttt tgctccttat taaattgggc tgtttgttct tttatctttg agttataaga   19020
gttcattgtg tattttggat accagcccct tatcagatat atcttttgca aatatttttt   19080
ccccaatctt tggcgtgtct ttttattcat ataatggttg atacatgttt ctgctttaag   19140
gaggaagggt tttaaaaata caatttacag tagcagtaaa aataaaaatt tattgcaaat   19200
gtcttatgtt cactctcagg tgatgtcagg gaactatgga cccagcaggg tttaattaaa   19260
ggggagtgtc aagtcctggg ggctgtggtt gacaatcctc ctttattggc aattgtgcag   19320
cagggctggg agtaagaaga caacccagtc ctgagctgca tcacttctaa attaagaata   19380
attcaggaac tgtgtttacg gtgaaatcct ggcccttctc acatagatta tattatgcat   19440
aggatatgaa tttctgtcca tgaatccaag tatatatgaa atcatcactt tgaaaatttc   19500
ctttaactca acttaatccc actggtgagc ctcaatcctg ccagttgaaa aagagactgt   19560
aactgggtca tgcaggagtc tccttccttt cctgcagccc agtcagaatt caagaagttc   19620
acctggtaac tggaaaatga tggaagggcc tcaagtccct agtctgtcct ggttgccatt   19680
ggcacccttA ctatctgagc ccatagtggt ctgtgaagtc cggcagctcc ctgcccccat   19740
gccacagtgg ggaatgagaa tatctactga tgctgggccc catgagcaaa gcatgctgcc   19800
tttctaggca tgagccatca cacctgaggt tgctaccccc tcgggagcac tgatggaggg   19860
gcagttgggt ttctactgct cacaggaccc agacaaccat cccctgccct cccttcttct   19920
tgcacttcaa aagcactctc ttcctctctt ttcacctcta agccaccggt atcatctctt   19980
ccatgggctt tcacaaaagt ctggatgaac ctttgaactt gtatctcttc tgctttcccc   20040
cttgcatcaa gaaagcttag aaaacaaaca ctaattaacg tttcaataaa taatgctgct   20100
ctaattattt gtggaaacta ttctgtatta gaactaccat cagcaccgcc tcctagagtg   20160
cttttagact tgaccactgg ccgcaggagg ccacttccat ataacaacaa acagatggct   20220
gaaattggaa aactcagcta aatgttcaga tgtttctaga ctcccacggg tttctggctc   20280
tggcacatgg agtagatcct gactgtgtgg tcctcagggg actctctctg gtgaagtttg   20340
gtgaggtcaa cttccacacc cacacacacc agctactgtg tgtagcctgt cctcctctgg   20400
ttgcttctac ttgcagcctt ggcctcttca gtcctgagag cgttggagaa tgaggcagtg   20460
gaggaagcag ccccacacag aaagcagttt ctgaagtaac ctcagcaact tcctcctcac   20520
caaacacaag gaactgatct tctccactgg gctcggcctc tggtcagcca aggcaacac   20580
tgttgaccac catcacggtt ggccccactc caccccttggc tctgatgaca tatgtgggag   20640
tcagaggaat tttgattggc tgactgctgg cctgtcacac aaacaagatg gggcaagggg   20700
gttgcgatat gacttgacat gtgaaaaaaa aaaagccgt ggtcagcaac cccctgcaac   20760
tgttgaaagg ctaattcaat ctctgactct ttaacaaaag tgatcttgtt cactgcctgt   20820
tctgccctga gagccttctc tgctaggagg taggttgact gactcaggga gaagggtgct   20880
ggtggcagag ctgccaatgg gtgagggtcc tagagactat cgacatgagg ggcagttgag   20940
aacactgtag tatttagctg agaggagaga ctattaataa aatttacaaa atcagctttc   21000
agctatttgg aagggtttat ataaaaggat aaaataatat gttctggtag ttctagaaaa   21060
caggacagag acaagtagct ggtacttatg gattggagga gtgagtggca gtagtttggg   21120
gattatttat aaaaaagaca ttttttctgtt aactctcttt tctaatagtg aatttcccaa   21180
cctgacaagt aagaaagcac aggctagaca cgcatctgtc atgacactga aggggtcctt   21240
gcttgagtga gagactggaa tgatgagttt tgaggtccct tacagtccag caactctagc   21300
```

```
taagttggag aataagagaa ttccatgaca ccatatcacc ccctcatttc tgctgcctgc    21360
ctcaccattc atctctcttt actccttta atatcattct acgttacagc attggaggag    21420
gctgctctaa ataggaactg aaataagtag attaaagaag tgctatggaa gggaaaacaa    21480
taaaacaact tgtttttta gagcctacta ttgccaggat ctgtgctaag caccatatat    21540
atgccatgtt atttaaccgt catgacatgc ctatgagata tttagtatta cttctgtgag    21600
gaagccaaag ctcagagagg ttaaataact gccccaagaa cacacaggca ttaagtagtg    21660
gagcagggtt tgaacacagg tctctatgac tccaaagtgc agtgtgatat gttattttta    21720
ctgatctgtt tatggaaaat gatactgctt tctaatttag tattaacaca aagatttttt    21780
tctaaataga tttacttaaa gtatgttata aaaatactat ataaataatg aaacagattt    21840
tacatgagta tgaagtggta ctagtagcta gaatgatgaa agtttgggga atactactcc    21900
aaatattttg atagctagcc tttcaattta gcctgtctta tatttggact gctgagtaca    21960
aggaaaagaa ggaaacatga aaattaagtg aaatatgagt tacttcccct gtgctctgat    22020
aggtgggtaa ttgatcatat gtcacaataa gaaaatcaaa tgaaccctt caaacaacag    22080 caaaatctgt gattgtaaaa tccagaggaa accccaggt gggatctatc tgtatgaagg    22140
atgaaatttc caaggtctga acatagaatg gctgagagga agtgatgacc ctgtgagtca    22200
agaccctgga ccctgggga gccctgtggg tttgagaagc cctgggtgaa aggtgaaggg    22260
ttttacaggc ctgtttacag acctctgtag tgacagaagg gagatctttg tgcaaaggtc    22320
aaagtaagaa ttgggaaagt ctgaaaagaa aacaggaaag taataatgaa gatgaaataa    22380
ctacttggca tactctgcca catgatttac aggcaaggtt tcctttgttt ttcacaacaa    22440
tgcagcaaag aagtgattat gagtcacatt tcataagtga aagactgac attcaaacat    22500 gttcaataac tggcccaggg tccagtggtc aagccaggac tggacttcgg accaccagtt    22560
ccaaacccac accccttccc ttgcaccaca cgcttttgtg tggatgagcc tccccaaccc    22620
tgtcaacaac aaactgtcac tttgtcactt ttaatgtctc ctgcttcaca ggacacagct    22680
agcctccaag agatcaggga ggcatgccca gagggtgctg cttctctctt ttgaagctca    22740
agtgccacag acctcagagg cacataaatg tcccccacac tgagcagagg actttgcagt    22800
gcctgatcag ggcagaaaaa ggaggcatgc acctggggga ggatcacata cgagtgaaac    22860
ctgtccccgc tgaagcacta ggtttggaga aatctactgg gcatttacac accttttccca    22920 cttctgctta tgacttgtag ccaaactcaa gagtaccacc cacttccagg aatagtgtac    22980
caaggtaaca gaaacattct agattcatac aattggggtt agattaggat catctgaaaa    23040
tgaaggttgt gtatgtcaat tgccttctaa caggatgggt ggagagatgt acttaatgaa    23100
tgattttggg gaagggctag aagtgaagca catggcctct ctgcctcac tcattgaagg    23160 ctgtcttctg aagccccgtg gagctcagtc cctgtcacat ggttgcccac atttgttgaa    23220
ctgaactgca ttttcatcta tgggcttcaa aggctgtgtg tactctggga tctctgggaa    23280
tctgtcaggg aaggtgtctt tgtcatgttt gtggatgggg ctcccttgg gggtttccca    23340 gggctttaca ctcatgctcc gagggtacgt ttgtagtcat tctcatcagt ggaaatgccc    23400
acctgccggc agaagttatt tggaaccaag caagagcact gtccctggct gtggtgttgt    23460
ttctctagtc agttcccctt tctgtatttg agttctaccg tcagtcctgg cattatttct    23520
ctctctacaa ggagccttag gaggtacggg gagctcgcaa atactccttt tggtttattc    23580
ttaccacctt gcttctgtgt tccttgggaa tgctgctgtg cttatgcatc tggtctcttt    23640
ttggagctac agtggacagg catttgtgac aggtatgttt gtggaggctc agacgcctag    23700
```

```
ggagtggcat gagataaagc tgcaagctgc atctggggca gaaatgctga tgtgctaatg    23760
gccggccaga gaatgagtaa aagggattgc agagagcatg cttaaaacct ctgaccatca    23820
ggtttgcttc tcagattgac tacattggag gtgggatatt acaaaaatct gtctcttcct    23880
gccagatccc ttcatctgtt tttcgtgagc taagagacaa aataggcagg aaatagaagg    23940
tgccacttac caaataattg gcagctgttc ttggctttgg ggtgctgggg tctccgagca    24000
gcctctgctc tagaagaagc agtccaaaga tgtcagctcg cctcgcctga gtccctgtg    24060 ccagtgggaa atccagagaa gggggatttc ctcctcttgc agcctctctg caatggactt    24120
acttggcttt cctgtttgac ctttcccttc tctggtccag agaccctcc ccaatatttc    24180 ttcccatcca agtgcccat cccaatatta gccccacttg gcaccagaga ccaagatcta    24240
atttaaaaag aaatattctt gggtcaaaaa agagcccaag caagtgattg aacataatgt    24300
gtttcacata cggtgaacct atttgcattt gcatttgcaa acgggcttaa aatatcatct    24360
ctattaatag caatttaagg ttctggagag ccaggtgaaa atagttttg acaagggaa    24420 cttcctactc cccttaaact gtaataatga aggaaatgaa ctgtttatct tacatgtaac    24480
ctcaatcttg ggactaaggc cctgtactaa aatgcgtcta tttatgtgct cagacttgca    24540
gttcgtgtta tgtctgctgc tgcagatacc gttaatatta tttatgtgag ctatcctgtg    24600
tataatggaa gcttttataa atctctattt atttattcct aatatagtta ttaagtgctt    24660
gctatgttcc aggtactagg gacttaacag gtagcataaa agacataagg aaaagctgca    24720
ctcttgtttt ctagcctagt ggggaaatca cattaattta atcacactaa acatgactac    24780
atagcaatag tgctttaaag ggaaggaaat tgttctatgt gactatatca gctgattaat    24840
taccaagcct ttgcatttga tattttggtt agtctattct tcttgaattt catatgcctc    24900
ttcctgggtg ggggtgagga tgggatttta tggagttgag gctagggcag gtagggagaa    24960
aacatgagaa agatgaagag ataagccaag ccagattctt cagcagaaaa atcaaggttg    25020
aaataccatg tttcaaaaat cagactgagg tgggagttga ggttaggggt ccctaggcca    25080
ggggattgaa gcttcaaaga gataaaacta gagcaaaagc aagcacagag agtggcagag    25140
aggtccctgg gcatttttcc acagtccatt ctagtgctgg caatccacct ttcatggcca    25200
ggcaggtaag agtatttgtg gggtgggaga aaggacaggg ccataggctg ggcacacagc    25260
cctttactgg cccttatctc tcctctcttc tcctatacag tgctgtttcc gaactgtaca    25320
ttggcttaca ctcgggctga ggtttgggaa ataggcgcca ttttgaatat gtgtggagga    25380
agaaaagtgt gtcttcagca cttttccacct ccccatcacg gccctgagac ctcaacaccg    25440
ggaagcatct cgttccctat cggtcctcct ttattcatgg acggatatga ttcctttcta    25500
agttccatgt cctttttaga taaattaact tgaacctaat gcctaatggc ttaaaaacaa    25560
acaaaaaaaa ccctcttcct tccagctagc atttgcattt taacagggc tttcaaaaaa    25620 tgccttagcc caaggaatga gtaatgtggg aattccaagc agcagggtag gactggtgca    25680
cagtatgggg agagaaggcc cctcaagttg tggccctgaa atgttggctt cctctctttg    25740
accatgatgc tgtttctgag aaaacaagaa tcaggctacc ttaggggacc aggatgggca    25800
tggctccctt ttagtgagtt ctatgagcct catacctgac agtcagagcc ctcgagtgga    25860
tgagcacaga ctagaagaag cactgtgaaa cttttgcatga tccttacctt tttggcaaaa    25920
aggaaaaaaa atcgttctca aattcatcaa tagtttgaaa tagggtgtgc cttgattcag    25980
aaagtttcga ttctagatac aactcggaga actaggcgtg tcttgtacac agatttgctc    26040
ttgggggacc ggaaaagcta aatgctatcg ccatgctatg ctccttcttc taggccagtg    26100
```

```
aggggaacgc attcttcatt ttaatatttc agttgcctac aatattggaa ggtggataaa   26160
agcaccctct gctccttcta aatctgcgaa gacatttctt ctctgcacct actcatcctt   26220
gatgcagctc tcctcatgtc tgtatggaaa cactgtgctc tcaaatgagt ttcagaaaga   26280
acaactcacg aaagaaaaca agcattcggt cagaaaaatc tccacaaatg gggaataagg   26340
gggatttgct ccaaggagag actggaaacc aagtcagaca taaaatccag cctaagctag   26400
aaggagacat ggctggtggg agcttgagga aaacagagct caggatggag gacgtctcca   26460
cctccagtca tgtcctctgt ccaccagaca ccaagaagtg ttcatgttcc atcgaggcag   26520
ccctcacacc catcccttcc tcatcatgcc gactgcctct ttactgcttc aggctcacca   26580
tctcaagtcg acgagcctgt aatactggct ttcttgatca ccctgatacc agccgtcacc   26640
tcttgacagg cttattttct ttaagctgtc attacaccat ttttctgctc ccaaactatt   26700
aattccaaac ttccaatttt ctgttaaatt aaatatgaat tccttatttg acttccatg    26760 ccctattagg ctatcttgct ccttgcttta cttatagaaa ctaatctccc attatttatc   26820
caaagacaac ctctgctgca ggccagtcag cttttcttac tgtcctgtaa aaattccatg   26880
gtcactcctc catttccatg tgtccttaaa aactgttatt tgattgtgtc tcagaaagtc   26940
gtcaaagaat atataccaat gaaaagcatc aaaaaggtta tacttgatgt tatgtgtgta   27000
tcaaaaatat ggctgaaata tttatccagt gaaactcaat caacactaaa aagtggttct   27060
ttcggaagca tcagttcttt gagacccatt aaacagatgc ctcggatgca gggttatata   27120
ttatcaggaa tctgtctagg gaagaattat tggaagcttg caaagccttt caaggacaga   27180
ggacgatagc taccacgttg agttctagga aattaaccat tgttattgtt aaaggaagac   27240
agcgtttctc agaggaagac tgttaaacag tgcagtggcc caggctaaca gccctcataa   27300
gtgggagtat cagaatgagt ggacttaatt acttaaaacc aatacagggt ggaacttcat   27360
ctgctataac agaaatcaac tcgtgcaagt tctaacatgc agggtacagt tctgagacca   27420
agtctgactc acctgtcaaa gctcagctca actattacca cctttacacc cccttccaa    27480 gctgtaggag tgcttgctgt tctccatgtc ttctgaagcc ctggatcact tgtagccagc   27540
tcagcagact ctacccagac agggatcctt taaatgtacc atattgtcta ctgtgttaaa   27600
aatgagagga actgactcag ggtgagagcg atggagtgtc cagatgttct cctttatttc   27660
tccttattcc tggaaatgta atgagaatct tagaggtgaa ctgaaaagtt atgagttcaa   27720
ccacttactc aattcgagat tcgctcctaa aatgtctctt ctgtgttatc accccactt    27780 tggtttgaat agtacttgtg acagggagct tatcacctca caagaaaatc cagtcattgc   27840
ttgtagctct ctattaaaag ttttccatca tctggaactg aaatctggct ccctgtaact   27900
tttagttatt ggaactactt gcccttcagc aacagtgtat gtatcctccc atggaagggc   27960
ccttacatat ttgcagacac ccagcatata cttgcaatct tttcttcttc aggttcatta   28020
ccctagtcct tttagttgtt cttcatttga cataatttca ttattcacta gtgaaccttg   28080
ctgcccttcc ccttgataaa ccgaatttgt cagtgtcatt caagtataac tgacctcaca   28140
gaacgtgata ccacaagcga tgtggtctga ttagcacaga gttcagtgaa tgaatcctac   28200
actaggattg gatgaaattt acttagccat accacactaa cacttatgtg attttatgt    28260 ttactatgga tagactattt ctcctgtgtc cacttcttcc tcttacacag ttgttatttc   28320
aaaactgaag tacagattct tacacttacc ctcaggagat tcatcatgtt agtattagtc   28380
tctcttttca ggctttatga atgttaattc agctaactca tttttgagct atctgtctca   28440
ttttgtgcca tctgcacagc ataagtttga tttctgttgc ttttattagt agtttacta   28500
```

```
aatacataaa agtgaaatag tgaaacacag agtcttgtag catccactgt gggatcagtc    28560
ttttagacaa gaatgatgca gttgctgagt caaatgaata aatgaataaa tcaaacaata    28620
ctttgtcctc atttcccata ttgatctatc accatatcct gttaattata attctaaata    28680
tttcttgatc tatccacttt tcccttactt cacctgctac tatcccagac caaacagcca    28740
tcttctttca ctcaaacaat tgcagtagcc aactgattgg tcttcctgca tctgtcctgg    28800
cttccctatc atccatttgc tacacagaaa ccatggtcat cttttcaaaa tgcaaatctg    28860
atgatatcag tctcagctct aatttctttg gtggttcaca tataaagact gaaatcttta    28920
actgaccaat aacacacgtg tgatctggcc cctgctcacc tcttcagcct tgtctttcac    28980
ctgtctcttc attttggcca cagggacctc ctcgtacctt ctctcacgtg ccctcctgcc    29040
tcagcgcctt tgcatatgct gttccctttg ccgagaactc ttcctgtcaa ctcccaagcc    29100
cttcacctac ttagcaccta cctattcaat ctgttctgtt tgcctcttgg tatgttacaa    29160
actgtctcca aacttagcag cttagaacaa tgaatccttt accctctctc acaatgtttg    29220
gggtcaggaa tttgagcggg ccttggctga ttttctgtt cctcatgcca tcaattgata     29280
tcacctgatg ttattaagct gatggatggg ctgatctgga gatgcactgt ccagtttggt    29340
agccactggt tacctgaaat gcagccagtc ctaattgaga tgtgctataa ctataaaaca    29400
cccacatgat tattgaagat ttggtgccac caaaaattt aaaatattcg ttaataattt     29460
gtattctgat tacatgttga gattataata tttcacatac atcagataac ataaaatgtc    29520
attaaaatta atgtcaccta tttctttta atttctttaa tgtgactact acaagttttc     29580
aaattatatc tgtggcttgt aattgtggct tgtattgtat tctttttttc tgagatggag    29640
tcttactctg ttgcccaggc tggagtgcag tggcgagatc tctgctcatc gcaagctctg    29700
cctcccaggt tcaagtgatt ctcctgcctc agcctcctga gtagctgaaa ttacaggtgc    29760
ccgccactat gcccagctaa ttttgtatt tttagtagag acggggtttc cccataatgg     29820
ccaggctggt ctcaaactcc tgacctcagg taatctgccc acctcggcct cccaaagtgc    29880
tgggattaca agcatgagcc accacacctg gcctgtttta tattcttact ggacagtgct    29940
gatctagagc aggagtcaag cagttttttc tatgaaaggc cacatagaaa atgttttcag    30000
ctttgcaggc catgcagtct ccatcatagc tgttcaactc ttccattgca ctgcaaaagc    30060
agccatagat aataatttac aatagacata gcagtgttcc agtacaacta ttaataaaaa    30120
taggtggtag ccagatttgg cctacaggct gtagtttgct gacccctgat ctagaagatc    30180
caagatttta ttcatatgtc tggtggcttg gcagggatag gtggaaggct cagctgggac    30240
cattgaccca aacagctata cagtcctctc cagcatgatg gtctcggggt agtgggacat    30300
cttacgtggt ggctcagaac tccagataag gtactcccag agagacaggt agaagctgtg    30360
aggcttctta tgaccaagct ctcgaagtcc cagaatatcc cttgtactgt attctatggt    30420
caaacaggtc actcaggcta gcccagattc aaagagagga gatccaactc tacctcttca    30480
tgggaggagg agtagccaag gatatgtgtt tctttttaat ctattatatc attcttcaga    30540
tctcagttta ggctggtcct gttatgggct ctcaaagtac catgaacctc tcttttgtag    30600
cacttgtcat agctagtttt acatttctct gtatgattac ttgatcacta tcttgctttt    30660
ctactaaact gtaggcaacc acgtgaagag gaactgtttc tggttttgct cattatattc    30720
ctagcaccaa acacaatgct tggttcaata aatatttgtg gaagaaacga atgaatgaat    30780
gaaccaatag caaatgaatg aatgagtaat aactgtatca atattaatcc tacatttctc    30840
catattgctg tcacgtatat cataagatac tctgtcagaa gccttgctaa aattcaaata    30900
```

```
tatttgattc ccagtaacct tcttattttg tagttcagaa actttataaa gaaggaaata    30960
agcctatctt actcttccca gtatctcaaa gagggtttct gccctgagct gctcaagagg    31020
gtttctgccc tgagctgctg ttcattctgc aaacactgct cgaataccca ctgtgtgcca    31080
ggtacagaga gttcttctct gctgtaatct ggacaggcac cagcttccca gcgtgggttt    31140
aggcttcagg tgcacactac tgtgtaccgt ctaagccaca cctagaagag ctctggggaa    31200
atatgactac ttgggcagaa aaggaaggaa ctaagaagag gtatctttgt gtctgaggtc    31260
tgaaggagcg tgtgggctct tgttcaggca aagggcagga tgaggggagg tggggtggca    31320
gcagccagta atgggtgggg acagcggaat gcagaggatg aaacttcagg tcctggtgct    31380
ctgagaagta acgctgtgca gcatgtcaca cccagaggca aaccaaggcc cagggagct    31440 gatgttgcac tggagctcta ctctcctctc agcgagctgg tgacgtgcca gtccagcagg    31500
cctggcttat ccaaccacaa gtatgaatcg gcagaaggca atgagctggg ccctgagtgc    31560
tgctgggctg aggccgacct aatccttcct ccacagagac tgtggtgtcc cctgctttgc    31620
tcagggtaag aactcttgta tacctcacaa gaagccaagg actacctacc accttccaca    31680
ctggccctgg agcctgcatt gtagttattt gtggacactt tttcttctct ttagtgccag    31740
gtgggggacc aaggcctaca tgtctttaca acccctcaat ctctagaaca agtctgacac    31800
tgagtagatg tagcaaatgt ttgcctgaaa gactacctca ataaataacc ttctgaggca    31860
ccagcaaact tctcagcatt tttcctgata ctccggttac cactaacatt ctacacaaag    31920
ttgtgaaata agtcttttc tttgttgctc tccaacatct actgtggacc cctcctctca    31980
cttcctgttt catcctctct gcactcccct gtcccacccc attactggct gctgccattc    32040
cacctccctc atcctgccct ttgcctgaat gagagcccac atgctccttc agacctcaga    32100
tacaaagata ccccttctta gttccttcct tttctgccca agtagtcata tttccccaga    32160
gctcttctag atatggctta gatggtccac agtagtgtgc acctgaagcc taaatccacg    32220
ctgggaagct ggtgcctgtc caggttaaag tggagaagta ctctctgtac ctggcacaca    32280
gtgggtattc gagcagtgtt tgcagaatga acagcagctc agggcagaaa ccctcttgat    32340
gcaaagggat actttggggc cccttcttct cccaccccag tctgtctctc tgagagtcct    32400
ctcgattcca ggagccacca tcacacctgg ccctaggctg tgctgctccc gtctgtctca    32460
gaggctagat aacatcagag tcctttccac tggctcctgt ggcagagcaa aaactggttg    32520
gcatttttaa acgtgctaca ccagtgtgtg aaagaaacac aggctgcatg ggttaaatc    32580 tcagctgtac catttactag ctgggcagcc tagggcaagt actgtgaccct ctctgagact    32640 ccattccttc atctgtaaca tggggacaaa taatctcacc ctgttgtgag cagtaataat    32700
atgattaatc atttagccaa ctcttattca tgttctctga tgggccagac atacaaagta    32760
agtgaaagtg gattacggca ggtgctcttc ttggtttctg gagtgaacct ccatttacat    32820
ggaggctcct cttttagat ttctgactag ttcacccacc ttattcatag accttattct    32880
gtgcttagct gacagaaatc tcctctcaga gaatcccccc ggtaaattct taggttcttt    32940
cctcttccat tcccctttt gctctctccc tccgaaggca agagtttcca ctttacaggc    33000
ccactgagaa aagttatggc ttctggttgt ggttggaggt tcattcctga gggagtgggg    33060
acatttctac acttcttcac ggccaatgac attggagaaa ctggcttcct aacccagccc    33120
acaccctcgc acacacacat cacacatcat ggctagaatg gagagaaatt cttcatatgg    33180
ggcacttgta cttcatgaaa gaaaatcata tcaatcttga gtattttaac atcctattac    33240
agcagggtca ctgataaact aagtgtccag agtgtttct aggatggtgt gtggtctcca    33300
```

```
aattaacatt agtgaagctt actggaagga ttgttactcc tgggccaggc caggattttg    33360
aggagagatg tgtttgctgt caccaaatcc ttgacagact ttggcagaag tgtgttaggc    33420
ttactctgga tagcttcaga ggacaaaact agtattgacg gaaggaaggt aaggagaagc    33480
agcttctaac ccaggggaag agagagtttc caaactgaga aatcaaaaat ggtactgatt    33540
ccttgtcagg gtcagtgctt ctccccactg tgtgaattac aggggccatt tgtccaagat    33600
tccttagagc aatactgatt tcatgtaatt atttgaatga aaggtgattt gttaaattta    33660
tagtaaaata taatttgatt tgtgtccctg tttgtcatgc caccccagaa gaaaaattgt    33720
ctttggttag gtcgaacata atggtttttt ggtttgcaaa ccatgagcga ttcccatatt    33780
aggtgggagt tcagattcaa agggccctct tttttttttt ttttttttg tagtagccag     33840 cctaatgagt aggaagttgt tctcactgtc attttatatt gaatttcttt tattttgagt    33900
atgaccatct tttcaaatgt atgagatagt tatttccagt tccacatact atctgtacat    33960
ttcttttgcc cgcttttagt ttgggtcttt ggccttttc ttattgattt atagaagctc     34020
ttttatacat agaaaattaa tactttgtga ctagttgcaa atattttcag ttgctgaaat    34080
acacagtagg tgttccatgt aagagctgaa cagctggttc ctgattgctg tctccctccc    34140
ttccagccaa tagatttcag agtttgggca ttacctattg agccaaagct gacaccacac    34200
aagcgcagag tatgggaaca gagttctctg tctgattcct gtgagcttcc tcatactaaa    34260
tcaccaacag caacctactt atcacagaat atgagaattg aacaagtgtt ggcaaggatg    34320
tggagaaatt ggagctcttg ttccagttgt cgatgggaat gtaaagtgat gtcgctgcta    34380
tggaaaatag tgtagcagtt cctcagaaaa ttaaaaatag aatgaccaca tgatctagca    34440
attccccttc tgggtatata cccaaaagaa ctgaaagcag agtcttaaag agatattcat    34500
acagccttgt tcataccagc attatgcaca atagccaaaa ggtggaagca actcaaatgt    34560
ccatcaaaaa tgaatggata aacaaaatgt agtatgtaca tacagtgaa tatcatttag     34620 tcttagaaag aaaggaaatt caaacacatg ctacaatgtg gatggccctt gaatacatta    34680
tactaagtga aataagccag tcacaaaaag acaaatactg tatgagttta cttatacct    34740 aagcagtcaa attcatggaa acagaaggtg gaatggtggt tggcaagagc tgagaggagg    34800
agagaaagaa gagttattgt ttaataggta tagaggctta gttttgcaag atgaaagagt    34860
tctgaagatg gatgtagtga tgactgtaca acaatgtgaa tgtatttcat accactgtac    34920
actcaaaagg tgaagatggc aaattttatg tgtattatgc cacaactaat aaagatttct    34980
aaaacttatg agatctaatt tcaccgtttc ctattgctaa agatcacaaa ttagaaaaca    35040
cgttggcaaa aggtacatga aaataagcac tcttgtgttg atcagagcat aaacgtataa    35100
tctcataaac taataaagat ttctaaataa caaagatttc taaaacttat gagatgtaat    35160
ttcaccattt cctattgcta aagatcacaa attagaaaac atgttggcaa aaggtacatg    35220
aaaataagca ctcttgtgtt gatcagagca taaacgtata atctcagggg agaacaattt    35280
gcaactattc ttcaacccctt tggtcaaacg attctgcttc taggaatata gcttactccc    35340
acctgtgtga tatggcatat aatcaaggtt ttccattgca acaaaagatt ggaaacaacg    35400
ttaagtatcc atcactagtg gtctggaaat atatatatat tattgtcatc caatagaata    35460
caatagacta atatgcaact tttagcatga ggatactcgt tacatgctga tacagaataa    35520
tctccaaggt agtcatatgt gtgcaaaacc gtacatagta tgctaccatt tgtgcttaaa    35580
aataaaaaga aaacagaata tgggtcaatg ttttgtttta gttttgtcta aagtaacttt    35640
aagtagaggc aagaaactgg taacatgtaa cagtgatcac ccctgttacc tctgtggaag    35700
```

```
aaaactagac agctaaggga caaggctggg aggcagactt gctttccact atttatcacc   35760
tttatctttc aaatttagta ccatctacat ttagtaccat gatctattca aaaatattta   35820
ttaaaaaaag aaaaggtata gtctagaagg aaaaaaaaca taacagacac ttctagccca   35880
atgtcctgca ctgggtgcta tgagagcaga ggaaagaaac acatatggct tctagacaac   35940
accgtctggg gcatacattt ctgctattcg atcaagaata gttgtgcatc ttttcctgga   36000
aagaattgat ttgttttat caacagacct atgaatttag tggacagacc tgtgaattaa    36060
ttcactggtt aggttttcct ttttacattg gctgttaaaa agctataagc caaatttatg   36120 tcccctcag tgcaaattgg gcagatttct agggcaagca tttagcactg gccttgtcct    36180
tggctctgta tcatattcct gtatttggtt tgcttttcca cctgtttctc atgttggtca   36240
tctttcctgt gtatggccat accatcctga atgtgcctga tcgcatctaa tgttggtcac   36300
ctctccttat tctttgcttc cttataagcc actaagcagc ctttttggtg ctagttaggg   36360
taagtgcgtg ggtagtgaag gagggaggag ggagaggaag aaagaagata gaggttataa   36420
agcaaagcat atccttttc ttggcttcat catgtagatt aagtgaattg ctctcaaagc    36480
gtggtcctta ggccggcagc attgtcatca ccttatgttg ttaaacataa aaattcatgg   36540
gtttcatccc aacttactaa gccagacttt ctgtggttga ggcccaggaa actctccagg   36600
tgatttttac tcacattcaa gtttgagaac cacaggaaaa caaaggaag gcagatttct    36660 aagcgtaaat gcaatactaa ccgattgccc ccatcatgcc tgttatgttg gtcaagataa   36720
ataatactag ctactgcaat aatcaatccc tcaaatttta tttttgcca atatcacaat    36780 ccattgtaga tcagttgtgg gagaggtgta aagagagctg ctttattagt ttattaagca   36840
aaccagatct cttccattgt gagactttgc gattttctag gcccttggac atttcctctg   36900
gatcccctgc tgctaagaag gcaggagagg gaggaaagag aagagacttt agcagccaga   36960
tctggaagaa acatcttttc tgcccacaat tccattggct agaagccagt ctcatggcct   37020
gtataactgc aggggaggct gggaaatgtg acctatcgat ggagctaaga gcaaaaggaa   37080
atggctttga tgaagccctg gcattgtctc tgcacacccg agaacccaag tgaatcccaa   37140
actccacgtc caggtcatgt tttggtgaac atcggttttc agtttccttt tctaatcaag   37200 ttttacctttt tttttctcg actctagcac tatgggactg agtaacattc tctttgtgat   37260
ggccttcctg ctctctggta agaaccttc agctttgtta agtcctggaa tcctactgtc    37320
tcctgatgag tctgaccaca gcaagcccag gcctgagact tggtgggttt tactcacttt   37380
ctactgagca ttgtacaaga ccacatgcaa aaaagacttt cctggagaag aaggaagtgt   37440
tatgattgag agcagctgat ggcaggcagc tgggatggag ctctcccccc cgtgtgcttc   37500
ttcctcctct gcagtctcac atcagtgagc ctagatgctc agagtagggt agcctggccc   37560
atcccatggg gatgggggaa ggctgctgca ctgaggcccc tgagacttga ctcttttgtt    37620
ccacacatat tctcttctgg tcttctctga ccctgtttct gtctttctca ggctcctagg   37680
aaacaactga cagaattcca aaagtctccc ttcattcgga gcactggctt tcacgtccct   37740
gacttcccta ccctctctca ctcccttccc tacagcccat gcataccct catggttgcc     37800 acggcttcct gacaactatg gatgttcagc taattgtgtc agctgattta tagtggagcc   37860
aatgaagctg aagcttcaga gccctccatt tgcacaaccc tttctaaatc cccctcaaga   37920
ccctgtgaag ggcccctag cagtgtggtc acctgtctta tgctttggta aaatttgaat    37980
aagtaagata ttgtaaccac aataagttat gaccactgtc tccttcctct gcaacttttc   38040
cctccatgcc attctcctgt ctggtggtgt tagcagtcag gggcattttg tatttgaatt   38100
```

```
ctacattctt tttcttaact atccaccacc tccctcaaa attttaacag catccagcct  38160
cacaaaactc agatcttccc tgtttacagt tccactttga gtttcagttt cttcatctat  38220
aaacaggagt tggctgcggt ccctgccatg tatcctgtga ctcagtgtct cgtagttact  38280 cctgcccac ccttcctgc tgctccttgt ctccacctgc aggcctgaga gggaagccac    38340
cccactaaga cagggaggtg aactgagcct gaagtttggc tacagcaccc acaggccacc  38400
agccatgagt tcacctcctc cagatggcca cacaccaggc ccttggccac tgtccccatg  38460
tctgctgtgg atgatgagga gtcagggaac tacaaagaga tggtccctca gatccatgct  38520
ggctgggata agccttttca gatttctgtt tttctgctta gcaccttgag cttgtggagt  38580
ccttgagtgc aaggtctgta gatgtgccag ctgatcactg acttaggtaa caacagcagc  38640
ttccaacccc cagggcccat gacctgctac cttagctcct ggggatgtgg gaggtatgtg  38700
tgtgtcagag agcaaggcaa gaagactcta gagaacatta tccagtaaga ttcccttctc  38760
atcccacttc ttattattt atttttattta tttttatttt tgagacagca tctttctctg  38820
tcacccaggc tggagtacag tggcacagtc acagctcact gtggcctcga ttacctgggc  38880
tcaagcaatt ctcccacctc agcctcccca agtgctagaa ttatatgcat gagccatcgc  38940
acatgactta ttttatttat ttgataaatg catatataca cacagtcatg aatcgtttaa  39000
caacaggggt acgttctgag aaacacatta ttaggcgatt ttgtcattgt ataatcatca  39060
tagggtgtcc ttacacaaaa ctagatagca tagcctgctc catacttagg ctacctggca  39120
cagcctattg ctcctaggct acaagcctgc acagcatgtt actgtgctga atactgtagg  39180
tgttgtaaca caatggtatg tatttttgta tctgaacata tctaagcata gaaaagatac  39240
agtaaaaata tggtgttata atcttatggg accaccattg tatatgactg aaatgtggct  39300
gtgcaataca tgacagtata tgcatatata tatatatccc ttactttgtg cctggtactg  39360
ttctaagtac ctcataaata ttaactcatt tgagcctcac aataactctc tgctttaggt  39420
cttgttgtta tttcccattt taagatgtgg acactaaagc ccagagagat gaagtaattt  39480
acccaagatc gacagagcta ctaagtggca gagcttggat tcacacccag caatgtgat   39540 ttagcattcg ttcacttgac tcttctccta actcttgtgg taaaccatga ataagtggta  39600
agacttcttc catggggcct gaacagcttt ggtggataat atagcttctg cctcatccgt  39660
gttcatccag tgcctcctcc ccatcacctg cagctgacac ctcagttgac ccaagagctt  39720
gggcccaagc ccttctcatc aaagtgacca gcccagctct caagatctgg gagagaagga  39780
agaaaaatgc cctggaaaca catttccaga aaacactaaa ctggaacacc atttcccacc  39840
aaattttctg actccgcaca ctgaaagtga gaaagtaaag ccgagacact ctatgaaaac  39900
tgagttcagg tgtcactttt gcccttgatt tgccattgac acttcttaga agtttcttag  39960
ctcctgagaa aagagttacc aatattgaaa gcaacaacct caaatggtaa ccgtttaagt  40020
tttatggtgg tgagagaata agtgactata ttttggcag tacaattta aagtggaata    40080 gaaagcccat gacatcagat cagaaaataa cattgccagt aattcacaca cgatgaaaag  40140
caacaaaaaa tcagattcta tttgaattct ttcttctcag gcacacctc tgcttactgg   40200 gctggtgaac agtgacctag ccacagggcc ggcttcaaaa gggagaaagg agatgcaatt  40260
ggcccacata atccaccctc aaaatgtaga gctgaataat tcatttcatg gcatagaaat  40320
agcaatacag tgaagcaatt ctgtttaact tttccctccc tatattttgt gtcctctgtc  40380
atggaaattt gacacagtag tatttgctgc ccctgctctt gaggataaaa ttggatggga  40440
gtttaagact gaaacgggca cctgtggcct tgcagaatta ggttacagtt tgtgccttgt  40500
```

```
atttacaaag cgaaaggaat tcctagtgcc acctgcagag gcacttctaa ctttcaagct   40560
ctgtttgcca ctgtcctggc acctccatca cacttttagg ctggagccag agaggttttt   40620
gaaaaatcag tagctcccac atcaggagga agtatctttc cagtttgagt tttggtagct   40680
gctctctttt tgtctgaggg ttctctgggt cctagggctt tctcatttct cttgaacaac   40740
acctctagtt aatttcatgt acctggagtg gtagttggaa tatttcttca ctttaagatt   40800
tttttttttt tttttttgaga tggagtctca ctctgttgcc caggctaaag tgcaatggca   40860
tgatcttggc tcacggcaac ccccgcctcc caggttcaag tgattctctt gcctcagcct   40920
cccaagtagc tgggattaca cctaccacca caaaatacaa aaatacacaa ataatttttg   40980 tattttggt agagacgggg tttcaccatg ttggccatgc tagtctcgaa ctcctgacct   41040
caggtgatct gcccgcctcg acctcccaaa gtgctgggat tacagacagg catgagccac   41100
tgcgcccggc ccaccttaag atttatgtaa gattggctca aaagctcatt cctgtggaaa   41160
ggtccactgt tttcctccca agattttgc agatatctgc gtgggtggtt acttttgact   41220
cccatttcct gctgttgttg atagccctca ttaaaaccat cacctggagg tgaatagaca   41280
gtcgagacct atcattccca aagaattgtc atggagccta atagttctat tggattcacc   41340
cctttatgtt aagccaccat ttcagtgttt ttcaaaatag atatatgtta tctagtaggg   41400
agtatcttac ccccaaatta gttgattgtt tcaggagggc ttttagtggg ttccagagaa   41460
aatgagcaat cagacaagtt gatttagtgg aagacagtca ctgaatagga tgtgtatagg   41520
gttgtttggg agcaagagtg aaattggtat ggaacagaga ggctcccaag gcaagcagac   41580
attttttttg gaagaagcaa gtgtttgaga gactgtggct tattttttcct ttgtgagagg   41640 ggagttttaa taccatttcc aaaatatgta acctggtatt ttgtccccag aagtactgtt   41700
gagatttatg gaagcaaaaa actctgtcac ccaggctaga ggagtgcagt ggtgctatca   41760
aagcttactg cagcctctaa ttcccaggct caagagatgt ttctgcctca gccacctgaa   41820
tagctggcac tataagtaca tgccaccatg cctggctagt ttttttttgtt gttgttttgt   41880 tttgctttag agacggggtc tcgctttgtg cccaggctgg tcttgaactc cttttaagtg   41940
attatctctt ctcagcttct taaagtcctg ggattatagg catggcctat ctatttttat   42000
gttttataat ttcttgtact ttttgatgtt acttcaaata tcttttttaag tatcctaaat   42060 atacttattt aaattttttt tgagtaaatt tatctataaa ttattgattt tatgtcgata   42120
gacattgttc tctatcatta ataatgttaa aaataaataa aaaaacaaaa acaagtaaat   42180
caattaatgc ttaccacagg ccagtatttg atccaacact aactcaaata ttcatttctt   42240
taatcctcac aacaaaccta tgaggtaggt accattattg ttcctgcttt ttgcaagagg   42300
aaactgagac acagggaagt taagtaattt gcctatggta acacaggcag tgagtagttg   42360
agctgagatt gaactcacgc tgtccagaat ccatgctatt agttataata gtgtactgcc   42420
ctatagcttt ctgtttcaca gctacatggc attactttgt atggatgtat cattatttgt   42480
taaaccattt aacttatttc cagtgtattg ttcttataaa caatgaatac ctgtgtacct   42540 ctaatttgt gcacatgtat cttttttgtag aatgaattct taagaaattg agttgctaag   42600
tcaatgctta agcccataat taattttctt acatattacc aactgtcctc caaaaaggtt   42660
gtaccaattt agaattttac cagcagtaaa ttcagcagtt aggacccatt ttcctaacac   42720
tctcgcggac actgggtatt accagtattt ttttaatac gtgccaatca aatgggcaaa   42780
aagaatggtt tctcactgag gtttaaattg catttcccta gttattcttg agattttcc    42840 tttcctttct tcaacaatta cttattgagt gcttcatatt tgtaagggac aattgcaggt   42900
```

```
actggaaatg tcacagtgag gaaaagtgac aaagcccctg ctgtcatgga gcttattcta   42960
atgggagatg tcaggtgctc agctgagctg ggagagagag agctgagttg tcaggtgtca   43020
gaggagccaa ttatagcagc aaaacaaaaa taaaatagtt cagcttttaa tctcttacta   43080
cgacggtata atcaagaggc taaaatggga ggaagggcag actctgcctg ttccatttcc   43140
ccacatagag tgagtatacc agtcgagggt caggtaatca gtgcagactt aggggggtcgc   43200 cttaccattg aagaagcccc aaatgaaagg ctctagcagt tttatggacc tgggggtgga   43260
ggaatccaag ggtggggaga attcatgagg aaaatgaggt gagagggcta ggagtggaaa   43320
agtacaaagt actgagttag cgtggggaat agtgtcttta gggctaggag tggaaaaaat   43380
actaggtact gagtcagagt ggaaaacagt gtcttcaagg cagggagtgg aaaagtgcta   43440
ggtactgagt ccgagtggag aaaagtgtct tctctatgat gaggaggctt cagcagaggt   43500
gcctgaagac ctcaccccag agcctcagat aaagagacct aagaatgagg gtgcctgggc   43560
taagattgca agtatgtgaa aaagcatgac tggcggagg ctgagatctt gattgcagcc   43620
cccttcagag actgccatgc actgactgtg caccaagtct gctgtagaaa gggcaacttc   43680
ctcagcaagg cttgtcagat taagcctctt taattgcctg tggtcaggtc tgaaaaatca   43740
cacatagatt tttaatcaga acccagacat ctcaggagag acagacaata accaaacata   43800
ccgtgtcatg tcatgtcatg ataagtacca caataaatat aagtcagcat gagggacaga   43860
atgcccagga tgctatcttc aatagaatgg ttagagaaat ctccctggga ggtagcattt   43920
aatgaaagac ctcatgaag tgaaggagaa gctatgagac tgtctggagg aagaaccttc   43980
tggacagagg gaacaacatg agaagaggac ttgagacaga gtgtgtgatc ttttggagga   44040
atgtcaaggg aggcagtgtg gctggggaga gtaagcaggg gaaagaggcc tgataggtac   44100
tggggaccca attacatgag gtcttgtaag gccaggggaa ggactttgga tgtagttctc   44160
agtgtgaggg gaagggatct ggatatattt ttcagtttgg tggaaggcat cagaggcttc   44220
tgaacaggag gattatgtga ttggagctgt attttaagg gatcattttg gcttgagaaa   44280
ctagacccgg ggacaaggac ggagcaggca gatgagttag gagacaatta cattagtctc   44340 ctctacccttt ttcttaacat attggagttc agctctggct gtagtagttc tagatctcct   44400
cagacacact tgtgtagagc ctctgttggg tattttgggt acacaaatga ttcatcttgg   44460
ttatacagat gatttagatg attgtagaca gaagaggggtt gtctggtcat tcccagacag   44520
gggagcattc cttgagatag agtagaggaa ggctgaaggg gaggaagaca gtacctgttg   44580
ctatctagat agagacatcc agcaggaagt tgaatacagg tatctgaaac tctagtgaaa   44640
gttataggct ggcaataagc acctgggagt tattagcttt tacttgacag ttgaatccgt   44700
ggggctagag gagaaaaacc aggaaagtat ggagaataag aagaccaaga acatgcactc   44760
aaggttacca aaattaaaga gtgatttgag aaaattaaca aggaaatcag agattgggaa   44820
agaatagagc atttcaatga ggagagatgc caacacttgc atttgacaca gcggtcaaat   44880
gagttgagat ctgaaaagag ctcaagcctt ggccatggtg tgaagtcacc aacaaccttt   44940
gtcagggagt tcagtagag aggtgggggt gggaggctgg gaataaaggc agcaattgct   45000
gcttactctt tcagggagtt tgactccaag ggaaagagaa actaaaagca gtagcacaag   45060
gtttgtgttt gaagtaatgg aggtgaacca ggtgaatagc ctggaggccg agtgaagtga   45120
gacaggacac tgcagatttg gaatgtcacc agtccgcaca actgaataat ttcctccaga   45180
actgctcaat tgcccagttg taagaacaga tatgtagacc aaaagtagag tgtccccagg   45240 gtaaattttta tagagacaaa ggggtgtgtt tattgaagtt gtggaaagga ataattacaa   45300
```

```
agacatacta ttgttgcatt gtccaatata ataaccacta gccatatgtg actacttaaa    45360
tttcaattaa ttaaaattaa ataagattaa aaattcatct tctcagtcat actagctatg    45420
tatcaattgc tcaatagcca caggggctgg tggctatcat attgttcagc acagagacag    45480
agcatttcca ttatcactaa gagttcttgt ggaaaacact gcactacagg gtctggataa    45540
agctgaggtc ttgattaagt tgaacaacag ttgtagaagg agtaagcaag agcaaaacct    45600
ggatgaatag gaggttgtgg acggagatta gtatattgag attaagattc tagggactga    45660
gctgctccag gtgaaaagtt tcaggttat gtcataagaa ggtgggggc agctgctgaa     45720 atagtctgcg ggtgtagacc tgtggagttg acaagatcaa agaaatttga ggcaaggttg    45780
ttagactcat tcatgaagaa gtcacccaaa ttgttagcaa gaccttgcat ctaatgccaa    45840
aatcctcatt tagcaaggtg gtagtgactt agtagctaca agcaatgaga aagtcagaca    45900
cctcaaaagg ggaaggtgtt gctcaaagtc cccacaaagt gtgataaaac aaacagtagc    45960
tggggctgga gcaagtggct tcctttgggt gaagccagat ttcactgaaa taataacctc    46020
agggaaacag tcaatgaagg ggttaaagat gtgggagagt ttccttgtag taagtaatgg    46080
aatgaggctt tcaaagggcc aagtaaaact ttggaggaag tttagtaaaa gaaggaattt    46140
tttttagtac agataagcat aggaacataa agaagagata attcttaaac atataagata    46200
tgcatttggg gatagcagcc agggaacact gaagtcccag tggggtcaga gacttcataa    46260
ggctagcaaa ttacagtttt tgagtggcat tccaacagta gagtgtattg ctcaggaagt    46320
ccttaattat cctttgaaac aaattccttc agctgattac gaaggcatct agctggattc    46380
ttgagcgact tgttcctgac atcatagcaa cccattgtaa ctagacttcg accattcctc    46440
ttacccaagt gctggggaag ggagagattc tcaatgctta cccacctatg gaatcccagt    46500
aagtccagtt gctaggtggc ttgaggtctg gggtcataaa atggaaggcc tgaagtcatt    46560
tggtgatcac agaccttgag ccaaactttc cccatttagt cagagaaagg attagcagca    46620
tcccccatgc ctggctctgt gtgagatcat ggaagccagt ggttggtgag gtgctatgga    46680
gtataaattg caaatactt tcagttccac tcagaatgga tttcaaagtg atttccaccc     46740 catgggagg agggagtc tgaggaggga tggatggaaa aaaaattttc atgtcatttt        46800
ctgtgatcca ctctggagac agaggcagag attctctaca acagctgctc aaactatagc    46860
tcttgttaaa atggaggttc tgaatcagta agtcttgggt ggggccagag attccgtgtt    46920
tcagaccagc ccacatgtga cgtgaatctc attggtccat acatcacact ttcagttgct    46980
aggtgaagaa gggagcactc gatgagtgga agagaaagcc gttgtaatct ttgggagaag    47040
gggcctgggt cagcggagtt agactggtct gtgagtggac agaatggatg ggaaggaaag    47100
aagatactgt gaggctctac agaaaaaaaa aaaaaaaaa atatatatat atatatatat    47160
atatatatgt aaatcaagaa gacagaagca gctaaagacg aagtcatttc caggtccaga    47220
aggcacaact gacagctgag taataacata acattgactg ttaattggca gaattttaa     47280 ctgtgtgttt ggtttctcca tcaggtcatc tgtcctatat tacatgacaa tttagactaa    47340
aaccagtatt tcctcagaga caatgctaga agcttttaca gtaggggca ctcttgcatt     47400 acattaagag ctcagcaaag aagatgcaga agcctcaggt ttgccttgta aggtgattca    47460
taaacacact aaatcttcct taggtctccc tttcactgtc agggtacgca tatagatttt    47520
ccttcctccc tccaataccg gtacgcatcc tctacaggtg gtgcatttta tacctcaagt    47580
acttcacagg gtcctagtga gtgtagtgaa ataggcagtg attcatattt gtgcaaactc    47640
ccactgatgc ctgctgtctg cttccctaag agttcaagac caccaccaac cccttgatta    47700
```

```
tgtgttctca ctgggccact ctgtacacag tttagtttga caagtgcatg tcactgttat   47760
ctgtccttct attccctctt tcaagagaaa ccacatcaat ttaattactc ccccacttag   47820
aactcttcaa atgaagctcc tctcatctct ctcatcaacc catctcctcc ctttcctcct   47880
caatgtcaac atgccttcac ataaatcctg aatgatgaaa ttttatttag aacttacact   47940
aacttcctct ccaaggtggc atctaacttc atattaagta agaaacagcc ttcccactct   48000 ccaccccgc acttctcacc caccactgct tacttttttt tttttttttt tttttttttt    48060
gccaagtctc aagtaattct gtaacctaga aaaggtccta cacaaacccc gtgatcattc   48120
acatttaagt agttgggtgg cccacatcct tcccacaaac cccaaagtgt cctcaaggac   48180
taaagccttt ctctcaaccc ttccagcatg atgtctatgg ttgtaaaatt gtccagggtc   48240
agtgcatact gggagcagca agtttgtggt gcctggggtt tccccaatac tcccaaagca   48300
catcctcacc tgcccatcta tgattcattt tcagcatttc actcatgtgc cttaaatggt   48360
cattgaccac cacaatccga aaacagccat caaatttgcc cagttctctt tctgatctct   48420
gaaagagctt agagaggtca ctgaaaataa aggccttggt tcactatcga agtcatttct   48480
aaagcatttg acatccttgg aagtgctggc catgggagca gcagtcatag gggaagttct   48540
gtaaagggag ctatttgaat ttcaaagatg ttactcaacg tgattcccca actaatgaag   48600
tataataaag gggggctata atttattacc attatcagca atcttttcac catagcagac   48660
caaggaatat gtggatggga ggggagggga aagcttttgg tgatggtgta gaagttatgg   48720
aacctgtaac agctacagtg atgaaaacta aaattaaggt tataggaagg taactggtgg   48780
gtgaatgggt tgtctaactc tactggtttt tccctgtctt gcaatttaaa ttcacagaac   48840
cacagtacta gaaagaccct tggaacattt agtcaaccac ttcattaatc agatgaggaa   48900
actgaggctc ataaagattg cagtttgtac aaggccacac atttagtcag cggtgaagca   48960
aggacaaagg tcctaatctc cagatgccaa gcagatgtgc acagttccag agcttaatat   49020
cttattcttc agcatgatta ctgataagat agtatctggg tattgtataa agagaaatgg   49080
aggttttttc cccttttcctc ttgttttctcc ctccctaatc cttaaccttc ttttttaggt   49140
gctgctcctc tgaagattca agcttatttc aatgagactg cagacctgcc atgccaattt   49200
gcaaactctc aaaaccaaag cctgagtgag ctagtagtat tttggcagga ccaggaaaac   49260
ttggttctga atgaggtata cttaggcaaa gagaaatttg acagtgttca ttccaagtat   49320
atgggccgca caagttttga ttcggacagt tggaccctga gacttcacaa tcttcagatc   49380
aaggacaagg gcttgtatca atgtatcatc catcacaaaa agcccacagg aatgattcgc   49440
atccaccaga tgaattctga actgtcagtg cttggtatgt ggtcaatggt gtgtgttcag   49500
attcttagcc ttctcagatg agactgcaaa tgagttagaa aaacactgga gggggacttg   49560
aggggcccag gggaaaaggg gggtctatag agagaaggca gaggacagcc acttctggga   49620
agtgcatttg aagggagtgt agagtctggg agtagggaac tgaaagtctt ttgtacttttt  49680 tatagtctgc ttctgaagga tcagtaaaaa tctgctttgg ggaaaaaata gagctaattg   49740
aacaaagata atatggctaa ttacctatag taaaaaccat ggataatttg gccatcacaa   49800
agtttatata accataaagg cctcagatgt cttacattca ttttttcctt gggtccaaga   49860
tttttcacct actaaatctt tgcctggagc tcctagcaaa gcggacagct gacacatttg   49920
ggttttccct tcagcctcct ctaggttgct tatgagttgt ttgctgccac aaccatgagc   49980
ctggtagaca gaagggaaaa aaacccaaca aacataaccc acaaacttac aaaccagctc   50040
ctctgcttca cgagaccttg gaaggcctaa atgccactac agattttttt aaaactatca   50100
```

```
cacagtaaaa ttatttttt  ttgttttgat atactgttct actgattgta tagatcttgt   50160
atagatttag gtaaccgcca caggacatag agcatttcta tcaccctaaa aatttccctc   50220
aggctgtccc ttcatagagt catacccctg ctgcactcat aacccttgtt gggcatccta   50280
tagttttgtc ttttttgacag tgtcacataa gtgaagccac acagtatgta acctttttaag  50340 cctggcttct ttcgtttagc gcgccttcga gattcaccca agttgttgca catatcgagc   50400
ttgtcccttt ttattgctga gtagcatttt attgtttatc cattcaactc agtaaaagac   50460
attgggttgt ttctggtttg gggctcttat gaataaggct gctgtaaacg ttcatgtaca   50520 ggttttttgtg tgaacataag ttctcagttc tctagaggaa atacccaggt gtggtattac   50580
tggatccagg ttaattttttg atgaaacttg aaaaggcaga tcaacaccta ttctaaaacc   50640
atagagtaaa acagaagcaa agtaaaaat  agaatggaga gctgctccct ttgaaccctg    50700
tgtgatttaa actaggctgc agggctttag gaatagttaa ccaagtgcta aatccgtgtt    50760
ttcaaaatgt ggtcaggtac cattggaaat gtttaggtg  ggacacagat aagcatttttg   50820 aaaagccatg ttgtattttgt tttaatgtat attagaaaaa ctctaactta cgcaacatgt   50880
gatttcacag atcttgttaa tgaagctaaa cacggtctgg caattcaccct tctacaggcc   50940 acatagactc caagaagact gctcaaatag tacactgata tagcaaaact tataaagatg   51000
acatgcaaat gacagacctt ttagtaagaa tacactaaat tataaattag tttgtagaac   51060
ctgcaaacta cctagtaact ataaaagaac aagggatttt ttctgacaga aggcacatga   51120
cacaggtcta gggactccat gccagtgatc ctgaacagcc agaaaagtga gaatggcaaa   51180
ggcaagagaa acactgtgtt tattaagatc atgtatttttt ccctaaaata gctggattttg  51240 gccttcttct tagagtatgt tatgaagaca ctttgatgct catgccaaaa atcagtgttc   51300
tgaatttcga attccaaaat atccacccac tcacttacca caatcctgct tgggtttctg   51360
aaagatatga cgcagggcat ctcagcacca tgaactctgt cagttcctgg tgagactcca   51420
gctcaattcc ttcctgctct cttagtctgg ggagctggaa tgtgccccat gggacacctg   51480
ggccctagag tcagaccact tctccttcca aagactctac tccctggaaa cagtggcttc   51540
attgtaaatc tttggtgact caattacagc cctcctgtca cttagagagc accccttttga  51600 tttggataag caggaagtaa gcatggctgc aaactctatt gttgaaaaat aaacatgaag   51660
tcattatgtg gcactcacct tgggctgagg gtcacatttt agacaccctg aggctcccag   51720
gtgtgcccca atgagcccca gatcaagtac ccagttatttt gctattccct cctagataca  51780
tctaaactta gattgatttt ttttttatctc tcttctgctt tcagctaact tcagtcaacc   51840
tgaaatagta ccaatttcta atataacaga aaatgtgtac ataaatttga cctgctcatc   51900
tatacacggt tacccagaac ctaagaagat gagtgttttg ctaagaacca agaattcaac   51960
tatcgagtat gatggtgtta tgcagaaatc tcaagataat gtcacagaac tgtacgacgt   52020
ttccatcagc ttgtctgttt cattccctga tgttacgagc aatatgacca tcttctgtat   52080
tctggaaact gacaagacgc ggcttttatc ttcacctttc tctataggta aagctgttt   52140 ccaagactat ttctttcagc aggtattata cacaaatgct taaggcagat catccaatgt   52200 cccccgacttg ctaggaaacc tccaactggg ccattttatg acgctgttag gaaggaccca  52260
gatggaggtc tcctgcttct cctgagtgat gcagggtcca ggaggctacg agcctatgtt   52320
gcacttgaag aaatatgctt ttagccctga aactgactca gtctcttggt ttaccttttgg  52380 atggaggatt ctgaagttttt gatttaaaaa tacaggattc ctccaggcta gaattctttc   52440
tttgattaca acacatacat gcgcttgcac acacacacac acacacacac acacacacca   52500
```

```
tgcatacatg cagacataca aatgatattt attgtgagta tagaaccatt tgggacatta    52560
ttggtcacag gagtgaaaac aaaaagatat gacacccct  ctgcccttga ggaccttcca    52620
atagaatcag aaccctgtaa tgtgcacaca tgaaaaactg gatttttaaa aggttgaatt    52680
ggaatctaaa tttattcca  tggaaatatc tgactaaatt taaaataaaa gtgactggta    52740
atgagattta tgggcattca gaggtaggca agatccctga gggtcaggga atggttccta    52800
aaggaagggg taccttgtaa catgtaaaat aaattattgg ggttaataaa tgtggtgagg    52860
aggggagggc attctggatg acaggttccc aaaactgtgg tgacttccgt agctgaaaaa    52920
atttgagaca gtatctgggc taagcaggtg agaggaccac agtggatcag ctgtatctga    52980
cgtaagtgca ggaggtatgt caaagaaagc cttggaggca gaaatgcttg tgtgttcaca    53040
agtattcttc agggacaagt tcagtggagg aaaggattga aactaagcag tagccactaa    53100
taggagcctg acatttaaa  gtcctggctt tacccaggag ggcatgtgtc tatatttgac    53160
tcctctttta agaagctgta actgcaagat tccctcctgg aataaaggtg gtctgcatct    53220
accctgtccc atcactgcct gtgctgacct tgacacccac atctgccttc ttcttacctt    53280 gacccttct  ccagcggtga tttcttggct tgccccctcc agtgacatcc atccaactcc    53340
ttgctccata ccctggcttt gtcacctcct ttctcccagt gtcttgttgt tcagatataa    53400
cttggtctgt gaacagccca cggggccagt ccccatgaac caactttaca actgggccaa    53460
tctcatctcc tgctactgac ttcttcctat tcagacactt cagcctctga gaatccagta    53520
aatggtggag ccaactcgtc ctgtcccagt tgcttctcct gtatcctctc ttggccagat    53580
agaagcctct ccaagctatg cctgaagttc agtacctcct tcaatgtgta attagtttga    53640
ttggtggcca caagatggcc atatatgaca tgccccaggg ccctctgtta cggctcccat    53700
agtctacaaa ttaacagggg cttgccacca ctataacctc atcatggctc accttcctgc    53760
tgcttctcaa ctactgttct gccaaacttc aacaggtacc cccatcttca gaaatgtttc    53820
agctctagct gcctcaggaa gatggggctt gcctctctgg gtttcccatt ctatcgcttg    53880
atcagagata ggttagaccc tgagtcaagg ggcctttttt gcatgttaaa aggtagcagc    53940
ctccacgtta gtaagtataa cccctaaccc cctttactgg gagtgccaaa ctggctcaag    54000
tggaatagac tgggacagac tcaaaaggga ttaaatatgg cctgcaatgc caacaacttc    54060
ttaacatccc agaaacaggg catgtgtcta caaattatag ctaagctaat agatcagctg    54120
gtcctaattt tcctgaaatt tgggattagc taccagaact gttcccaaaa atgtctttaa    54180
agtgggcgac tccgttctaa gttttcccca caaagcctgt tttccaactc cccagaaact    54240
taggagttct catgtaagga agtagttcct gaaggcgtga aggttcctca aggcatgaag    54300
aaacatcaaa ggttttcag  tagatgagat atgctgaaag ccatgcagag gaaacctgct    54360
gtgacctcag taggaaaaaa ctaaacaaac aagcaaatga aaactagagg taggggcctg    54420
tggaagctgt tccatttgtc caagtgagag gtgtctggag attatagtgg acagaagaat    54480
catcacgaga ggaacttcag ggcctgggaa ctgactgcag aggggggcag atagcaggc    54540 acggcacaaa tgactgcacg tgcagagcct cagcacagac acctcaccca gattccgaaa    54600
tcacgggcca ggctgaccct cttcttcctg atcatggtcg gtgttatccc cacctccatg    54660
aaggcatggc agctcagtcc aggcatttgg ccagaggcat gggctcgatt cttaggtcgc    54720
tgctgaggcc ctgagcctgg gactttctat ggcctcctat tgtggatttc aggcttctct    54780
ggccttagag ccctggggag aggctggcag gtaaataaag agaagagcag ctagcagaaa    54840
ccttttgtaa atgactctcc tggctgattg aaaatttgtg gtcatttgta gagcttgagg    54900
```

```
accctcagcc tcccccagac cacattcctt ggattacagc tgtacttcca acagttatta   54960
tatgtgtgat ggttttctgt ctaattctat ggaaatggaa gaagaagaag cggcctcgca   55020
actcttataa atgtggtgag tgagtccttg tcctccccac agactgtcac tttgcaccta   55080
cttcccaatc ggctggctgc cttccggagc ttgttggctg agcctagact ggcaaaaagt   55140
caggaagttg ttgggaaaaa aggttttccc ttggagtttt gagcctatac agactggcag   55200
tagcagataa tgctgctctt ggacttcaaa gaaaggcgac atttctaacc tctggtttac   55260
aaatgtactt ctggttttcca gggaaaactg attattactt gctttatcta cctcacttca   55320
tgaggttact gtgacatata cataaagtaa aatggtgaaa ccactcctaa atgttaaaga   55380
ttgtggacct ggtggtgttt aagcagggat atttgctaaa tgaccacaag aatcagcttc   55440
tcgtctctaa aaaaatctag gtttcttatg aaataagtta gatgaattat tgcccattga   55500
cttataacaa acaatattaa ctttaactaa tttctaagta atacatatcc attatcatat   55560
ataccaaaaa taaaataatc tataactcca ctaataagaa aaaatgatta cacaaatatt   55620
tttggtgcct atctttaaga ttttctgtg tatcaatcta tgttgttttc cataattagg   55680
attatcataa gggttatttt tcacaatttg gataatatat gtactgtgtt ctaattttgt   55740
tatactaaat gtagcaagac aattttcaat gtcataaata tcattctaca gcatcatttt   55800
taatggctgc aagatattcc cttttgtgga tacaccataa tttatttatt taaccaacct   55860
cattttttgg acacttgagt tagtccaata gttttgttat tataaacacc ctccccactg   55920
acttctgtta taaaaatgtt tcatggggac aaagtggtcc ctaactttat aataatgcca   55980 tgccttttg tagtttggtc tggttctaag ctaagattgg actttatctc agtaattgcc   56040
tccagtagta attagtttga ttggtgctaa taattaaggt aaccttctaa ctcacttatg   56100
gtagaaagca caagatgagt attgcctctg gccagcatct tgttttttcag tatactgatt   56160 ttaaaatcta actagaaaat agatggatga cattagcagt cattcaatgc atcctgctgt   56220
actttaaaaa taagaaattg gggagcaacg atcgaattta aataaattaa cacaaagcat   56280
gtggcagagc cattcaaact gccaatgtat ggagtgtgct gcgagatttc tatgatataa   56340
aagtataaaa ttcctagcac agatgtaaag acatatcatg cttgtccagg ctttgacttt   56400
tcaaggtgag agttttgagc ttcactttct ttcaacctca ttgccattta aaattagtca   56460
aatatgaaga agtgacttac atcttgggaa taagctgttt gctagatttt tcttcacatt   56520
agaatgatca gcttacaaat gaaacaaaga agggttggag aaaaagatta aggatgtttc   56580
ttcctccatg aggcaatcag aaaaaaatca ggagactaga tagggagat aaagaggata   56640 tgtgtgttca catgagagaa gttagaaggt ggttaaataa gctctgtagg tacagatgag   56700
atggtcagat tgggctgagt ggcacataca tgaccccta gaatgtaatg aagaatattg   56760
gtaagaaaaa gttatttatt cagacagtca tccatgccac tgagtttgat caaagagaga   56820
agccttgcta tcactgtagg gagggaggtg caacaggtat aactatgcca ttatagatat   56880
gatatatttg taaatttgga ttctgtaact tcagcaatat ctgccattgc tttgtgggta   56940
ctcctggcat tggctatgtg ataggtaaaa taatgccccc cacaagacgt ccacctccta   57000
tactccagaa cctgtaatat gttatcttac atggcaaaag gaacttcaca taggtgatta   57060
aggcaccaag cttgagatgg tgagattaac ctggattatc caggtgggcc caatgtaatc   57120
acatgagtca gagaaccttt cctagctggg atggagaaat gaactggaag aaggagagat   57180
ctgaaacttg agaagctcaa cccagcattt ctagctttga agatgaagg aggaagccat   57240 gagccaagga atgtaagtag cttctagaag ctggaagtgg ctctcagttg acagccagcc   57300
```

```
attaaggaaa ttaggatctc agttctgcaa ctataaggag ctgaattctg ccaagagacc   57360
aatgtggaaa cagcagatcc ctccacagag acacaagctt actgataact ggtaggaatt   57420
tctccaaaag tggagcttcc tcctactcca gtgttaatcc ctttctcaga ggagacggtc   57480
ctcaaactaa ctaacttggc accaaaagtc ctatccagtg ttttctcatt atagttttc    57540 tatgcctcaa ctgtatatat ttacccagtt taggctgttt aaatgaataa aaaggaaatg   57600
ccatagttat tctagccagt ttccaatctc tcttctcttt ttttgttttg tcaaataggg   57660
cagataaggc atgagaattt ataactatga attactgtct tttcccaaac agaaatcacc   57720
ctatcagctt acccattggg agaaaaacta aaatagctcc ccctgaaatt ttacttcctc   57780
atttgggtct tgtgtgactg aaatctgtat acaatgccct agcaacaacg gtttttacag   57840
cttgcctccc tagaacaaac ctaggagtct cagctgtttc aggaatgatt tcttaaaggt   57900
aaagtgcctt tttcaaaaga aattattatt attttttttt aattttttt ttgtgtgtgt    57960 gtgagacaga gcctcactct gtcaccaggc tggagtgcag tggcacgatc tcagcacact   58020
gcaacctctg cctcccaggt tcaagcgatt ctcctgcctc agcctcccaa gtagctggga   58080
ctacaggcac gtgccaccaa gcccaggtaa ttttgtatt ttcagtagag atgggttttc     58140
accatgttgg ccaggatggt ctcgatctct tgacctcgtg atccgttttt aaccaacatt   58200
taaacagaaa tattcacagg cttaaagact gaaagttagt gatatcatca catttcccct   58260
tcaaaatgct gaatttgtaa gcaaatttaa aagtttagaa tctaccttt aattgtctgc     58320 tttcattttt ttgacagtgg cttttttga tatggtgact attttgtcat gggtataaaa     58380
ggataattca ttttgtgtta atctgaagac atctgaaata ctgtattcaa ctataagtac   58440 cttttttac atttataaga ttcttttca aaattttat ttgaatagtt ttttgggaac       58500
tactgaacta aactaggtgg ttttttggtta catggataag ttatttagtg gtgatttctg   58560
agactttggt gccacctgtc actcgagcag tgtacactgc accagtgtgt agtcttttat   58620
ctctcacccc tcccactctt tcctctgagt ccccaaagtc cattatatta ttcttatgtc   58680
tttgcatcct catagtttag ctcccactta tcagtgaaaa catacaatat tgtttctcc    58740 attcttgagt tacttcactt agaataatgg tctctggttc catcaaagtt gctgcaaatg   58800
ccattatttt gttctttttt atggctgagt aatattccat gagggatatt taccacattt   58860
tccttatcca ctcatggggtt gatggacatt taggttggtt ccttattttt ggaattgcaa   58920
attgtgctgc tataaacatg cgtgtgcatg tgtcttttc atataatgaa ttatttttcct   58980 ttgggtatat acccagtagt aggattgctg aattaaatag tagagttcta cttttagttc   59040
tttaaggaat ctccatactg ttttccatag tgtttgtact agtttacatt cccaccagca   59100
gtgtaaacat gttccctttt caccacatcc atgccaacat ctattatttt tgatttttt    59160 aataatggcc attcttgcag gagtaaggtg gtatctcatg gtggttttaa tttgcatttc   59220
cctgatagtt agtgatattg aactttttt catgtttgtt ggccatttgt atatttctt     59280 ttcagaattg tctattcatg tccttataaa caccattatt tttaagaaga actttacaa    59340 aaatagaaca taaccagatt tataaagcat ctgggaactc agtcaattaa gaaatagctc   59400
aagtaactga tgatgcttca cctgaaagaa ggcctggaga gaacagagat actgtcttca   59460
aatatctgaa gagctaccat gggatgcaaa gattgagctt gatggtatga ctctgaaggg   59520
catctctatg aatgaaggtt atgagagggt ataaggaatt aagagagact tttctaacaa   59580
ttaaaaggtc ttttaggcca ggggtggtgg ctcacacctg taatcccagc acttttggag   59640
gctgaggcag gcagatcacc ttagatcagg agttcgagac ccgcctggcc aacatggtga   59700
```

```
aaccccattt ctactaaaca tacaaaaatt agctgggtgt ggtggcaggc acctgtaatc   59760
ccagctactt gggaggctga gagaggagaa tcgcttgaac ctgggaggca gaggttgcag   59820
tgagccaaga tcacaccact gcactccagc ctgggtgaca agatcaag attccgtctt    59880 aaaaaatata aataaataaa taaataaata aatagtcttt aaaattgtat agaagaagta   59940
gacttctgct tcctccaaca aaggattaac tgctatagga attgccctct ttccataaac   60000
aactagaaag cagacaaaat atatgaaaca actgttttca gagatcggat gacagacagc   60060
agaaaactgt agtccctgag tgaaggaaag aaaaaatgag ataagcccta tgattgctct   60120
agtttgctgc ctggagccag tgtccaggcc cctctgaagg caggggagcc ctgatactga   60180
actaggaaaa gacattgcaa gaaagaaaa ctacaaacat ctctcgtgaa atgcttaaca    60240
aaattagcaa ctaaaatcta gcaatatgtt aaaagtataa tacatcatga tcaagtgggg   60300
tttattcaag aaacacaggt aagctcaaca ttcaaaaatc aggcaataac ctttactaca   60360
taaataaact aaaaagaaaa aaacatatga tcatgtcaat ggatacagga aaaacttttg   60420
acaaaattaa tacccattca tagttttaaa tggaaagaaa agctctcata aaaataggaa   60480
tacaagatga cttcctcaac ctgacaaagg acatctacca aaaattcttc tgttagcata   60540
atatttcatg atagaagact gattgctttt accttaagat ggcgaatgtg gggaggatgt   60600
ctactctctc tacttttgtt ccacattgta ctggaggtca tagccagaga aacaagacta   60660 gaaaagaaa taaagacat acagattgga aaggaagtaa aactgtcttt tttcacagat    60720
aatgatcatg cttgtagaaa atcctgagga atctatcaaa aacctattaa aactgataag   60780
tgagtgtagc aaagacacag gatacaaagt caatacacaa aatcaattat ttctatatac   60840
taacaaaagc aattgtacat tgaaaaaaat taatagcatt tataatagca tcaaataata   60900
ttaaaaactt ggaaataaat ttaacaaaac aagtacaagg tctatatact gaaaactata   60960
caatattact actggagaaa ttaaagtaaa ccaaaataaa tggagacata ggccatgttt   61020
atgaatcaga agactagatg ttaagataac cattctctcc aagttgatct atggattaaa   61080
tgtaatcaca atcaaaatcc tggtaagctc tctaatagat actaaaaatc ttactcgaaa   61140
agttataggg aaatgcaaag aatctacaat tgccaaaaca attctgaaaa ataagaacaa   61200
aggttaaaaa tacaaaatta gccaggcatg gtggcgcatg cctgtaatcc cagctactct   61260
ggaggctgag gcaggagaat tgcttgaacc cgggaggcag aggttgctgt gagctgagat   61320
cgtgccattg cactccagcc tgggcaacaa gagtgaaact ccctctcaaa aaaaaaaaaa   61380 aaaaaaaaa aaagaacaa aggtggactt aacctaccta atttcaatat ttactatata     61440
tagtaattaa tacagtgtga tattggtaaa aggacagaca tatcagtcaa tggaacaaaa   61500
tagagagtca aaaatagatt cacactgttg acaaagctac caaggtaatt ccatgcagaa   61560
aggatagtat tttcaacaaa tagtgttggg acaattagat atccacatgg aaaaagtatg   61620
aacctagaca cacacaaagt aacttatata ttaagaatta aaatgaaagg acttccaaaa   61680 gaaacagag gagaaaatct ttgtaacctt aagttaggca agtcttctta gataggacac    61740
agaaagcaaa aaccatatca taaaaagata aaatggatgt catcaatatg gaaaactttt   61800
gttctttgac tttgttaaaa aaacgaaaag tcaaaccaca gacagggaga aaacgtttgc   61860
aaaatatata tctgataaag gacttgtatc cagtatataa ttacatattg ctactcatta   61920
gtaagaagac aatccattta ataaaggca agaagaagag acttgaacag atacataaca    61980
gaagaagata tacagatggc cgatgagcac agtcacaaca tcattagtca tcagggaagt   62040
acaaattaaa acgataatga gataccactg cacaccctct agaatggcta aaattaaaag   62100
```

```
gtctgataaa catcaagtgt tggagaggat atgaagcaac tgaaactctc atatactgct   62160
atacaaccca gaaatcctag acatttacca aacagaaatt ttaaaaaatt taaaaatata   62220
taaagactca tacacaaatg ttcatagcag cttgcttcat aataccaaac ctggcattct   62280
aaattttcat cagttggcgg tggtatattt atacaatgaa atactgcaaa gctatagaaa   62340
ggaatggact actaataata cacaagaaca tagataaatt tcaaaagcat tatgctaagt   62400
gaaacaatcc aggcacaaga agaatacaca ttatacaatt tcatgtatat gaaatttgag   62460
aaaaagcaaa actattttaa gtagattcat ggttatccat gggatggggg aaaggaatca   62520
gctgaaaagc gaactatttt ggcttataaa aatgttctcg atcttgattg tggtggtggt   62580
tacgtgacta tatatattcg ttaaaatcac caaactctaa actgaaaatg attgggtttt   62640
attatttatt aattatacct ccataaagct gattgttttt atcttttatt tttattttat   62700
ttcaatagtt tttggggaac agatggtttt cggttacatg gatgagttct ttagtggtga   62760
tttctgagat tttgatgcac ctgtcacccg agcaatgtcc actgtaccca atgtgtagtc   62820
ttttatcctt catccacctc tctctcactc ttcccccaa gtacccaagt ccattatatc   62880
attcttatga ctttgtggcc tcataaaagc tgattgtttt taaatacaca catcacaca   62940 taaaagagaa cttccagtga caggaagtgt tcaagaatgc tctatttagt aaagacagaa   63000
tcacaaaacc atcagaggta ttgttgagtg gattcttgtg gtctataaat acctccatgg   63060
acacccaggt tagcaacctg ttggagttta cgtgggacaa tagcatcatc acaacagtca   63120
gcctagagaa atttacatcc caagttgtgt cagtagcaag tccctatcaa tagcaactca   63180
ggctttgtga ggtctagctg gctagaaatt tcccacttgg ccttgcccat gcaacattgt   63240
gtaatattct tagcaccatc tggctagccg atttaggcat caacatcttc aagacttctt   63300
ctcctcctcc ttataaacct tgctttcaga aaaggattag aaactcttcc aatcacaaaa   63360
tgattgctaa aactaaatat attacccctc ccaatggtat tttttggtta gccaggatag   63420
agatataagt gaaaaatcta tttccagtgt tagaatttaa ggcacagtga gaaagggaag   63480
gcatatactt tttgaatgca agaaacttct tcccaatccc cctgaaattg catcatttga   63540
gtaactatct cttccatata taaagtcaca acaatttctc tctcagtccc agaactttga   63600
agccttttca aactttcctt cttttggtat ctaggaggaa tacattttg aagattgttc   63660 ttggtgtctt tcaggaacca acacaatgga gagggaagag agtgaacaga ccaagaaaag   63720
gtaaatcctg accctgagac attgatgaga gagaggtata atccccagag tgcctgttac   63780
ttgaataggc ttatgcctaa catatgttga gacctcagca aacctgaact aatggagagg   63840
gagaggaaaa taaaactagt taagaactgg aagaaaataa cctgataatg gatgacaggg   63900
tatccaatgc acaatgccca gaaagcatga caagctctgt catggtcaag taaaagtcaa   63960
taccaaagac ttcagaggtg gtgaacatgg gcttcatctt atctgccaca gtaaccccag   64020
tacctggcac agtgcctaga ttagtgggca tcctacatgt gtggaatgaa taaatgaaga   64080
agtggggaat gataacatgt ttgcttcagc ctgagcatct tagtatttgc tatggccctg   64140
tttagatgtt cttctgccac ttctttacct cattcttcag atcttgcctc aagcagcact   64200
ttcttaaaaa ccctttccca aactagaaaa tgtcaacttg ttacagtgtc atgtggatcc   64260
cttggctttt tcttaataac accagattat gcttacatat ttgtgtaatt atcttattaa   64320
actctataaa ctagacttaa ctaaatccta tgaagagcag agaccatacc agttaagctc   64380
atcattgtgc tgctagcact tagcatggtg cctggcatat agcaggttct caataaatgt   64440
tgaaagaatg attgatgcat gatgaataca taaaagttcg tggtgatcag tcctttcaca   64500
```

```
acgtgaagct atcagatagt ctgtacctct atccctcctg agaaattaag ctctcaggaa    64560
tatcaaggct ctgactgcat acccatagga tcaaagcaac cctcagtcac aagcctggtt    64620
tcagagatag ggtcataacc cccagggtgc agagacaacc gagagtaccc agcactaatc    64680
cagatatacc agccactgtg attctagcaa caaaactaat aattccgggc acccttggac    64740
aatgagaaag ggtgctgaaa tcctgcctac cctgtcacac tcagtttcag aaatggtctg    64800
gaagagcctg cagagggcag gcagcagaga accggcagag ggcatgggaa gggccaggca    64860
gaaataaagg gtagctcttg aagcatagat gacagtgtag accgtggttc ttttctcttg    64920
ctttctccac ctttctcttc aatagtttgt ttctcctcat tgctgttcca atggcaacct    64980
ctattctgcc ctatcattga aatctagaaa aagaaagtag ctcaaatgtg aaatatcacc    65040 taatctttc ttctatttct ccagagaaaa aatccatata cctgaaagat ctgatgaagc    65100
ccagcgtgtt tttaaaagtt cgaagacatc ttcatgcgac aaaagtgata catgttttta    65160
attaaagagt aaagcccata caagtattca ttttttctac cctttccttt gtaagttcct    65220
gggcaacctt tttgatttct tccagaaggc aaaaagacat taccatgagt aataagggg    65280 ctccaggact ccctctaagt ggaatagcct ccctgtaact ccagctctgc tccgtatgcc    65340
aagaggagac tttaattctc ttactgcttc ttttcacttc agagcacact tatgggccaa    65400
gcccagctta atggctcatg acctggaaat aaaatttagg accaatacct cctccagatc    65460
agattcttct cttaatttca tagattgtgt ttttttttta aatagacctc tcaatttctg    65520
gaaaactgcc ttttatctgc ccagaattct aagctggtgc cccactgaat tttgtgtgta    65580
cctgtgacta acaactacc tcctcagtct gggtgggact tatgtattta tgaccttata    65640
gtgttaatat cttgaaacat agagatctat gtactgtaat agtgtgatta ctatgctcta    65700
gagaaaagtc taccctgct aaggagttct catccctctg tcagggtcag taaggaaaac    65760
ggtggcctag ggtacaggca acaatgagca gaccaaccta aatttgggga aattaggaga    65820
ggcagagata gaacctggag ccacttctat ctgggctgtt gctaatattg aggaggcttg    65880
ccccacccaa caagccatag tggagagaac tgaataaaca ggaaaatgcc agagcttgtg    65940
aaccctgttt ctcttgaaga actgactagt gagatggcct ggggaagctg tgaaagaacc    66000
aaaagagatc acaatactca aaagagagag agagagaaaa aagagagatc ttgatccaca    66060
gaaatacatg aaatgtctgg tctgtccacc ccatcaacaa gtcttgaaac aagcaacaga    66120
tggatagtct gtccaaatgg acataagaca gacagcagtt tccctggtgg tcagggaggg    66180
gttttggtga tacccaagtt attgggatgt catcttcctg gaagcagagc tggggaggga    66240
gagccatcac cttgataatg ggatgaatgg aaggaggctt aggactttcc actcctggct    66300
gagagaggaa gagctgcaac ggaattagga agaccaagac acagatcacc cggggcttac    66360
ttagcctaca gatgtcctac gggaacgtgg gctggcccag catagggcta gcaaatttga    66420
gttggatgat tgttttgct caaggcaacc agaggaaact tgcatacaga gacagatata    66480 ctggagaaa tgactttgaa aacctggctc taaggtggga tcactaaggg atggggcagt    66540
ctctgcccaa acataaagag aactctgggg agcctgagcc acaaaaatgt tcctttattt    66600
tatgtaaacc ctcaagggtt atagactgcc atgctagaca agcttgtcca tgtaatattc    66660
ccatgttttt accctgcccc tgccttgatt agactcctag cacctggcta gtttctaaca    66720
tgttttgtgc agcacagttt ttaataaatg cttgttacat tcatttaaaa gtctacattt    66780
tctgctttgg cttcaagagt actactcaac ccttgtggtc tgatgttccc tgctctgtcc    66840
tctgaatgta cttcctttct ctttacatct ctatggctag aagcctctca cgcatcctgt    66900
```

-continued

```
atcttctcct cctcccttt ccctaccatt atttgagaaa ggaggcttgt atacttctat    66960
atgtttatct cagtaataag tcataaaaaa tcaagtaaga atggttgttt ttgaggacaa    67020
ctaagaaatc tggaataagg aagggaagct tacttttgag tttgtaacct gtagtgtgta    67080
attttttaat tatgtactta catgtacatt aaacaaaagc ttaatgtaaa aatattcctt    67140
gaaaacacca tgattataaa ataaatgcat atatacacat acagcatgtg agaggagcca    67200
ggaaaactct ggaaaaaaga aaattaccta gactctgtga gggcaggaat gtgtttaatt    67260
tctctccaat ggatcctcag acaactaaga tagttgtcta ttctattgtc catcttttg    67320
tcttttgttg tatttcttaa agattccctc aactttatct tctaacttct gttgtatttt    67380
tatttctgct atcatgtatt cttttcagaa ttctttttg ttctctcaaa acatatctgt    67440
ttaaagattg aatgaaatat taacatgccc tttggtgaga acatccctcc tttgtatatt    67500
aaattctctg aactgctgta ttctaagact aggggaaaga aaagaaggt tgaaagaggt    67560
cattaggcag aatagtacta gctaacatta tttcacattt accatatacc cgtcactcat    67620
ctaaacctt aaactcatta tcctatttaa tcctcacaat gaccctgtga cgtaggtaat    67680
ggaatattat gcccattatg ctgatgagaa aatataaaca cagagataag tcagagtaat    67740
ttacccaaca ttgttaactt tgtaagtggc agagctttgt aacaggcaga ggttggaaca    67800
gtttggaggg ctcagaagaa gacaggaaga tgtaggaaag tttggaactt cccagagcct    67860
tgttgaatgg ctttgaccaa aatgctgata gtaatatgga caatgaaata caggctgagg    67920
tggtctcaga tagagaagag gaacttgttg ggaactggaa taaaggtgac tcttgctatg    67980
ttttagcaaa gacactggtg g                                              68001
```

<210> SEQ ID NO 298  
<211> LENGTH: 20  
<212> TYPE: DNA  
<213> ORGANISM: Artificial Sequence  
<220> FEATURE:  
<223> OTHER INFORMATION: Antisense Oligonucleotide
<400> SEQUENCE: 298
accaaaagga gtatttgcga                                              20

<210> SEQ ID NO 299  
<211> LENGTH: 20  
<212> TYPE: DNA  
<213> ORGANISM: Artificial Sequence  
<220> FEATURE:  
<223> OTHER INFORMATION: Antisense Oligonucleotide
<400> SEQUENCE: 299
cattcccaag gaacacagaa                                              20

<210> SEQ ID NO 300  
<211> LENGTH: 20  
<212> TYPE: DNA  
<213> ORGANISM: Artificial Sequence  
<220> FEATURE:  
<223> OTHER INFORMATION: Antisense Oligonucleotide
<400> SEQUENCE: 300
actgtagctc caaaaagaga                                              20

<210> SEQ ID NO 301  
<211> LENGTH: 20  
<212> TYPE: DNA  
<213> ORGANISM: Artificial Sequence

```
<220> FEATURE:
<223> OTHER INFORMATION: Antisense Oligonucleotide

<400> SEQUENCE: 301
ctgtcacaaa tgcctgtcca                                               20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302
tcagtcccat agtgctgtca                                               20

<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303
ctgttacagc agcagagaag                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 304
tccctgttac agcagcagag                                               20

<210> SEQ ID NO 305
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 305
atctggaaat gaccccactc                                               20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306
gtgacctaat atctggaaat                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307
cattttggct gcttctgctg                                               20
```

```
<210> SEQ ID NO 308
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 308
ggaacttaca aaggaaaggg                                               20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309
aaaaaggttg cccaggaact                                               20

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310
tgccttctgg aagaaatcaa                                               20

<210> SEQ ID NO 311
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 311
tttttgcctt ctggaagaaa                                               20

<210> SEQ ID NO 312
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 312
ctattccact tagagggagt                                               20

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313
tctgatctgg aggaggtatt                                               20

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314
```
agaaattgag aggtctattt                                        20

<210> SEQ ID NO 315
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 315
caccagctta gaattctggg                                        20

<210> SEQ ID NO 316
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 316
aggtagttgt ttagtcacag                                        20

<210> SEQ ID NO 317
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 317
ccagactgag gaggtagttg                                        20

<210> SEQ ID NO 318
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 318
cagtacatag atctctatgt                                        20

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319
ttacagtaca tagatctcta                                        20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320
gatgagaact ccttagcagg                                        20

<210> SEQ ID NO 321
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 321
tagcaacagc ccagatagaa                                               20

<210> SEQ ID NO 322
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 322
tctgttgctt gtttcaagac                                               20

<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323
tccatttgga cagactatcc                                               20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 324
gggaaactgc tgtctgtctt                                               20

<210> SEQ ID NO 325
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325
tgcttccagg aagatgacat                                               20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326
attcatccca ttatcaaggt                                               20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327
agccaggagt ggaaagtcct                                               20
```

```
<210> SEQ ID NO 328
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 328
cttcctaatt ccgttgcagc                                                 20

<210> SEQ ID NO 329
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 329
catctgtagg ctaagtaagc                                                 20

<210> SEQ ID NO 330
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 330
cccgtaggac atctgtaggc                                                 20

<210> SEQ ID NO 331
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 331
gccctatgct gggccagccc                                                 20

<210> SEQ ID NO 332
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 332
gtctctgtat gcaagtttcc                                                 20

<210> SEQ ID NO 333
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 333
ccagtatatc tgtctctgta                                                 20

<210> SEQ ID NO 334
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 334
```
ccaggttttc aaagtcattt                    20

<210> SEQ ID NO 335
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 335
agccaggttt tcaaagtcat                    20

<210> SEQ ID NO 336
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 336
cccttagtga tcccacctta                    20

<210> SEQ ID NO 337
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 337
ctgccccatc ccttagtgat                    20

<210> SEQ ID NO 338
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 338
tttatgtttg ggcagagact                    20

<210> SEQ ID NO 339
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 339
catggcagtc tataaccctt                    20

<210> SEQ ID NO 340
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 340
tagcatggca gtctataacc                    20

<210> SEQ ID NO 341
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 341
tctagcatgg cagtctataa                                           20

<210> SEQ ID NO 342
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 342
ttgtctagca tggcagtcta                                           20

<210> SEQ ID NO 343
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 343
aagcttgtct agcatggcag                                           20

<210> SEQ ID NO 344
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 344
acatggacaa gcttgtctag                                           20

<210> SEQ ID NO 345
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 345
ttacatggac aagcttgtct                                           20

<210> SEQ ID NO 346
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 346
gaatattaca tggacaagct                                           20

<210> SEQ ID NO 347
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 347
aactagccag gtgctaggag                                           20
```

```
<210> SEQ ID NO 348
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 348
aattattact caccactggg                                              20

<210> SEQ ID NO 349
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 349
taatatttag ggaagcatga                                              20

<210> SEQ ID NO 350
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 350
ggaccctggg ccagttattg                                              20

<210> SEQ ID NO 351
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 351
caaacatacc tgtcacaaat                                              20

<210> SEQ ID NO 352
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 352
gtgatatcaa ttgatggcat                                              20

<210> SEQ ID NO 353
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 353
tgctacatct actcagtgtc                                              20

<210> SEQ ID NO 354
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 354
```
tggaaactct tgccttcgga                                          20

<210> SEQ ID NO 355
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 355
ccatccacat tgtagcatgt                                          20

<210> SEQ ID NO 356
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 356
tcaggatggt atggccatac                                          20

<210> SEQ ID NO 357
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 357
tcccatagtg ctagagtcga                                          20

<210> SEQ ID NO 358
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 358
aggttcttac cagagagcag                                          20

<210> SEQ ID NO 359
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 359
cagaggagca gcacctaaaa                                          20

<210> SEQ ID NO 360
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 360
gaccacatac caagcactga                                          20

<210> SEQ ID NO 361
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 361
atctttcaga aacccaagca                                               20

<210> SEQ ID NO 362
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 362
gagtcaccaa agatttacaa                                               20

<210> SEQ ID NO 363
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 363
ctgaagttag ctgaaagcag                                               20

<210> SEQ ID NO 364
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 364
acagctttac ctatagagaa                                               20

<210> SEQ ID NO 365
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 365
tcctcaagct ctacaaatga                                               20

<210> SEQ ID NO 366
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 366
gactcactca ccacatttat                                               20

<210> SEQ ID NO 367
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 367
agtgatagca aggcttctct                                               20
```

```
<210> SEQ ID NO 368
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 368
cttggagaga atggttatct                                          20

<210> SEQ ID NO 369
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 369
gaagatgttg atgcctaaat                                          20

<210> SEQ ID NO 370
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 370
gtgttggttc ctgaaagaca                                          20

<210> SEQ ID NO 371
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 371
caggatttac cttttcttgg                                          20

<210> SEQ ID NO 372
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 372
agggcagaat agaggttgcc                                          20

<210> SEQ ID NO 373
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 373 ttttctctg gagaaataga                                           20

<210> SEQ ID NO 374
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 374
```
gttactcagt cccatagtgc                                              20

<210> SEQ ID NO 375
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 375
caaagagaat gttactcagt                                              20

<210> SEQ ID NO 376
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 376
ccatcacaaa gagaatgtta                                              20

<210> SEQ ID NO 377
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 377
ggaaggccat cacaaagaga                                              20

<210> SEQ ID NO 378
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 378
gagcaggaag gccatcacaa                                              20

<210> SEQ ID NO 379
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 379
ccagagagca ggaaggccat                                              20

<210> SEQ ID NO 380
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 380
aaataagctt gaatcttcag                                              20

<210> SEQ ID NO 381
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 381
agtctcattg aaataagctt                                               20

<210> SEQ ID NO 382
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 382
aggtctgcag tctcattgaa                                               20

<210> SEQ ID NO 383
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 383
ctactagctc actcaggctt                                               20

<210> SEQ ID NO 384
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 384
aaatactact agctcactca                                               20

<210> SEQ ID NO 385
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 385
ctgccaaaat actactagct                                               20

<210> SEQ ID NO 386
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 386
ttcagaacca agttttcctg                                               20

<210> SEQ ID NO 387
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 387
cctcattcag aaccaagttt                                               20
```

```
<210> SEQ ID NO 388
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 388
gtatacctca ttcagaacca                                              20

<210> SEQ ID NO 389
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 389
gcctaagtat acctcattca                                              20

<210> SEQ ID NO 390
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 390
ctctttgcct aagtatacct                                              20

<210> SEQ ID NO 391
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 391
cccatatact tggaatgaac                                              20

<210> SEQ ID NO 392
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 392
cttgtgcggc ccatatactt                                              20

<210> SEQ ID NO 393
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 393
atcaaaactt gtgcggccca                                              20

<210> SEQ ID NO 394
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 394
```

```
cccttgtcct tgatctgaag                                              20

<210> SEQ ID NO 395
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 395
acaagccctt gtccttgatc                                              20

<210> SEQ ID NO 396
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 396
ttgatacaag cccttgtcct                                              20

<210> SEQ ID NO 397
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 397
atacattgat acaagccctt                                              20

<210> SEQ ID NO 398
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 398
tggatgatac attgatacaa                                              20

<210> SEQ ID NO 399
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 399
gaattcatct ggtggatgcg                                              20

<210> SEQ ID NO 400
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 400
gttcagaatt catctggtgg                                              20

<210> SEQ ID NO 401
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 401
tgacagttca gaattcatct                                          20

<210> SEQ ID NO 402
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 402
agcactgaca gttcagaatt                                          20

<210> SEQ ID NO 403
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 403
tagcaagcac tgacagttca                                          20

<210> SEQ ID NO 404
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 404
tgaagttagc aagcactgac                                          20

<210> SEQ ID NO 405
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 405
ttgactgaag ttagcaagca                                          20

<210> SEQ ID NO 406
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 406
ctatttcagg ttgactgaag                                          20

<210> SEQ ID NO 407
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 407
tctgttatat tagaaattgg                                          20
```

```
<210> SEQ ID NO 408
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 408
gcaggtcaaa tttatgtaca                                               20

<210> SEQ ID NO 409
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 409
gtatagatga gcaggtcaaa                                               20

<210> SEQ ID NO 410
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 410
gggtaaccgt gtatagatga                                               20

<210> SEQ ID NO 411
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 411
aggttctggg taaccgtgta                                               20

<210> SEQ ID NO 412
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 412
tagcaaaaca ctcatcttct                                               20

<210> SEQ ID NO 413
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 413
gttcttagca aaacactcat                                               20

<210> SEQ ID NO 414
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 414
```
attcttggtt cttagcaaaa                                               20

<210> SEQ ID NO 415
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 415
gatagttgaa ttcttggttc                                               20

<210> SEQ ID NO 416
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 416
accatcatac tcgatagttg                                               20

<210> SEQ ID NO 417
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 417
atcttgagat ttctgcataa                                               20

<210> SEQ ID NO 418
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 418
acattatctt gagatttctg                                               20

<210> SEQ ID NO 419
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 419
cgtacagttc tgtgacatta                                               20

<210> SEQ ID NO 420
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 420
agacaagctg atggaaacgt                                               20

<210> SEQ ID NO 421
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 421
gaaacagaca agctgatgga                                               20

<210> SEQ ID NO 422
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 422
ggaatgaaac agacaagctg                                               20

<210> SEQ ID NO 423
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 423
catcagggaa tgaaacagac                                               20

<210> SEQ ID NO 424
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 424
cgtaacatca gggaatgaaa                                               20

<210> SEQ ID NO 425
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 425
agctctatag agaaaggtga                                               20

<210> SEQ ID NO 426
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 426
cctcaagctc tatagagaaa                                               20

<210> SEQ ID NO 427
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 427
ggaggctgag ggtcctcaag                                               20
```

```
<210> SEQ ID NO 428
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 428
agtacagctg taatccaagg                                               20

<210> SEQ ID NO 429
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 429
ttggaagtac agctgtaatc                                               20

<210> SEQ ID NO 430
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 430
ataataactg ttggaagtac                                               20

<210> SEQ ID NO 431
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 431
catcacacat ataataactg                                               20

<210> SEQ ID NO 432
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 432
tccatttcca tagaattaga                                               20

<210> SEQ ID NO 433
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 433
tcttcttcca tttccataga                                               20

<210> SEQ ID NO 434
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 434
```
atttataaga gttgcgaggc                                          20

<210> SEQ ID NO 435
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 435
ttggttccac atttataaga                                          20

<210> SEQ ID NO 436
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 436
ctctccattg tgttggttcc                                          20

<210> SEQ ID NO 437
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 437
cttccctctc cattgtgttg                                          20

<210> SEQ ID NO 438
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 438
tggtctgttc actctcttcc                                          20

<210> SEQ ID NO 439
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 439
ttcatcagat ctttcaggta                                          20

<210> SEQ ID NO 440
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 440
atcacttttg tcgcatgaag                                          20

<210> SEQ ID NO 441
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 441
gctttactct ttaattaaaa                                               20

<210> SEQ ID NO 442
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 442
gtatgggctt tactctttaa                                               20

<210> SEQ ID NO 443
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 443
atacttgtat gggctttact                                               20

<210> SEQ ID NO 444
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 444
aatgaatact tgtatgggct                                               20

<210> SEQ ID NO 445
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 445
cgagaggcgg acgggaccg                                                19

<210> SEQ ID NO 446
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1-19
<223> OTHER INFORMATION: bases at these positions are RNA

<400> SEQUENCE: 446
cgagaggcgg acgggaccgt t                                             21

<210> SEQ ID NO 447
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
```

```
<222> LOCATION: 1, 2, 3, 5, 6, 7, 8, 10
      11, 12, 13, 14, 16, 18, 19
<223> OTHER INFORMATION: bases at these position are RNA

<400> SEQUENCE: 447
cggtcccgtc cgcctctcgt t                                              21
```

US 7,897,582 B2

OLIGONUCLEOTIDE COMPOSITIONS AND METHODS FOR THE MODULATION OF THE EXPRESSION OF B7 PROTEIN

RELATED APPLICATIONS

This application is a Continuation of U.S. application Ser. No. 10/641,962, filed Aug. 15, 2003, now allowed, which is a application claiming the benefit under 35 USC 119(e) of U.S. Provisional Patent Application Ser. No. 60/651,504, filed May 23, 2003, now expired; each of which is herein incorporated by reference in its entirety.

SEQUENCE LISTING

The present application is being filed along with a Sequence Listing in electronic format. The Sequence Listing is provided as a file entitled BIOL0020US.C1, created on May 14, 2007 which is 180 Kb in size. The information in the electronic format of the sequence listing is incorporated herein by reference in its entirety.

FIELD OF THE INVENTION

This invention relates to diagnostics, research reagents and therapeutics for disease states which respond to modulation of T cell activation. In particular, this invention relates to antisense oligonucleotide interactions with certain messenger ribonucleic acids (mRNAs) or DNAs involved in the synthesis of proteins that modulate T cell activation. Antisense oligonucleotides designed to hybridize to nucleic acids encoding B7 proteins are provided. These oligonucleotides have been found to lead to the modulation of the activity of the RNA or DNA, and thus to the modulation of T cell activation. Palliative, therapeutic and prophylactic effects result.

BACKGROUND OF THE INVENTION

Inflammation is a localized protective response mounted by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. In general, the first inflammatory cells to appear at the site of inflammation are neutrophils, followed by monocytes and lymphocytes. Cell-cell interactions are also critical for activation of both B-lymphocytes (B cells) and T-lymphocytes (T cells) with resulting enhanced humoral and cellular immune responses, respectively.

The hallmark of the immune system is its ability to distinguish between self (host) and nonself (foreign invaders). This remarkable specificity exhibited by the immune system is mediated primarily by T cells. T cells participate in the host's defense against infection but also mediate organ damage of transplanted tissues and contribute to cell attack in graft-versus-host disease (GVHD) and some autoimmune diseases. In order to induce an antigen-specific immune response, a T cell must receive signals delivered by an antigen-presenting cell (APC). T cell-APC interactions can be divided into three stages: cellular adhesion, T cell receptor (TCR) recognition, and costimulation. At least two discrete signals are required from an APC for induction of T cell activation. The first signal is antigen-specific and is provided when the TCR interacts with an antigen in the context of a major histocompatibility complex (MHC) protein, or an MHC-related CD1 protein, expressed on the surface of an APC ("CD," standing for "cluster of differentiation," is a term used to denote different T cell surface molecules). The second (costimulatory) signal involves the interaction of the T cell surface antigen, CD28, with its ligand on the APC, which is a member of the B7 family of proteins.

CD28, a disulfide-linked homodimer of a 44 kilodalton polypeptide and a member of the immunoglobulin superfamily, is one of the major costimulatory signal receptors on the surface of a resting T cell for T cell activation and cytokine production (Allison, *Curr. Opin. Immunol.*, 1994, 6, 414; Linsley and Ledbetter, *Annu. Rev. Immunol.*, 1993, 11, 191; June et al., *Immunol. Today*, 1994, 15, 321). Signal transduction through CD28 acts synergistically with TCR signal transduction to augment both interleukin-2 (IL-2) production and proliferation of naive T cells. B7-1 (also known as CD80) was the first ligand identified for CD28 (Liu and Linsley, *Curr. Opin. Immunol.*, 1992, 4, 265). B7-1 is normally expressed at low levels on APCs, however, it is upregulated following activation by cytokines or ligation of cell surface molecules such as CD40 (Lenschow et al., *Proc. Natl. Acad. Sci. U.S.A.*, 1993, 90, 11054; Nabavi et al., *Nature*, 1992, 360, 266). Initial studies suggested that B7-1 was the CD28 ligand that mediated costimulation (Reiser et al., *Proc. Natl. Acad. Sci. U.S.A.*, 1992, 89, 271; Wu et al., *J. Exp. Med.*, 1993, 178, 1789; Harlan et al., *Proc. Natl. Acad. Sci. U.S.A.*, 1994, 91, 3137). However, the subsequent demonstration that anti-B7-1 monoclonal antibodies (mAbs) had minimal effects on primary mixed lymphocyte reactions and that B7-1-deficient mice responded normally to antigens (Lenschow et al., *Proc. Natl. Acad. Sci. U.S.A.*, 1993, 90, 11054; Freeman et al., *Science*, 1993, 262, 909) resulted in the discovery of a second ligand for the CD28 receptor, B7-2 (also known as CD86). In contrast with anti-B7-1 mAbs, anti-B7-2 mAbs are potent inhibitors of T cell proliferation and cytokine production (Wu et al., *J. Exp. Med.*, 1993, 178, 1789; Chen et al., *J. Immunol.*, 1994, 152, 2105; Lenschow et al., *Proc. Natl. Acad. Sci. U.S.A.*, 1993, 90, 11054). B7:CD28 signaling may be a necessary component of other T cell costimulatory pathways, such as CD40:CD40L (CD40 ligand) signaling (Yang et al., *Science*, 1996, 273, 1862).

In addition to binding CD28, B7-1 and B7-2 bind the cytolytic T-lymphocyte associated protein CTLA4. CTLA4 is a protein that is structurally related to CD28 but is expressed on T cells only after activation (Linsley et al., *J. Exp. Med.*, 1991, 174, 561). A soluble recombinant form of CTLA4, CTLA4-Ig, has been determined to be a more efficient inhibitor of the B7:CD28 interaction than monoclonal antibodies directed against CD28 or a B7 protein. In vivo treatment with CTLA4-Ig results in the inhibition of antibody formation to sheep red blood cells or soluble antigen (Linsley et al., *Science*, 1992, 257, 792), prolongation of cardiac allograft and pancreatic islet xenograft survival (Lin et al., *J. Exp. Med.*, 1993, 178, 1801; Lenschow et al., 1992, *Science*, 257, 789; Lenschow et al., *Curr. Opin. Immunol.*, 1991, 9, 243), and significant suppression of immune responses in GVHD (Hakim et al., *J. Immun.*, 1995, 155, 1760). It has been proposed that CD28 and CTLA4, although both acting through common B7 receptors, serve opposing costimulatory and inhibitory functions, respectively (Allison et al., *Science*, 1995, 270, 932). CTLA4-Ig, which binds both B7-1 and B7-2 molecules on antigen-presenting cells, has been shown to block T-cell costimulation in patients with stable psoriasis vulgaris, and to cause a 50% or greater sustained improvement in clinical disease activity in 46% of the patients to which it was administered. This result was dose-dependent. Abrams et al., *J. Clin. Invest.*, 1999, 9, 1243-1225.

European Patent Application No. EP 0 600 591 discloses a method of inhibiting tumor cell growth in which tumor cells from a patient are recombinantly engineered ex vivo to express a B7-1 protein and then reintroduced into a patient. As a result, an immunologic response is stimulated against both B7-transfected and nontransfected tumor cells.

International Publication No. WO95/03408 discloses nucleic acids encoding novel CTLA4/CD28 ligands which costimulate T cell activation, including B7-2 proteins. Also disclosed are antibodies to B7-2 proteins and methods of producing B7-2 proteins.

International Publication No. WO95/05464 discloses a polypeptide, other than B7-1, that binds to CTLA4, CD28 or CTLA4-Ig. Also disclosed are methods for obtaining a nucleic acid encoding such a polypeptide.

International Publication No. WO 95/06738 discloses nucleic acids encoding B7-2 (also known as B70) proteins. Also disclosed are antibodies to B7-2 proteins and methods of producing B7-2 proteins.

European Patent Application No. EP 0 643 077 discloses a monoclonal antibody which specifically binds a B7-2 (also known as B70) protein. Also disclosed are methods of producing monoclonal antibodies which specifically bind a B7-2 protein.

U.S. Pat. No. 5,434,131 discloses the CTLA4 protein as a ligand for B7 proteins. Also disclosed are methods of producing CTLA4 fusion proteins (e.g., CTLA4-Ig) and methods of regulating immune responses using antibodies to B7 proteins or CTLA4 proteins.

International Publication No. WO95/22619 discloses antibodies specific to B7-1 proteins which do not bind to B7-2 proteins. Also disclosed are methods of regulating immune responses using antibodies to B7-1 proteins.

International Publication No. WO95/34320 discloses methods for inhibiting T cell responses using a first agent which inhibits a costimulatory agent, such as a CTLA4-Ig fusion protein, and a second agent which inhibits cellular adhesion, such as an anti-LFA-1 antibody. Such methods are indicated to be particularly useful for inhibiting the rejection of transplanted tissues or organs.

International Publication No. WO95/32734 discloses Fc RII bridging agents which either prevent the upregulation of B7 molecules or impair the expression of ICAM-3 on antigen presenting cells. Such FcRII bridging agents include proteins such as aggregated human IgG molecules or aggregated Fc fragments of human IgG molecules.

International Publication No. WO96/11279 discloses recombinant viruses comprising genetic sequences encoding (1) one or more immunostimulatory agents, including B7-1 and B7-2, and (2) antigens from a disease causing agent. Also disclosed are methods of treating diseases using such recombinant viruses.

To date, there are no known therapeutic agents which effectively regulate and prevent the expression of B7 proteins such as B7-1 and B7-2. Thus, there is a long-felt need for compounds and methods which effectively modulate critical costimulatory molecules such as the B7 proteins.

SUMMARY OF THE INVENTION

In accordance with the present invention, oligonucleotides are provided which specifically hybridize with nucleic acids encoding B7-1 or B7-2. Certain oligonucleotides of the invention are designed to bind either directly to mRNA transcribed from, or to a selected DNA portion of, the B7-1 or B7-2 gene, thereby modulating the amount of protein translated from a B7-1 or B7-2 mRNA or the amount of mRNA transcribed from a B7-1 or B 7-2 gene, respectively.

Oligonucleotides may comprise nucleotide sequences sufficient in identity and number to effect specific hybridization with a particular nucleic acid. Such oligonucleotides are commonly described as "antisense." Antisense oligonucleotides are commonly used as research reagents, diagnostic aids, and therapeutic agents.

It has been discovered that the B7-1 and B7-2 genes, encoding B7-1 and B7-2 proteins, respectively, are particularly amenable to this approach. As a consequence of the association between B7 expression and T cell activation and proliferation, inhibition of the expression of B7-1 or B7-2 leads to inhibition of the synthesis of B7-1 or B7-2, respectively, and thereby inhibition of T cell activation and proliferation. Additionally, the oligonucleotides of the invention may be used to inhibit the expression of one of several alternatively spliced mRNAs of a B7 transcript, resulting in the enhanced expression of other alternatively spliced B7 mRNAs. Such modulation is desirable for treating various inflammatory or autoimmune disorders or diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, rhinitis, various allergies, and cancers and their metastases. Such modulation is further desirable for preventing or modulating the development of such diseases or disorders in an animal suspected of being, or known to be, prone to such diseases or disorders.

In one embodiment, the invention provides methods of inhibiting the expression of a nucleic acid molecule encoding B7-1 or B7-2 in an individual, comprising the step of administering to said individual a compound of the invention targeted to a nucleic acid molecule encoding B7-1 or B7-2, wherein said compound specifically hybridizes with and inhibits the expression of a nucleic acid molecule encoding B7-1 or B7-2.

The invention further provides methods of inhibiting expression of a nucleic acid molecule encoding B7-1 or B7-2 in an individual, comprising the step of administering to an individual a compound of the invention which specifically hybridizes with at least an 8-nucleobase portion of an active site on a nucleic acid molecule encoding B7-1 or B7-2. Regions in the nucleic acid which when hybridized to a compound of the invention effect significantly lower B7-1 or B7-2 expression compared to a control, are referred to as active sites.

The invention also provides methods of inhibiting expression of a nucleic acid molecule encoding B7-1 or B7-2 in an individual, comprising the step of administering a compound of the invention targeted to a nucleic acid molecule encoding B7-1 or B7-2, wherein the compound specifically hybridizes with the nucleic acid and inhibits expression of B7-1 or B7-2.

In another aspect the invention provides methods of inhibiting expression of a nucleic acid molecule encoding B7-1 or B7-2 in an individual, comprising the step of administering a compound of the invention targeted to a nucleic acid molecule encoding B7-1 or B7-2, wherein the compound specifically hybridizes with the nucleic acid and inhibits expression of B7-1 or B7-2, said compound comprising at least 8 contiguous nucleobases of any one of the compounds of the invention.

The invention also provides methods of inhibiting the expression of a nucleic acid molecule encoding B7-1 or B7-2 in an individual, comprising the step of administering a compound of the invention targeted to a nucleic acid molecule encoding B7-1 or B7-2, wherein the compound specifically hybridizes with an active site in the nucleic acid and inhibits expression of B7-1 or B7-2, and the compound comprises at least 8 contiguous nucleobases of any one of the compounds of the invention.

In another aspect the invention provides methods of inhibiting expression of a nucleic acid molecule encoding B7-1 or B7-2 in an individual, comprising the step of administering an oligonucleotide mimetic compound targeted to a nucleic acid molecule encoding B7-1 or B7-2, wherein the compound specifically hybridizes with the nucleic acid and inhibits expression of B7-1 or B7-2, and the compound comprises at least 8 contiguous nucleobases of a compound of the invention.

In another aspect, the invention provides methods of inhibiting the expression of a nucleic acid molecule encoding B7-1 or B7-2 in an individual comprising the step of administering a compound of the invention targeted target to a nucleic acid encoding B7-1 or B7-2, wherein the compound inhibits B7-1 or B7-2 mRNA expression by at least 5% in 80% confluent HepG2 cells in culture at an optimum concentration compared to a control. In yet another aspect, the compounds inhibit expression of mRNA encoding B7-1 or B7-2 in 80% confluent HepG2 cells in culture at an optimum concentration by at least 10%, at least 15%, at least 20%, at least 25%, at least 30%, at least 35%, at least 40%, or at least 50%, compared to a control.

The invention also relates to pharmaceutical compositions which comprise an antisense oligonucleotide to a B7 protein in combination with a second anti-inflammatory agent, such as a second antisense oligonucleotide to a protein which mediates intercellular interactions, e.g., an intercellular adhesion molecule (ICAM) protein.

Methods comprising contacting animals with oligonucleotides specifically hybridizable with nucleic acids encoding B7 proteins are herein provided. These methods are useful as tools, for example, in the detection and determination of the role of B7 protein expression in various cell functions and physiological processes and conditions, and for the diagnosis of conditions associated with such expression. Such methods can be used to detect the expression of B7 genes (i.e., B7-1 or B7-2) and are thus believed to be useful both therapeutically and diagnostically. Methods of modulating the expression of B7 proteins comprising contacting animals with oligonucleotides specifically hybridizable with a B7 gene are herein provided. These methods are believed to be useful both therapeutically and diagnostically as a consequence of the association between B7 expression and T cell activation and proliferation. The present invention also comprises methods of inhibiting B7-associated activation of T cells using the oligonucleotides of the invention. Methods of treating conditions in which abnormal or excessive T cell activation and proliferation occurs are also provided. These methods employ the oligonucleotides of the invention and are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

The methods disclosed herein are also useful, for example, as clinical research tools in the detection and determination of the role of B7-1 or B7-2 expression in various immune system functions and physiological processes and conditions, and for the diagnosis of conditions associated with their expression. The specific hybridization exhibited by the oligonucleotides of the present invention may be used for assays, purifications, cellular product preparations and in other methodologies which may be appreciated by persons of ordinary skill in the art. For example, because the oligonucleotides of this invention specifically hybridize to nucleic acids encoding B7 proteins, sandwich and other assays can easily be constructed to exploit this fact. Detection of specific hybridization of an oligonucleotide of the invention with a nucleic acid encoding a B7 protein present in a sample can routinely be accomplished. Such detection may include detectably labeling an oligonucleotide of the invention by enzyme conjugation, radiolabeling or any other suitable detection system. A number of assays may be formulated employing the present invention, which assays will commonly comprise contacting a tissue or cell sample with a detectably labeled oligonucleotide of the present invention under conditions selected to permit hybridization and measuring such hybridization by detection of the label, as is appreciated by those of ordinary skill in the art.

The present invention provides an antisense oligonucleotide which specifically hybridizes to a nucleic acid encoding human B7.2 protein, said antisense oligonucleotide comprising at least an 8 nucleobase portion of SEQ ID NO: 374, 391 or 440, wherein said antisense oligonucleotide inhibits expression of said human B7.2 protein.

In one aspect, the invention provides the antisense oligonucleotide of the invention, wherein said antisense oligonucleotide has the sequence shown in SEQ ID NO: 374, 391 or 440.

In another aspect, the antisense oligonucleotide of the invention has at least one modified internucleotide linkage.

In yet another aspect, the invention encompasses the antisense oligonucleotide of the invention wherein said modified linkage is a phosphorothioate. The antisense oligonucleotide of claim 2, wherein all internucleotide linkages are phosphorothioate linkages.

In another aspect, the invention encompasses the antisense oligonucleotide of the invention having at least one 2' sugar modification. The antisense oligonucleotide of claim 2, wherein nucleotides 1-5 and 16-20 comprise 2'-MOE modifications.

In yet another aspect, the invention provides the antisense oligonucleotide of the invention wherein said 2' sugar modification is a 2'-MOE.

In another aspect, the invention encompasses the antisense oligonucleotide of the invention having at least one base modification.

In another aspect, the invention provides the antisense oligonucleotide of the invention wherein said base modification is a 5-methylcytidine. The antisense oligonucleotide of claim 2, wherein all cytidine residues are replaced with 5'methylcytidines.

In yet another aspect, the invention provides an antisense oligonucleotide having the sequence of SEQ ID NO: 374, 391 or 440, wherein all internucleotide linkages are phosphorothioate linkages, all cytidine residues are replaced with 5'methylcytidines and nucleotides 1-15 and 16-20 comprise 2'-MOE modifications.

In another aspect, the invention also provides a method of inhibiting expression of human B7.2 protein in cells or tissues comprising contacting said cells or tissues with the antisense oligonucleotide of the invention.

BRIEF DESCRIPTION OF THE DRAWINGS

FIG. 20 is a graph showing that treatment with an antisense oligonucleotide targeted to B7.1 (ISIS 121844) reduces allergen-induced eosinophilia in the ovalbumin-induced mouse model of asthma.

DETAILED DESCRIPTION OF THE INVENTION

Figure 1:
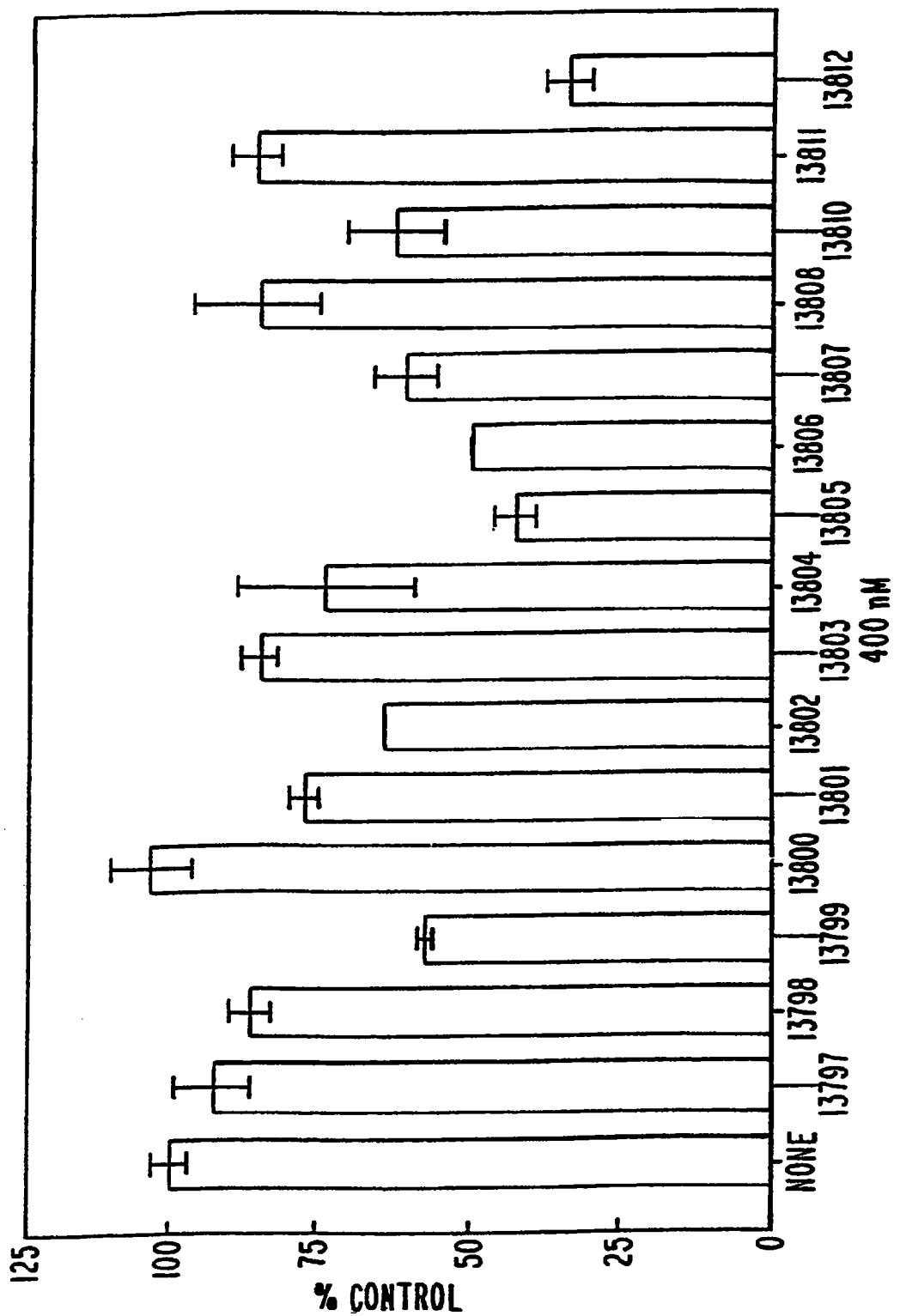
FIG. 1 is a bar graph showing the inhibitory effect of the indicated oligonucleotides on B7-1 protein expression in COS-7 cells.

The present invention employs oligonucleotides for use in antisense inhibition of the function of RNA and DNA encoding B7 proteins including B7-1 and B7-2. The present invention also employs oligonucleotides which are designed to be specifically hybridizable to DNA or messenger RNA (mRNA) encoding such proteins and ultimately to modulate the amount of such proteins transcribed from their respective genes. Such hybridization with mRNA interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of a B7 protein, wherein "modulation" means either an increase (stimulation) or a decrease (inhibition) in the expression of a B7 protein. In the context of the present invention, inhibition is the preferred form of modulation of gene expression.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses.

"Hybridization", in the context of this invention, means hydrogen bonding, which may be Watson-Crick, Hoogsteen or reversed Hoogsteen hydrogen bonding, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of activity, and there is a sufficient degree of complementarity to avoid non-specific binding of the oligonucleotide to non-target nucleic acid sequences under conditions in which specific binding is desired, i.e., under physiological conditions in the case of in vivo assays or therapeutic treatment or, in the case of in vitro assays, under conditions in which the assays are conducted.

It is understood in the art that the sequence of the oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). It is preferred that the oligomeric compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention; "stringent conditions" under which oligomeric compounds hybridize to a target sequence are determined by the nature and composition of the oligomeric compounds and the assays in which they are being investigated.

The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenza virus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to CMV. U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent EBV infections.

Oligonucleotides capable of modulating the expression of B7 proteins represent a novel therapeutic class of anti-inflammatory agents with activity towards a variety of inflammatory or autoimmune diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, eczema, atopic dermatitis, seborrheic dermatitis, nummular dermatitis, generalized exfoliative dermatitis, rhinitis and various allergies. In addition, oligonucleotides capable of modulating the expression of B7 proteins provide a novel means of manipulating the ex vivo proliferation of T cells.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with several immune system disorders and diseases (such as inflammation and autoimmune diseases), as well as with ostensibly "normal" immune reactions (such as a host animal's rejection of transplanted tissue), for which modulation is desired in certain instances. The targeting process also includes determination of a region (or regions) within this gene for the oligonucleotide interaction to occur such that the desired effect, either detection or modulation of expression of the protein, will result. Once the target regions have been identified, oligonucleotides are chosen which are sufficiently complementary to the target, i.e., hybridize sufficiently well and with sufficient specificity to give the desired effect.

Generally, there are five regions of a gene that may be targeted for antisense modulation: the 5' untranslated region (hereinafter, the "5'-UTR"), the translation initiation codon region (hereinafter, the "tIR"), the open reading frame (hereinafter, the "ORF"), the translation termination codon region (hereinafter, the "tTR") and the 3' untranslated region (hereinafter, the "3'-UTR"). As is known in the art, these regions are arranged in a typical messenger RNA molecule in the following order (left to right, 5' to 3'): 5'-UTR, tIR, ORF, tTR, 3'-UTR. As is known in the art, although some eukaryotic transcripts are directly translated, many ORFs contain one or more sequences, known as "introns" which are excised from a transcript before it is translated; the expressed (unexcised) portions of the ORF are referred to as "exons" (Alberts et al., Molecular Biology of the Cell, 1983, Garland Publishing Inc., New York, pp. 411-415). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites. Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., Growth Factors, 1990, 4, 45; Gelbert et al., Somat. Cell. Mol. Genet., 1990, 16, 173; Gold and Stormo, in: Escherichia coli and Salmonella typhimurium: Cellular and Molecular Biology, Vol. 2, 1987, Neidhardt et al., eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., Development, 1995, 121, 3723; Gao et al., Cancer Res., 1995, 55, 743; McDermott et al, Gene, 1992, 117, 193; Perri et al., J. Biol. Chem., 1991, 266, 12536; French et al., J. Virol., 1989, 63, 3270; Pushpa-Rekha et al., J. Biol. Chem., 1995, 270, 26993; Monaco et al., J. Biol. Chem., 1994, 269, 347; DeVirgilio et al., Yeast, 1992, 8, 1043; Kanagasundaram et al., Biochim. Biophys. Acta, 1992, 1171, 198; Olsen et al., Mol. Endocrinol., 1991, 5, 1246; Saul et al., Appl. Environ. Microbiol., 1990, 56, 3117; Yaoita et al., Proc. Natl. Acad. Sci. USA, 1990, 87, 7090; Rogers et al., EMBO J., 1990, 9, 2273). In the context of the invention, "start codon" and "translation initiation codon" refer to the codon or codons that are used in vivo to initiate translation of an mRNA molecule transcribed from a gene encoding a B7 protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses from about 25 to about 50 contiguous nucleotides in either direction (i.e., 5' or 3') from a translation initiation codon. Similarly, the terms "stop codon region" and "translation termination region" refer to a portion of such an mRNA or gene that encompasses from about 25 to about 50 contiguous nucleotides in either direction (i.e., 5' or 3') from a translation termination codon.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, Caenorhabditis elegans (Guo and Kempheus, Cell, 1995, 81, 611-620).

Montgomery et al. have shown that the primary interference effects of dsRNA are posttranscriptional (Montgomery et al., Proc. Natl. Acad. Sci. USA, 1998, 95, 15502-15507). The posttranscriptional antisense mechanism defined in Caenorhabditis elegans resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391, 806-811). Recently, it has been shown that it is, in fact, the single-stranded RNA oligomers of antisense polarity of the dsRNAs which are the potent inducers of RNAi (Tijsterman et al., Science, 2002, 295, 694-697).

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$—[known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester internucleotide linkage is represented as —O—P(=O)(OH)—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., *Science*, 1991, 254, 1497-1500.

One oligonucleotide mimetic that has been reported to have excellent hybridization properties is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

PNA has been modified to incorporate numerous modifications since the basic PNA structure was first prepared. The basic structure is shown below:

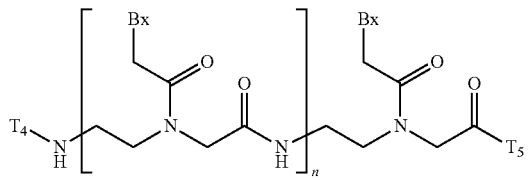

wherein

Bx is a heterocyclic base moiety;

$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

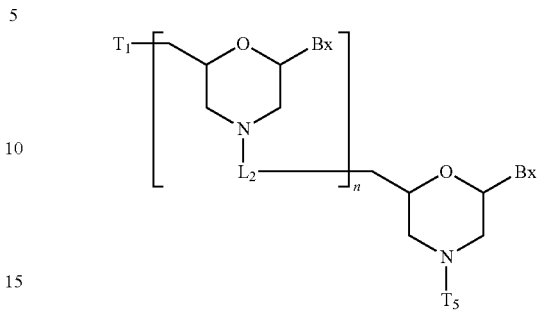

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

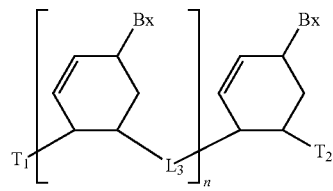

wherein each Bx is a heterocyclic base moiety;

$T_1$ is hydroxyl or a protected hydroxyl; and

T2 is hydroxyl or a protected hydroxyl.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

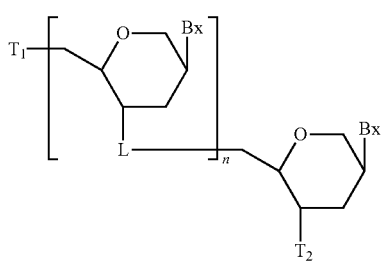

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene ($-CH_2-$)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

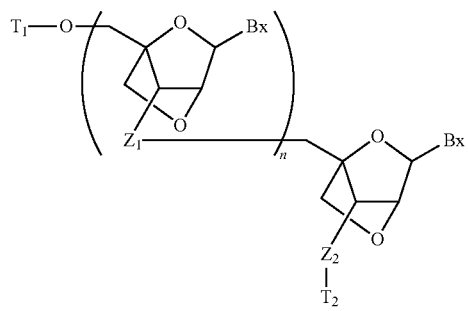

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs. Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

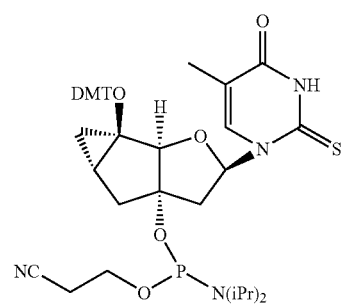

-continued

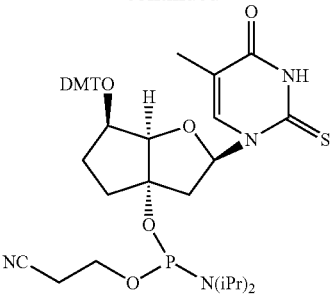

(see Steffens et al., *Helv. Chim. Acta*, 1997, 80, 2426-2439; Steffens et al., *J. Am. Chem. Soc.*, 1999, 121, 3249-3255; and Renneberg et al., *J. Am. Chem. Soc.*, 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic referred to as phosphonomonoester nucleic acids incorporate a phosphorus group in the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

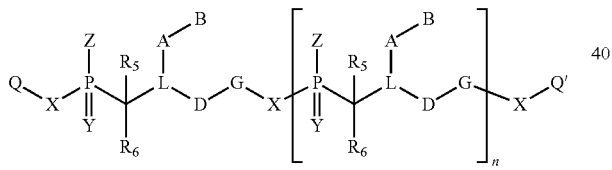

Another oligonucleotide mimetic has been reported wherein the furanosyl ring has been replaced by a cyclobutyl moiety.

Modified Sugars

Oligomeric compounds of the invention may also contain one or more substituted sugar moieties. Preferred oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, amino alkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other preferred sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula $I_a$ or $II_a$:

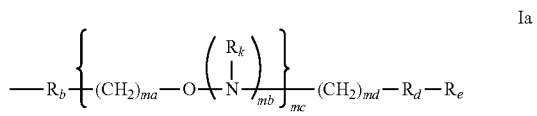

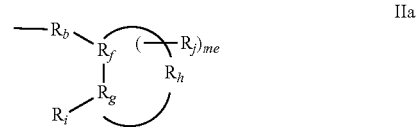

wherein:

$R_b$ is O, S or NH;

$R_d$ is a single bond, O, S or C(=O);

$R_e$ is $C_1$-$C_{10}$ alkyl, $N(R_k)(R_m)$, $N(R_k)(R_n)$, $N=C(R_p)(R_q)$, $N=C(R_p)(R_r)$ or has formula $III_a$;

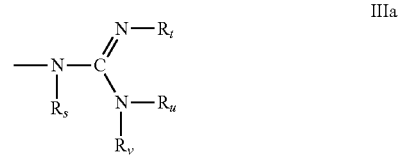

$R_p$ and $R_q$ are each independently hydrogen or $C_1$-$C_{10}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, a nitrogen protecting group or —$R_x$—$R_y$;
$R_p$ is hydrogen, a nitrogen protecting group or —$R_x$—$R_y$;
$R_x$ is a bond or a linking moiety;
$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;
each $R_z$ is, independently, H, $C_1$-$C_8$ alkyl, $C_1$-$C_8$ haloalkyl, $C(=NH)N(H)R_u$, $C(=O)N(H)R_u$ or $OC(=O)N(H)R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;

$m_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

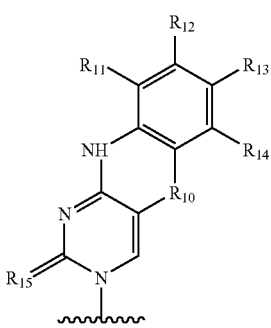

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of HCV mRNA and/or HCV replication.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al.,

*Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within an oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

3'-Endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

SCHEME 1

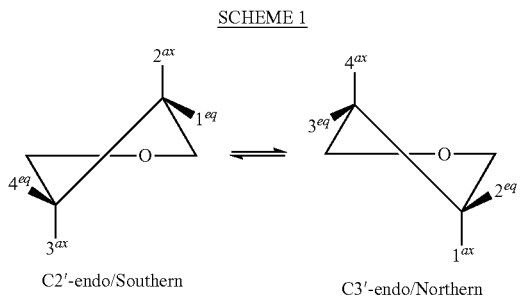

Figure 2:
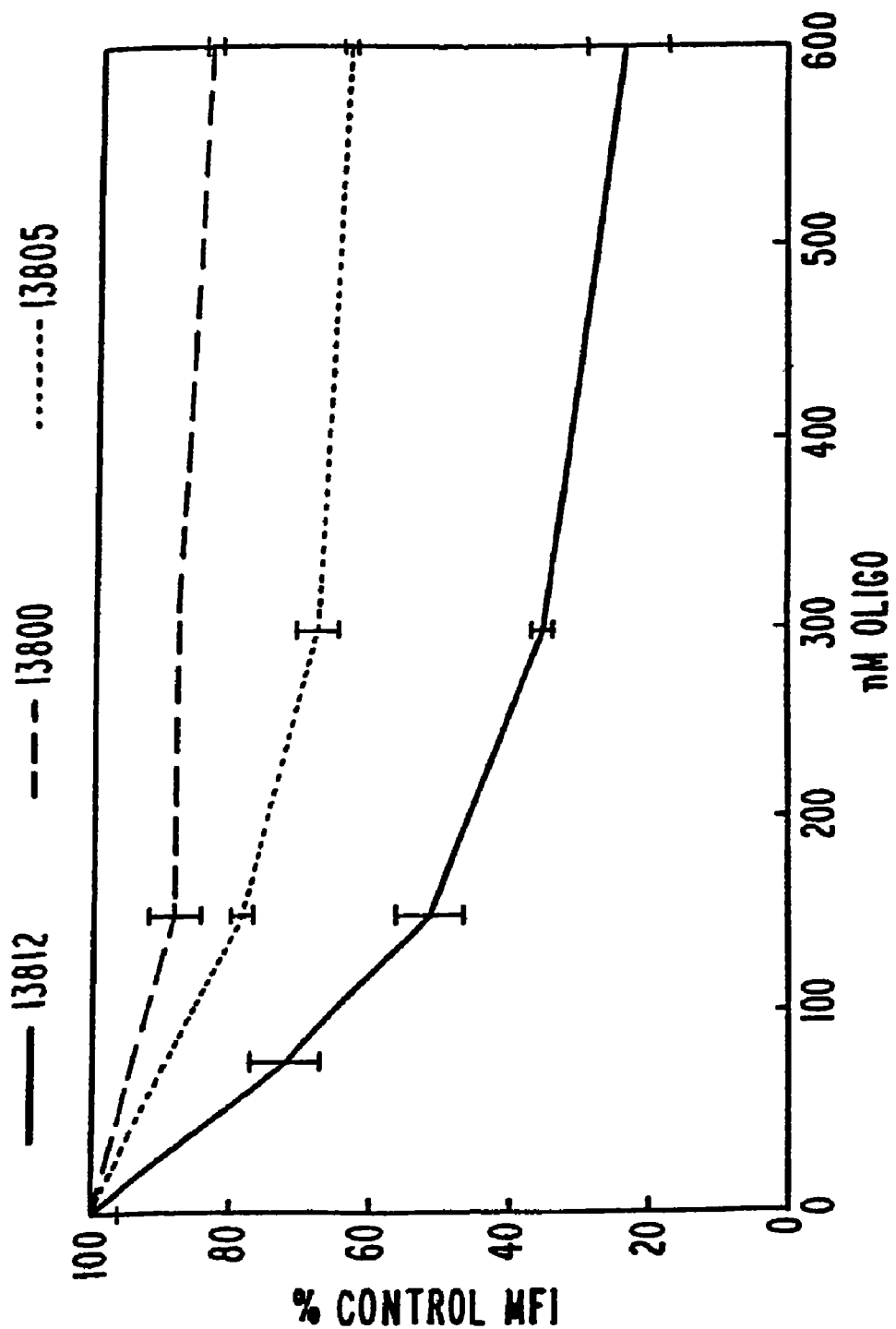
FIG. 2 is a dose-response curve showing the inhibitory effect of oligonucleotides on cell surface expression of B7-1 protein. Solid line, ISIS 13812; dashed line, ISIS 13800; dotted line, ISIS 13805.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Table I. These examples are meant to be representative and not exhaustive.

TABLE I

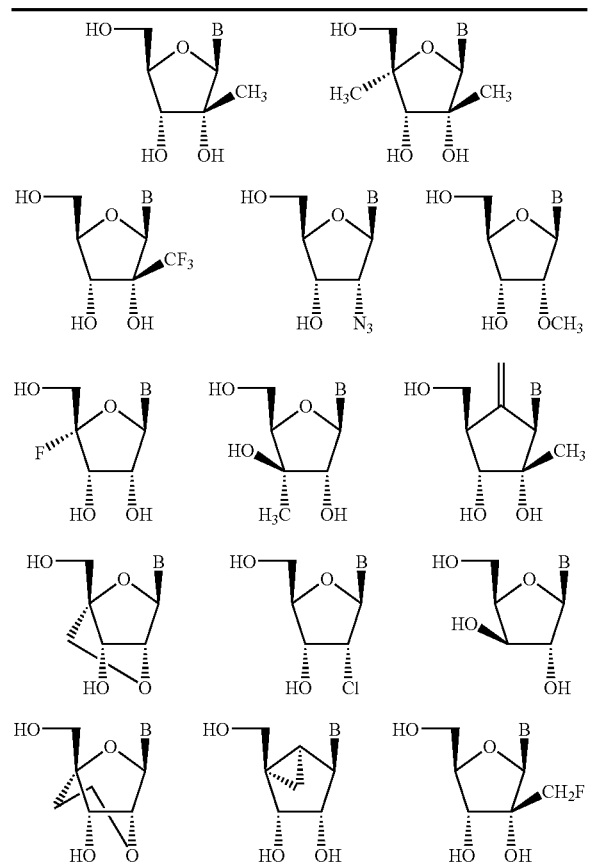

TABLE I-continued

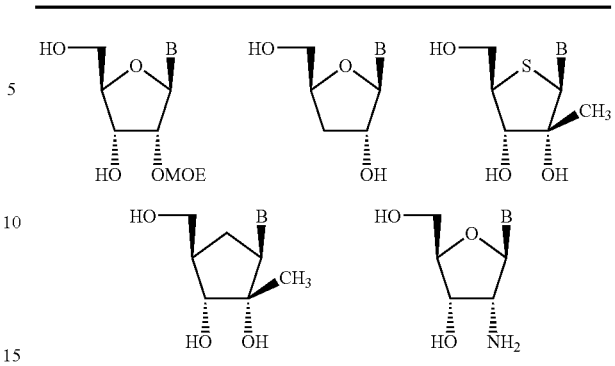

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B).

In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research,* 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.,* 1993, 21, 2051-2056). The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533). The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.,* 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. $—CO_2H$, $—OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

The oligonucleotides in accordance with this invention (single stranded or double stranded) preferably comprise from about 8 to about 80 nucleotides, more preferably from about 12-50 nucleotides and most preferably from about 15 to 30 nucleotides. As is known in the art, a nucleotide is a base-sugar combination suitably bound to an adjacent nucleotide through a phosphodiester, phosphorothioate or other covalent linkage.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of B7.1 or B7.2 mRNA.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

The oligonucleotides of the present invention can be utilized as therapeutic compounds, diagnostic tools and as research reagents and kits. The term "therapeutic uses" is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention. While not intending to be bound to a particular utility, the ex vivo modulation of, e.g., T cell proliferation by the oligonucleotides of the invention can be employed in, for example, potential therapeutic modalities wherein it is desired to modulate the expression of a B7 protein in APCs.

As an example, oligonucleotides that inhibit the expression of B7-1 proteins are expected to enhance the availability of B7-2 proteins on the surface of APCs, thus increasing the costimulatory effect of B7-2 on T cells ex vivo (Levine et al., *Science*, 1996, 272, 1939).

For therapeutic uses, an animal suspected of having a disease or disorder which can be treated or prevented by modulating the expression or activity of a B7 protein is, for example, treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans.

The oligonucleotides of the present invention can be further used to detect the presence of B7-specific nucleic acids in a cell or tissue sample. For example, radiolabeled oligonucleotides can be prepared by $^{32}P$ labeling at the 5' end with polynucleotide kinase (Sambrook et al., *Molecular Cloning. A Laboratory Manual*, Cold Spring Harbor Laboratory Press, 1989, Volume 2, pg. 10.59). Radiolabeled oligonucleotides are then contacted with cell or tissue samples suspected of containing B7 message RNAs (and thus B7 proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of B7 proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a B7 gene. Quantitation of the silver grains permits detection of the expression of mRNA molecules encoding these proteins and permits targeting of oligonucleotides to these areas.

Analogous assays for fluorescent detection of expression of B7 nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va.

The present invention employs oligonucleotides targeted to nucleic acids encoding B7 proteins and oligonucleotides targeted to nucleic acids encoding such proteins. Kits for detecting the presence or absence of expression of a B7 protein may also be prepared. Such kits include an oligonucleotide targeted to an appropriate gene, i.e., a gene encoding a B7 protein. Appropriate kit and assay formats, such as, e.g., "sandwich" assays, are known in the art and can easily be adapted for use with the oligonucleotides of the invention. Hybridization of the oligonucleotides of the invention with a nucleic acid encoding a B7 protein can be detected by means known in the art. Such means may include conjugation of an enzyme to the oligonucleotide, radiolabeling of the oligonucleotide or any other suitable detection systems. Kits for detecting the presence or absence of a B7 protein may also be prepared.

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 μg to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

In some cases, it may be more effective to treat a patient with an oligonucleotide of the invention in conjunction with other therapeutic modalities in order to increase the efficacy of a treatment regimen. In the context of the invention, the term "a treatment regimen" is meant to encompass therapeutic, palliative and prophylactic modalities. In a preferred embodiment, the oligonucleotides of the invention are used in conjunction with an anti-inflammatory and/or immunosuppressive agent, preferably one or more antisense oligonucleotides targeted to an intercellular adhesion molecule (ICAM), preferably to ICAM-1. Other anti-inflammatory and/or immunosuppressive agents that may be used in combination with the oligonucleotides of the invention include, but are not limited to, soluble ICAM proteins (e.g., sICAM-1), antibody-toxin conjugates, prednisone, methylprednisolone, azathioprine, cyclophosphamide, cyclosporine, interferons, sympathomimetics, conventional antihistamines (histamine $H_1$ receptor antagonists, including, for example, brompheniramine maleate, chlorpheniramine maleate, dexchlorpheniramine maleate, tripolidine HCl, carbinoxamine maleate, clemastine fumarate, dimenhydrinate, diphenhydramine HCl, diphenylpyraline HCl, doxylamine succinate, tripelennamine citrate, tripelennamine HCl, cyclizine HCl, hydroxyzine HCl, meclizine HCl, methdilazine HCl, promethazine HCl, trimeprazine tartrate, azatadine maleate, cyproheptadine HCl, terfenadine, etc.), histamine $H_2$ receptor antagonists (e.g., ranitidine). See, generally, *The Merck Manual of Diagnosis and Therapy*, 15th Ed., Berkow et al., eds., 1987, Rahway, N.J., pages 302-336 and 2516-2522). When used with the compounds of the invention, such agents may be used individually, sequentially, or in combination with one or more other such agents.

In another preferred embodiment of the invention, an antisense oligonucleotide targeted to one B7 mRNA species (e.g., B7-1) is used in combination with an antisense oligonucleotide targeted to a second B7 mRNA species (e.g., B7-2) in order to inhibit the costimulatory effect of B7 molecules to a more extensive degree than can be achieved with either oligonucleotide used individually. In a related version of this embodiment, two or more oligonucleotides of the invention, each targeted to an alternatively spliced B7-1 or B7-2 mRNA, are combined with each other in order to inhibit expression of both forms of the alternatively spliced mRNAs. It is known in the art that, depending on the specificity of the modulating agent employed, inhibition of one form of an alternatively spliced mRNA may not result in a sufficient reduction of expression for a given condition to be manifest. Thus, such combinations may, in some instances, be desired to inhibit the expression of a particular B7 gene to an extent necessary to practice one of the methods of the invention.

Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years. In the case of in individual known or suspected of being prone to an autoimmune or inflammatory condition, prophylactic effects may be achieved by administration of preventative doses, ranging from 0.01 µg to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer or metered dose inhaler; intratracheal, intranasal, epidermal and transdermal, oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for oral administration also include pulsatile delivery compositions and bioadhesive composition as described in copending U.S. patent application Ser. No. 09/944,493, filed Aug. 22, 2001, and 09/935, 316, filed Aug. 22, 2001, the entire disclosures of which are incorporated herein by reference.

Compositions for parenteral, intrathecal or intraventricular administration may include sterile aqueous solutions which may also contain buffers, diluents and other suitable additives.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

The following examples are provided for illustrative purposes only and are not intended to limit the invention.

EXAMPLES

Example 1

Synthesis of Nucleic Acids Oligonucleotides

Oligonucleotides were synthesized on an automated DNA synthesizer using standard phosphoramidite chemistry with oxidation using iodine. β-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages. The thiation cycle wait step was increased to 68 seconds and was followed by the capping step.

The 2'-fluoro phosphorothioate oligonucleotides of the invention were synthesized using 5'-dimethoxytrityl-3'-phosphoramidites and prepared as disclosed in U.S. patent application Ser. No. 463,358, filed Jan. 11, 1990, and Ser. No. 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

The 2'-methoxy (2'-O-methyl)oligonucleotides of the invention were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va. The 3'-base used to start the synthesis was a 2'-deoxyribonucleotide. The 2'-O-propyl oligonucleotides of the invention are prepared by a slight modification of this procedure.

The 2' methoxyethoxy (2'-O—$CH_2CH_2OCH_3$) oligonucleotides of the invention were synthesized according to the method of Martin, Helv. Chim. Acta 1995, 78, 486. For ease of synthesis, the last nucleotide was a deoxynucleotide. All 2'-O—$CH_2CH_2OCH_3$-cytosines were 5-methyl cytosines, which were synthesized according to the following procedures.

Synthesis of 5-Methyl Cytosine Monomers 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added to the later solution dropwise, over a 45 minute period. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10 M) was dissolved in $CH_2Cl_2$ (1 L).

Tetrazole diisopropylamine (7.1 g) and 2-cyanoethoxy-tetra (isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

2'-O-(Aminooxyethyl)nucleoside amidites and 2'-O-(dimethylaminooxyethyl)nucleoside amidites 2'-(Dimethylaminooxyethoxy)nucleoside amidites 2'-(Dimethylaminooxyethoxy)nucleoside amidites [also known in the art as 2'-O-(dimethylaminooxyethyl)nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O2-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for are-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl)thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O—[N,N-dimethylaminooxyethyl]-5

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH$_2$Cl$_2$). Aqueous NaHCO$_3$ solution (5%, 10 mL) was added and extracted with ethyl acetate (2×20 mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO$_3$ (25 mL) solution was added and extracted with ethyl acetate (2×25 mL). Ethyl acetate layer was dried over anhydrous Na2SO4 and evaporated to dryness. The residue obtained was purified by flash column chromatography and eluted with 5% MeOH in CH$_2$Cl$_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P2O5 under high vacuum overnight at 40° C. Then the reaction mixture was dissolved in anhydrous acetonitrile (8.4 mL) and 2-cyanoethyl-N,N,N1,N1-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy)nucleoside amidites

2'-(Aminooxyethoxy)nucleoside amidites [also known in the art as 2'-O-(aminooxyethyl)nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl)diaminopurine riboside may be resolved and converted to 2'-O-(2-ethylacetyl)guanosine by treatment with adenosine deaminase. (PCT WO94/02501). Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl) guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE)nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O2-,2'-anhydro-5-methyluridine (1.2 g, 5 mmol), and sodium bicarbonate (2.5 mg) are added and the bomb is sealed, placed in an oil bath and heated to 155 C for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylamino-ethoxy)ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated NaHCO3 solution, followed by saturated NaCl solution and dried over anhydrous sodium sulfate. Evaporation of the solvent followed by silica gel chromatography using MeOH:CH2Cl2:Et3N (20:1, v/v, with 1% triethylamine) gives the title compound.

5'-O-Dimethoxytrityl-2'-O-[2(2-N,N-dimethylamino-ethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Purification:

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

B7 Antisense Oligonucleotides

A series of oligonucleotides with sequences designed to hybridize to the published human B7-1 (hB7-1) and murine B7-1 (mB7-1) mRNA sequences (Freeman et al., *J. Immunol.*, 1989, 143, 2714, and Freeman et al., *J. Exp. Med.*, 1991, 174, 625 respectively). The sequences of and modifications to these oligonucleotides, and the location of each of their target sites on the hB7-1 mRNA, are given in Tables 1 and 2. Similarly, a series of oligonucleotides with sequences designed to hybridize to the human B7-2 (hB7-2) and murine B7-2 (mB7-2) mRNA published sequences (respectively, Azuma et al., *Nature*, 1993, 366, 76; Chen et al., *J. Immunol.*, 1994, 152, 4929) were synthesized. The sequences of and modifications to these oligonucleotides and the location of each of their target sites on the hB7-2 mRNA are described in Tables 3 and 4. Antisense oligonucleotides targeted to ICAM-1, including ISIS 2302 (SEQ ID NO: 17), have been described in U.S. Pat. No. 5,514,788, which issued May 7, 1996, hereby incorporated by reference. ISIS 1082 (SEQ ID NO: 102) and ISIS 3082 (SEQ ID NO: 101) have been previously described (Stepkowski et al., *J. Immunol.*, 1994, 153, 5336).

Subsequent to their initial cloning, alternative splicing events of B7 transcripts have been reported. The reported alternative splicing for B7-1 is relatively simple, in that it results in messages extended 5' relative to the 5' terminus of the human and murine B7-1 cDNA sequences originally reported (Borriello et al., J. Immunol., 1994, 153, 5038; Inobe et al., J. Immunol., 1996, 157, 588). In order to retain the numbering of the B7-1 sequences found in the references initially reporting B7-1 sequences, positions within these 5' extensions of the initially reported sequences have been given negative numbers (beginning with position −1, the most 3' base of the 5' extension) in Tables 1 and 2. The processing of murine B7-2 transcripts is considerably more complex than that so far reported for B7-1; for example, at least five distinct murine B7-2 mRNAs, and at least two distinct human B7-2 mRNAs, can be produced by alternative splicing events (Borriello et al., *J. Immunol.*, 1995, 155, 5490; Freeman et al., WO 95/03408, published Feb. 2, 1995; see also Jellis et al., Immunogenet., 1995, 42, 85). The nature of these splicing events is such that different 5' exons are used to produce distinct B7-2 mRNAs, each of which has a unique 5' sequence but which share a 3' portion consisting of some or all of the B7-2 sequence initially reported. As a result, positions within the 5' extensions of B7-2 messages cannot be uniquely related to a position within the sequence initially reported. Accordingly, in Table 3, a different set of coordinates (corresponding to those of SEQ ID NO: 1 of WO 95/03408) and, in Table 4, the exon number (as given in Borriello et al., J. Immunol., 1995, 155, 5490) is used to specify the location of targeted sequences which are not included in the initially reported B7-2 sequence. Furthermore, although these 5' extended messages contain potential in-frame start codons upstream from the ones indicated in the initially published sequences, for simplicity's sake, such additional potential start codons are not indicated in the description of target sites in Tables 1-4.

In Tables 1-4, the following abbreviations are used: UTR, untranslated region; ORF, open reading frame; tIR, translation initiation region; tTR, translation termination region; FITC, fluorescein isothiocyanate. Chemical modifications are indicated as follows. Residues having 2' fluoro (2'F), 2'-methoxy (2'MO) or 2'-methoxyethoxy (2'ME) modification are emboldened, with the type of modification being indicated by the respective abbreviations. Unless otherwise indicated, interresidue linkages are phosphodiester linkages; phosphorothioate linkages are indicated by an "s" in the superscript position (e.g., $T^SA$). Target positions are numbered according to Freeman et al., *J. Immunol.*, 1989, 143: 2714 (human B7-1 cDNA sequence; Table 1), Freeman et al., *J. Exp. Med.*, 1991, 174, 625 (murine B7-1 cDNA sequence; Table 2), Azuma et al., *Nature*, 1993, 366:76 (human B7-2 cDNA sequence; Table 3) and Chen et al., *J. Immunol.*, 1994, 152:4929 (murine B7-2 cDNA sequence; Table 4). Nucleotide base codes are as given in 37 C.F.R. §1.822(b)(1).

TABLE 1

Sequences of Oligonucleotides Targeted to Human B7-1 mRNA

| ISIS # | Target Position; Site (and/or Description) | Oligonucleotide Sequence (5'->3') and Chemical Modifications | SEQ ID NO: |
|---|---|---|---|
| 13797 | 0053-0072; 5' UTR | $G^SG^SG^ST^SA^SA^SG^SA^SC^ST^SC^SC^SA^SC^ST^ST^SC^ST^SG^SA$ | 22 |
| 13798 | 0132-0151; 5' UTR | $G^SG^SG^ST^SC^ST^SC^SC^SA^SA^SA^SG^SG^ST^ST^SG^ST^SG^SG^SA$ | 23 |

TABLE 1-continued

Sequences of Oligonucleotides Targeted to Human B7-1 mRNA

| ISIS # | Target Position; Site (and/or Description) | Oligonucleotide Sequence (5'->3') and Chemical Modifications | SEQ ID NO: |
|---|---|---|---|
| 13799 | 0138-0157; 5' UTR | $G^STT^SC^SC^ST^SG^SG^SG^ST^SC^ST^SG^SC^SA^SA^SA^SG^SG^ST$ | 24 |
| 13800 | 0158-0177; 5' UTR | $A^SC^SA^SC^SA^SG^SA^SG^SA^ST^ST^SG^SG^SA^SG^SG^SG^ST$ | 25 |
| 13801 | 0193-0212; 5' UTR | $G^SC^ST^SC^SA^SC^SG^ST^SA^SG^SA^SA^SG^SA^SC^SC^SC^ST^SC^SC$ | 26 |
| 13802 | 0217-0236; 5' UTR | $G^SG^SC^SA^SG^SG^SC^ST^SG^SA^ST^SG^SA^SC^SA^SA^ST^SC^SC$ | 27 |
| 13803 | 0226-0245; 5' UTR | $T^SG^SC^SA^SA^SA^SA^SC^SA^SG^SG^SC^SA^SG^SG^SG^SC^ST^SG^SA$ | 28 |
| 13804 | 0246-0265; 5' UTR | $A^SG^SA^SC^SG^SA^SG^SG^SG^SC^SA^SC^ST^ST^SC^SC^SC^SA^SG^SG$ | 29 |
| 13805 | 0320-0339; tIR | $C^SC^ST^SG^SC^SC^ST^SC^SC^SG^ST^SG^ST^SG^ST^SG^SG^SC^SC^SC$ | 30 |
| 13806 | 0380-0399; 5' ORF | $G^SA^SC^SA^SG^SC^SC^SA^SG^SC^SA^SC^SC^SA^SA^SG^SA^SG^SC$ | 31 |
| 13807 | 0450-0469; 5' ORF | $C^SC^SA^SC^SA^SG^SG^SA^SC^SA^SG^SC^SG^ST^ST^SG^SC^SC^SA^SC$ | 32 |
| 13808 | 0568-0587; 5' ORF | $C^SC^SG^SG^ST^ST^SC^ST^ST^SG^ST^SA^SC^ST^SC^SG^SG^SG^SC^SC$ | 33 |
| 13809 | 0634-0653; central ORF | $G^SC^SC^ST^ST^SC^SG^ST^SC^SA^SG^SA^ST^SG^SG^SG^SC^SG^SC^SA$ | 51 |
| 13810 | 0829-0848; central ORF | $C^SC^SA^SA^SC^SC^SA^SG^SG^SA^SG^SA^SG^SG^ST^SG^SA^SG^SG^SC$ | 34 |
| 13811 | 1102-1121; 3' ORF | $G^SC^SA^SA^SG^SC^SA^SG^ST^SA^SG^SG^ST^SC^SA^SG^SG^SC$ | 35 |
| 13812 | 1254-1273; 3'-UTR | $G^SC^SC^ST^SC^SA^ST^SG^SA^ST^SC^SC^SC^SA^SC^SG^SA^ST^SC$ | 36 |
| 13872 | (scrambled # 13812) | $A^SG^ST^SC^SC^ST^SA^SC^ST^SA^SC^SC^SA^SG^SC^SC^SG^SC^SC^ST$ | 52 |
| 12361 | 0056-0075; 5' UTR | $T^SC^SA^SG^SG^SG^ST^SA^SA^SG^SA^SC^ST^SC^SC^SA^SC^ST^ST^SC$ | 38 |
| 12348 | 0056-0075; 5' UTR | T C A G G G$^ST^SA^SA^SG^SA^SC^ST^SC^SC$C A C T T C (2'ME) | 38 |
| 12473 | 0056-0075; 5' UTR | $T^S$C$^S$A$^S$G$^S$G$^ST^SA^SA^SG^SA^SC^ST^SC^SC$C$^S$A$^S$C$^S$T$^S$T$^S$C (2'FI) | 38 |
| 12362 | 0143-0162; 5' UTR | $A^SG^SG^SG^ST^SG^ST^ST^SC^SC^ST^SG^SG^SG^ST^SC^ST^SC^SC^SA$ | 39 |
| 12349 | 0143-0162; 5' UTR | A G G G T G$^ST^ST^SC^SC^ST^SG^SG^SG^S$T C T C C A (2'ME) | 39 |
| 12474 | 0143-0162; 5' UTR | $A^S$G$^S$G$^S$G$^S$T$^S$G$^ST^ST^SC^SC^ST^SG^SG^SG^S$T$^S$C$^S$T$^S$C$^S$C$^S$A (2'F1) | 39 |
| 12363 | 0315-0334; tIR | $C^ST^SC^SC^SG^ST^SG^ST^SG^ST^SG^SG^SC^SC^SC^SA^ST^SG^SG^SC$ | 40 |
| 12350 | 0315-0334; tIR | C T C C G T$^SG^ST^SG^ST^SG^SG^SC^S$C A T G G C (2'ME) | 40 |
| 12475 | 0315-0334; tIR | C$^S$T$^S$C$^S$C$^S$G$^S$T$^SG^ST^SG^ST^SG^SG^SC^SC^S$C$^S$A$^S$T$^S$G$^S$G$^S$C (2'FI) | 40 |
| 12364 | 0334-0353; 5' ORF | $G^SG^SA^ST^SG^SG^ST^SG^SA^ST^SG^ST^ST^SC^SC^SC^ST^SG^SC^SC$ | 41 |
| 12351 | 0334-0353; 5' ORF | G G A T G G$^ST^SG^SA^ST^SG^ST^ST^SC$C C T G C C (2'ME) | 41 |
| 12476 | 0334-0353; 5' ORF | G$^S$G$^S$A$^S$T$^S$G$^S$G$^ST^SG^SA^ST^SG^ST^ST^SC^S$C$^S$C$^S$T$^S$G$^S$C$^S$C (2'FI) | 41 |
| 12365 | 0387-0406; 5' ORF | $T^SG^SA^SG^SA^SA^SA^SG^SA^SC^SC^SA^SG^SC^SC^SA^SG^SC^SA^SC$ | 42 |
| 12352 | 0387-0406; 5' ORF | T G A G A A$^SA^SG^SA^SC^SC^SA^SG^SC^S$C A G C A C (2'ME) | 42 |
| 12477 | 0387-0406; 5' ORF | T$^S$G$^S$A$^S$G$^S$A$^S$A$^SA^SG^SA^SC^SC^SA^SG^SC^S$C$^S$A$^S$G$^S$C$^S$A$^S$C (2'FI) | 42 |
| 12366 | 0621-0640; central ORF | $G^SG^SG^SC^SG^SC^SA^SG^SA^SG^SC^SC^SA^SG^SG^SA^ST^SC^SA^SC$ | 43 |

TABLE 1-continued

Sequences of Oligonucleotides Targeted to Human B7-1 mRNA

| ISIS # | Target Position; Site (and/or Description) | Oligonucleotide Sequence (5'->3') and Chemical Modifications | SEQ ID NO: |
|---|---|---|---|
| 12353 | 0621-0640; central ORF | G G G C G C$^S$A$^S$G$^S$A$^S$G$^S$C$^S$C$^S$A$^S$G A T C A C (2'ME) | 43 |
| 12478 | 0621-0640; central ORF | G$^S$G$^S$G$^S$C$^S$G$^S$C$^S$A$^S$G$^S$A$^S$G$^S$C$^S$C$^S$A$^S$G$^S$G$^S$A$^S$T$^S$C$^S$A$^S$C (2'FI) | 43 |
| 12367 | 1042-1061; 3' ORF | G$^S$G$^S$C$^S$C$^S$C$^S$A$^S$G$^S$G$^S$A$^S$T$^S$G$^S$G$^S$G$^S$A$^S$G$^S$C$^S$A$^S$G$^S$G$^S$T | 44 |
| 12354 | 1042-1061; 3' ORF | G G C C C A$^S$G$^S$G$^S$A$^S$T$^S$G$^S$G$^S$G$^S$A G C A G G T (2'ME) | 44 |
| 12479 | 1042-1061; 3' ORF | G$^S$G$^S$C$^S$C$^S$C$^S$A$^S$G$^S$G$^S$A$^S$T$^S$G$^S$G$^S$G$^S$A$^S$G$^S$C$^S$A$^S$G$^S$G$^S$T (2'FI) | 44 |
| 12368 | 1069-1088; tTR | A$^S$G$^S$G$^S$G$^S$C$^S$G$^S$T$^S$A$^S$C$^S$A$^S$C$^S$T$^S$T$^S$T$^S$T$^S$C$^S$C$^S$C$^S$T$^S$T$^S$C | 45 |
| 12355 | 1069-1088; tTR | A G G G C G$^S$T$^S$A$^S$C$^S$A$^S$C$^S$T$^S$T$^S$T$^S$T C C C T T C (2'ME) | 45 |
| 12480 | 1069-1088; tTR | A$^S$G$^S$G$^S$G$^S$C$^S$G$^S$T$^S$A$^S$C$^S$A$^S$C$^S$T$^S$T$^S$T$^S$T$^S$C$^S$C$^S$C$^S$T$^S$T$^S$C (2'FI) | 45 |
| 12369 | 1100-1209; tTR | C$^S$A$^S$G$^S$C$^S$C$^S$C$^S$C$^S$T$^S$T$^S$G$^S$C$^S$T$^S$T$^S$T$^S$C$^S$T$^S$G$^S$C$^S$G$^S$G$^S$A | 46 |
| 12356 | 1100-1209; tTR | C A G C C C$^S$C$^S$T$^S$T$^S$G$^S$C$^S$T$^S$T$^S$T$^S$C$^S$T G C G G A (2'ME) | 46 |
| 12481 | 1100-1209; tTR | C$^S$A$^S$G$^S$C$^S$C$^S$C$^S$C$^S$T$^S$T$^S$G$^S$C$^S$T$^S$T$^S$T$^S$C$^S$T$^S$G$^S$C$^S$G$^S$G$^S$A (2'FI) | 46 |
| 12370 | 1360-1380; 3' UTR | A$^S$A$^S$G$^S$G$^S$A$^S$G$^S$A$^S$G$^S$G$^S$G$^S$A$^S$T$^S$G$^S$C$^S$C$^S$A$^S$G$^S$C$^S$C$^S$A | 47 |
| 12357 | 1360-1380; 3' UTR | A A G G A G$^S$A$^S$G$^S$G$^S$G$^S$A$^S$T$^S$G$^S$C C A G C C A (2'ME) | 47 |
| 12482 | 1360-1380; 3' UTR | A$^S$A$^S$G$^S$G$^S$A$^S$G$^S$A$^S$G$^S$G$^S$G$^S$A$^S$T$^S$G$^S$C$^S$C$^S$A$^S$G$^S$C$^S$C$^S$A (2'FI) | 47 |
| 12914 | (-0038 to -0059; 5' UTR of alternative mRNA) | C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$T$^S$G (2'MO) | 48 |
| 12915 | (-0035 to -0059; 5' UTR of alternative mRNA) | C$^S$T$^S$T$^S$C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$T$^S$G (2'MO) | 49 |
| 13498 | (-0038 to -0058; 5' UTR of alternative mRNA) | C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$T (2'ME) | 50 |
| 13499 | (-0038 to -0058; 5' UTR of alternative mRNA) | C T G T T A C T T T A C A G A G G G T T T (2'ME) | 50 |

TABLE 2

Sequences of Oligonucleotides Targeted to Murine B7-1 mRNA

| ISIS # | Target Position; Site | Oligonucleotide Sequence (5'->3') Chemical Modifications | SEQ ID NO: |
|---|---|---|---|
| 14419 | 0009-0028; 5' UTR | A$^S$G$^S$T$^S$A$^S$A$^S$G$^S$A$^S$G$^S$T$^S$C$^S$T$^S$A$^S$T$^S$T$^S$G$^S$A$^S$G$^S$G$^S$T$^S$A | 53 |
| 14420 | 0041-0060; 5' UTR | G$^S$G$^S$T$^S$T$^S$G$^S$A$^S$G$^S$T$^S$T$^S$T$^S$C$^S$A$^S$C$^S$A$^S$A$^S$C$^S$C$^S$T$^S$G$^S$A | 54 |
| 14421 | 0071-0091; 5' UTR | G$^S$T$^S$C$^S$C$^S$A$^S$G$^S$A$^S$A$^S$G$^S$A$^S$A$^S$T$^S$G$^S$G$^S$A$^S$A$^S$C$^S$A$^S$G$^S$A$^S$G | 55 |
| 14422 | 0109-0128; 5' UTR | G$^S$G$^S$C$^S$A$^S$T$^S$C$^S$C$^S$A$^S$C$^S$C$^S$C$^S$G$^S$G$^S$C$^S$A$^S$G$^S$A$^S$T$^S$G$^S$C | 56 |
| 14423 | 0114-0133; 5' UTR | T$^S$G$^S$G$^S$A$^S$T$^S$G$^S$G$^S$C$^S$A$^S$T$^S$C$^S$C$^S$A$^S$C$^S$C$^S$C$^S$G$^S$G$^S$C$^S$A | 57 |

TABLE 2-continued

Sequences of Oligonucleotides Targeted to Murine B7-1 mRNA

| ISIS # | Target Position; Site | Oligonucleotide Sequence (5'->3') Chemical Modifications | SEQ ID NO: |
|---|---|---|---|
| 14424 | 0168-0187; 5' UTR | $A^SG^SG^SC^SA^SC^SC^ST^SC^SC^ST^SA^SG^SG^SC^ST^SC^SA^SC^SA$ | 58 |
| 14425 | 0181-0200; 5' UTR | $G^SC^SC^SA^SA^ST^SG^SA^SG^SC^ST^ST^SA^SG^SG^SC^SA^SC^SC$ | 59 |
| 14426 | 0208-0217; 5' UTR | $C^SA^ST^SG^SA^ST^SG^SG^SG^SG^SA^SA^SG^SC^SC^SA^SG^SG^SA$ | 60 |
| 14427 | 0242-0261; tIR | $A^SA^ST^ST^SG^SC^SA^SA^SG^SC^SC^SA^ST^SA^SG^SC^ST^ST^SC^SA$ | 61 |
| 14428 | 0393-0412; 5' ORF | $C^SG^SG^SC^SA^SA^SG^SG^SC^SA^SG^SC^SA^SA^ST^SA^SC^SC^ST^ST$ | 62 |
| 14909 | 0478-0497; 5' ORF | $C^SC^SC^SA^SG^SC^SA^SA^ST^SG^SA^SC^SA^SG^SA^SC^SA^SG^SC^SA$ | 63 |
| 14910 | 0569-0588; central ORF | $G^SG^ST^SC^ST^SG^SA^SA^SG^SG^SA^SC^SC^SA^SG^SG^SC^SC^SC$ | 64 |
| 14911 | 0745-0764; central ORF | $T^SG^SG^SG^SA^SA^SA^SC^SC^SC^SC^SG^SG^SA^SA^SG^SC^SA^SA$ | 65 |
| 14912 | 0750-0769; central ORF | $G^SG^SC^ST^ST^SG^SG^SG^SA^SA^SA^SC^SC^SC^SC^SG^SG^SA$ | 66 |
| 14913 | 0825-0844; 3' ORF | $T^SC^SA^SG^SA^ST^ST^SC^SA^SG^SG^SA^ST^SC^SC^ST^SG^SG^SA$ | 67 |
| 14914 | 0932-0951; 3' ORF | $C^SC^SC^SA^SG^SG^ST^SG^SA^SG^ST^SC^SC^ST^SC^ST^SG^SA^SC$ | 68 |
| 14915 | 1001-1020; 3' ORF | $C^ST^SG^SC^SG^SC^SC^SG^SA^SA^ST^SC^SC^ST^SG^SC^SC^SC^SA$ | 69 |
| 14916 | 1125-1144; tTR | $C^SA^SG^SG^SC^SC^SC^SG^SA^SA^SG^SG^ST^SA^SA^SG^SG^SC^ST^SG$ | 70 |
| 14917 | 1229-1248; 3' UTR | $T^SC^SA^SG^SC^ST^SA^SG^SC^SA^SC^SG^ST^SG^SC^ST^SG^SA^SA$ | 71 |
| 14918 | 1329-1348; 3' UTR | $G^SC^SC^SC^SA^SG^SC^SA^SA^SA^SG^ST^ST^SG^SC^SC^SC^SG^ST$ | 72 |
| 14919 | 1377-1393; 3' UTR | $C^SC^SA^SC^SC^SA^SC^SA^SG^ST^SG^SG^SC^ST^SC^SA^SG^SC^SC$ | 73 |
| 12912 | -0067 to -0049; 5' UTR | $G^SG^SC^SC^SA^ST^SG^SA^SG^SG^SG^SC^SA^SA^ST^SC^ST^SA^SA$ (2'MO) | 74 |
| 12913 | -0067 to -0047; 5' UTR | $G^ST^SG^SG^SC^SC^SA^ST^SG^SA^SG^SG^SG^SC^SA^SA^ST^SC^ST^SA^SA$ (2'MO) | 75 |
| 13496 | -0067 to -0047; 5' UTR | $G^ST^SG^SG^SC^SC^SA^ST^SG^SA^SG^SG^SG^SC^SA^SA^ST^SC^ST^SA^SA$ (2'ME) | 75 |
| 13497 | -0067 to -0047; 5' UTR | G T G G C C A T G A G G G C A A T C T A A (2'ME) | 75 |

TABLE 3

Sequences of Oligonucleotides Targeted to Human B7-2 mRNA

| ISIS # | Target Position*; Site** | Oligonucleotide Sequence (5'->3') | SEQ ID NO: |
|---|---|---|---|
| 9133 | 1367-1386; 3'-UTR | $T^ST^SC^SC^SA^SG^SG^ST^SC^SA^ST^SG^SA^SG^SC^SC^SA^ST^ST^SA$ | 3 |
| 10715 | scrambled control of # 9133 | $G^SA^ST^ST^ST^SA^SC^SA^ST^ST^ST^SG^SG^SC^SG^SC^SC^SC^SA$ | 76 |
| 9134 | 1333-1352; 3'-UTR | $C^SA^ST^SA^SA^SG^ST^SG^ST^SG^SC^ST^SC^ST^SG^SA^SA^SG^ST^SG$ | 4 |
| 9135 | 1211-1230; 3'-UTR | $T^ST^SA^SC^ST^SC^SA^ST^SG^SG^ST^SA^SA^ST^SG^ST^SC^ST^ST^ST^S$ | 5 |
| 9136 | 1101-1120; tTR | $A^ST^ST^SA^SA^SA^SA^SG^SG^ST^SG^ST^SA^SC^ST^SC^ST^ST^S$ | 6 |
| 10716 | (scrambled # 9136) | $A^SA^SA^SG^ST^SA^SC^SA^SA^SC^SA^ST^ST^SA^ST^SA^ST^SC^ST$ | 77 |
| 9137 | 0054-0074; 5'-UTR | $G^SG^SA^SC^SA^SC^SA^SG^SA^SA^SG^SC^SA^SA^SG^SG^ST^SG^SG^ST$ | 7 |
| 9138 | 0001-0020; 5'-UTR | $C^SC^SG^ST^SA^SC^ST^SC^ST^SA^SG^SG^SC^ST^SC^SC^ST$ | 8 |
| 9139 | 0133-0152; tIR | $C^SC^SC^SA^SG^ST^SC^SC^SA^ST^SG^ST^SC^SA^ST^SA^SA^ST$ | 9 |
| 10877 | (scrambled # 9139) | $A^SG^ST^SG^SC^SG^SA^ST^ST^SC^ST^SC^SA^SA^SA^SC^SC^ST^SA^SC$ | 78 |
| 10367 | 0073-0092; 5'-UTR | $G^SC^SA^SG^SA^SG^SA^SG^SC^SA^ST^SC^SC^SC^SA^SA^SG^SG$ | 10 |
| 10368 | 0240-0259; 5' ORF | $T^ST^SG^SC^SA^SA^ST^ST^SG^SC^SA^ST^SG^SC^SA^SG^SG$ | 11 |
| 10369 | 1122-1141; 3'-UTR | $T^SG^SG^ST^SA^ST^SG^ST^SC^ST^ST^ST^SA^SC^ST^SC^ST^ST^ST$ | 12 |
| 10370 | 1171-1190; 3'-UTR | $A^SA^SA^SA^SG^SG^ST^ST^SG^SC^SC^SC^SA^SG^SG^SA^SA^SC^SG$ | 13 |
| 10371 | 1233-1252; 3'-UTR | $G^SG^SA^SG^ST^SC^ST^ST^SG^SC^SA^SC^SC^SC^SC^ST^ST$ | 14 |
| 10372 | 1353-1372; 3'-UTR | $C^SA^ST^ST^SA^SA^SG^SC^ST^SG^SG^SC^ST^ST^SG^SG^SC^SC$ | 15 |
| 11149 | 0019-0034; 5'-UTR | $T^SA^ST^ST^SG^SC^SG^SA^SG^SC^ST^SC^SC^SC$ | 79 |
| 11151 | 0020-0034; 5'-UTR | $T^SA^ST^ST^SG^SC^SG^SA^SG^SC^ST^SC^SC$ | 80 |

TABLE 3-continued

Sequences of Oligonucleotides Targeted to Human B7-2 mRNA

| ISIS # | Target Position*; Site** | Oligonucleotide Sequence (5'->3') | SEQ ID NO: |
|---|---|---|---|
| 11150 | 0021-0034; 5'-UTR | $T^SA^ST^ST^SG^SC^SG^SA^SG^SC^ST^SC^SC$ | 81 |
| 10373 | 0011-0030; 5'-UTR | $T^SG^SC^SG^SA^SG^SC^ST^SC^SC^SC^SC^SG^ST^SA^SC^SC^ST^SC^SG$ | 16 |
| 10721 | (scrambled # 10373) | $C^SG^SA^SC^SA^SG^SC^ST^SC^SC^ST^SG^SC^SG^SC^ST^SC^SC^ST^SC$ | 82 |
| 10729 | (5'FITC # 10373) | $T^SG^SC^SG^SA^SG^SC^ST^SC^SC^SC^SC^SG^ST^SA^SC^SC^ST^SC^SC$ | 16 |
| 10782 | (5'cholesterol # 10373) | $T^SG^SC^SG^SA^SG^SC^ST^SC^SC^SC^SC^SG^ST^SA^SC^SC^ST^SC^SC$ | 16 |
| | # 10373 Deletion Derivatives: | | |
| 10373 | 0011-0030; 5'-UTR | $T^SG^SC^SG^SA^SG^SC^ST^SC^SC^SC^SC^SG^ST^SA^SC^SC^ST^SC^SC$ | 16 |
| 10888 | 0011-0026; 5'-UTR | $A^SG^SC^ST^SC^SC^SC^SC^SG^ST^SA^SC^SC^ST^SC^SC$ | 83 |
| 10889 | 0015-0030; 5'-UTR | $T^SG^SC^SG^SA^SG^SC^ST^SC^SC^SC^SC^SG^ST^SA^SC$ | 84 |
| 10991 | 0015-0024; 5'-UTR | $C^ST^SC^SC^SC^SC^SG^ST^SA^SC$ | 85 |
| 10992 | 0015-0025; 5'-UTR | $G^SC^ST^SC^SC^SC^SC^SG^ST^SA^SC$ | 86 |
| 10993 | 0015-0026; 5'-UTR | $A^SG^SC^ST^SC^SC^SC^SC^SG^ST^SA^SC$ | 87 |
| 10994 | 0015-0027; 5'-UTR | $G^SA^SG^SC^ST^SC^SC^SC^SC^SG^ST^SA^SC$ | 88 |
| 10995 | 0015-0028; 5'-UTR | $C^SG^SA^SG^SC^ST^SC^SC^SC^SC^SG^ST^SA^SC$ | 89 |
| 10996 | 0015-0029; 5'-UTR | $G^SC^SG^SA^SG^SC^ST^SC^SC^SC^SC^SG^ST^SA^SC$ | 90 |
| 11232 | 0017-0029; 5' UTR | $G^SC^SG^SA^SG^SC^ST^SC^SC^SC^SC^SG^ST$ | 91 |
| | # 10996 Derivatives: | | |
| 10996 | 0015-0029; 5'-UTR | $G^SC^SG^SA^SG^SC^ST^SC^SC^SC^SC^SG^ST^SA^SC$ | 90 |
| 11806 | (scrambled # 10996) | $G^SC^SC^SG^SC^SC^SG^SC^SC^SA^SA^SG^ST^SC^ST$ | 92 |
| 11539 | (fully 2'MO # 10996) | G$^S$C$^S$G$^S$A$^S$G$^S$C$^S$T$^S$C$^S$C$^S$C$^S$C$^S$G$^S$T$^S$A$^S$C (2'MO) | 90 |
| 11540 | (control for # 11539) | G$^S$C$^S$C$^S$G$^S$C$^S$C$^S$G$^S$C$^S$C$^S$A$^S$A$^S$G$^S$T$^S$C$^S$T (2'MO) | 92 |
| 11541 | (# 10996 7-base "gapmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11542 | (control for # 11541) | G$^S$C$^S$C$^S$G$^S$C$^S$C$^S$G$^S$C$^S$C$^S$A$^S$A$^S$G$^S$T$^S$C$^S$T (2'MO) | 92 |
| 11543 | (# 10996 9-base "gapmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11544 | (control for # 11543) | G$^S$C$^S$C$^S$G$^S$C$^S$C$^S$G$^S$C$^S$C$^S$A$^S$A$^S$G$^S$T$^S$C$^S$T (2'MO) | 92 |
| 11545 | (# 10996 5' "wingmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11546 | (control for # 11545) | G$^S$C$^S$C$^S$G$^S$C$^S$C$^S$G$^S$C$^S$C$^S$A$^S$A$^S$G$^S$T$^S$C$^S$T (2'MO) | 92 |
| 11547 | (# 10996 3' "wingmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11548 | (control for # 11547) | G$^S$C$^S$C$^S$G$^S$C$^S$C$^S$G$^S$C$^S$C$^S$A$^S$A$^S$G$^S$T$^S$C$^S$T (2'MO) | 92 |
| 12496 | ((2'-5')A₄ # 10996) | GCGAGCTCCCCGTAC | 90 |
| 13107 | ((2'-5')A₄ # 10996) | $G^SC^SG^SA^SG^SC^ST^SC^SC^SC^SC^SG^ST^SA^SC$ | 90 |
| 12492 | ((2'-5')A₄ # 10996) | G$^S$C$^S$G$^S$A$^S$G$^S$C$^S$T$^S$C$^S$C$^S$C$^S$C$^S$G$^S$T$^S$A$^S$C (2'MO) | 90 |
| 12495 | ((2'-5')A₄ # 10996) | G$^S$C$^S$G$^S$A$^S$G$^S$C$^S$T$^S$C$^S$C$^S$C$^S$C$^S$G$^S$T$^S$A$^S$C (2'MO) | 90 |
| 12887 | (1-24 of SEQ ID NO:1 of WO 95/03408; alternative mRNA) | G$^S$A$^S$G$^S$A$^S$G$^S$C$^S$A$^S$A$^S$A$^S$G$^S$C$^S$T$^S$T$^S$T$^S$C$^S$A$^S$C$^S$C$^S$C$^S$T$^S$G$^S$T$^S$G (2'MO) | 93 |
| 12888 | (1-22 of SEQ ID NO:1 of WO 95/03408; alternative mRNA) | G$^S$A$^S$G$^S$C$^S$A$^S$A$^S$A$^S$G$^S$C$^S$T$^S$T$^S$T$^S$C$^S$A$^S$C$^S$C$^S$C$^S$T$^S$G$^S$T$^S$G (2'MO) | 94 |
| 12889 | (1-19 of SEQ ID NO:1 of WO 95/03408; alternative mRNA) | G$^S$C$^S$A$^S$A$^S$A$^S$G$^S$C$^S$T$^S$T$^S$T$^S$C$^S$A$^S$C$^S$C$^S$C$^S$T$^S$G$^S$T$^S$G (2'MO) | 95 |
| 12890 | 0001-0024 | C$^S$T$^S$C$^S$C$^S$C$^S$G$^S$T$^S$A$^S$C$^S$C$^S$T$^S$C$^S$C$^S$T$^S$A$^S$A$^S$G$^S$G$^S$C$^S$T$^S$C$^S$C$^S$T (2'MO) | 96 |
| 12891 | 0001-0022 | C$^S$C$^S$C$^S$C$^S$G$^S$T$^S$A$^S$C$^S$C$^S$T$^S$C$^S$C$^S$T$^S$A$^S$A$^S$G$^S$G$^S$C$^S$T$^S$C$^S$C$^S$T (2'MO) | 97 |
| 12892 | 0001-0020 | C$^S$C$^S$G$^S$T$^S$A$^S$C$^S$C$^S$T$^S$C$^S$C$^S$T$^S$A$^S$A$^S$G$^S$G$^S$C$^S$T$^S$C$^S$C (2'MO) | 98 |

TABLE 4

Sequences of Oligonucleotides Targeted to Murine B7-2 mRNA

| ISIS # | Target Position; Site | Oligonucleotide Sequence (5'->3') | SEQ ID NO: |
|---|---|---|---|
| 11347 | 1094-1113; 3' UTR | $A^SG^SA^SA^ST^ST^SC^SC^SA^SA^ST^SC^SA^SG^SC^ST^SG^SA^SG^SA$ | 121 |
| 11348 | 1062-1081; 3' UTR | $T^SC^ST^SG^SA^SG^SA^SA^SA^SC^ST^SC^ST^SG^SC^SA^SC^ST^ST^SC$ | 122 |
| 11349 | 1012-1031; 3' UTR | $T^SC^SC^ST^SC^SA^SG^SG^SC^ST^SC^ST^SC^SA^SC^ST^SG^SC^SC^ST$ | 123 |
| 11350 | 0019-1138; 5' UTR | $G^SG^ST^ST^SG^ST^ST^SC^SA^SA^SG^ST^SC^SC^SG^ST^SG^SC^ST^SG$ | 124 |
| 11351 | 0037-0056; 5' UTR | $A^SC^SA^SC^SG^ST^SC^ST^SA^SC^SA^SG^SG^SA^SG^ST^SC^ST^SG^SG$ | 103 |
| 11352 | 0089-0108; tIR | $C^SA^SG^SC^SC^SC^SA^ST^SG^SG^ST^SG^SC^SA^ST^SC^ST^SG^SG$ | 104 |
| 11353 | 0073-0092; tIR | $C^ST^SG^SG^SG^SG^ST^SC^SC^SA^ST^SC^SG^ST^SG^SG^SG^ST^SG^SC$ | 105 |

TABLE 4-continued

Sequences of Oligonucleotides Targeted to Murine B7-2 mRNA

| ISIS # | Target Position; Site | Oligonucleotide Sequence (5'->3') | SEQ ID NO: |
|---|---|---|---|
| 11354 | 0007-0026; 5' UTR | $C^SC^SG^ST^SG^SC^ST^SG^SC^SC^ST^SA^SC^SA^SG^SG^SA^SG^SC^SC$ | 106 |
| 11695 | 0058-0077; 5' UTR | $G^SG^ST^SG^SC^ST^ST^SC^SC^SG^ST^SA^SA^SG^ST^ST^SC^ST^SG^SG$ | 107 |
| 11696 | 0096-0117; tIR | $G^SG^SA^ST^ST^SG^SC^SC^SA^SA^SG^SC^SC^SC^SA^ST^SG^SG^ST^SG$ | 108 |
| 11866 | (scrambled # 11696) | $C^ST^SA^SA^SG^ST^SA^SG^ST^SG^SC^ST^SA^SG^SC^SC^SG^SG^SG^SA$ | 109 |
| 11697 | 0148-0167; 5' ORF | $T^SG^SC^SG^ST^SC^ST^SC^SC^SA^SC^SG^SG^SA^SA^SA^SC^SA^SG^SC$ | 110 |
| 11698 | 0319-0338; 5' ORF | $G^ST^SG^SC^SG^SG^SC^SC^SC^SA^SG^SG^ST^SA^SC^ST^ST^SG^SG^SC$ | 111 |
| 11699 | 0832-0851; 3' ORF | $A^SC^SA^SA^SG^SG^SA^SG^SG^SA^SG^SG^SG^SC^SC^SA^SC^SA^SG^ST$ | 112 |
| 11700 | 0753-0772; 3' ORF | $T^SG^SA^SG^SA^SG^SG^ST^ST^ST^SG^SG^SA^SG^SG^SA^SA^SA^ST^SC$ | 113 |
| 11701 | 0938-0957; 3' ORF | $G^SA^ST^SA^SG^ST^SC^ST^SC^ST^SC^ST^SG^ST^SC^SA^SG^SC^SG^ST$ | 114 |
| 11702 | 0890-0909; 3' ORF | $G^ST^ST^SG^SC^ST^SG^SG^SG^SC^SC^ST^SG^SC^ST^SA^SG^SG^SC^ST$ | 115 |
| 11865 | (scrambled # 11702) | $C^ST^SA^SG^SG^ST^SC^ST^SC^SG^ST^SC^SG^ST^SC^SG^SG^ST^SG^SG$ | 116 |
| 11703 | 1003-1022; tTR | $T^SC^ST^SC^SA^SC^ST^SG^SC^SC^ST^ST^SC^SA^SC^ST^SC^ST^SG^SC$ | 117 |
| 13100 | Exon 1 (Borriello et al., J. Immun., 1995, 155, 5490; 5' UTR of alternative mRNA) | $G^ST^SA^SC^SC^SA^SG^SA^ST^SG^SA^SA^SG^SG^ST^ST^SA^ST^SC^SA$ $^SA$(2'MO) | 118 |
| 13101 | Exon 4 (Borriello et al.; 5' UTR of alternative mRNA) | $C^ST^ST^ST^SG^SG^SA^SG^SA^ST^ST^SA^ST^ST^SC^SG^SA^SG^ST^ST$ (2'MO) | 119 |
| 13102 | Exon 5 (Borriello et al.; 5' UTR of alternative mRNA) | $G^SC^SA^SA^SG^ST^SG^ST^SA^SA^SA^SG^SC^SC^SC^ST^SG^SA^SG^ST$ (2'MO) | 120 | cDNA Clones:

A cDNA encoding the sequence for human B7-1 was isolated by using the reverse transcription/polymerase chain reaction (RT-PCR). Poly A+ RNA from Daudi cells (ATCC accession No. CCL 213) was reverse transcribed using oligo-dT primer under standard conditions. Following a 30 minute reaction at 42° C. and heat inactivation, the reaction mixture (20 µL) was brought to 100 µL with water. A 10 µL aliquot from the RT reaction was then amplified in a 50 µL PCR reaction using the 5' primer,

```
the 5' primer,
5'-GAT-CAG-GGT-ACC-CCA-AAG-AAA-AAG-TGA-TTT-GTC-
ATT-GC-3' (sense, SEQ ID NO: 20), and the 3' primer,
5'-GAT-AGC-CTC-GAG-GAT-AAT-GAA-TTG-GCT-GAC-AAG-
AC-3' (antisense, SEQ ID NO: 21)
```

The primers included unique restriction sites for subcloning of the PCR product into the vector pcDNA-3 (Invitrogen, San Diego, Calif.). The 5' primer was designed to have identity with bases 1 to 26 of the published human B7-1 sequence (Freeman et al., J. Immunol., 1989, 143, 2714; positions 13-38 of the primer) and includes a Kpn I restriction site (positions 7-12 of the primer) for use in cloning. The 3' primer was designed to be complementary to bases 1450 to 1471 of the published sequence for B7-1 (positions 14-35 of the primer) and includes a Xho I restriction site (positions 7-12 of the primer). Following PCR, the reaction was extracted with phenol and precipitated using ethanol. The product was digested with the appropriate restriction enzymes and the full-length fragment purified by agarose gel and ligated into the vector pcDNA-3 (Invitrogen, San Diego, Calif.) prepared by digesting with the same enzymes. The resultant construct, pcB7-1, was confirmed by restriction mapping and DNA sequence analysis using standard procedures. A mouse B7-1 clone, pcmB7-1, was isolated in a similar manner by RT-PCR of RNA isolated from a murine B-lymphocyte cell line, 70Z3.

A cDNA encoding the sequence for human B7-2, position 1 to 1391, was also isolated by RT-PCR. Poly A+ RNA from Daudi cells (ATCC accession No. CCL 213) was reverse transcribed using oligo-dT primer under standard conditions. Following a 30 minute reaction at 42° C. and heat inactivation, the reaction mixture (20 µL) was brought to 100 µL with water. A 10 µL aliquot from the RT reaction was then amplified in a 50 µL PCR reaction using

```
the 5' primer,
5'-GAT-CAG-GGT-ACC-AGG-AGC-CTT-AGG-AGG-TAC-GG-3'
(sense, SEQ ID NO: 1), and the 3' primer,
5'-GAT-AGC-CTC-GAG-TTA-TTT-CCA-GGT-CAT-GAG-CCA-3'
(antisense, SEQ ID NO: 2).
```

The 5' primer was designed to have identity with bases 1-20 of the published B7-2 sequence (Azuma et al., Nature, 1993, 366, 76 and Genbank Accession No. L25259; positions 13-32 of the primer) and includes a Kpn I site (positions 7-12 of the primer) for use in cloning. The 3' primer was designed to have complementarity to bases 1370-1391 of the published sequence for B7-2 (positions 13-33 of the primer) and includes an Xho I restriction site (positions 7-12 of the primer). Following PCR, the reaction was extracted with phenol and precipitated using ethanol. The product was digested with Xho I and Kpn I, and the full-length fragment purified by agarose gel and ligated into the vector pcDNA-3 (Invitrogen, San Diego, Calif.) prepared by digesting with the same enzymes. The resultant construct, pcB7-2, was confirmed by restriction mapping and DNA sequence analysis using standard procedures.

A mouse B7-2 clone, pcmB7-2, was isolated in a similar manner by RT-PCR of RNA isolated from P388D1 cells using the 5' primer,

```
the 5' primer,
5'-GAT-CAG-GGT-ACC-AAG-AGT-GGC-TCC-TGT-AGG-CA
(sense, SEQ ID NO: 99), and the 3' primer,
5'-GAT-AGC-CTC-GAG-GTA-GAA-TTC-CAA-TCA-GCT-GA
(antisense, SEQ ID NO: 100).
```

The 5' primer has identity with bases 1-20, whereas the 3' primer is complementary to bases 1096-1115, of the published murine B7-2 sequence (Chen et al., *J. Immun.*, 1994, 152, 4929). Both primers incorporate the respective restriction enzyme sites found in the other 5' and 3' primers used to prepare cDNA clones. The RT-PCR product was restricted with Xho I and Kpn I and ligated into pcDNA-3 (Invitrogen, Carlsbad, Calif.).

Other cDNA clones, corresponding to mRNAs resulting from alternative splicing events, are cloned in like fashion, using primers containing the appropriate restriction sites and having identity with (5' primers), or complementarity to (3' primers), the selected B7 mRNA.

Example 2

Modulation of hB7-1 Expression by Oligonucleotides

The ability of oligonucleotides to inhibit B7-1 expression was evaluated by measuring the cell surface expression of B7-1 in transfected COS-7 cells by flow cytometry.
Methods:
A T-175 flask was seeded at 75% confluency with COS-7 cells (ATCC accession No. CRL 1651). The plasmid pcB7-1 was introduced into cells by standard calcium phosphate transfection. Following a 4 hour transfection, the cells were trypsinized and seeded in 12-well dishes at 80% confluency. The cells were allowed to adhere to the plastic for 1 hour and were then washed with phosphate-buffered saline (PBS). OptiMEM™ (GIBCO-BRL, Gaithersburg, Md.) medium was added along with 15 µg/mL of Lipofectin™ (GIBCO-BRL, Gaithersburg, Md.) and oligonucleotide at the indicated concentrations. After four additional hours, the cells were washed with phosphate buffered saline (PBS) and incubated with fresh oligonucleotide at the same concentration in DMEM (Dulbecco et al., *Virol.*, 1959, 8, 396; Smith et al., *Virol.*, 1960, 12, 185) with 10% fetal calf sera (FCS).

In order to monitor the effects of oligonucleotides on cell surface expression of B7-1, treated COS-7 cells were harvested by brief trypsinization 24-48 hours after oligonucleotide treatment. The cells were washed with PBS, then resuspended in 100 µL of staining buffer (PBS, 0.2% BSA, 0.1% azide) with 5 µL conjugated anti-B7-1-antibody (i.e., anti-hCD80-FITC, Ancell, Bayport, Minn.; FITC: fluorescein isothiocyanate). The cells were stained for 30 minutes at 4° C., washed with PBS, resuspended in 300 µL containing 0.5% paraformaldehyde. Cells were harvested and the fluorescence profiles were determined using a flow cytometer.
Results:
The oligonucleotides shown in Table 1 were evaluated, in COS-7 cells transiently expressing B7-1 cDNA, for their ability to inhibit B7-1 expression. The results (FIG. 1) identified ISIS 13805, targeted to the translation initiation codon region, and ISIS 13812, targeted to the 3' untranslated region (UTR), as the most active oligonucleotides with greater than 50% inhibition of B7-1 expression. These oligonucleotides are thus highly preferred. ISIS 13799 (targeted to the 5' untranslated region), ISIS 13802 (targeted to the 5' untranslated region), ISIS 13806 and 13807 (both targeted to the 5' region of the ORF), and ISIS 13810 (targeted to the central portion of the ORF) demonstrated 35% to 50% inhibition of B7-1 expression. These sequences are therefore also preferred. Oligonucleotide ISIS 13800, which showed essentially no inhibition of B7-1 expression in the flow cytometry assay, and ISIS Nos. 13805 and 13812 were then evaluated for their ability to inhibit cell surface expression of B7-1 at various concentrations of oligonucleotide. The results of these assays are shown in FIG. 2. ISIS 13812 was a superior inhibitor of B7-1 expression with an $IC_{50}$ of approximately 150 nM. ISIS 13800, targeted to the 5' UTR, was essentially inactive.

Example 3

Modulation of hB7-2 Protein by Oligonucleotides

Figure 3:
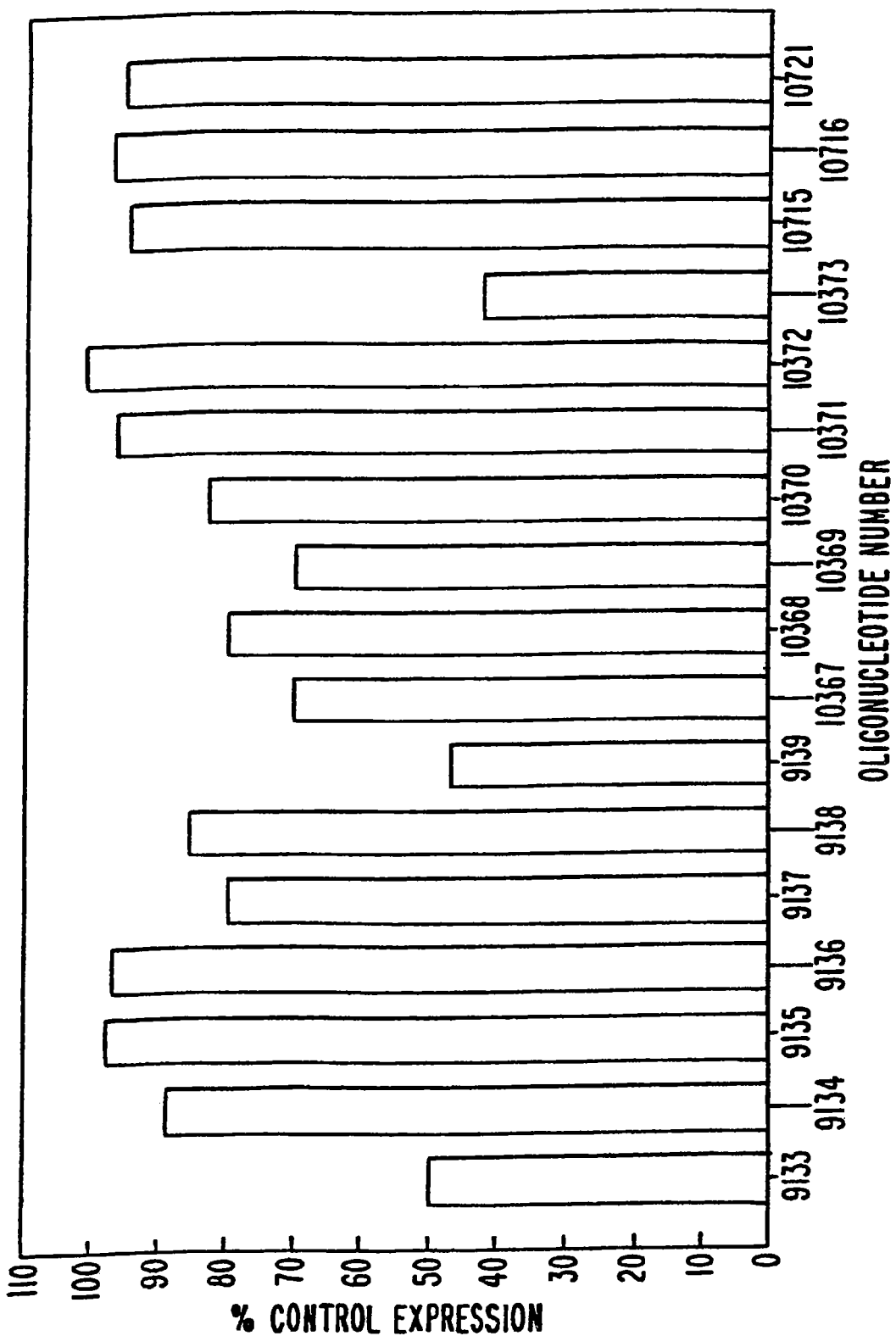
FIG. 3 is a bar graph showing the inhibitory effect of the indicated oligonucleotides on cell surface expression of B7-2 in COS-7 cells.

In an initial screen, the ability of hB7-2 oligonucleotides to inhibit B7-2 expression was evaluated by measuring the cell surface expression of B7-2 in transfected COS-7 cells by flow cytometry. The methods used were similar to those given in Example 2, with the exceptions that (1) COS-7 cells were transfected with the plasmids pbcB7-2 or BBG-58, a human ICAM-1 (CD54) expression vector (R&D Systems, Minneapolis, Minn.) introduced into cells by standard calcium phosphate transfection, (2) the oligonucleotides used were those described in Table 2, and (3) a conjugated anti-B7-2 antibody (i.e., anti-hCD86-FITC or anti-CD86-PE, PharMingen, San Diego, Calif.; PE: phycoerythrin) was used during flow cytometry.
Results:
The results are shown in FIG. 3. At a concentration of 200 nM, ISIS 9133, ISIS 9139 and ISIS 10373 exhibited inhibitory activity of 50% or better and are therefore highly preferred. These oligonucleotides are targeted to the 3' untranslated region (ISIS 9133), the translation initiation codon region (ISIS 9139) and the 5' untranslated region (ISIS 10373). At the same concentration, ISIS 10715, ISIS 10716 and ISIS 10721, which are scrambled controls for ISIS 9133, ISIS 9139 and ISIS 10373, respectively, showed no inhibitory activity. Treatment with ISIS 10367 and ISIS 10369 resulted in greater than 25% inhibition, and these oligonucleotides are thus also preferred. These oligonucleotides are targeted to the 5' (ISIS 10367) and 3' (ISIS 10369) untranslated regions.

Example 4

Modulation of hB7-2 mRNA by Oligonucleotides

Methods:
For ribonuclease protection assays, cells were harvested 18 hours after completion of oligonucleotide treatment using a Totally RNA™ kit (Ambion, Austin, Tex.). The probes for the assay were generated from plasmids pcB7-2 (linearized by digestion with Bgl II) and pTRI-b-actin (Ambion Inc., Austin, Tex.). In vitro transcription of the linearized plasmid from the SP6 promoter was performed in the presence of $\alpha\text{-}^{32}\text{P-UTP}$ (800 Ci/mmole) yielding an antisense RNA complementary to the 3' end of B7-2 (position 1044-1391). The probe was gel-purified after treatment with DNase I to remove DNA template. Ribonuclease protection assays were carried out using an RPA II™ kit (Ambion) according to the manufacturer's directions. Total RNA (5 μg) was hybridized overnight, at 42° C., with $10^5$ cpm of the B7-2 probe or a control beta-actin probe. The hybridization reaction was then treated, at 37° C. for 30 minutes, with 0.4 units of RNase A and 2 units of RNase T1. Protected RNA was precipitated, resuspended in 10 μL of gel loading buffer and electrophoresed on a 6% acrylamide gel with 50% w/v urea at 20 W. The gel was then exposed and the lanes quantitated using a PhosphorImager (Molecular Dynamics, Sunnyvale, Calif.) essentially according to the manufacturer's instructions.

Results:

The extent of oligonucleotide-mediated hB7-2 mRNA modulation generally paralleled the effects seen for hB7-2 protein (Table 5). As with the protein expression (flow cytometry) assays, the most active oligonucleotides were ISIS 9133, ISIS 9139 and 10373. None of the oligonucleotides tested had an inhibitory effect on the expression of b-actin mRNA in the same cells.

TABLE 5

Activities of Oligonucleotides Targeted to hB7-2 mRNA

| ISIS NO. | SEQ ID NO. | % Control Protein | % Control RNA Expression |
|---|---|---|---|
| 9133 | 3 | 70.2 | 46.0 |
| 9134 | 4 | 88.8 | 94.5 |
| 9135 | 5 | 98.2 | 83.4 |
| 9136 | 6 | 97.1 | 103.1 |
| 9137 | 7 | 80.5 | 78.1 |
| 9138 | 8 | 86.4 | 65.9 |
| 9139 | 9 | 47.9 | 32.6 |
| 10367 | 10 | 71.3 | 52.5 |
| 10368 | 11 | 81.0 | 84.5 |
| 10369 | 12 | 71.3 | 81.5 |
| 10370 | 13 | 84.3 | 83.2 |
| 10371 | 14 | 97.3 | 92.9 |
| 10372 | 15 | 101.7 | 82.5 |
| 10373 | 16 | 43.5 | 32.7 |

Example 5

Additional hB7-1 and hB7-2 Oligonucleotides

Figure 4:
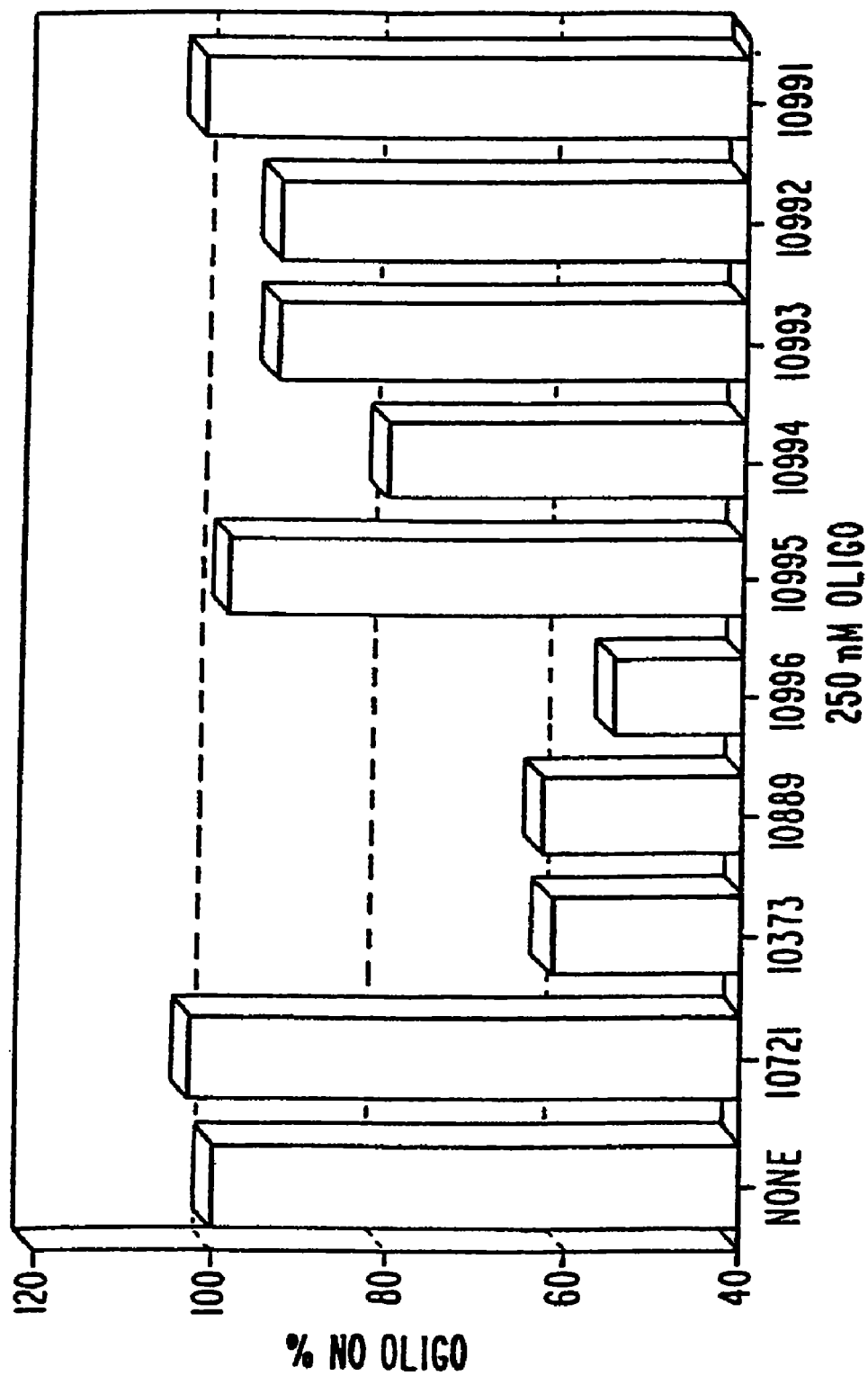
FIG. 4 is a bar graph showing the inhibitory effect of the indicated oligonucleotides, including ISIS 10373 (a 20-mer) and ISIS 10996 (a 15-mer) on cell surface expression of B7-2 in COS-7 cells.

Oligonucleotides having structures and/or sequences that were modified relative to the oligonucleotides identified during the initial screening were prepared. These oligonucleotides were evaluated for their ability to modulate human B7-2 expression using the methods described in the previous examples. ISIS 10996, an oligonucleotide having a 15 nucleotide sequence derived from the 20 nucleotide sequence of ISIS 10373, was also prepared and evaluated. ISIS 10996 comprises 15 nucleotides, 5'-GCG-AGC-TCC-CCG-TAC (SEQ ID NO: 90) contained within the sequence of ISIS 10373. Both ISIS 10373 and 10996 overlap a potential stem-loop structure located within the B7-2 message comprising bases 1-67 of the sequence of hB7-2 presented by Azuma et al. (Nature, 1993, 366, 76). While not intending to be bound be any particular theory regarding their mode(s) of action, ISIS 10373 and ISIS 10996 have the potential to bind as loop 1 pseudo-half-knots at a secondary structure within the target RNA. U.S. Pat. No. 5,5152,438, the contents of which are hereby incorporated by reference, describes methods for modulating gene expression by the formation of pseudo-half-knots. Regardless of their mode(s) of action, despite having a shorter length than ISIS 10373, the 15-mer ISIS 10886 is as (or more) active in the B7-2 protein expression assay than the 20-mer from which it is derived (FIG. 4; ISIS 10721 is a scrambled control for ISIS 10373). A related 16-mer, ISIS 10998, was also active in the B7-2 protein expression assay. However, a structurally related 14-mer (ISIS 10995), 13-mer (ISIS 10994), 12-mer (ISIS 10993), 11-mer (ISIS 10992) and 10-mer (ISIS 10991) exhibited little or no activity in this assay. ISIS 10996 was further derivatized in the following ways.

ISIS 10996 derivatives having 2' methoxyethoxy substitutions were prepared, including a fully substituted derivative (ISIS 11539), "gapmers" (ISIS 11541 and 11543) and "wingmers" (ISIS 11545 and 11547). As explained in Example 5, the 2' methoxyethoxy substitution prevents the action of some nucleases (e.g., RNase H) but enhances the affinity of the modified oligonucleotide for its target RNA molecule. These oligonucleotides are tested for their ability to modulate hB7-2 message or function according to the methods of Examples 3, 4, 7 and 8.

ISIS 10996 derivatives were prepared in order to be evaluated for their ability to recruit RNase L to a target RNA molecule, e.g., hB7-2 message. RNase L binds to, and is activated by, $(2'\text{-}5')(A)_n$, which is in turn produced from ATP by $(2'\text{-}5')(A)_n$ synthetase upon activation by, e.g., interferon. RNase L has been implicated in antiviral mechanisms and in the regulation of cell growth as well (Sawai, Chemica Scripta, 1986, 21, 169; Charachon et al., Biochemistry, 1990, 29, 2550). The combination of anti-B7 oligonucleotides conjugated to $(2'\text{-}5')(A)_n$, is expected to result in the activation of RNase L and its targeting to the B7 message complementary to the oligonucleotide sequence. The following oligonucleotides have identical sequences (i.e., that of ISIS 10996) and identical $(2'\text{-}5')(A)_4$ "caps" on their 5' termini: ISIS 12492, 12495, 12496 and 13107. The adenosyl residues have 3' hydroxyl groups and are linked to each other by phosphorothioate linkages. The (3'-5') portion of the oligonucleotide, which has a sequence complementary to a portion of the human B7-2 RNA, is conjugated to the $(2'\text{-}5')(A)_4$ "cap" via a phosphorothioate linkage from the 5' residue of the (3'-5') portion of the oligonucleotide to an n-aminohexyl linker which is bonded to the "cap" via another phosphorothioate linkage. In order to test a variety of chemically diverse oligonucleotides of this type for their ability to recruit RNase L to a specific message, different chemical modifications were made to this set of four oligonucleotides as follows. ISIS 12496 consists of unmodified oligonucleotides in the (3'-5') portion of the oligonucleotide. In ISIS 13107, phosphorothioate linkages replace the phosphate linkages found in naturally occurring nucleic acids. Phosphorothioate linkages are also employed in ISIS 12492 and 12495, which additionally have 2'-methoxyethoxy substitutions. These oligonucleotides are tested for their ability to modulate hB7-2 message or function according to the methods of Examples 3, 4, 7 and 8.

Derivatives of ISIS 10996 having modifications at the 2' position were prepared and evaluated. The modified oligonucleotides included ISIS 11539 (fully 2'-O-methyl), ISIS 11541 (having 2'-O-methyl wings and a central 7-base gap), ISIS 11543 (2'-O-methyl wings with a 9-base gap), ISIS 11545 (having a 5'2'-O-methyl wing) and ISIS 11547 (having a 3'2'-O-methyl wing). The results of assays of 2'-O-methyl oligonucleotides were as follows. ISIS 11539, the fully 2'O-methyl version of ISIS 10996, was not active at all in the protein expression assay. The gapped and winged oligonucleotides (ISIS 11541, 11543, 11545 and 11547) each showed some activity at 200 nM (i.e., from 60 to 70% expression relative to untreated cells), but less than that demonstrated by the parent compound, ISIS 10996 (i.e., about 50% expression). Similar results were seen in RNA expression assays.

ISIS 10782, a derivative of ISIS 10373 to which cholesterol has been conjugated via a 5' n-aminohexyl linker, was prepared. Lipophilic moieties such as cholesterol have been reported to enhance the uptake by cells of oligonucleotides in some instances, although the extent to which uptake is enhanced, if any, remains unpredictable. ISIS 10782, and other oligonucleotides comprising lipophilic moieties, are tested for their ability to modulate B7-2 message or function according to the methods of Examples 3, 4, 7 and 8.

A series of 2'-methoxyethoxy (herein, "2'ME") and 2'-fluoride (herein, "2'F") "gapmer" derivatives of the hB7-1 oligonucleotides ISIS 12361 (ISIS Nos. 12348 and 12473, respectively), ISIS 12362 (ISIS Nos. 12349 and 12474), ISIS 12363 (ISIS Nos. 12350 and 12475), ISIS 12364 (ISIS Nos. 12351 and 12476), ISIS 12365 (ISIS Nos. 12352 and 12477), ISIS 12366 (ISIS Nos. 12353 and 12478), ISIS 12367 (ISIS Nos. 12354 and 12479), ISIS 12368 (ISIS Nos. 12355 and 12480), ISIS 12369 (ISIS Nos. 12356 and 12481) and ISIS 12370 (ISIS Nos. 12357 and 12482) were prepared. The central, non-2'-modified portions ("gaps") of these derivatives support RNase H activity when the oligonucleotide is bound to its target RNA, even though the 2'-modified portions do not. However, the 2'-modified "wings" of these oligonucleotides enhance their affinity to their target RNA molecules (Cook, Chapter 9 In: Antisense Research and Applications, Crooke et al., eds., CRC Press, Boca Raton, 1993, pp. 171-172).

Another 2' modification is the introduction of a methoxy (MO) group at this position. Like 2'ME- and 2'F-modified oligonucleotides, this modification prevents the action of RNase H on duplexes formed from such oligonucleotides and their target RNA molecules, but enhances the affinity of an oligonucleotide for its target RNA molecule. ISIS 12914 and 12915 comprise sequences complementary to the 5' untranslated region of alternative hB7-1 mRNA molecules, which arise from alternative splicing events of the primary hB7-1 transcript. These oligonucleotides include 2' methoxy modifications, and the enhanced target affinity resulting therefrom may allow for greater activity against alternatively spliced B7-1 mRNA molecules which may be present in low abundance in some tissues (Inobe et al., J. Immun., 1996, 157, 582). Similarly, ISIS 13498 and 13499, which comprise antisense sequences to other alternative hB7-1 mRNAs, include 2' methoxyethoxy modifications in order to enhance their affinity for their target molecules, and 2' methoxyethoxy or 2'methoxy substitutions are incorporated into the hB7-2 oligonucleotides ISIS 12912, 12913, 13496 and 13497. These oligonucleotides are tested for their ability to modulate hB7-1 essentially according to the methods of Example 2 or hB7-2 according to the methods of Examples 3, 4, 7 and 8, with the exception that, when necessary, the target cells are transfected with a cDNA clone corresponding to the appropriate alternatively spliced B7 transcript.

Example 6

Specificity of Antisense Modulation

Figure 5:
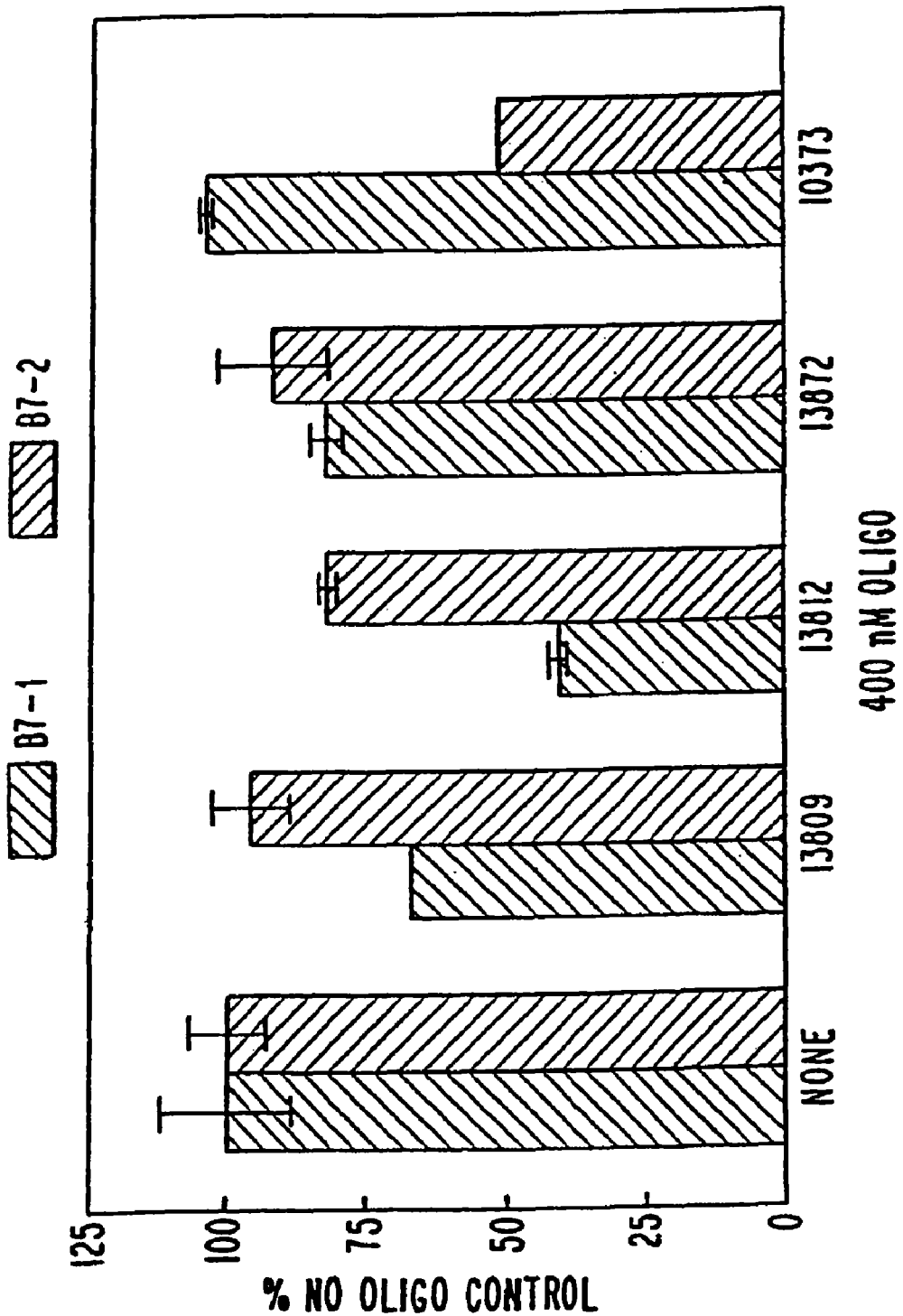
FIG. 5 is a bar graph showing the specificity of inhibition of B7-1 or B7-2 protein expression by oligonucleotides. Cross-hatched bars, B7-1 levels; striped bars, B7-2 levels.

Several oligonucleotides of the invention were evaluated in a cell surface expression flow cytometry assay to determine the specificity of the oligonucleotides for B7-1 as contrasted with activity against B7-2. The oligonucleotides tested in this assay included ISIS 13812, an inhibitor of B7-1 expression (FIG. 1; Example 2) and ISIS 10373, an inhibitor of B7-2 expression (FIG. 3; Example 3). The results of this assay are shown in FIG. 5. ISIS 13812 inhibits B7-1 expression with little or no effect on B7-2 expression. As is also seen in FIG. 5, ISIS 10373 inhibits B7-2 expression with little or no effect on B7-1 expression. ISIS 13872 (SEQ ID NO: 37, AGT-CCT-ACT-ACC-AGC-CGC-CT), a scrambled control of ISIS 13812, and ISIS 13809 (SEQ ID NO: 51) were included in these assays and demonstrated essentially no activity against either B7-1 or B7-2.

Example 7

Modulation of hB7-2 Expression by Oligonucleotides in Antigen Presenting Cells

The ability of ISIS 10373 to inhibit expression from the native B7-2 gene in antigen presenting cells (APCs) was evaluated as follows.

Methods:

Monocytes were cultured and treated with oligonucleotides as follows. For dendritic cells, EDTA-treated blood was layered onto Polymorphprep™ (1.113 g/mL; Nycomed, Oslo, Norway) and sedimented at 500×g for 30 minutes at 20° C. Mononuclear cells were harvested from the interface. Cells were washed with PBS, with serum-free RPMI media (Moore et al., N.Y. J. Med., 1968, 68, 2054) and then with RPMI containing 5% fetal bovine serum (FBS). Monocytes were selected by adherence to plastic cell culture cell culture dishes for 1 h at 37° C. After adherence, cells were treated with oligonucleotides in serum-free RPMI containing Lipofectin™ (8 µg/mL). After 4 hours, the cells were washed. Then RPMI containing 5% FBS and oligonucleotide was added to cells along with interleukin-4 (IL-4; R&D Systems, Minneapolis, Minn.) (66 ng/mL) and granulocyte-macrophage colony-stimulating factor (GM-CSF; R&D Systems, Minneapolis, Minn.) (66 ng/mL) to stimulate differentiation (Romani et al., J. Exp. Med., 1994, 180, 83, 1994). Cells were incubated for 48 hours, after which cell surface expression of various molecules was measured by flow cytometry.

Mononuclear cells isolated from fresh blood were treated with oligonucleotide in the presence of cationic lipid to promote cellular uptake. As a control oligonucleotide, ISIS 2302 (an inhibitor of ICAM-1 expression; SEQ ID NO: 17) was also administered to the cells. Expression of B7-2 protein was measured by flow cytometry according to the methods of Example 2. Monoclonal antibodies not described in the previous Examples included anti-hCD3 (Ancell, Bayport, Minn.) and anti-HLA-DR (Becton Dickinson, San Jose, Calif.).

Figure 6:
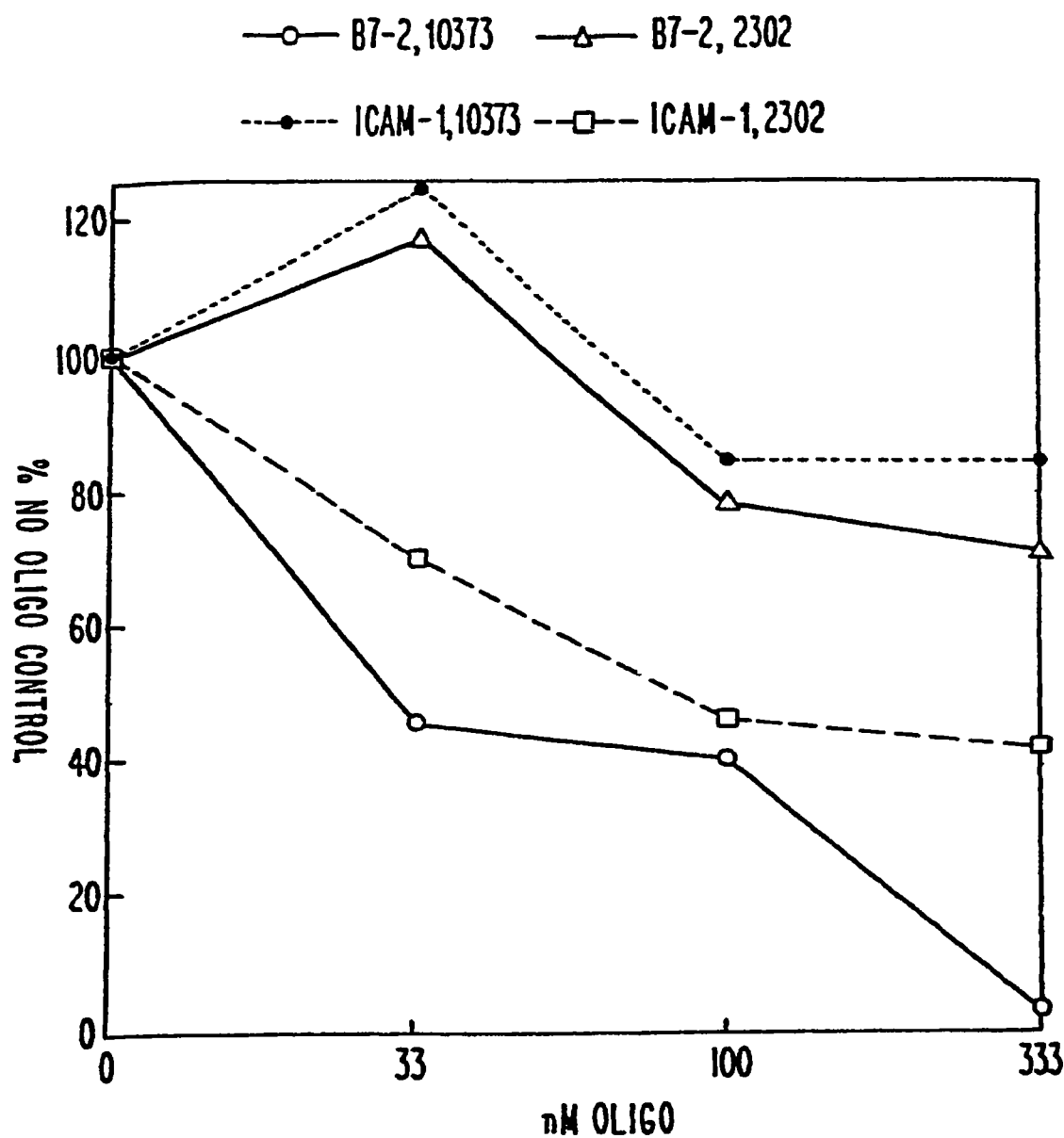
FIG. 6 is a dose-response curve showing the inhibitory effect of oligonucleotides having antisense sequences to ICAM-1 (ISIS 2302) or B7-2 (ISIS 10373) on cell surface expression of the ICAM-1 and B7-2 proteins. Solid line with X's, levels of B7-1 protein on cells treated with ISIS 10373; dashed line with asterisks, levels of ICAM-1 protein on cells treated with ISIS 10373; solid line with triangles, levels of B7-1 protein on cells treated with ISIS 2302; solid line with squares, levels of ICAM-1 protein on cells treated with ISIS 10373.

Results:

As shown in FIG. 6, ISIS 10373 has a significant inhibitory effect on B7-2 expression with an $IC_{50}$ of approximately 250 nM. ISIS 10373 had only a slight effect on ICAM-1 expression even at a dose of 1 µM. ISIS 2302 (SEQ ID NO: 17), a control oligonucleotide which has been shown to inhibit ICAM-1 expression, had no effect on B7-2 expression, but significantly decreased ICAM-1 levels with an $IC_{50}$ of approximately 250 nM. Under similar conditions, ISIS 10373 did not affect the cell surface expression of B7-1, HLA-DR or CD3 as measured by flow cytometry.

Example 8

Modulation of T Cell Proliferation by Oligonucleotides

The ability of ISIS 2302 and ISIS 10373 to inhibit T cell proliferation was evaluated as follows. Monocytes treated with oligonucleotide and cytokines (as in Example 6) were used as antigen presenting cells in a T cell proliferation assay. The differentiated monocytes were combined with CD4+ T cells from a separate donor. After 48 hours, proliferation was measured by [$^3$H]thymidine incorporation.

Methods:

For T cell proliferation assays, cells were isolated from EDTA-treated whole blood as described above, except that a faster migrating band containing the lymphocytes was harvested from just below the interface. Cells were washed as described in Example 6 after which erythrocytes were removed by NH$_4$Cl lysis. T cells were purified using a T cell enrichment column (R&D Systems, Minneapolis, Minn.) essentially according to the manufacturer's directions. CD4+ T cells were further enriched from the entire T cell population by depletion of CD8+ cells with anti-CD8-conjugated magnetic beads (AMAC, Inc., Westbrook, Me.) according to the manufacturer's directions. T cells were determined to be >80% CD4+ by flow cytometry using Cy-chrome-conjugated anti-CD4 mAb (PharMingen, San Diego, Calif.).

Antigen presenting cells (APCs) were isolated as described in Example 6 and treated with mitomycin C (25 µg/mL) for 1 hour then washed 3 times with PBS. APCs (10$^5$ cells) were then combined with 4×10$^4$ CD4+ T cells in 350 µL of culture media. Where indicated, purified CD3 mAb was also added at a concentration of 1 µg/mL. During the last 6 hours of the 48 hour incubation period, proliferation was measured by determining uptake of 1.5 µCi of [$^3$H]-thymidine per well. The cells were harvested onto filters and the radioactivity measured by scintillation counting.

Figure 7:
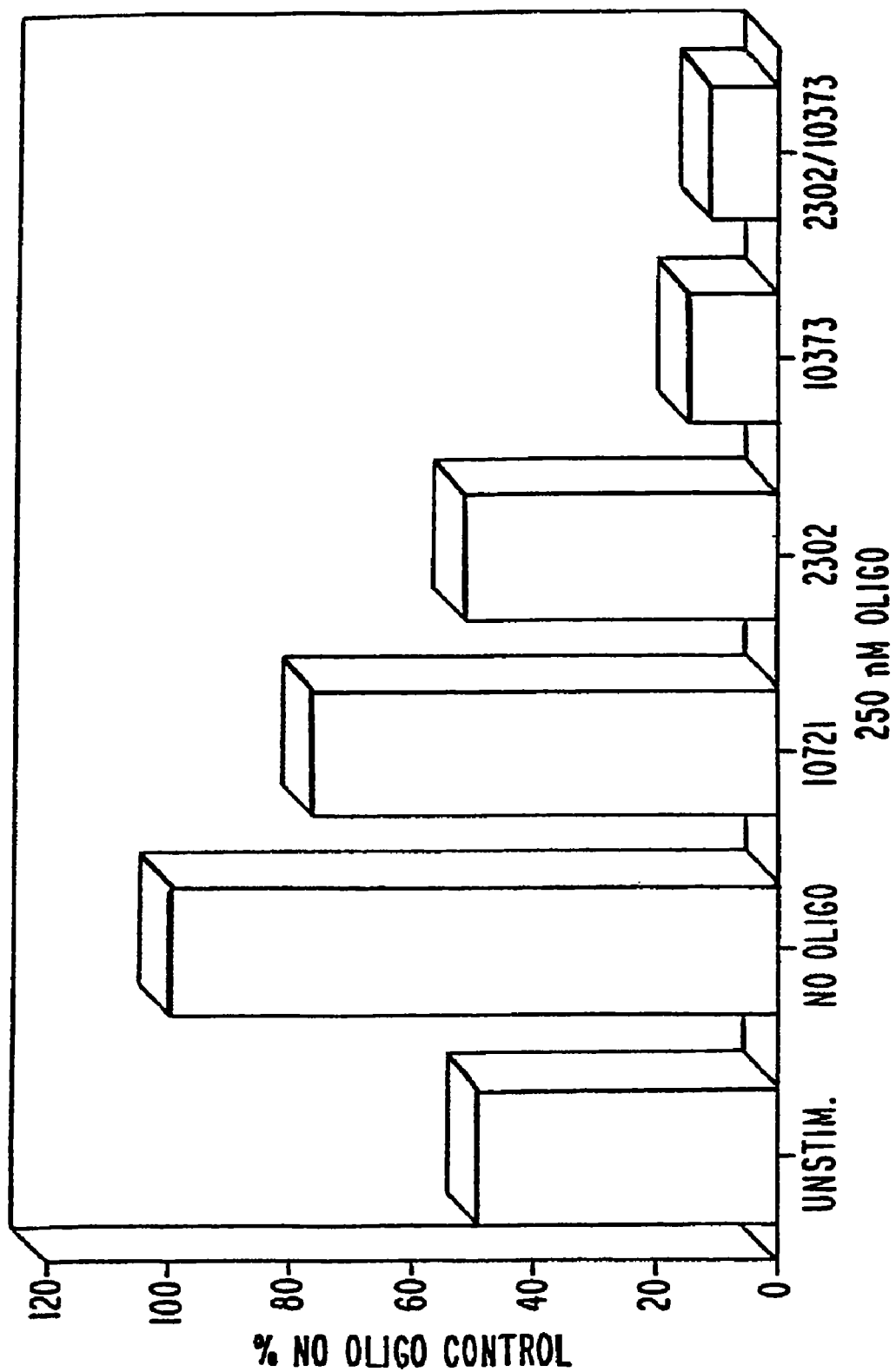
FIG. 7 is a bar graph showing the effect of the indicated oligonucleotides on T cell proliferation.

Results:

As shown in FIG. 7, mononuclear cells which were not cytokine-treated slightly induced T cell proliferation, presumably due to low levels of costimulatory molecules expressed on the cells. However, when the cells were treated with cytokines and induced to differentiate to dendritic-like cells, expression of both ICAM-1 and B7-2 was strongly upregulated. This resulted in a strong T cell proliferative response which could be blocked with either anti-ICAM-1 (ISIS 2302) or anti-B7-2 (ISIS 10373) oligonucleotides prior to induction of the mononuclear cells. The control oligonucleotide (ISIS 10721) had an insignificant effect on T cell proliferation. A combination treatment with both the anti-ICAM-1 (ISIS 2302) and anti-B7-2 (ISIS 10373) oligonucleotides resulted in a further decrease in T cell response.

Example 9

Modulation of Murine B7 Genes by Oligonucleotides

Oligonucleotides (see Table 4) capable of inhibiting expression of murine B7-2 transiently expressed in COS-7 cells were identified in the following manner. A series of phosphorothioate oligonucleotides complementary to murine B7-2 (mB7-2) cDNA were screened for their ability to reduce mB7-2 levels (measured by flow cytometry as in Example 2, except that a conjugated anti-mB7-2 antibody (i.e., anti-mCD86-PE, PharMingen, San Diego, Calif.) in COS-7 cells transfected with an mB7-2 cDNA clone. Anti-mB7-2 antibody may also be obtained from the hybridoma deposited at the ATCC under accession No. HB-253. Oligonucleotides (see Table 2) capable of modulating murine B7-1 expression are isolated in like fashion, except that a conjugated anti-mB7-1 antibody is used in conjunction with COS-7 cells transfected with an mB7-1 cDNA clone.

Figure 8:
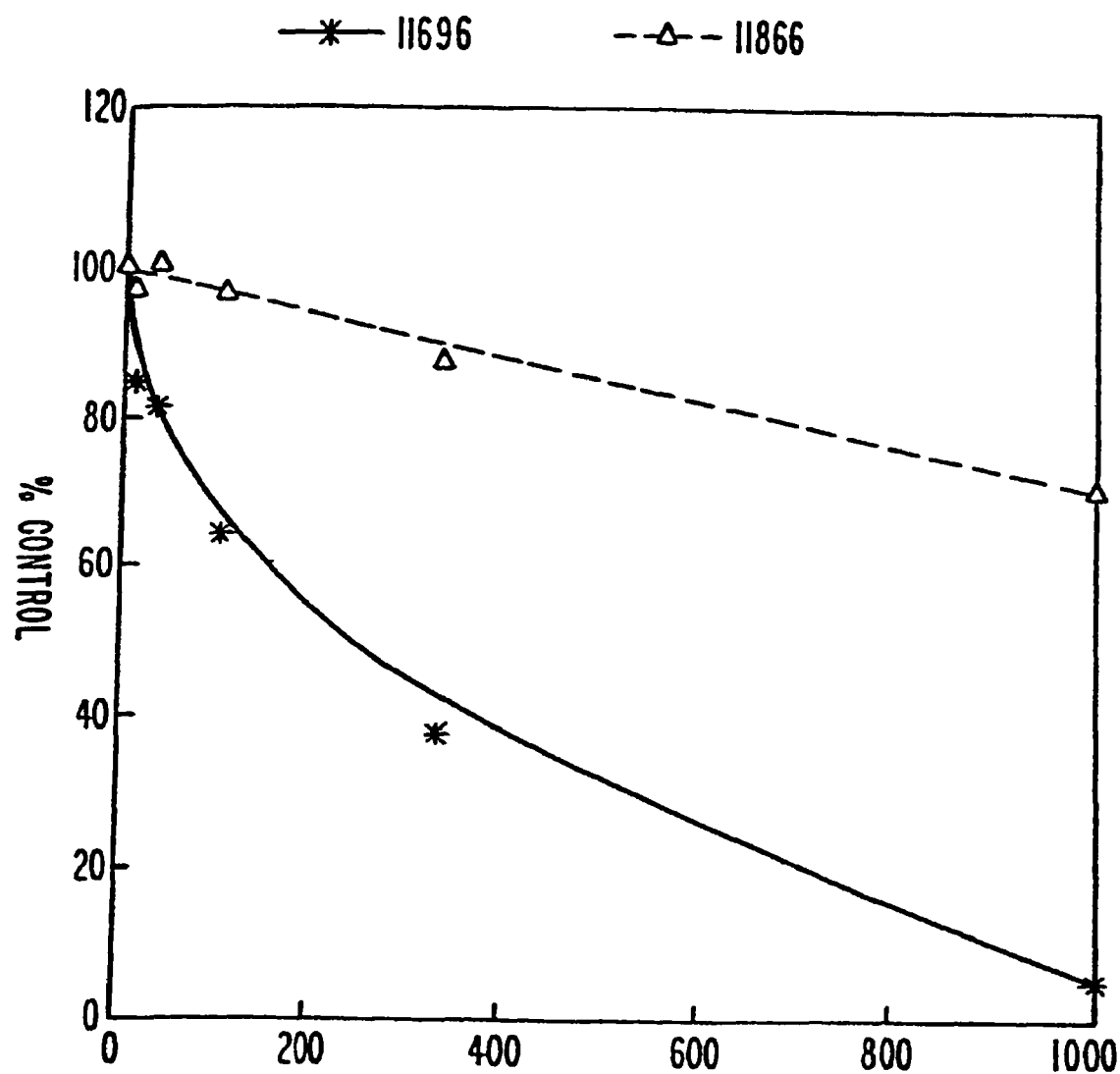
FIG. 8 is a dose-response curve showing the inhibitory effect of oligonucleotides on murine B7-2 protein expression in COS-7 cells. Solid line with asterisks, ISIS 11696; dashed line with triangles, ISIS 11866.

For murine B7-2, the most active oligonucleotide identified was ISIS 11696 (GGA-TTG-CCA-AGC-CCA-TGG-TG, SEQ ID NO: 18), which is complementary to position 96-115 of the cDNA, a site which includes the translation initiation (AUG) codon. FIG. 8 shows a dose-response curve for ISIS 11696 and a scrambled control, ISIS 11866 (CTA-AGT-AGT-GCT-AGC-CGG-GA, SEQ ID NO: 19). ISIS 11696 inhibited cell surface expression of B7-2 in COS-7 cells with an IC$_{50}$ in the range of 200-300 nM, while ISIS 11866 exhibited less than 20% inhibition at the highest concentration tested (1000 nM).

In order to further evaluate the murine B7-2 antisense oligonucleotides, the IC-21 cell line was used. IC-21 monocyte/macrophage cell line expresses both B7-1 and murine B7-2 (mB7-2) constitutively. A 2-fold induction of expression can be achieved by incubating the cells in the presence of lipopolysaccharide (LPS; GIBCO-BRL, Gaithersburg, Md.) (Hathcock et al., Science, 1993, 262, 905).

IC-21 cells (ATCC; accession No. TIB 186) were seeded at 80% confluency in 12-well plates in DMEM media with 10% FCS. The cells were allowed to adhere to the plate overnight. The following day, the medium was removed and the cells were washed with PBS. Then 500 µL of OptiMEM™ (GIBCO-BRL, Gaithersburg, Md.) supplemented with 15 µg/mL of Lipofectin™ (GIBCO-BRL, Gaithersburg, Md.) was added to each well. Oligonucleotides were then added directly to the medium at the indicated concentrations. After incubation for 4 hours, the cells were washed with PBS and incubated overnight in culture medium supplemented with 15 µg/mL of LPS. The following day, cells were harvested by scraping, then analyzed for cell surface expression by flow cytometry.

Figure 9:
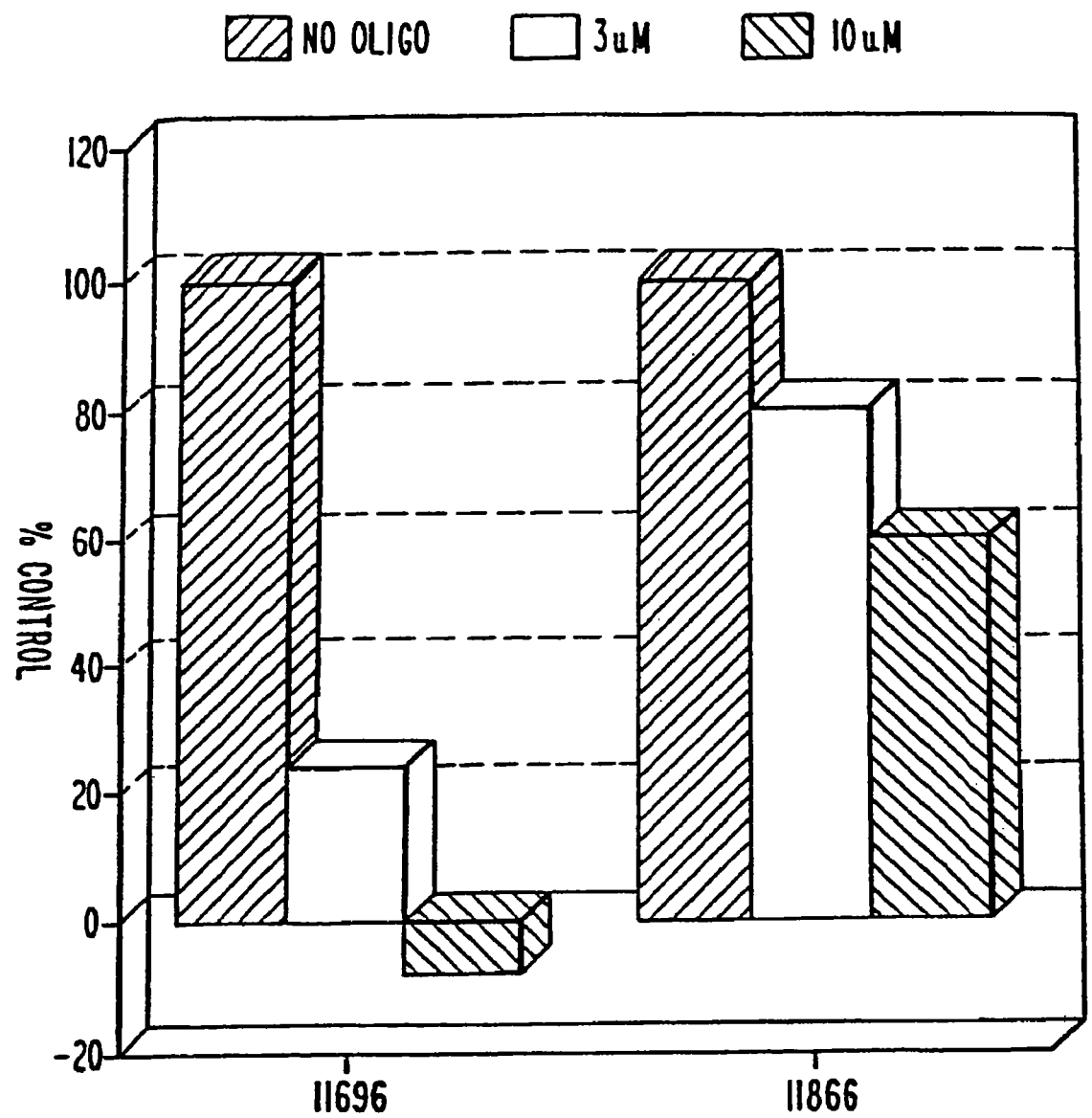
FIG. 9 is a bar graph showing the effect of oligonucleotides ISIS 11696 and ISIS 11866 on cell surface expression of murine B7-2 protein in IC-21 cells. Left (black) bars, no oligonucleotide; middle bars, 3 µM indicated oligonucleotide; right bars, 10 µM indicated oligonucleotide.
Figure 10:
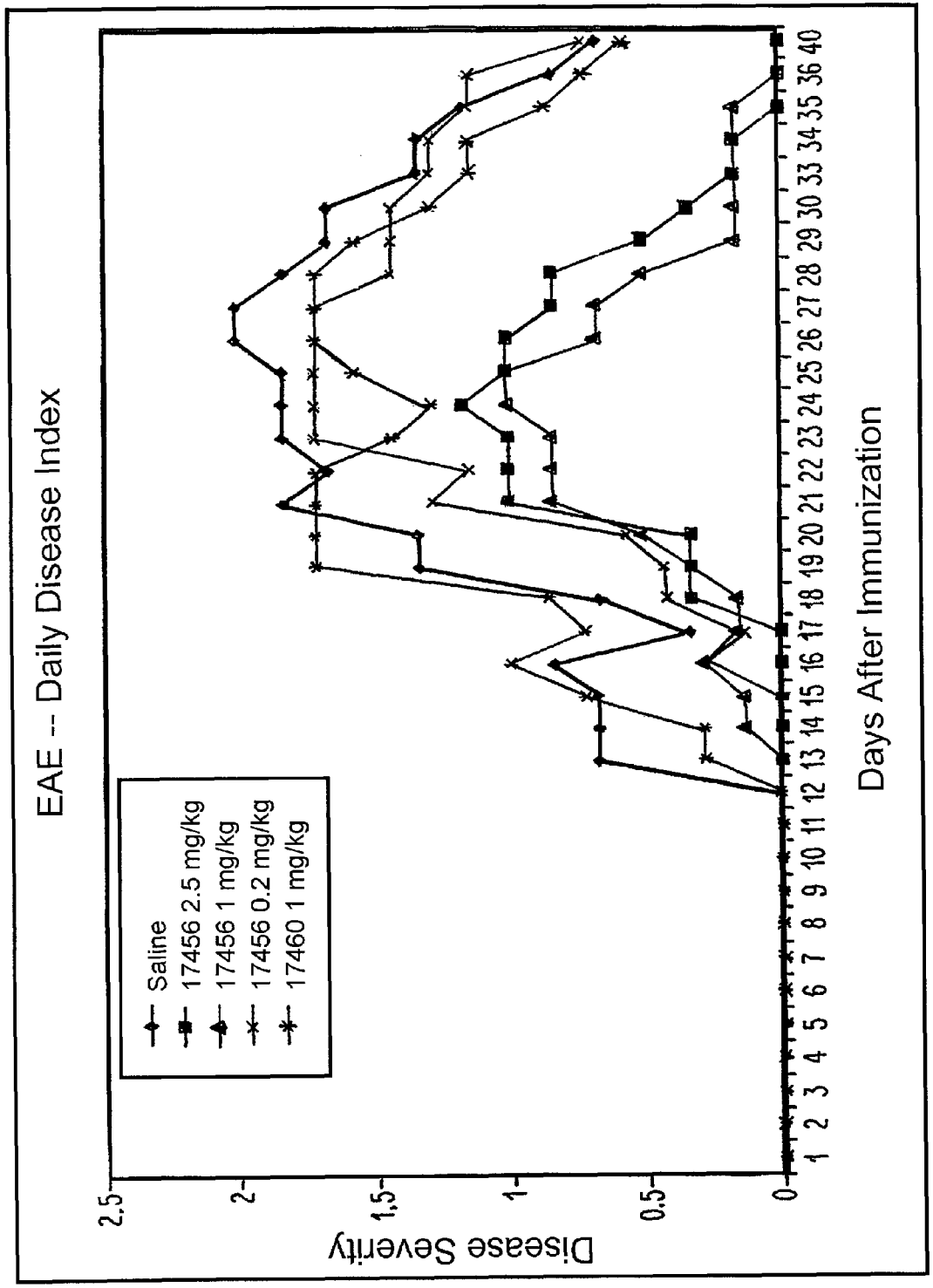
FIG. 10 is a graph showing the effect of ISIS 17456 on severity of EAE at various doses.

ISIS 11696 and ISIS 11866 were administered to IC-21 cells in the presence of Lipofectin™ (GIBCO-BRL, Gaithersburg, Md.). The results are shown in FIG. 9. At a concentration of 10 µM, ISIS 11696 inhibited mB7-2 expression completely (and decreased mB7-2 levels below the constitutive level of expression), while the scrambled control oligonucleotide, ISIS 11866, produced only a 40% reduction in the level of induced expression. At a concentration of 3 µM, levels of induced expression were greatly reduced by ISIS 11696, while ISIS 11866 had little effect.

Modified oligonucleotides, comprising 2' substitutions (e.g., 2' methoxy, 2' methoxyethoxy) and targeted to alternative transcripts of murine B7-1 (ISIS 12914, 12915, 13498, 13499) or murine B7-2 (ISIS 13100, 13100 and 13102) were prepared. These oligonucleotides are tested for their ability to modulate murine B7 essentially according to the above methods using IC-21 cells or COS-7 transfected with a cDNA clone corresponding to the appropriate alternatively spliced B7 transcript.

Example 10

Modulation of Allograft Rejection by Oligonucleotides

A murine model for evaluating compounds for their ability to inhibit heart allograft rejection has been previously described (Stepkowski et al., J. Immunol., 1994, 153, 5336). This model was used to evaluate the immunosuppressive capacity of antisense oligonucleotides to B7 proteins alone or in combination with antisense oligonucleotides to intercellular adhesion molecule-1 (ICAM-1).

Methods:

Heart allograft rejection studies and oligonucleotide treatments of BALB/c mice were performed essentially as previously described (Stepkowski et al., J. Immunol., 1994, 153, 5336). Antisense oligonucleotides used included ISIS 11696, ISIS 3082 (targeted to ICAM-1) and ISIS 1082 (a control oligonucleotide targeted to the herpes virus UL-13 gene sequence). Dosages used were 1, 2, 2.5, 5 or 10 mg/kg of individual oligonucleotide (as indicated below); when combinations of oligonucleotides were administered, each oligonucleotide was given at a dosage of 1, 5 or 10 mg/kg (total oligonucleotide dosages of 2, 10 and 20 mg/kg, respectively). The survival times of the transplanted hearts and their hosts were monitored and recorded.

Results:

The mean survival time for untreated mice was 8.2±0.8 days (7, 8, 8, 8, 9, 9 days). Treatment of the mice for 7 days with ISIS 1082 (SEQ ID NO: 125, unrelated control oligonucleotide) slightly reduced the mean survival times to 7.1±0.7 days (5 mg/kg/day; 6, 7, 7, 7, 8, 8) or 7.0±0.8 days (10 mg/kg/day; 6, 7, 7, 8). Treatment of the mice for seven days with the murine B7-2 oligonucleotide ISIS 11696 (SEQ ID NO: 108) increased the mean survival time to 9.3 days at two doses (2 mg/kg/day, 9.3±0.6 days, 9, 9, 10; 10 mg/kg/day, 9.3±1.3 days, 8, 9, 9, 11). Treatment of mice for seven days with an ICAM-1 oligonucleotide, ISIS 3082, also increased the mean survival of the mice over several doses. Specifically, at 1 mg/kg/day, the mean survival time (MSD) was 11.0±0.0 (11, 11, 11); at 2.5 mg/kg/day, the MSD was 12.0±2.7 (10, 12, 13, 16); at 5 mg/kg/day, the MSD was 14.1±2.7 (10, 12, 12, 13, 16, 16, 17, 17); and, at 10 mg/kg/day, the MSD was 15.3±5.8 (12, 12, 13, 24). Some synergistic effect was seen when the mice were treated for seven days with 1 mg/kg/day each of ISIS 3082 and 11696: the MSD was 13.8±1.0 (13, 13, 14, 15).

Example 11

Detection of Nucleic Acids Encoding B7 Proteins

Oligonucleotides are radiolabeled after synthesis by $^{32}$P-labeling at the 5' end with polynucleotide kinase. Sambrook et al., "Molecular Cloning. A Laboratory Manual," Cold Spring Harbor Laboratory Press, 1989, Volume 2, pg. 11.31. Radiolabeled oligonucleotide capable of hybridizing to a nucleic acid encoding a B7 protein is contacted with a tissue or cell sample suspected of B7 protein expression under conditions in which specific hybridization can occur, and the sample is washed to remove unbound oligonucleotide. A similar control is maintained wherein the radiolabeled oligonucleotide is contacted with a normal tissue or cell sample under conditions that allow specific hybridization, and the sample is washed to remove unbound oligonucleotide. Radioactivity remaining in the samples indicates bound oligonucleotide and is quantitated using a scintillation counter or other routine means. A greater amount of radioactivity remaining in the samples, as compared to control tissues or cells, indicates increased expression of a B7 gene, whereas a lesser amount of radioactivity in the samples relative to the controls indicates decreased expression of a B7 gene.

Radiolabeled oligonucleotides of the invention are also useful in autoradiography. A section of tissues suspected of expressing a B7 gene is treated with radiolabeled oligonucleotide and washed as described above, then exposed to photographic emulsion according to standard autoradiography procedures. A control of a normal tissue section is also maintained. The emulsion, when developed, yields an image of silver grains over the regions expressing a B7 gene, which is quantitated. The extent of B7 expression is determined by comparison of the silver grains observed with control and test samples.

Analogous assays for fluorescent detection of expression of a B7 gene use oligonucleotides of the invention which are labeled with fluorescein or other fluorescent tags. Labeled oligonucleotides are synthesized on an automated DNA synthesizer (Applied Biosystems, Foster City, Calif.) using standard phosphoramidite chemistry. b-Cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described above for radiolabeled oligonucleotides except that, instead of a scintillation counter, a fluorescence microscope is used to detect the fluorescence. A greater amount of fluorescence in the samples, as compared to control tissues or cells, indicates increased expression of a B7 gene, whereas a lesser amount of fluorescence in the samples relative to the controls indicates decreased expression of a B7 gene.

Example 12

Chimeric (Deoxy Gapped) Human B7-1 Antisense Oligonucleotides

Additional oligonucleotides targeting human B7-1 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 6.

Oligonucleotides were screened as described in Example 4. Results are shown in Table 7.

Oligonucleotides 22315 (SEQ ID NO: 128), 22316 (SEQ ID NO: 26), 22317 (SEQ ID NO: 129), 22320 (SEQ ID NO: 132), 22324 (SEQ ID NO: 135), 22325 (SEQ ID NO: 136), 22334 (SEQ ID NO: 145), 22335 (SEQ ID NO: 146), 22337 (SEQ ID NO: 148), and 22338 (SEQ ID NO: 36) resulted in 50% or greater inhibition of B7-1 mRNA in this assay.

TABLE 6

Nucleotide Sequences of Human B7-1 Chimeric (deoxy gapped) Oligodeoxynucleotides

| ISIS NO. | NUCLEOTIDE SEQUENCE[1] (5'->3') | SEQ ID NO: | TARGET GENE NUCLEOTIDE COORDINATES[2] | GENE TARGET REGION |
|---|---|---|---|---|
| 22313 | AGACTCCACTTCTGAGATGT | 126 | 0048-0067 | 5'-UTR |
| 22314 | TGAAGAAAAATTCCACTTTT | 127 | 0094-0113 | 5'-UTR |
| 22315 | TTTAGTTTCACAGCTTGCTG | 128 | 0112-0129 | 5'-UTR |
| 22316 | GCTCACGTAGAAGACCCTCC | 26 | 0193-0212 | 5'-UTR |
| 22317 | TCCCAGGTGCAAAACAGGCA | 129 | 0233-0252 | 5'-UTR |
| 22318 | GTGAAAGCCAACAATTTGGA | 130 | 0274-0293 | 5'-UTR |
| 22319 | CATGGCTTCAGATGCTTAGG | 131 | 0301-0320 | AUG |
| 22320 | TTGAGGTATGGACACTTGGA | 132 | 0351-0370 | coding |
| 22321 | GACCAGCCAGCACCAAGAGC | 31 | 0380-0399 | coding |
| 22322 | GCGTTGCCACTTCTTTCACT | 133 | 0440-0459 | coding |
| 22323 | TTTTGCCAGTAGATGCGAGT | 134 | 0501-0520 | coding |

TABLE 6-continued

Nucleotide Sequences of Human B7-1 Chimeric (deoxy gapped) Oligodeoxynucleotides

| ISIS NO. | NUCLEOTIDE SEQUENCE[1] (5'->3') | SEQ ID NO: | TARGET GENE NUCLEOTIDE COORDINATES[2] | GENE TARGET REGION |
|---|---|---|---|---|
| 22324 | GGCCATATATTCATGTCCCC | 135 | 0552-0571 | coding |
| 22325 | GCCAGGATCACAATGGAGAG | 136 | 0612-0631 | coding |
| 22326 | GTATGTGCCCTCGTCAGATG | 137 | 0640-0659 | coding |
| 22327 | TTCAGCCAGGTGTTCCCGCT | 138 | 0697-0716 | coding |
| 22328 | GGAAGTCAGCTTTGACTGAT | 139 | 0725-0744 | coding |
| 22329 | CCTCCAGAGGTTGAGCAAAT | 140 | 0798-0817 | coding |
| 22330 | CCAACCAGGAGAGGTGAGGC | 141 | 0827-0846 | coding |
| 22331 | GAAGCTGTGGTTGGTTGTCA | 142 | 0940-0959 | coding |
| 22332 | TTGAAGGTCTGATTCACTCT | 143 | 0987-1006 | coding |
| 22333 | AAGGTAATGGCCCAGGATGG | 144 | 1050-1069 | coding |
| 22334 | AAGCAGTAGGTCAGGCAGCA | 145 | 1098-1117 | coding |
| 22335 | CCTTGCTTCTGCGGACACTG | 146 | 1185-1204 | 3'-UTR |
| 22336 | AGCCCCTTGCTTCTGCGGAC | 147 | 1189-1208 | 3'-UTR |
| 22337 | TGACGGAGGCTACCTTCAGA | 148 | 1216-1235 | 3'-UTR |
| 22338 | GCCTCATGATCCCCACGATC | 36 | 1254-1273 | 3'-UTR |
| 22339 | GTAAAACAGCTTAAATTTGT | 149 | 1286-1305 | 3'-UTR |
| 22340 | AGAAGAGGTTACATTAAGCA | 150 | 1398-1417 | 3'-UTR |
| 22341 | AGATAATGAATTGGCTGACA | 151 | 1454-1473 | 3'-UTR |
| 24733 | GCGTCATCATCCGCACCATC | 152 | | control |
| 24734 | CGTTGCTTGTGCCGACAGTG | 153 | | control |
| 24735 | GCTCACGAAGAACACCTTCC | 154 | | control |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. M27533, locus name "HUMIGB7".

TABLE 7

Inhibition of Human B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100% | — |
| 13805 | 30 | AUG | 46% | 54% |
| 13812 | 36 | 3'-UTR | 22% | 78% |
| 22313 | 126 | 5'-UTR | 75% | 25% |
| 22314 | 127 | 5'-UTR | 69% | 31% |
| 22315 | 128 | 5'-UTR | 49% | 51% |
| 22316 | 26 | 5'-UTR | 42% | 58% |
| 22317 | 129 | 5'-UTR | 43% | 57% |
| 22318 | 130 | 5'-UTR | 63% | 37% |
| 22319 | 131 | AUG | 68% | 32% |
| 22320 | 132 | coding | 45% | 55% |
| 22321 | 31 | coding | 57% | 43% |
| 22324 | 135 | coding | 46% | 54% |
| 22325 | 136 | coding | 46% | 54% |
| 22326 | 137 | coding | 62% | 38% |
| 22328 | 139 | coding | 64% | 36% |
| 22329 | 140 | coding | 59% | 41% |
| 22330 | 141 | coding | 54% | 46% |
| 22331 | 142 | coding | 62% | 38% |
| 22332 | 143 | coding | 67% | 33% |
| 22333 | 144 | coding | 73% | 27% |
| 22334 | 145 | coding | 43% | 57% |
| 22335 | 146 | 3'-UTR | 43% | 57% |
| 22336 | 147 | 3'-UTR | 55% | 45% |
| 22337 | 148 | 3'-UTR | 42% | 58% |
| 22338 | 36 | 3'-UTR | 40% | 60% |
| 22339 | 149 | 3'-UTR | 69% | 31% |
| 22340 | 150 | 3'-UTR | 71% | 29% |
| 22341 | 151 | 3'-UTR | 59% | 41% |

Dose response experiments were performed on several of the more active oligonucleotides. The oligonucleotides were screened as described in Example 4 except that the concentration of oligonucleotide was varied as shown in Table 8. Mismatch control oligonucleotides were included. Results are shown in Table 8.

All antisense oligonucleotides tested showed a dose response effect with inhibition of mRNA approximately 60% or greater.

TABLE 8

Dose Response of COS-7 Cells to B7-1 Chimeric (deoxy gapped) Antisense Oligonucleotides

| ISIS # | SEQ ID NO: | Gene Target | Dose | % mRNA Expression | % mRNA Inhibition |
|---|---|---|---|---|---|
| basal | — | — | — | 100% | — |
| 22316 | 26 | 5'-UTR | 10 nM | 99% | 1% |
| " | " | " | 30 nM | 73% | 27% |
| " | " | " | 100 nM | 58% | 42% |
| " | " | " | 300 nM | 33% | 67% |
| 24735 | 154 | control | 10 nM | 100% | — |
| " | " | " | 30 nM | 95% | 5% |
| " | " | " | 100 nM | 81% | 19% |
| " | " | " | 300 nM | 75% | 25% |
| 22335 | 146 | 3'-UTR | 10 nM | 81% | 19% |
| " | " | " | 30 nM | 63% | 37% |
| " | " | " | 100 nM | 43% | 57% |
| " | " | " | 300 nM | 35% | 65% |
| 24734 | 153 | control | 10 nM | 94% | 6% |
| " | " | " | 30 nM | 96% | 4% |
| " | " | " | 100 nM | 94% | 6% |
| " | " | " | 300 nM | 84% | 16% |
| 22338 | 36 | 3'-UTR | 10 nM | 68% | 32% |
| " | " | " | 30 nM | 60% | 40% |
| " | " | " | 100 nM | 53% | 47% |
| " | " | " | 300 nM | 41% | 59% |
| 24733 | 152 | control | 10 nM | 90% | 10% |
| " | " | " | 30 nM | 91% | 9% |
| " | " | " | 100 nM | 90% | 10% |
| " | " | " | 300 nM | 80% | 20% |

Example 13

Chimeric (Deoxy Gapped) Mouse B7-1 Antisense Oligonucleotides

Additional oligonucleotides targeting mouse B7-1 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 9.

Oligonucleotides were screened as described in Example 4. Results are shown in Table 10. Oligonucleotides 18105 (SEQ ID NO: 156), 18106 (SEQ ID NO: 157), 18109 (SEQ ID NO: 160), 18110 (SEQ ID NO: 161), 18111 (SEQ ID NO: 162), 18112 (SEQ ID NO: 163), 18113 (SEQ ID NO: 164), 18114 (SEQ ID NO: 165), 18115 (SEQ ID NO: 166), 18117 (SEQ ID NO: 168), 18118 (SEQ ID NO: 169), 18119 (SEQ ID NO: 170), 18120 (SEQ ID NO: 171), 18122 (SEQ ID NO: 173), and 18123 (SEQ ID NO: 174) resulted in greater than approximately 50% inhibition of B7-1 mRNA in this assay.

TABLE 9

Nucleotide Sequences of Mouse B7-1 Chimeric (deoxy gapped) Oligodeoxynucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 18104 | AGAGAAACTAGTAAGAGTCT | 155 | 0018-0037 | 5'-UTR |
| 18105 | TGGCATCCACCCGGCAGATG | 156 | 0110-0129 | 5'-UTR |
| 18106 | TCGAGAAACAGAGATGTAGA | 157 | 0144-0163 | 5'-UTR |
| 18107 | TGGAGCTTAGGCACCTCCTA | 158 | 0176-0195 | 5'-UTR |
| 18108 | TGGGGAAAGCCAGGAATCTA | 159 | 0203-0222 | 5'-UTR |
| 18109 | CAGCACAAAGAGAAGAATGA | 160 | 0310-0329 | coding |
| 18110 | ATGAGGAGAGTTGTAACGGC | 161 | 0409-0428 | coding |
| 18111 | AAGTCCGGTTCTTATACTCG | 162 | 0515-0534 | coding |
| 18112 | GCAGGTAATCCTTTTAGTGT | 163 | 0724-0743 | coding |
| 18113 | GTGAAGTCCTCTGACACGTG | 164 | 0927-0946 | coding |
| 18114 | CGAATCCTGCCCCAAAGAGC | 165 | 0995-1014 | coding |
| 18115 | ACTGCGCCGAATCCTGCCCC | 166 | 1002-1021 | coding |
| 18116 | TTGATGATGACAACGATGAC | 167 | 1035-1054 | coding |
| 18117 | CTGTTGTTTGTTTCTCTGCT | 168 | 1098-1117 | coding |
| 18118 | TGTTCAGCTAATGCTTCTTC | 169 | 1134-1153 | coding |
| 18119 | GTTAACTCTATCTTGTGTCA | 170 | 1263-1282 | 3'-UTR |
| 18120 | TCCACTTCAGTCATCAAGCA | 171 | 1355-1374 | 3'-UTR |
| 18121 | TGCTCAATACTCTCTTTTTA | 172 | 1680-1699 | 3'-UTR |
| 18122 | AGGCCCAGCAAACTTGCCCG | 173 | 1330-1349 | 3'-UTR |
| 18123 | AACGGCAAGGCAGCAATACC | 174 | 0395-0414 | coding |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. X60958, locus name "MMB7BLAA".

TABLE 10

Inhibition of Mouse B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100.0% | — |
| 18104 | 155 | 5'-UTR | 60.0% | 40.0% |
| 18105 | 156 | 5'-UTR | 32.0% | 68.0% |
| 18106 | 157 | 5'-UTR | 51.0% | 49.0% |
| 18107 | 158 | 5'-UTR | 58.0% | 42.0% |

TABLE 10-continued

Inhibition of Mouse B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 18108 | 159 | 5'-UTR | 82.0% | 18.0% |
| 18109 | 160 | coding | 45.5% | 54.5% |
| 18110 | 161 | coding | 21.0% | 79.0% |
| 18111 | 162 | coding | 38.0% | 62.0% |
| 18112 | 163 | coding | 42.0% | 58.0% |
| 18113 | 164 | coding | 24.6% | 75.4% |
| 18114 | 165 | coding | 25.6% | 74.4% |
| 18115 | 166 | coding | 33.5% | 66.5% |
| 18116 | 167 | coding | 65.6% | 34.4% |
| 18117 | 168 | coding | 46.7% | 53.3% |
| 18118 | 169 | coding | 31.7% | 68.3% |
| 18119 | 170 | 3'-UTR | 24.0% | 76.0% |
| 18120 | 171 | 3'-UTR | 26.7% | 73.3% |
| 18121 | 172 | 3'-UTR | 114.0% | — |
| 18122 | 173 | 3'-UTR | 42.0% | 58.0% |
| 18123 | 174 | coding | 42.0% | 58.0% |

Example 14

Chimeric (Deoxy Gapped) Human B7-2 Antisense Oligonucleotides

Additional oligonucleotides targeting human B7-2 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 11.

Oligonucleotides were screened as described in Example 4. Results are shown in Table 12. Oligonucleotides 22284 (SEQ ID NO: 16), 22286 (SEQ ID NO: 176), 22287 (SEQ ID NO: 177), 22288 (SEQ ID NO: 178), 22289 (SEQ ID NO: 179), 22290 (SEQ ID NO: 180), 22291 (SEQ ID NO: 181), 22292 (SEQ ID NO: 182), 22293 (SEQ ID NO: 183), 22294 (SEQ ID NO: 184), 22296 (SEQ ID NO: 186), 22299 (SEQ ID NO: 189), 22300 (SEQ ID NO: 190), 22301 (SEQ ID NO: 191), 22302 (SEQ ID NO: 192), 22303 (SEQ ID NO: 193), 22304 (SEQ ID NO: 194), 22306 (SEQ ID NO: 196), 22307 (SEQ ID NO: 197), 22308 (SEQ ID NO: 198), 22309 (SEQ ID NO: 199), 22310 (SEQ ID NO: 200), and 22311 (SEQ ID NO: 201) resulted in greater than 50% inhibition of B7-2 mRNA in this assay.

TABLE 11

Nucleotide Sequences of Human B7-2 Chimeric (deoxy gapped) Oligodeoxynucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 22284 | TGCGAGCTCCCCGTACCTCC | 16 | 0011-0030 | 5'-UTR |
| 22285 | CAGAAGCAAGGTGGTAAGAA | 175 | 0049-0068 | 5'-UTR |
| 22286 | GCCTGTCCACTGTAGCTCCA | 176 | 0113-0132 | 5'-UTR |
| 22287 | AGAATGTTACTCAGTCCCAT | 177 | 0148-0167 | AUG |
| 22288 | TCAGAGGAGCAGCACCAGAG | 178 | 0189-0208 | coding |
| 22289 | TGGCATGGCAGGTCTGCAGT | 179 | 0232-0251 | coding |
| 22290 | AGCTCACTCAGGCTTTGGTT | 180 | 0268-0287 | coding |
| 22291 | TGCCTAAGTATACCTCATTC | 181 | 0324-0343 | coding |
| 22292 | CTGTCAAATTTCTCTTTGCC | 182 | 0340-0359 | coding |
| 22293 | CATATACTTGGAATGAACAC | 183 | 0359-0378 | coding |
| 22294 | GGTCCAACTGTCCGAATCAA | 184 | 0392-0411 | coding |
| 22295 | TGATCTGAAGATTGTGAAGT | 185 | 0417-0436 | coding |
| 22296 | AAGCCCTTGTCCTTGATCTG | 186 | 0430-0449 | coding |
| 22297 | TGTGATGGATGATACATTGA | 187 | 0453-0472 | coding |
| 22298 | TCAGGTTGACTGAAGTTAGC | 188 | 0529-0548 | coding |
| 22299 | GTGTATAGATGAGCAGGTCA | 189 | 0593-0612 | coding |
| 22300 | TCTGTGACATTATCTTGAGA | 190 | 0694-0713 | coding |
| 22301 | AAGATAAAAGCCGCGTCTTG | 191 | 0798-0817 | coding |
| 22302 | AGAAAACCATCACACATATA | 192 | 0900-0919 | coding |
| 22303 | AGAGTTGCGAGGCCGCTTCT | 193 | 0947-0968 | coding |
| 22304 | TCCCTCTCCATTGTGTTGGT | 194 | 0979-0998 | coding |
| 22305 | CATCAGATCTTTCAGGTATA | 195 | 1035-1054 | coding |
| 22306 | GGCTTTACTCTTTAATTAAA | 196 | 1115-1134 | stop |
| 22307 | GAAATCAAAAAGGTTGCCCA | 197 | 1178-1197 | 3'-UTR |
| 22308 | GGAGTCCTGGAGCCCCCTTA | 198 | 1231-1250 | 3'-UTR |
| 22309 | TTGGCATACGGAGCAGAGCT | 199 | 1281-1300 | 3'-UTR |
| 22310 | TGTGCTCTGAAGTGAAAAGA | 200 | 1327-1346 | 3'-UTR |
| 22311 | GGCTTGGCCCATAAGTGTGC | 201 | 1342-1361 | 3'-UTR |
| 22312 | CCTAAATTTTATTTCCAGGT | 202 | 1379-1398 | 3'-UTR |
| 24736 | GCTCCAAGTGTCCCAATGAA | 203 | control | |
| 24737 | AGTATGTTTCTCACTCCGAT | 204 | control | |
| 24738 | TGCCAGCACCCGGTACGTCC | 205 | control | |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. U04343 locus name "HSU04343".

TABLE 12

Inhibition of Human B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100% | 0% |
| 10373 | 16 | 5'-UTR | 24% | 76% |
| 22284 | 16 | 5'-UTR | 30% | 70% |
| 22285 | 175 | 5'-UTR | 74% | 26% |
| 22286 | 176 | 5'-UTR | 39% | 61% |
| 22287 | 177 | AUG | 27% | 73% |
| 22288 | 178 | coding | 38% | 62% |
| 22289 | 179 | coding | 41% | 59% |
| 22290 | 180 | coding | 42% | 58% |
| 22291 | 181 | coding | 41% | 59% |
| 22292 | 182 | coding | 39% | 61% |
| 22293 | 183 | coding | 43% | 57% |
| 22294 | 184 | coding | 21% | 79% |
| 22295 | 185 | coding | 66% | 34% |
| 22296 | 186 | coding | 42% | 58% |
| 22297 | 187 | coding | 54% | 46% |
| 22298 | 188 | coding | 53% | 47% |
| 22299 | 189 | coding | 46% | 54% |
| 22300 | 190 | coding | 39% | 61% |
| 22301 | 191 | coding | 51% | 49% |
| 22302 | 192 | coding | 41% | 59% |
| 22303 | 193 | coding | 46% | 54% |
| 22304 | 194 | coding | 41% | 59% |
| 22305 | 195 | coding | 57% | 43% |
| 22306 | 196 | stop | 44% | 56% |
| 22307 | 197 | 3'-UTR | 45% | 55% |
| 22308 | 198 | 3'-UTR | 40% | 60% |
| 22309 | 199 | 3'-UTR | 42% | 58% |
| 22310 | 200 | 3'-UTR | 41% | 59% |
| 22311 | 201 | 3'-UTR | 49% | 51% |
| 22312 | 202 | 3'-UTR | 83% | 17% |

Dose response experiments were performed on several of the more active oligonucleotides. The oligonucleotides were screened as described in Example 4 except that the concentration of oligonucleotide was varied as shown in Table 13. Mismatch control oligonucleotides were included. Results are shown in Table 13.

All antisense oligonucleotides tested showed a dose response effect with maximum inhibition of mRNA approximately 50% or greater.

TABLE 13

Dose Response of COS-7 Cells to B7-2 Chimeric (deoxy gapped) Antisense Oligonucleotides

| ISIS # | SEQ ID NO: | ASO Gene Target | Dose | % mRNA Expression | % mRNA Inhibition |
|---|---|---|---|---|---|
| basal | — | — | — | 100% | — |
| 22284 | 16 | 5'-UTR | 10 nM | 92% | 8% |
| " | " | " | 30 nM | 72% | 28% |
| " | " | " | 100 nM | 59% | 41% |
| " | " | " | 300 nM | 48% | 52% |
| 24738 | 205 | control | 10 nM | 81% | 19% |
| " | " | " | 30 nM | 92% | 8% |
| " | " | " | 100 nM | 101% | — |
| " | " | " | 300 nM | 124% | — |
| 22287 | 177 | AUG | 10 nM | 93% | 7% |
| " | " | " | 30 nM | 79% | 21% |
| " | " | " | 100 nM | 66% | 34% |
| " | " | " | 300 nM | 45% | 55% |
| 24737 | 204 | control | 10 nM | 85% | 15% |
| " | " | " | 30 nM | 95% | 5% |
| " | " | " | 100 nM | 87% | 13% |
| " | " | " | 300 nM | 99% | 1% |
| 22294 | 184 | coding | 10 nM | 93% | 7% |
| " | " | " | 30 nM | 95% | 5% |
| " | " | " | 100 nM | 58% | 42% |
| " | " | " | 300 nM | 45% | 55% |
| 24736 | 203 | control | 10 nM | 102% | — |
| " | " | " | 30 nM | 101% | — |
| " | " | " | 100 nM | 100% | — |
| " | " | " | 300 nM | 107% | — |

Example 15

Chimeric (Deoxy Gapped) Mouse B7-2 Antisense Oligonucleotides

Additional oligonucleotides targeting mouse B7-2 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 14.

Oligonucleotides were screened as described in Example 4. Results are shown in Table 15.

Oligonucleotides 18084 (SEQ ID NO: 206), 18085 (SEQ ID NO: 207), 18086 (SEQ ID NO: 208), 18087 (SEQ ID NO: 209), 18089 (SEQ ID NO: 211), 18090 (SEQ ID NO: 212), 18091 (SEQ ID NO: 213), 18093 (SEQ ID NO: 215), 18095 (SEQ ID NO: 217), 18096 (SEQ ID NO: 218), 18097 (SEQ ID NO: 219), 18098 (SEQ ID NO: 108), 18102 (SEQ ID NO: 223), and 18103 (SEQ ID NO: 224) resulted in 50% or greater inhibition of B7-2 mRNA expression in this assay.

TABLE 14

Nucleotide Sequences of Mouse B7-2 Chimeric (deoxy gapped) Oligodeoxynucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 18084 | GCTGCCTACAGGAGCCACTC | 206 | 0003-0022 | 5'-UTR |
| 18085 | TCAAGTCCGTGCTGCCTACA | 207 | 0013-0032 | 5'-UTR |
| 18086 | GTCTACAGGAGTCTGGTTGT | 208 | 0033-0052 | 5'-UTR |
| 18087 | AGCTTGCGTCTCCACGGAAA | 209 | 0152-0171 | coding |
| 18088 | TCACACTATCAAGTTTCTCT | 210 | 0297-0316 | coding |
| 18089 | GTCAAAGCTCGTGCGGCCCA | 211 | 0329-0348 | coding |
| 18090 | GTGAAGTCGTAGAGTCCAGT | 212 | 0356-0375 | coding |
| 18091 | GTGACCTTGCTTAGACGTGC | 213 | 0551-0570 | coding |
| 18092 | CATCTTCTTAGGTTTCGGGT | 214 | 0569-0588 | coding |
| 18093 | GGCTGTTGGAGATACTGAAC | 215 | 0663-0682 | coding |
| 18094 | GGGAATGAAAGAGAGAGGCT | 216 | 0679-0698 | coding |
| 18095 | ACATACAATGATGAGCAGCA | 217 | 0854-0873 | coding |
| 18096 | GTCTCTCTGTCAGCGTTACT | 218 | 0934-0953 | coding |
| 18097 | TGCCAAGCCCATGGTGCATC | 219 | 0092-0111 | AUG |
| 18098 | GGATTGCCAAGCCCATGGTG | 108 | 0096-0115 | AUG |
| 18099 | GCAATTTGGGGTTCAAGTTC | 220 | 0967-0986 | coding |
| 18100 | CAATCAGCTGAGAACATTTT | 221 | 1087-1106 | 3'-UTR |
| 18101 | TTTTGTATAAAACAATCATA | 222 | 0403-0422 | coding |
| 18102 | CCTTCACTCTGCATTTGGTT | 223 | 0995-1014 | stop |
| 18103 | TGCATGTTATCACCATACTC | 224 | 0616-0635 | coding |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. S70108 locus name "S70108".

TABLE 15

Inhibition of Mouse B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100.0% | 0.0% |
| 18084 | 206 | 5'-UTR | 36.4% | 63.6% |
| 18085 | 207 | 5'-UTR | 35.0% | 65.0% |
| 18086 | 208 | 5'-UTR | 40.1% | 59.9% |
| 18087 | 209 | coding | 42.1% | 57.9% |

TABLE 15-continued

Inhibition of Mouse B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 18088 | 210 | coding | 52.3% | 47.7% |
| 18089 | 211 | coding | 20.9% | 79.1% |
| 18090 | 212 | coding | 36.6% | 63.4% |
| 18091 | 213 | coding | 37.1% | 62.9% |
| 18092 | 214 | coding | 58.9% | 41.1% |
| 18093 | 215 | coding | 32.7% | 67.3% |
| 18094 | 216 | coding | 63.8% | 36.2% |
| 18095 | 217 | coding | 34.3% | 65.7% |
| 18096 | 218 | coding | 32.3% | 67.7% |
| 18097 | 219 | AUG | 24.5% | 75.5% |
| 18098 | 108 | AUG | 32.2% | 67.8% |
| 18099 | 220 | coding | 66.8% | 33.2% |
| 18100 | 221 | 3'-UTR | 67.2% | 32.8% |
| 18101 | 222 | coding | 88.9% | 11.1% |
| 18102 | 223 | stop | 33.8% | 66.2% |
| 18103 | 224 | coding | 30.2% | 69.8% |

Example 16

Effect of B7 Antisense Oligonucleotides on Cell Surface Expression

B7 antisense oligonucleotides were tested for their effect on cell surface expression of both B7-1 and B7-2. Cell surface expression was measured as described in Example 1. Experiments were done for both human B7 and mouse B7. Results for human B7 are shown in Table 16. Results for mouse B7 are shown in Table 17.

In both species, B7-1 antisense oligonucleotides were able to specifically reduce the cell surface expression of B7-1. B7-2 antisense oligonucleotides were specific for the B-7-2 family member. These oligonucleotides were also specific for their effect on B7-1 and B7-2 mRNA levels.

TABLE 16

Inhibition of Human B7 Cell Surface Expression by Chimeric (deoxy gapped) Phosphorothioate Oligodeoxynucleotides

| ISIS No: | SEQ ID NO: | GENE TARGET | % B7-1 EXPRESSION | % B7-2 EXPRESSION |
|---|---|---|---|---|
| basal | — | — | 100% | 0% |
| 22316 | 26 | B7-1 | 31% | 100% |
| 22317 | 129 | B7-1 | 28% | 91% |
| 22320 | 132 | B7-1 | 37% | 86% |
| 22324 | 135 | B7-1 | 37% | 91% |
| 22325 | 136 | B7-1 | 32% | 89% |
| 22334 | 145 | B7-1 | 28% | 92% |
| 22335 | 146 | B7-1 | 23% | 95% |
| 22337 | 148 | B7-1 | 48% | 101% |
| 22338 | 36 | B7-1 | 22% | 96% |
| 22284 | 16 | B7-2 | 88% | 32% |
| 22287 | 177 | B7-2 | 92% | 35% |
| 22294 | 184 | B7-2 | 77% | 28% |

TABLE 17

Inhibition of Mouse B7 Cell Surface Expression by Chimeric (deoxy gapped) Phosphorothioate Oligodeoxynucleotides

| ISIS No: | SEQ ID NO: | GENE TARGET REGION | % B7-1 EXPRESSION | % B7-2 EXPRESSION |
|---|---|---|---|---|
| basal | — | — | 100% | 0% |
| 18089 | 211 | B7-2 | 85% | 36% |
| 18097 | 219 | B7-2 | 87% | 28% |
| 18110 | 161 | B7-1 | 31% | 93% |
| 18113 | 164 | B7-1 | 25% | 91% |
| 18119 | 170 | B7-1 | 27% | 98% |

Dose response experiments were performed on several of the more active human B7-1 antisense oligonucleotides. The oligonucleotides were screened as described in Example 2 except that the concentration of oligonucleotide was varied as shown in Table 18. Results are shown in Table 18.

All antisense oligonucleotides tested showed a dose response effect with inhibition of cell surface expression approximately 60% or greater.

TABLE 18

Dose Response of COS-7 Cells to B7-1 Chimeric (deoxy gapped) Antisense Oligonucleotides

| ISIS # | SEQ ID NO: | ASO Gene Target | Dose | % Surface Expression | % Surface Inhibition |
|---|---|---|---|---|---|
| basal | — | — | — | 100% | — |
| 22316 | 26 | 5'-UTR | 10 nM | 74% | 26% |
| " | " | " | 30 nM | 74% | 26% |
| " | " | " | 100 nM | 47% | 53% |
| " | " | " | 300 nM | 34% | 66% |
| 22335 | 146 | 3'-UTR | 10 nM | 81% | 19% |
| " | " | " | 30 nM | 69% | 31% |
| " | " | " | 100 nM | 47% | 53% |
| " | " | " | 300 nM | 38% | 62% |
| 22338 | 36 | 3'-UTR | 10 nM | 78% | 22% |
| " | " | " | 30 nM | 65% | 35% |
| " | " | " | 100 nM | 50% | 50% |
| " | " | " | 300 nM | 40% | 60% |

Dose response experiments were performed on several of the more active human B7-2 antisense oligonucleotides. The oligonucleotides were screened as described in Example 2 except that the concentration of oligonucleotide was varied as shown in Table 19. Results are shown in Table 19.

All antisense oligonucleotides tested showed a dose response effect with maximum inhibition of cell surface expression 85% or greater.

TABLE 19

Dose Response of COS-7 Cells to B7-2 Chimeric (deoxy gapped) Antisense Oligonucleotides

| ISIS # | SEQ ID NO: | ASO Gene Target | Dose | % Surface Expression | % Surface Inhibition |
|---|---|---|---|---|---|
| basal | — | — | — | 100% | — |
| 22284 | 16 | 5'-UTR | 10 nM | 63% | 37% |
| " | " | " | 30 nM | 60% | 40% |
| " | " | " | 100 nM | 37% | 63% |
| " | " | " | 300 nM | 15% | 85% |
| 22287 | 177 | AUG | 10 nM | 93% | 7% |
| " | " | " | 30 nM | 60% | 40% |
| " | " | " | 100 nM | 32% | 68% |
| " | " | " | 300 nM | 15% | 85% |
| 22294 | 184 | coding | 10 nM | 89% | 11% |
| " | " | " | 30 nM | 62% | 38% |
| " | " | " | 100 nM | 29% | 71% |
| " | " | " | 300 nM | 12% | 88% |

Example 17

Effect of B7-1 Antisense Oligonucleotides in a Murine Model for Rheumatoid Arthritis Collagen-induced arthritis (CIA) was used as a murine model for arthritis (Mussener, A., et al., Clin. Exp. Immunol., 1997, 107, 485-493). Female DBA/1LacJ mice (Jackson Laboratories, Bar Harbor, Me.) between the ages of 6 and 8 weeks were used to assess the activity of B7-1 antisense oligonucleotides.

On day 0, the mice were immunized at the base of the tail with 100 µg of bovine type II collagen which is emulsified in Complete Freund's Adjuvant (CFA). On day 7, a second booster dose of collagen was administered by the same route. On day 14, the mice were injected subcutaneously with 100 µg of LPS. Oligonucleotide was administered intraperitoneally daily (10 mg/kg bolus) starting on day −3 (three days before day 0) and continuing for the duration of the study. Oligonucleotide 17456 (SEQ ID NO. 173) is a fully phosphorothioated analog of 18122.

Weights were recorded weekly. Mice were inspected daily for the onset of CIA. Paw widths are rear ankle widths of affected and unaffected joints were measured three times a week using a constant tension caliper. Limbs were clinically evaluated and graded on a scale from 0-4 (with 4 being the highest).

Results are shown in Table 20. Treatment with B7-1 and B7-2 antisense oligonucleotides was able to reduce the incidence of the disease, but had modest effects on severity. The combination of 17456 (SEQ ID NO. 173) and 11696 (SEQ ID NO. 108) was able to significantly reduce the incidence of the disease and its severity.

TABLE 20

Effect of B7 antisense oligonucleotide on CIA

| ISIS #(s) | SEQ ID NO | Dose mg/kg | % Inci-dence | Peak day[1] | Severity[2] |
|---|---|---|---|---|---|
| control | — | — | 70% | 6.7 ± 2.9 | 3.2 ± 1.1 |
| 17456 (B7-1) | 173 | 10 | 50% | 12.1 ± 4.6 | 2.7 ± 1.3 |
| 11696 (B7-2) | 108 | 10 | 37.5% | 11.6 ± 4.5 | 3.4 ± 1.8 |
| 17456/11696 | | 10 | 30% | 1.0 ± 0.6 | 0.7 ± 0.4 |
| 18110 (B7-1) | 161 | 10 | 55.6% | 2.0 ± 0.8 | 2.0 ± 1.3 |
| 18089 (B7-2) | 211 | 10 | 44.4% | 6.8 ± 2.2 | 2.3 ± 1.3 |
| 18110/18089 | | 10 | 60% | 11.6 ± 0.7 | 4.5 ± 1.7 |

[1]Peak day is the day from onset of maximum swelling for each joint measure.
[2]Severity is the total clinical score divided by the total number of mice in the group.

Example 18

Effect of B7-1 Antisense Oligonucleotides in a Murine Model for Multiple Sclerosis Experimental autoimmune encephalomyelitis (EAE) is a commonly accepted murine model for multiple sclerosis (Myers, K. J., et al., J. Neuroimmunol., 1992, 41, 1-8). SJL/H, PL/J, (SJLxPL/J)F1, (SJLxBalb/c)F1 and Balb/c female mice between the ages of 6 and 12 weeks are used to test the activity of a B7-1 antisense oligonucleotide.

The mice are immunized in the two rear foot pads and base of the tail with an emulsion consisting of encephalitogenic protein or peptide (according to Myers, K. J., et al., J. of Immunol., 1993, 151, 2252-2260) in Complete Freund's Adjuvant supplemented with heat killed *Mycobacterium tuberculosis*. Two days later, the mice receive an intravenous injection of 500 ng *Bordetella pertussis* toxin and additional adjuvant.

Alternatively, the disease may also be induced by the adoptive transfer of T-cells. T-cells are obtained from the draining of the lymph nodes of mice immunized with encephalitogenic protein or peptide in CFA. The T cells are grown in tissue culture for several days and then injected intravenously into naive syngeneic recipients.

Mice are monitored and scored daily on a 0-5 scale for signals of the disease, including loss of tail muscle tone, wobbly gait, and various degrees of paralysis.

Oligonucleotide 17456 (SEQ ID NO. 173), a fully phosphorothioated analog of 18122, was compared to a saline control and a fully phosphorothioated oligonucleotide of random sequence (Oligonucleotide 17460). Results of this experiment are shown in FIG. 11.

As shown in FIG. 11, for all doses of oligonucleotide 17456 tested, there is a protective effect, i.e. a reduction of disease severity. At 0.2 mg/kg, this protective effect is greatly reduced after day 20, but at the higher doses tested, the protective effect remains throughout the course of the experiment (day 40). The control oligonucleotide gave results similar to that obtained with the saline control.

Example 19

Additional Antisense Oligonucleotides Targeted to Human B7-1

Additional oligonucleotides targeting human B7-1 were synthesized. Oligonucleotides were synthesized as uniformly phosphorothioate chimeric oligonucleotides having regions of five 2'-O-methoxyethyl (2'-MOE) nucleotides at the wings and a central region often deoxynucleotides. Oligonucleotide sequences are shown in Table 21.

The human promonocytic leukaemia cell line, THP-1 (American Type Culture Collection, Manassas, Va.) was maintained in RPMI 1640 growth media supplemented with 10% fetal calf serum (FCS; Life Technologies, Rockville, Md.). A total of $1 \times 10^7$ cells were electroporated at an oligonucleotide concentration of 10 micromolar in 2 mm cuvettes, using an Electrocell Manipulator 600 instrument (Biotechnologies and Experimental Research, Inc.) employing 200 V, 1000 µF. Electroporated cells were then transferred to petri dishes and allowed to recover for 16 hrs. Cells were then induced with LPS at a final concentration of 1 µg/ml for 16 hours. RNA was isolated and processed as described in previous examples. Results are shown in Table 22.

Oligonucleotides 113492, 113495, 113498, 113499, 113501, 113502, 113504, 113505, 1113507, 113510, 113511, 113513 and 113514 (SEQ ID NO: 228, 231, 234, 235, 237, 238, 240, 241, 243, 246, 247, 249 and 250) resulted in 50% or greater inhibition of B7-1 mRNA expression in this assay.

TABLE 21

Nucleotide Sequences of Human B7-1 Chimeric (deoxy gapped) Oligodeoxynucleotides

| ISIS NO. | NUCLEOTIDE SEQUENCE[1] (5'->3') | SEQ ID NO. | TARGET GENE NUCLEOTIDE CO-ORDINATES[2] | GENE TARGET REGION |
|---|---|---|---|---|
| 113489 | CCCTCCAGTGATGTTTACAA | 225 | 179 | 5'UTR |
| 113490 | GAAGACCCTCCAGTGATGTT | 226 | 184 | 5'UTR |
| 113491 | CGTAGAAGACCCTCCAGTGA | 227 | 188 | 5'UTR |
| 113492 | TTCCCAGGTGCAAAACAGGC | 228 | 234 | 5'UTR |
| 113493 | TGGCTTCAGATGCTTAGGGT | 229 | 299 | 5'UTR |
| 113494 | CCTCCGTGTGTGGCCCATGG | 230 | 316 | AUG |
| 113495 | GGTGATGTTCCCTGCCTCCG | 231 | 330 | Coding |
| 113496 | GATGGTGATGTTCCCTGCCT | 232 | 333 | Coding |
| 113497 | AGGTATGGACACTTGGATGG | 233 | 348 | Coding |
| 113498 | GAAAGACCAGCCAGCACCAA | 234 | 384 | Coding |
| 113499 | CAGCGTTGCCACTTCTTTCA | 235 | 442 | Coding |
| 113500 | GTGACCACAGGACAGCGTTG | 236 | 454 | Coding |
| 113501 | AGATGCGAGTTTGTGCCAGC | 237 | 491 | Coding |
| 113502 | CCTTTTGCCAGTAGATGCGA | 238 | 503 | Coding |
| 113503 | CGGTTCTTGTACTCGGGCCA | 239 | 567 | Coding |
| 113504 | CGCAGAGCCAGGATCACAAT | 240 | 618 | Coding |
| 113505 | CTTCAGCCAGGTGTTCCCGC | 241 | 698 | Coding |
| 113506 | TAACGTCACTTCAGCCAGGT | 242 | 706 | Coding |
| 113507 | TTCTCCATTTTCCAACCAGG | 243 | 838 | Coding |
| 113508 | CTGTTGTGTTGATGGCATTT | 244 | 863 | Coding |
| 113509 | CATGAAGCTGTGGTTGGTTG | 245 | 943 | Coding |
| 113510 | AGGAAAATGCTCTTGCTTGG | 246 | 1018 | Coding |
| 113511 | TGGGAGCAGGTTATCAGGAA | 247 | 1033 | Coding |
| 113512 | TAAGGTAATGGCCCAGGATG | 248 | 1051 | Coding |
| 113513 | GGTCAGGCAGCATATCACAA | 249 | 1090 | Coding |
| 113514 | GCCCCTTGCTTCTGCGGACA | 250 | 1188 | 3'UTR |
| 113515 | AGATCTTTTCAGCCCCTTGC | 251 | 1199 | 3'UTR |
| 113516 | TTTGTTAAGGGAAGAATGCC | 252 | 1271 | 3'UTR |
| 113517 | AAAGGAGAGGGATGCCAGCC | 253 | 1362 | 3'UTR |
| 113518 | CAAGACAATTCAAGATGGCA | 254 | 1436 | 3'UTR |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. M27533 to which the oligonucleotides are targeted.

TABLE 22

Inhibition of Human B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 113489 | 225 | 5' UTR | 122 | — |
| 113490 | 226 | 5' UTR | 183 | — |
| 113491 | 227 | 5' UTR | 179 | — |
| 113492 | 228 | 5' UTR | 27 | 73 |
| 113493 | 229 | 5' UTR | 488 | — |
| 113494 | 230 | AUG | 77 | 23 |
| 113495 | 231 | Coding | 43 | 57 |
| 113496 | 232 | Coding | 71 | 29 |
| 113497 | 233 | Coding | 78 | 22 |
| 113498 | 234 | Coding | 37 | 63 |
| 113499 | 235 | Coding | 25 | 75 |
| 113500 | 236 | Coding | 83 | 17 |
| 113501 | 237 | Coding | 36 | 64 |
| 113502 | 238 | Coding | 26 | 74 |
| 113503 | 239 | Coding | 65 | 35 |
| 113504 | 240 | Coding | 46 | 54 |
| 113505 | 241 | Coding | 40 | 60 |
| 113506 | 242 | Coding | 105 | — |
| 113507 | 243 | Coding | 36 | 64 |
| 113508 | 244 | Coding | 117 | — |
| 113509 | 245 | Coding | 62 | 38 |
| 113510 | 246 | Coding | 43 | 57 |
| 113511 | 247 | Coding | 48 | 52 |
| 113512 | 248 | Coding | 73 | 27 |
| 113513 | 249 | Coding | 48 | 52 |
| 113514 | 250 | 3' UTR | 35 | 65 |
| 113515 | 251 | 3' UTR | 184 | — |
| 113516 | 252 | 3' UTR | 83 | 17 |
| 113517 | 253 | 3' UTR | 201 | — |
| 113518 | 254 | 3' UTR | 97 | 03 |

Example 20

Additional Antisense Oligonucleotides Targeted to Human B7-2

Additional oligonucleotides targeting human B7-2 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 23.

The human promonocytic leukaemia cell line, THP-1 (American Type Culture Collection, Manassas, Va.) was maintained in RPMI 1640 growth media supplemented with 10% fetal calf serum (FCS; Life Technologies, Rockville, Md.). A total of $1\times10^7$ cells were electroporated at an oligonucleotide concentration of 10 micromolar in 2 mm cuvettes, using an Electrocell Manipulator 600 instrument (Biotechnologies and Experimental Research, Inc.) employing 200 V, 1000 µF. Electroporated cells were then transferred to petri dishes and allowed to recover for 16 hrs Cells were then induced with LPS and dibutyryl cAMP (500 µM) for 16 hours. RNA was isolated and processed as described in previous examples. Results are shown in Table 24.

Oligonucleotides ISIS 113131, 113132, 113134, 113138, 113142, 113144, 113145, 113146, 113147, 113148, 113149, 113150, 113153, 113155, 113157, 113158, 113159 and 113160 (SEQ ID NO: 255, 256, 258, 262, 266, 268, 269, 270, 271, 272, 273, 274, 277, 279, 281, 282, 283 and 284) resulted in 50% or greater inhibition of B7-2 mRNA expression in this assay.

TABLE 23

Nucleotide Sequences of Human B7-2 Chimeric (deoxy gapped) Oligodeoxynucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 113131 | CGTGTGTCTGTGCTAGTCCC | 255 | 38 | 5'UTR |
| 113132 | GCTGCTTCTGCTGTGACCTA | 256 | 83 | 5'UTR |
| 113133 | TATTTGCGAGCTCCCCGTAC | 257 | 15 | 5'UTR |
| 113134 | GCATAAGCACAGCAGCATTC | 258 | 79 | 5'UTR |
| 113135 | TCCAAAAAGAGACCAGATGC | 259 | 97 | 5'UTR |
| 113136 | AAATGCCTGTCCACTGTAGC | 260 | 117 | 5'UTR |
| 113137 | CTTCAGAGGAGCAGCACCAG | 261 | 191 | Coding |
| 113138 | GAATCTTCAGAGGAGCAGCA | 262 | 195 | Coding |
| 113139 | CAAATTGGCATGGCAGGTCT | 263 | 237 | Coding |
| 113140 | GCTTTGGTTTTGAGAGTTTG | 264 | 257 | Coding |
| 113141 | AGGCTTTGGTTTTGAGAGTT | 265 | 259 | Coding |
| 113142 | GCTCACTCAGGCTTTGGTTT | 266 | 267 | Coding |
| 113143 | GGTCCTGCCAAAATACTACT | 267 | 288 | Coding |
| 113144 | AGCCCTTGTCCTTGATCTGA | 268 | 429 | Coding |
| 113145 | TGTGGGCTTTTTGTGATGGA | 269 | 464 | Coding |
| 113146 | AATCATTCCTGTGGGCTTTT | 270 | 473 | Coding |
| 113147 | CCGTGTATAGATGAGCAGGT | 271 | 595 | Coding |
| 113148 | ACCGTGTATAGATGAGCAGG | 272 | 596 | Coding |
| 113149 | TCATCTTCTTAGGTTCTGGG | 273 | 618 | Coding |
| 113150 | ACAAGCTGATGGAAACGTCG | 274 | 720 | Coding |
| 113151 | TGCTCGTAACATCAGGGAAT | 275 | 747 | Coding |
| 113152 | AAGATGGTCATATTGCTCGT | 276 | 760 | Coding |
| 113153 | CGCGTCTTGTCAGTTTCCAG | 277 | 787 | Coding |
| 113154 | CAGCTGTAATCCAAGGAATG | 278 | 864 | Coding |
| 113155 | GGGCTTCATCAGATCTTTCA | 279 | 1041 | Coding |
| 113156 | CATGTATCACTTTTGTCGCA | 280 | 1093 | Coding |
| 113157 | AGCCCCCTTATTACTCATGG | 281 | 1221 | 3'UTR |
| 113158 | GGAGTTACAGGGAGGCTATT | 282 | 1261 | 3'UTR |
| 113159 | AGTCTCCTCTTGGCATACGG | 283 | 1290 | 3'UTR |
| 113160 | CCCATAAGTGTGCTCTGAAG | 284 | 1335 | 3'UTR |

[1] Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2] For ISIS #113131 and 113132, co-ordinates are from Genbank Accession No. L25259, locus name "HUMB72A". For remaining oigonucleotides, co-ordinates are from Genbank Accession No. U04343, locus name "HSUU04343".

TABLE 24

Inhibition of Human B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 113131 | 255 | 5'UTR | 13 | 87 |
| 113132 | 256 | 5'UTR | 17 | 83 |
| 113133 | 257 | 5'UTR | 214 | — |
| 113134 | 258 | 5'UTR | 27 | 73 |
| 113135 | 259 | 5'UTR | 66 | 34 |
| 113136 | 260 | 5'UTR | 81 | 19 |
| 113137 | 261 | Coding | 57 | 43 |
| 113138 | 262 | Coding | 12 | 88 |
| 113140 | 264 | Coding | 214 | — |
| 113141 | 265 | Coding | 126 | — |
| 113142 | 266 | Coding | 35 | 65 |
| 113143 | 267 | Coding | 118 | — |
| 113144 | 268 | Coding | 41 | 59 |
| 113145 | 269 | Coding | 46 | 54 |
| 113146 | 270 | Coding | 32 | 68 |
| 113147 | 271 | Coding | 35 | 65 |
| 113148 | 272 | Coding | 23 | 77 |
| 113149 | 273 | Coding | 29 | 71 |
| 113150 | 274 | Coding | 19 | 81 |
| 113151 | 275 | Coding | 208 | — |
| 113152 | 276 | Coding | 89 | 11 |
| 113153 | 277 | Coding | 19 | 81 |
| 113154 | 278 | Coding | 63 | 37 |
| 113155 | 279 | Coding | 13 | 87 |
| 113156 | 280 | Coding | 83 | 17 |
| 113157 | 281 | 3tUTR | 13 | 87 |
| 113158 | 282 | 3'UTR | 20 | 80 |
| 113159 | 283 | 3'UTR | 43 | 57 |
| 113160 | 284 | 3'UTR | 09 | 91 |

Example 21

Human Skin Psoriasis Model

Animal models of psoriasis based on xenotransplantation of human skin from psoriatic patients are advantageous because they involve the direct study of affected human tissue. Psoriasis is solely a disease of the skin and consequently, engraftment of human psoriatic skin onto SCID mice allows psoriasis to be created with a high degree of fidelity in mice. BALB/cByJSmn-Prkdcscid/J SCID mice (4-6 weeks old) of either sex (Jackson Laboratory, Bar Harbor, Me.) were maintained in a pathogen free environment. At 6-8 weeks of age, mice were anesthetized by intraperitoneal injection of 30 mg/kg body weight ketamine-HCl and 1 mg/kg body weight acepromazine. After anesthesia, mice were prepared for transplantation by shaving the hair from the dorsal skin, 2 cm away from the head. The area was then sterilized and cleaned with povidone iodide and alcohol. Graft beds of about 1 cm×1 cm were created on the shaved areas by removing full thickness skin down to the fascia. Partial thickness human skin was then orthotopically transferred onto the graft bed. The transplants were held in place by gluing the human skin to mouse-to-mouse skin with Nexband liquid, a veterinary bandage (Veterinary Products Laboratories, Phoenix, Ariz.). Finally, the transplant and the wounds were covered with a thick layer of antibiotic ointment. After 4 weeks of transplantation, a 2 mm punch biopsy was obtained to confirm the acceptance of the graft and the origin of the skin in the transplant area. Only mice whose grafts did not show signs of infection were used for the study. Normal human skin was obtained from elective plastic surgeries and psoriatic plaques were obtained from shave biopsies from psoriatic volunteers. Partial thickness skin was prepared by dermatome shaving of the skin and transplanted to the mouse as described above for the psoriatic skin.

Animals (n=5) were topically treated with 2.5% (w/w) of each antisense oligonucleotide in a cream formulation comprising 10% isopropyl myristate, 10% glyceryl monooleate, 3% cetostearyl alcohol, 10% polyoxyl-20-cetyl ether, 6% poloxamer 407, 2.5% phenoxyethanol, 0.5% methylparaben, 0.5% propylparaben and water (final pH about 7.5).

The following oligonucleotides were used: human B7-1 (5'-TTCCCAGGTGCAAAACAGGC-3'; SEQ ID NO: 228) (ISIS 113492) and human B7-2 (5'-CGTGTGTCTGT-GCTAGTCCC-3'; SEQ ID NO: 255) (ISIS 113131). Both sequences contained only phosphorothioate linkages and had 2'-MOE modifications at nucleotides 1-5 and 16-20.

Plaques from the same patients were also transplanted onto control mice (n=5) and treated only with the vehicle of the active cream preparation. Both groups received the topical preparation twice a day for 4 weeks. Within 3-4 weeks the animals were sacrificed and 4 mm punch biopsies were taken from each xenograft. Biopsies were fixed in formalin for paraffin embedding and/or transferred to cryotubes and snap-frozen in liquid nitrogen and stored at −80° C.

Significant histological improvement marked by reduction of hyperkeratosis, acanthosis and lymphonuclear cellular infiltrates was observed in mice treated with the antisense oligonucleotides. Rete pegs, finger-like projections of the epidermis into the dermis, were also measured. These are phenotypic markers for psoriasis which lengthen as the disease progresses. The shortening of these rete pegs is a good measure of anti-psoriatic activity. In mice treated with the active agent, the rete pegs changed from 238.56±98.3 μm to 168.4±96.62 μm ($p<0.05$), whereas in the control group the rete pegs before and after treatment were 279.93±40.56 μm and 294.65±45.64 μm, respectively ($p>0.1$). HLA-DR positive lymphocytic infiltrates and intraepidermal CD8 positive lymphocytes were significantly reduced in the transplanted plaques treated with the antisense oligonucleotide cream. These results show that antisense oligonucleotides to B7 inhibit psoriasis-induced inflammation and have therapeutic efficacy in the treatment of psoriasis.

Example 22

Mouse Model of Allergic Inflammation

In the mouse model of allergic inflammation, mice were sensitized and challenged with aerosolized chicken ovalbumin (OVA). Airway responsiveness was assessed by inducing airflow obstruction with a methacholine aerosol using a noninvasive method. This methodology utilized unrestrained conscious mice that are placed into the main chamber of a plthysmograph (Buxco Electronics, Inc., Troy, N.Y.). Pressure differences between this chamber and a reference chamber were used to extrapolate minute volume, breathing frequency and enhanced pause (Penh). Penh is a dimensionless parameter that is a function of total pulmonary airflow in mice (i.e., the sum of the airflow in the upper and lower respiratory tracts) during the respiratory cycle of the animal. The lower the Penh, the greater the airflow. This parameter closely correlates with lung resistance as measured by traditional invasive techniques using ventilated animals (Hamelmann . . . Gelfand, 1997). Dose-response data were plotted as raw Penh values to increasing concentrations of methacholine. This system was used to test the efficacy of antisense oligonucleotides targeted to human B7-1 and B7-2.

There are several important features common to human asthma and the mouse model of allergic inflammation. One of these is pulmonary inflammation, in which cytokine expression and Th2 profile is dominant. Another is goblet cell hyperplasia with increased mucus production. Lastly, airway hyperresponsiveness (AHR) occurs resulting in increased sensitivity to cholinergic receptor agonists such as acetylcholine or methacholine. The compositions and methods of the present invention may be used to treat AHR and pulmonary inflammation.

Ovalbumin-Induced Allergic Inflammation

Female Balb/c mice (Charles Rivers Laboratory, Taconic Farms, N.Y.) were maintained in micro-isolator cages housed in a specific pathogen-free (SPF) facility. The sentinel cages within the animal colony surveyed negative for viral antibodies and the presence of known mouse pathogens. Mice were sensitized and challenged with aerosolized chicken OVA. Briefly, 20 μg alum-precipitated OVA was injected intraperitoneally on days 0 and 14. On day 24, 25 and 26, the animals were exposed for 20 minutes to 1.0% OVA (in saline) by nebulization. The challenge was conducted using an ultrasonic nebulizer (PulmoSonic, The DeVilbiss Co., Somerset, Pa.). Animals were analyzed about 24 hours following the last nebulization using the Buxco electronics Biosystem. Lung function (Penh), lung histology (cell infiltration and mucus production), target mRNA reduction in the lung, inflammation (BAL cell type & number, cytokine levels), spleen weight and serum AST/ALT were determined.

This method has been used to show that prophylactic treatment with an anti-B7.2 monoclonal antibody continued throughout the sensitization and challenge periods decreases OVA-specific serum IgE and IgE levels, IL-4 and IFN-γ levels in bronchoalveolar lavage (BAL) fluid, airway eosinophilia and airway hyperresponsiveness (Haczku et al., *Am. J. Respir. Crit. Care Med.* 159:1638-1643, 1999). Treatment during antigen challenge with both anti-B7.1 and anti-B7.2 mAbs is effective; however, either mAb alone is only partially active (Mathur et al., 21:498-509, 1999). However, the anti-B7.2 mAb had no activity when administered after the OVA challenge. The anti-B7.1 monoclonal antibody had no effect, either prophylactically or post-antigen challenge. Thus, there is a need for an effective B7 inhibitor which can be administered after antigen challenge, and which will reduce airway hyperresponsiveness and pulmonary inflammation. As described below, the antisense oligonucleotides of the present inventors fit this description.

Oligonucleotide Administration

Antisense oligonucleotides (ASOs) were dissolved in saline and used to intratracheally dose mice every day, four times per day, from days 15-26 of the OVA sensitization and challenge protocol. Specifically, the mice were anesthetized with isofluorane and placed on a board with the front teeth hung from a line. The nose was covered and the animal's tongue was extended with forceps and 251 μl of various doses of ASO, or an equivalent volume of saline (control) was placed at the back of the tongue until inhaled into the lung. The deposition pattern of an ASO in the lung, ISIS 13920 (5'-TCCGTCATCGCTCCTCAGGG-3'; SEQ ID NO:285) was also examined by immunohistochemical staining using a monoclonal antibody to the oligonucleotide, and showed that the ASO is taken up throughout the lung, most strongly by antigen presenting cells (APCs) and alveolar epithelium.

The B7 oligonucleotides used were:

```
B7-1:    5'-GCTCAGCCTTTCCACTTCAG-3' (ISIS 121844;
                                     SEQ ID NO: 286)

B7-2:    5'-GCTCAGCCTTTCCACTTCAG-3' (ISIS 121874;
                                     SEQ ID NO: 287)
```

Both of these oligonucleotides are phosphorothioates with 2'-MOE modifications on nucleotides 1-5 and 16-20, and 2'-deoxy at positions 6-15. These ASOs were identified by mouse-targeted ASO screening by target mRNA reduction in mouse cell lines. For B7-2, 19 mouse-targeted ASOs were screened by target mRNA reduction (Northern analysis) in IC-21 macrophages. Dose-response confirmation led to selection of ISIS 121874 (>70% reduction at 25 nM). For B7-1, 22 mouse-targeted ASOs were screened by target mRNA reduction (RT-PCR) in L-929 fibroblasts. Dose-response confirmation led to selection of ISIS 121844 (>70% reduction at 100 nM). No cross hybridization was predicted, and no cross-target reduction was detected in transfected cells.

RT-PCR Analysis

RNA was harvested from experimental lungs removed on day 28 of the OVA protocol. B7.2 and B7.1 levels were measured by quantitative RT-PCR using the Applied Biosystems PRISM 7700 Sequence Detection System (Applied Biosystems, Foster City, Calif.). Primers and probes used for these studies were synthesized by Operon Technologies (Alameda, Calif.). The primer and probe sequences were as follows:

```
B7-2:
                                       (SEQ ID NO: 288)
    forward: 5'-GGCCCTCCTCCTTGTGATG-3'

(SEQ ID NO: 289)
    probe:
    5'-/56-FAM/TGCTCATCATTGTATGTCACAAGAAGCCG/36-
    TAMTph/-3'

(SEQ ID NO: 290)
    reverse: 5'-CTGGGCCTGCTAGGCTGAT-3'
```

-continued

B7-1:
forward: 5'-CAGGAAGCTACGGGCAAGTT-3' (SEQ ID NO: 291)

probe:
5'-/56-FAM/TGGGCCTTTGATTGCTTGATGACTGAA/36-TAMTph/-3' (SEQ ID NO: 292)

reverse: 5'-GTGGGCTCAGCCTTTCCA-3' (SEQ ID NO: 293)

Collection of Bronchial Alveolar Lavage (BAL) Fluid and Blood Serum for the Determination of Cytokine and Chemokine Levels Animals were injected with a lethal dose of ketamine, the trachea was exposed and a cannula was inserted and secured by sutures. The lungs were lavaged twice with 0.5 ml aliquots of ice cold PBS with 0.2% FCS. The recovered BAL fluid was centrifuged at 1,000 rpm for 10 min at 4° C., frozen on dry ice and stored at −80° C. until used. Luminex was used to measure cytokine levels in BAL fluid and serum.

BAL Cell Counts and Differentials

Cytospins of cells recovered from BAL fluid were prepared using a Shandon Cytospin 3 (Shandon Scientific LTD, Cheshire, England). Cell differentials were performed from slides stained with Leukostat (Fisher Scientific, Pittsburgh, Pa.). Total cell counts were quantified by hemocytometer and, together with the percent type by differential, were used to calculate specific cell number.

Tissue Histology

Before resection, lungs were inflated with 0.5 ml of 10% phosphate-buffered formalin and fixed overnight at 4° C. The lung samples were washed free of formalin with 1×PBS and subsequently dehydrated through an ethanol series prior to equilibration in xylene and embedded in paraffin. Sections (6µ) were mounted on slides and stained with hematoxylin/eosin, massons trichome and periodic acid-schiff (PAS) reagent. Parasagittal sections were analyzed by bright-field microscopy. Mucus cell content was assessed as the airway epithelium staining with PAS. Relative comparisons of mucus content were made between cohorts of animals by counting the number of PAS-positive airways.

Figure 11A:
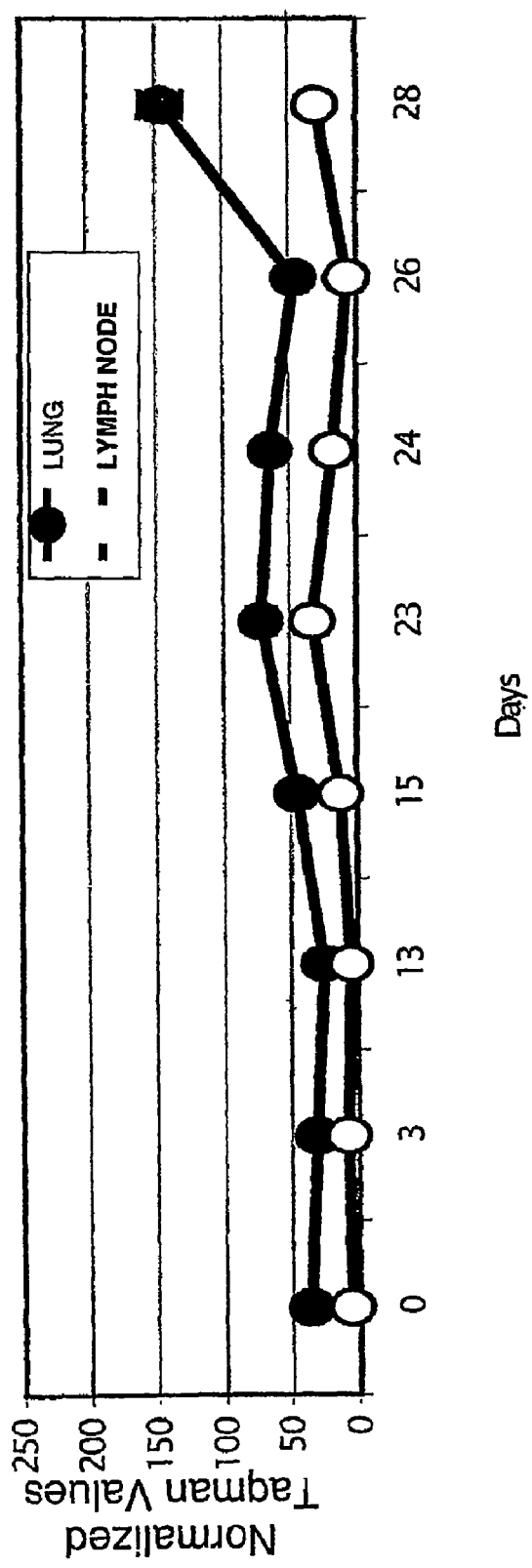
FIG. 11A-B are graphs showing the detection of B7.2 mRNA (FIG. 11A) and B7.1 mRNA (FIG. 11B) during the development of ovalbumin-induced asthma in a mouse model.
Figure 11B:
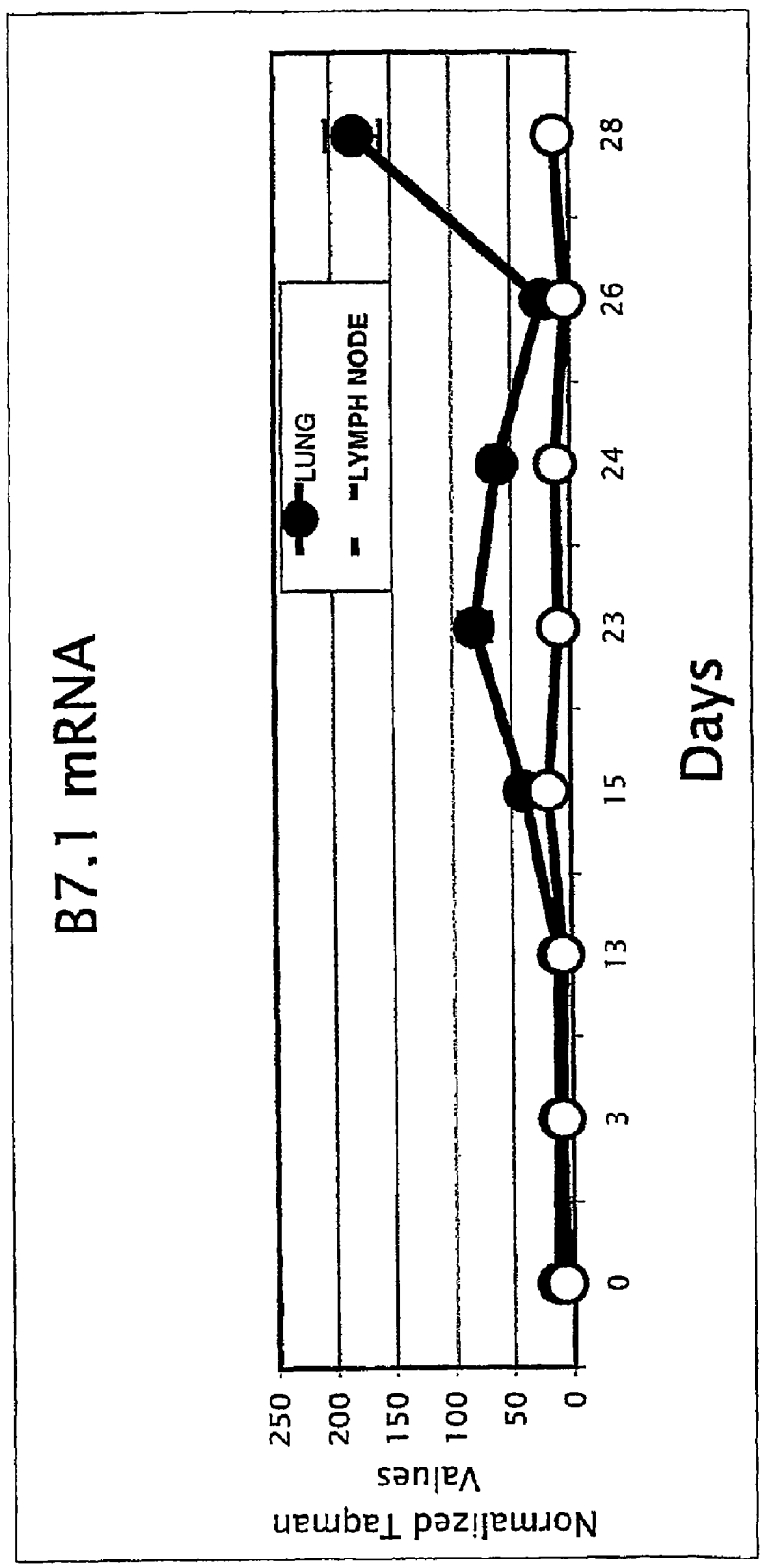
Figure 12:
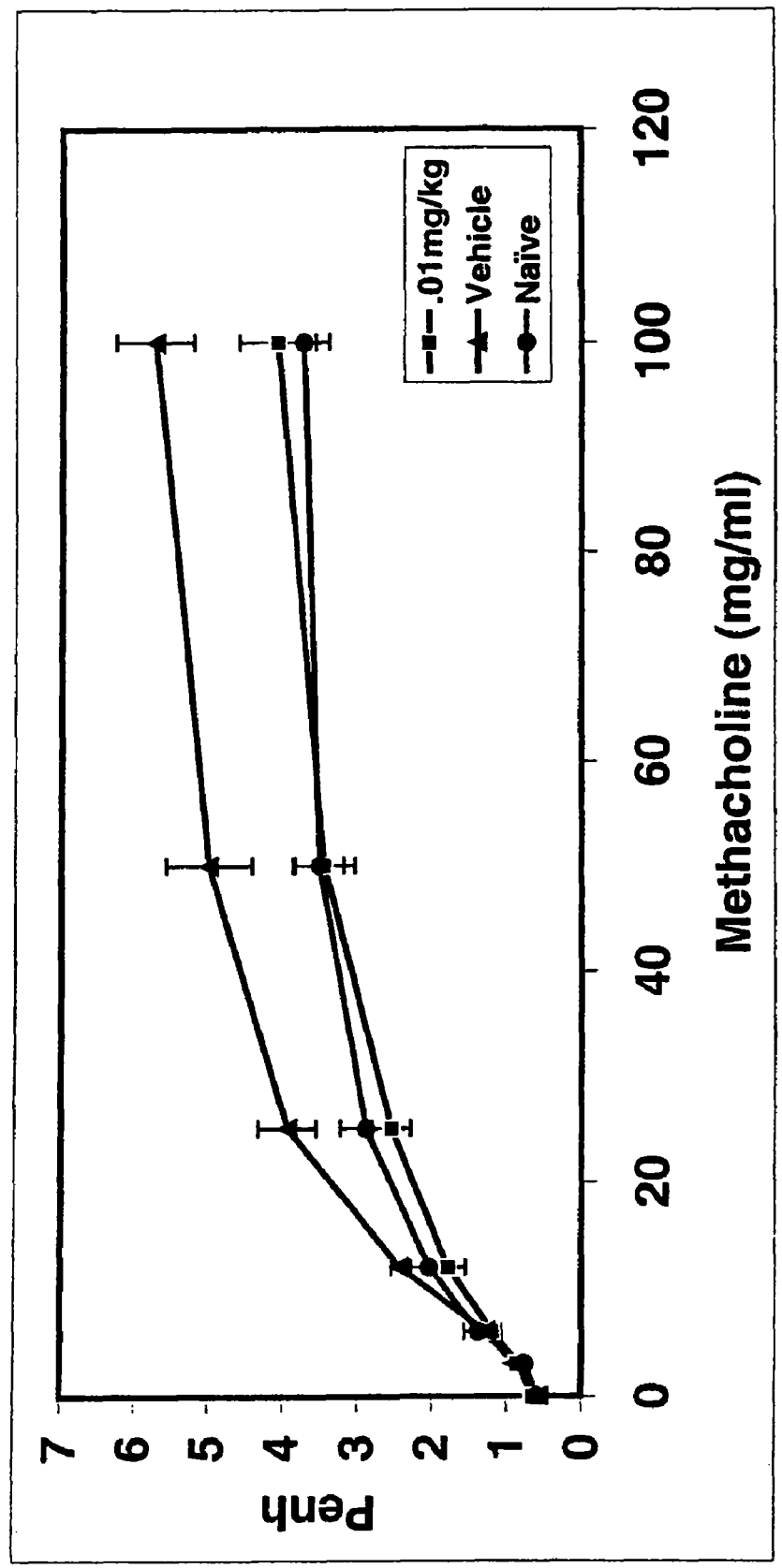
FIG. 12 is a graph showing that intratracheal administration of ISIS 121874, an antisense oligonucleotide targeted to mouse B7.2, following allergen challenge, reduces the airway response to methacholine.
Figure 13:
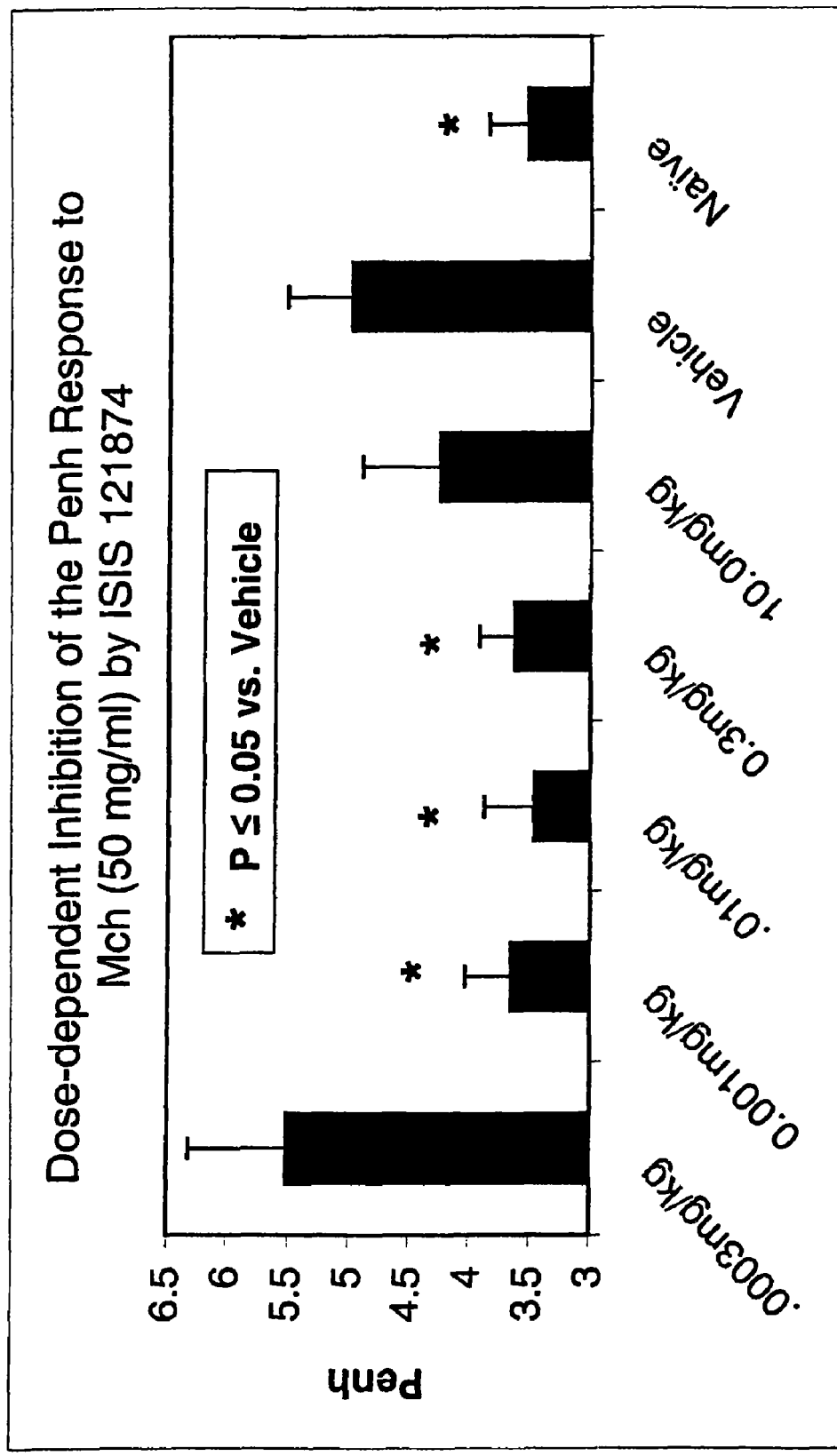
FIG. 13 is a graph showing the dose-dependent inhibition of the Penh response to 50 mg/ml methacholine by ISIS 121874. Penh is a dimensionless parameter that is a function of total pulmonary airflow in mice (i.e., the sum of the airflow in the upper and lower respiratory tracts) during the respiratory cycle of the animal. The lower the Penh, the greater the airflow. The dose of ISIS 121874 is shown on the x-axis.
Figure 14:
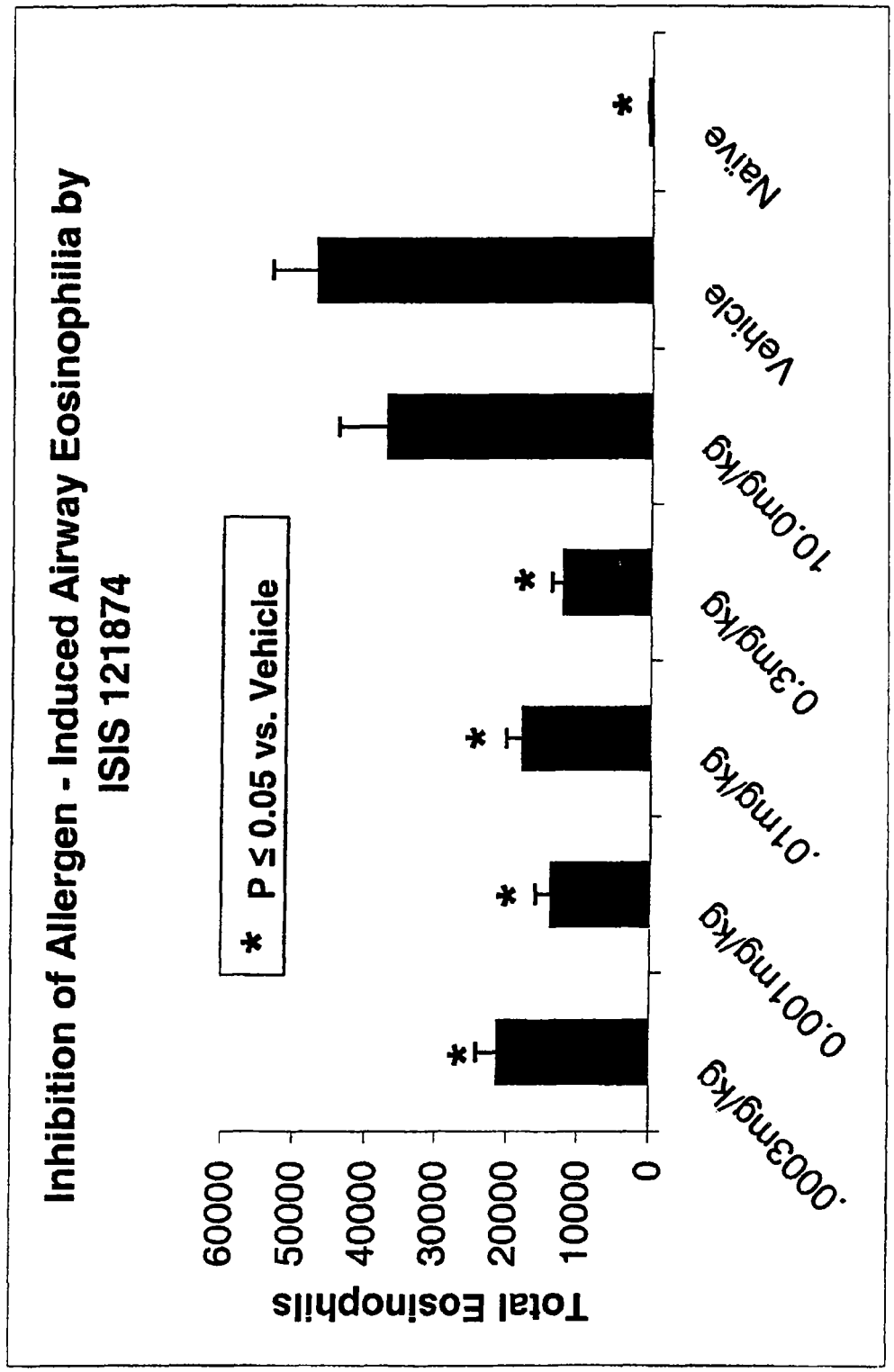
FIG. 14 is a graph showing the inhibition of allergen-induced eosinophilia by ISIS 121874. The dose of ISIS 121874 is shown on the x-axis.
Figure 15:
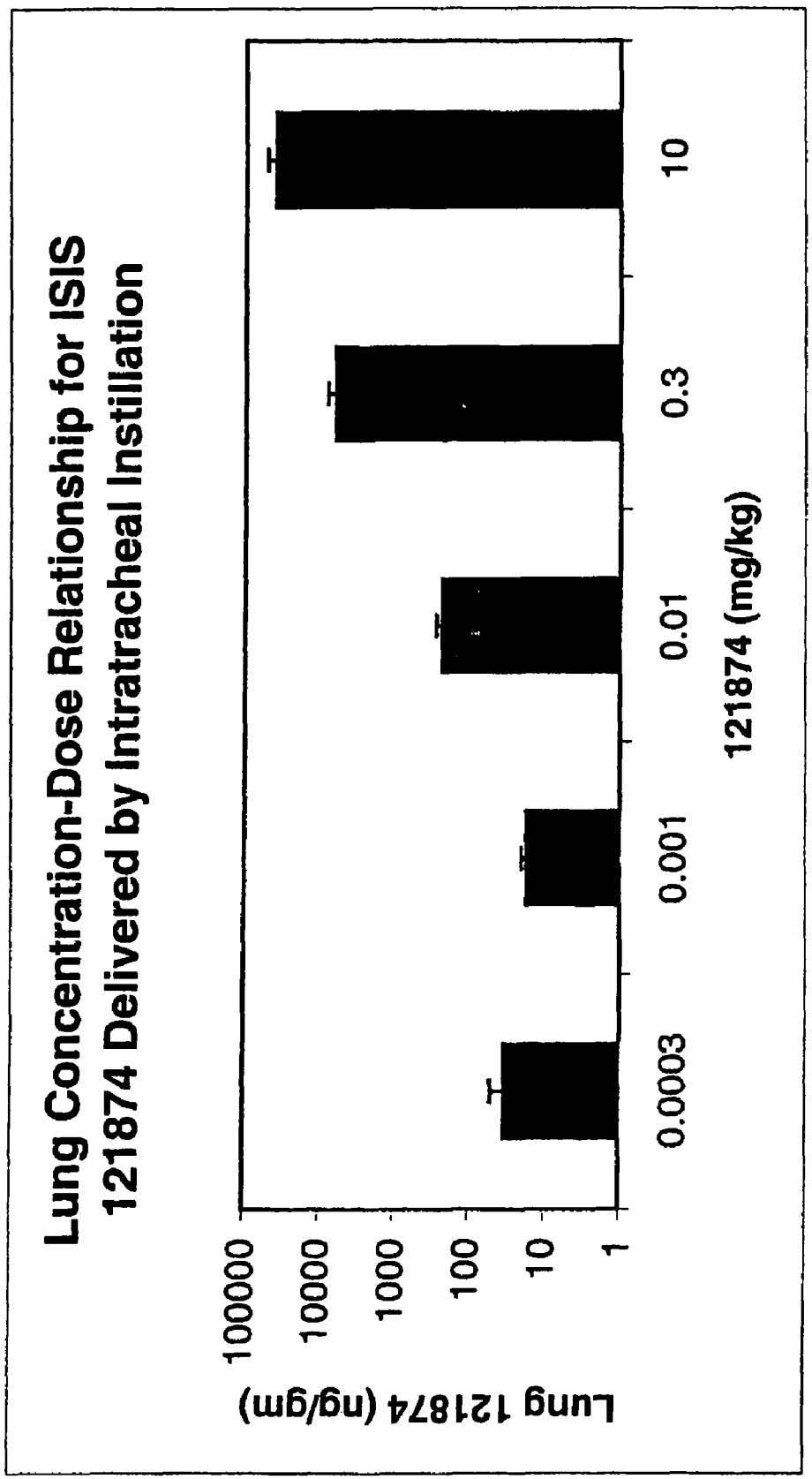
FIG. 15 is a graph showing the lung concentration-dose relationship for ISIS 121874 delivered by intratracheal administration.
Figure 16:
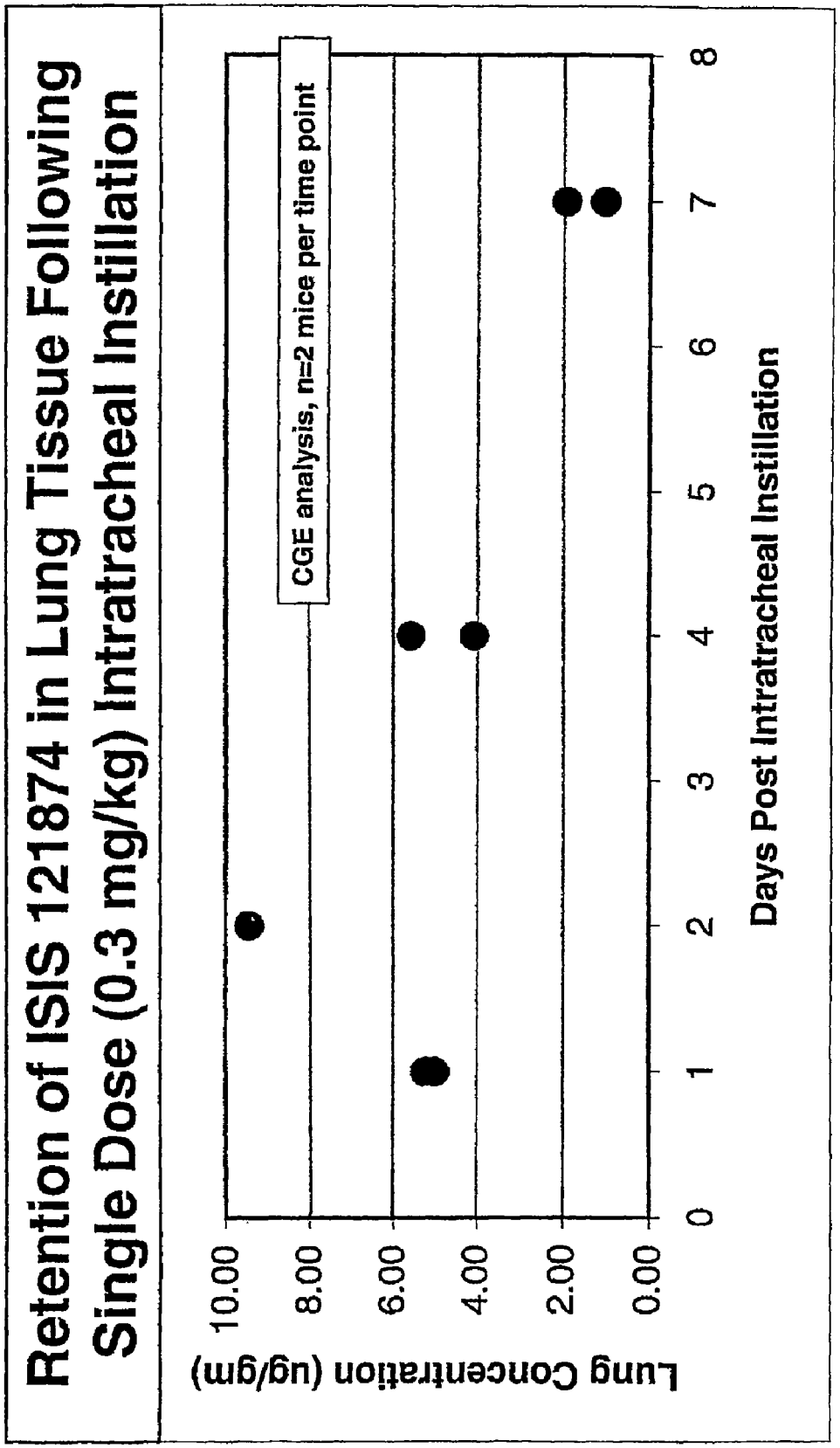
FIG. 16 is a graph showing the retention of ISIS 121874 in lung tissue following single dose (0.3 mg/kg) intratracheal instillation in the ovalbumin-induced mouse model of asthma.

As shown in FIGS. 11A-11B, B7.2 mRNA (FIG. 11A) and B7.1 mRNA (FIG. 11B) were detected in mouse lung and lymph node during the development of ovalbumin-induced asthma. Treatment with ISIS 121874 following allergen challenge reduces the airway response to methacholine (FIG. 12). The Penh value in B7.2 ASO-treated mice was about 40% lower than vehicle-treated mice, and was statistically the same as naïve mice which were not sensitized with the allergen or treated with the ASO. This shows that B7.2 ASO-treated mice had significantly better airflow, and less inflammation, than mice which were not treated with the ASO. The dose-dependent inhibition of the Penh response to methacholine by ISIS 121874 is shown in FIG. 13. The inhibition of allergen-induced eosinophilia by ISIS 121874 is shown in FIG. 14. ISIS 121874 at 0.3 mg/kg reduced the total number of eosinophils by about 75% compared to vehicle-treated mice. Since increased numbers of eosinophils result from inflammation, this provides further support for the anti-inflammatory properties of the B7.2 ASO. In addition, daily intratracheal delivery of ISIS 121874 does not induce splenomegaly, the concentration of ISIS 121874 achieved in lung tissue via daily intratracheal administration is proportional to the dose delivered (FIG. 15) and ISIS 121874 is retained in lung tissue for at least one week following single dose (0.3 mg/kg) intratracheal administration as determined by capillary gel electrophoresis (CGE) analysis (FIG. 16).

Example 23

Support for an Antisense Mechanism of Action for ISIS 121874

Two variants of ISIS 121874 were synthesized: a 7 base mismatch 5'-TCAAGTCCTTCCACACCCAA-3' (ISIS 306058; SEQ ID NO: 294) and a gap ablated oligonucleotide ISIS 306058 having the same sequence as ISIS 121874, but with 2'-MOE modifications at nucleotides 1, 2, 3, 6, 9, 13, 16, 18, 19 and 20. Because of the presence of 2'-MOE in the gap, this oligonucleotide is no longer an RNase H substrate and will not recruit RNase H to the RNA-DNA hybrid which is formed.

Figure 17:
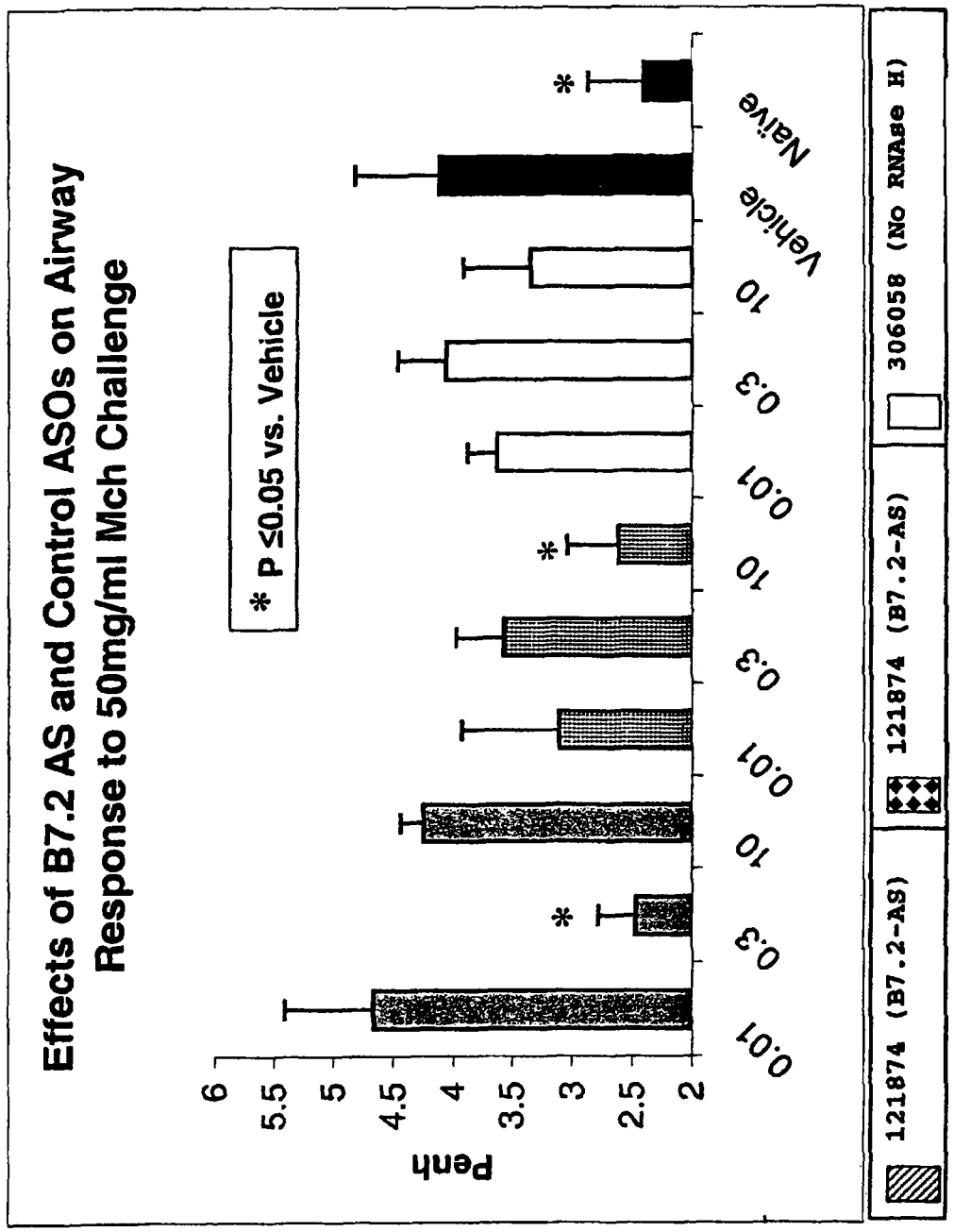
FIG. 17 is a graph showing the effects of ISIS 121874, a 7 base pair mismatched control oligonucleotide (ISIS 131906) and a gap ablated control oligonucleotide which does not promote cleavage by RNase H (ISIS 306058).

The results (FIG. 17) show that at 0.3 mg/kg, only ISIS 121874, and not the mismatch and gap ablated controls, significantly lowered Penh, which supports that ISIS 121874 is working by an antisense mechanism.

Figure 18A:
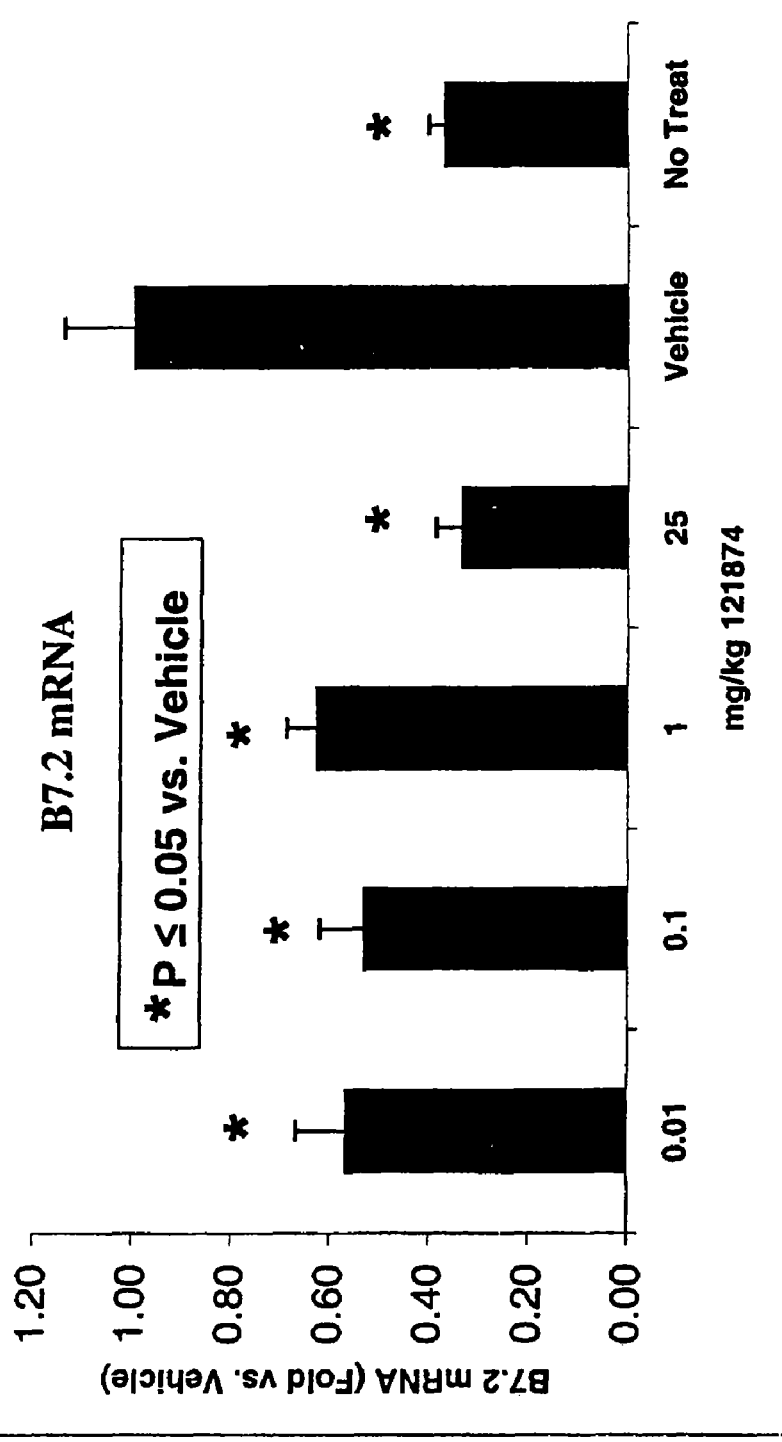
FIGS. 18A-B are graphs showing the effect of ISIS 121874 on B7.2 (FIG. 18A) and B7.1 (FIG. 18B) mRNA in lung tissue of ovalbumin-challenged mice.
Figure 18B:
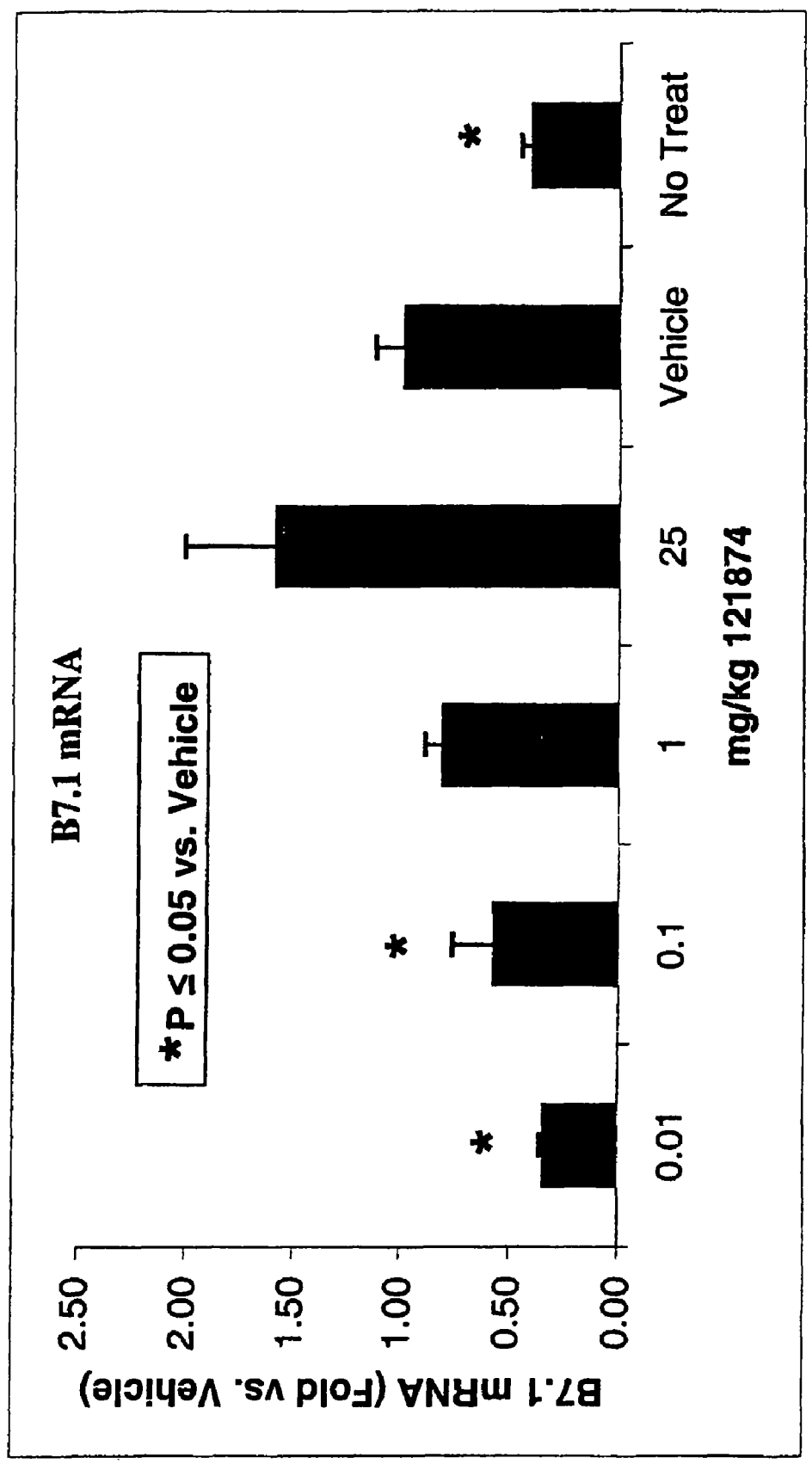

The effects of ISIS 121874 and the control oligonucleotides on airway mucus production in the ovalbumin-induced model were also tested. The results (FIG. 18) show that only ISIS 121874 significantly inhibited mucus production.

Figure 19A:
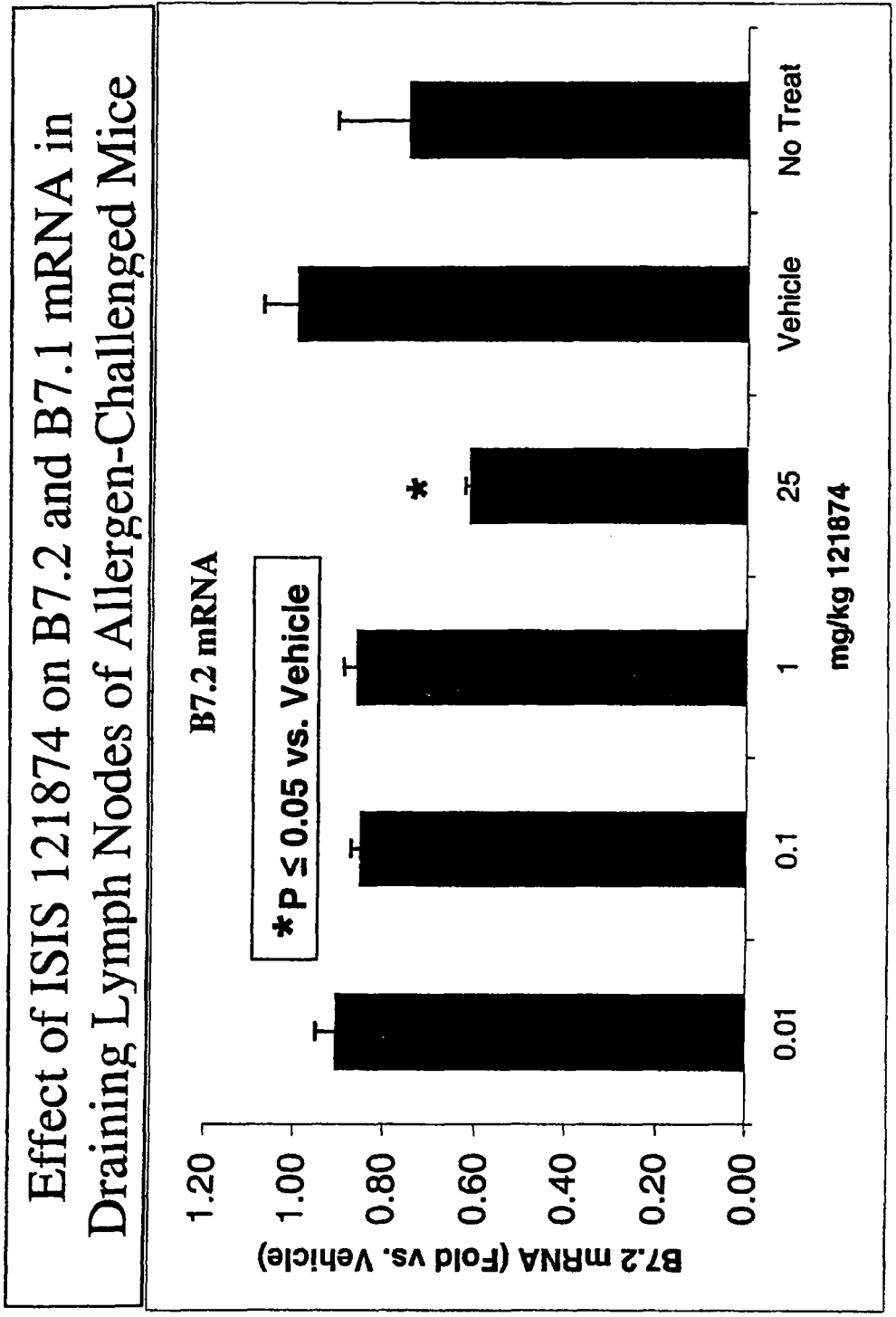
FIGS. 19A-B are graphs showing the effect of ISIS 121874 on B7.2 (FIG. 19A) and B7.1 (FIG. 19B) mRNA in draining lymph nodes of ovalbumin-challenged mice.
Figure 19B:
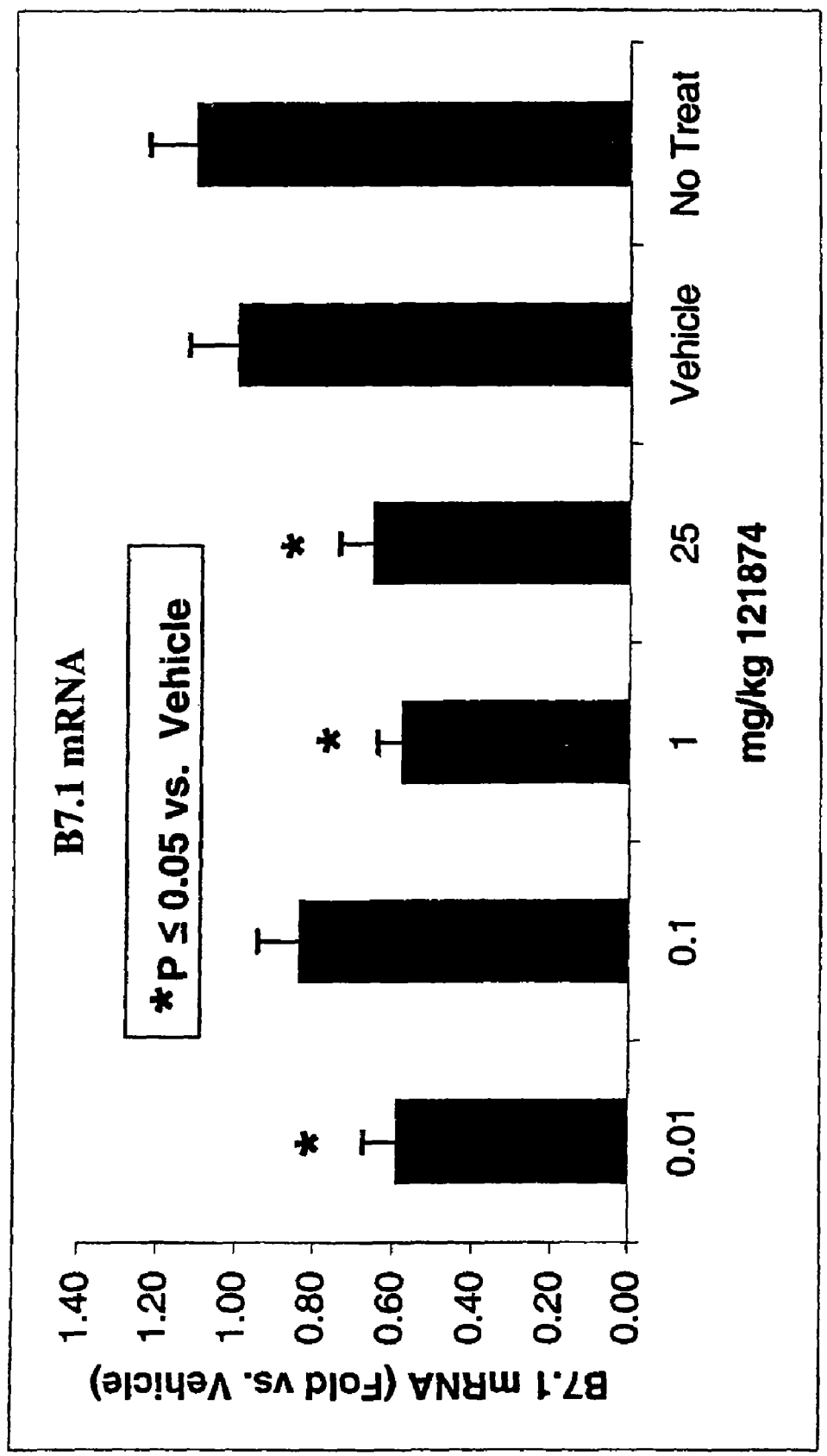

The effect of ISIS 121874 on B7.2 and B7.1 mRNA in lung tissue of allergen-challenged mice is shown in FIGS. 19A and 19B, respectively. The effect of ISIS 121874 on B7.2 and B7.1 mRNA in draining lymph nodes of allergen-challenged mice is shown in FIGS. 20A and 20B, respectively. This shows that ISIS 121874 reduces both B7.2 and B7.1 mRNA (greater in lung vs. node).

In summary, ISIS 121874 resulted in a dose-dependent inhibition of airway hypersensitivity, inhibited eosinophilia and reduced B7.1 and B7.2 expression in the lung and lymph nodes. In addition, ISIS 121874 reduced levels of the following inflammatory molecules: IgE mRNA in the lung and IgE protein in the serum; reduced IL-5 mRNA in the lung and IL-5 protein in the BAL fluid; and reduced the serum level of macrophage chemokine (KC).

In the aerosolized ISIS 121874 study, treatment with 0.001, 0.01, 0.1 or 1.0 mg/kg estimated inhaled dose was delivered by nose-only inhalation of an aerosol solution, four times per day, on days 15-26 (n=8 mice per group). The airway response to methacholine was reduced to the level seen in naïve mice at 0.001 mg/kg dose (estimated inhaled dose=1 µg/kg). No gross adverse effects were seen.

Example 24

B7.1 ASO in Ovalbumin Model of Asthma

Figure 21A:
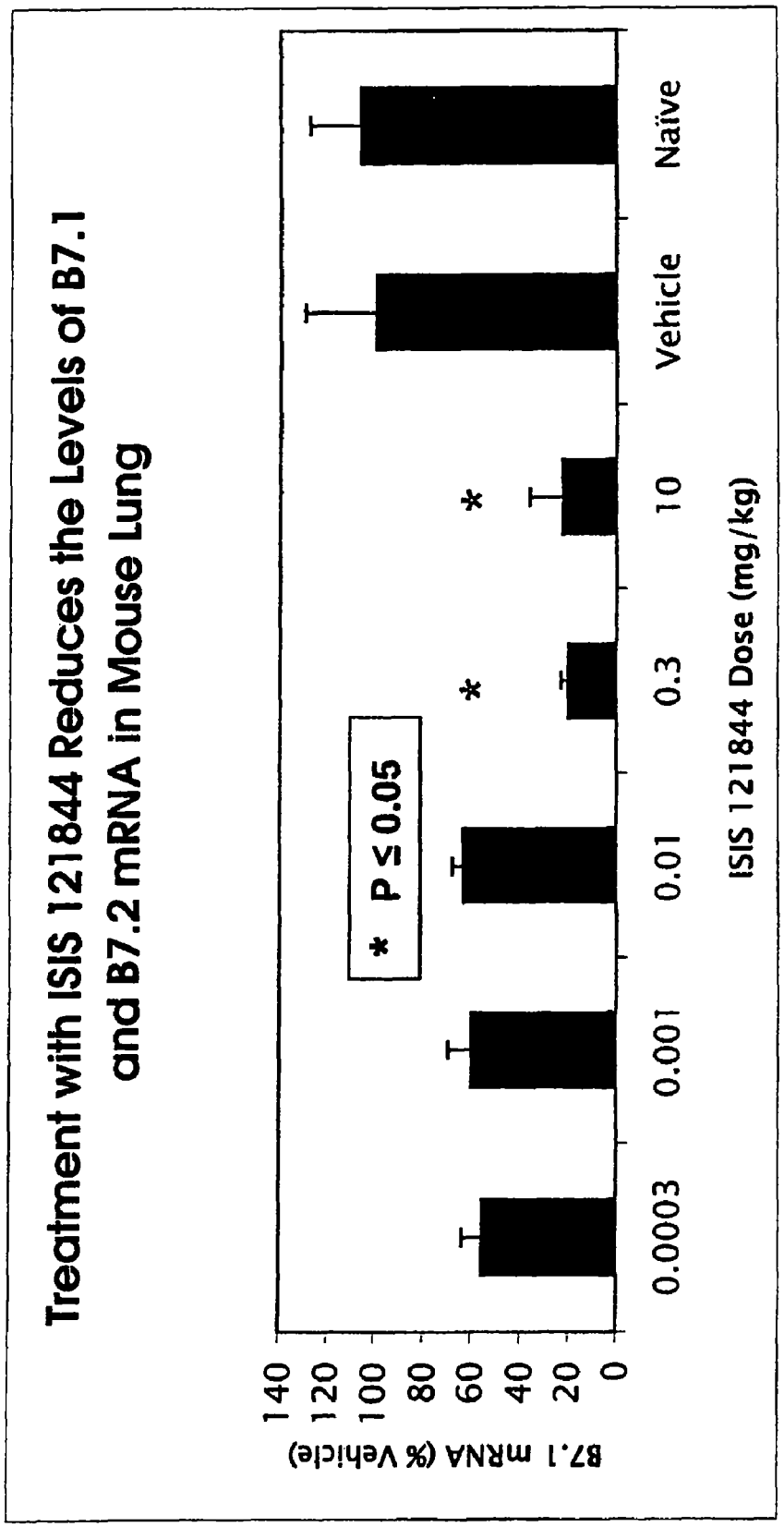
FIGS. 21A-B are graphs showing that treatment with ISIS 121844 reduces the levels of B7.1 mRNA (FIG. 21A) and B7.2 mRNA (FIG. 21B) in the mouse lung.
Figure 21B:
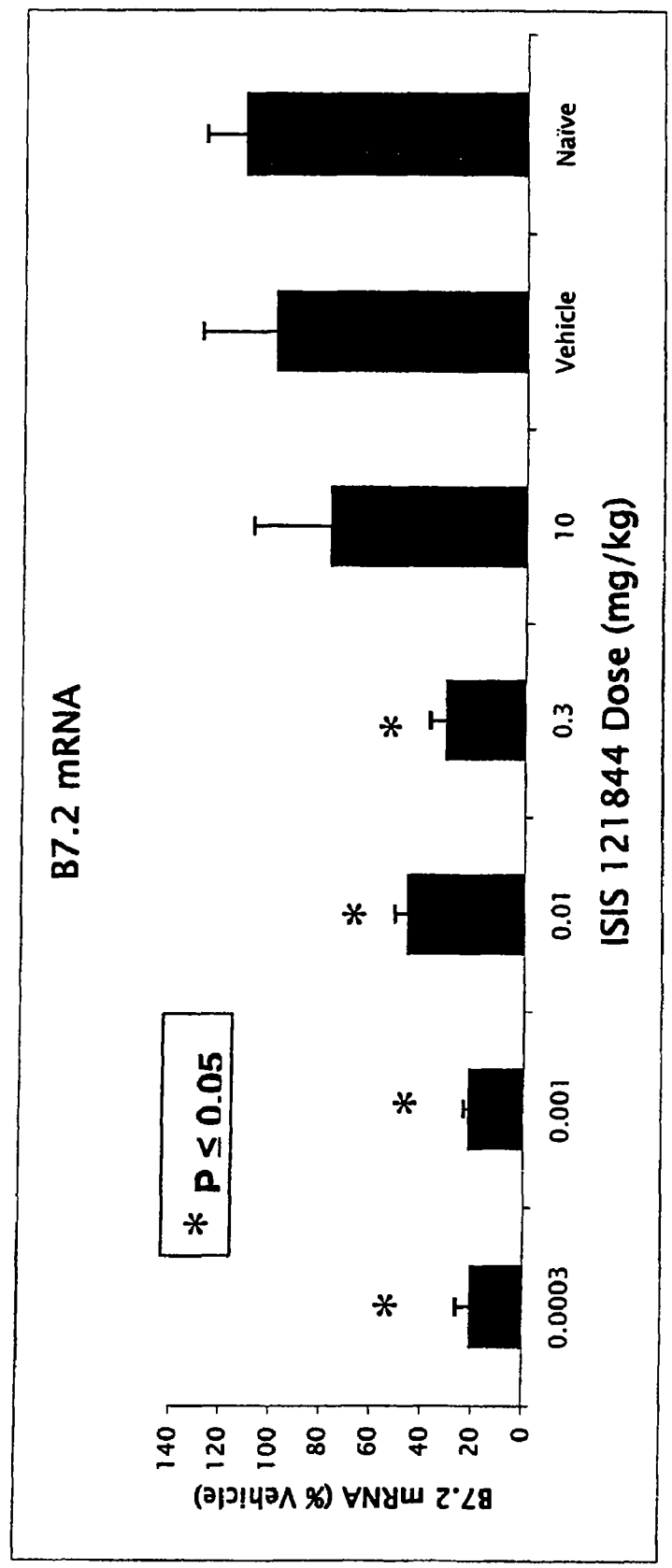

The same protocols described above for the B7.2 ASOs were used to test the effect of the B7.1 ASO ISIS 121844 (SEQ ID NO: 286). In contrast to the B7.2 ASO, ISIS 121844 had no effect on the Penh response in mice challenged with methacholine. Although there was no effect on Penh, ISIS 121844 reduced allergen-induced airway eosinophilia (FIG. 21) and reduced the levels of B7.1 and B7.2 in the mouse lung. (FIGS. 22A-B). Thus, treatment with B7.1 ASO produced anti-inflammatory effects, but did not prevent airway hyper-responsiveness. There was no effect of ISIS 121844 on the Penh response despite achieving an 80% reduction of B7.2 mRNA in the lung (FIG. 21B). Treatment with ISIS 121844 reduced eosinophil and PMN numbers in BAL fluid. This effect was associated with a reduction in lung B7.2 (not B7.1) mRNA.

The combined use of B7.1 or B7.2 with one or more conventional asthma medications including, but not limited to, montelukast sodium (Singulair™), albuterol, beclomethasone dipropionate, triamcinolone acetonide, ipratropium bromide (Atrovent™), flunisolide, fluticasone propionate (Flovent™) and other steroids is also contemplated. The combined use of oligonucleotides which target both B7.1 and B7.2 for the treatment of asthma is also within the scope of the present invention. B7.1 and B7.2 may also be combined with one or more conventional asthma medications as described above for B7.1 or B7.2 alone.

Example 25

Design and Screening of Duplexed Antisense Compounds Targeting B7.1 or B7.2

In accordance with the present invention, a series of nucleic acid duplexes comprising the antisense compounds of the present invention and their complements can be designed to target B7.1 or B7.2. The nucleobase sequence of the antisense strand of the duplex comprises at least a portion of an oligonucleotide to B7.1 or B7.2 as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. For example, a duplex comprising an antisense strand having the sequence CGAGAGGCGGACGGGACCG (SEQ ID NO: 445) and having a two-nucleobase overhang of deoxythymidine(dT) would have the following structure:

```
cgagaggcggacgggaccgTT    Antisense Strand
||||||||||||||||||||      (SEQ ID NO: 446)
TTgctctccgcctgccctggc    Complement (SEQ ID NO:
                         447)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed antisense compounds are evaluated for their ability to modulate B7.1 or B7.2 expression according to the protocols described herein.

Example 26

Design of Phenotypic Assays and In Vivo Studies for The Use of B7.1 or B7.2 Inhibitors Phenotypic Assays Once B7.1 or B7.2 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of B7.1 or B7.2 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with B7.1 or B7.2 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the B7.1 or B7.2 inhibitors. Hallmark genes, or those genes suspected to be associated with a specific disease state, condition, or phenotype, are measured in both treated and untreated cells.

Example 27

Antisense Inhibition of Human B7.2 Expression by Chimeric Phosphorothioate Oligonucleotides Having 2'-MOE Wings and a Deoxy Gap In accordance with the present invention, an additional series of antisense compounds were designed to target different regions of the human B7.2 RNA, using published sequences (GenBank accession number U04343.1, incorporated herein as SEQ ID NO: 295, GenBank accession number BC040261.1, incorporated herein as SEQ ID NO: 296 and GenBank accession number NT_005543.12, a portion of which is incorporated herein as SEQ ID NO: 297). The compounds are shown in Table 25. "Target site" indicates the first (5'-most) nucleotide number on the particular target sequence to which the compound binds. All compounds in Table 25 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S)

throughout the oligonucleotide. All cytidine residues are 5-methylcytidines. The compounds were analyzed for their effect on human B7.2 mRNA levels in THP-1 cells by quantitative real-time PCR as described in other examples herein. Data are averages from three experiments. If present, "N.D." indicates "no data".

TABLE 25

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 322216 | ACCAAAAGGAGTATTTGCGA | 298 | N.D. | U04343.1 | 26 | 5'UTR |
| 322217 | CATTCCCAAGGAACACAGAA | 299 | N.D. | U04343.1 | 64 | 5'UTR |
| 322218 | ACTGTAGCTCCAAAAAGAGA | 300 | N.D. | U04343.1 | 105 | 5'UTR |
| 322219 | CTGTCACAAATGCCTGTCCA | 301 | N.D. | U04343.1 | 124 | 5'UTR |
| 322220 | TCAGTCCCATAGTGCTGTCA | 302 | N.D. | U04343.1 | 138 | START |
| 322221 | CTGTTACAGCAGCAGAGAAG | 303 | N.D. | BC040261.1 | 29 | 5'UTR |
| 322222 | TCCCTGTTACAGCAGCACTC | 304 | N.D. | BC040261.1 | 32 | 5'UTR |
| 322223 | ATCTGGAAATGACCCCAAAT | 305 | N.D. | BC040261.1 | 71 | 5'UTR |
| 322224 | GTGACCTAATATCTGGACTG | 306 | N.D. | BC040261.1 | 81 | 5'UTR |
| 322225 | CATTTTGGCTGCTTCTGCTG | 307 | N.D. | BC040261.1 | 100 | START |
| 322226 | GGAACTTACAAAGGAAAGGG | 308 | N.D. | BC040261.1 | 1145 | 3'UTR |
| 322227 | AAAAAGGTTGCCCAGGAACT | 309 | N.D. | BC040261.1 | 1159 | 3'UTR |
| 322228 | TGCCTTCTGGAAGAAATCAA | 310 | N.D. | BC040261.1 | 1177 | 3'UTR |
| 322229 | TTTTTGCCTTCTGGAAGAAA | 311 | N.D. | BC040261.1 | 1181 | 3'UTR |
| 322230 | CTATTCCACTTAGAGGGAGT | 312 | N.D. | BC040261.1 | 1233 | 3'UTR |
| 322231 | TCTGATCTGGAGGAGGTATT | 313 | N.D. | BC040261.1 | 1389 | 3'UTR |
| 322232 | AGAAATTGAGAGGTCTATTT | 314 | N.D. | BC040261.1 | 1444 | 3'UTR |
| 322233 | CACCAGCTTAGAATTCTGGG | 315 | N.D. | BC040261.1 | 1484 | 3'UTR |
| 322234 | AGGTAGTTGTTTAGTCACAG | 316 | N.D. | BC040261.1 | 1524 | 3'UTR |
| 322235 | CCAGACTGAGGAGGTAGTTG | 317 | N.D. | BC040261.1 | 1535 | 3'UTR |
| 322236 | CAGTACATAGATCTCTATGT | 318 | N.D. | BC040261.1 | 1599 | 3'UTR |
| 322237 | TTACAGTACATAGATCTCTA | 319 | N.D. | BC040261.1 | 1602 | 3'UTR |
| 322238 | GATGAGAACTCCTTAGCAGG | 320 | N.D. | BC040261.1 | 1657 | 3'UTR |
| 322239 | TAGCAACAGCCCAGATAGAA | 321 | N.D. | BC040261.1 | 1787 | 3'UTR |
| 322240 | TCTGTTGCTTGTTTCAAGAC | 322 | N.D. | BC040261.1 | 2043 | 3'UTR |
| 322241 | TCCATTTGGACAGACTATCC | 323 | N.D. | BC040261.1 | 2064 | 3'UTR |
| 322242 | GGGAAACTGCTGTCTGTCTT | 324 | N.D. | BC040261.1 | 2087 | 3'UTR |
| 322243 | TGCTTCCAGGAAGATGACAT | 325 | N.D. | BC040261.1 | 2149 | 3'UTR |
| 322244 | ATTCATCCCATTATCAAGGT | 326 | N.D. | BC040261.1 | 2191 | 3'UTR |
| 322245 | AGCCAGGAGTGGAAAGTCCT | 327 | N.D. | BC040261.1 | 2223 | 3'UTR |
| 322246 | CTTCCTAATTCCGTTGCAGC | 328 | N.D. | BC040261.1 | 2255 | 3'UTR |
| 322247 | CATCTGTAGGCTAAGTAAGC | 329 | N.D. | BC040261.1 | 2297 | 3'UTR |
| 322248 | CCCGTAGGACATCTGTAGGC | 330 | N.D. | BC040261.1 | 2306 | 3'UTR |
| 322249 | GCCCTATGCTGGGCCAGCCC | 331 | N.D. | BC040261.1 | 2331 | 3'UTR |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 322250 | GTCTCTGTATGCAAGTTTCC | 332 | N.D. | BC040261.1 | 2396 | 3'UTR |
| 322251 | CCAGTATATCTGTCTCTGTA | 333 | N.D. | BC040261.1 | 2407 | 3'UTR |
| 322252 | CCAGGTTTTCAAAGTCATTT | 334 | N.D. | BC040261.1 | 2430 | 3'UTR |
| 322253 | AGCCAGGTTTTCAAAGTCAT | 335 | N.D. | BC040261.1 | 2432 | 3'UTR |
| 322254 | CCCTTAGTGATCCCACCTTA | 336 | N.D. | BC040261.1 | 2453 | 3'UTR |
| 322255 | CTGCCCCATCCCTTAGTGAT | 337 | N.D. | BC040261.1 | 2462 | 3'UTR |
| 322256 | TTTATGTTTGGGCAGAGACT | 338 | N.D. | BC040261.1 | 2480 | 3'UTR |
| 322257 | CATGGCAGTCTATAACCCTT | 339 | N.D. | BC040261.1 | 2556 | 3'UTR |
| 322258 | TAGCATGGCAGTCTATAACC | 340 | N.D. | BC040261.1 | 2559 | 3'UTR |
| 322259 | TCTAGCATGGCAGTCTATAA | 341 | N.D. | BC040261.1 | 2561 | 3'UTR |
| 322260 | TTGTCTAGCATGGCAGTCTA | 342 | N.D. | BC040261.1 | 2564 | 3'UTR |
| 322261 | AAGCTTGTCTAGCATGGCAG | 343 | N.D. | BC040261.1 | 2568 | 3'UTR |
| 322262 | ACATGGACAAGCTTGTCTAG | 344 | N.D. | BC040261.1 | 2576 | 3'UTR |
| 322263 | TTACATGGACAAGCTTGTCT | 345 | N.D. | BC040261.1 | 2578 | 3'UTR |
| 322264 | GAATATTACATGGACAAGCT | 346 | N.D. | BC040261.1 | 2583 | 3'UTR |
| 322265 | AACTAGCCAGGTGCTAGGAG | 347 | N.D. | BC040261.1 | 2636 | 3'UTR |
| 322266 | AATTATTACTCACCACTGGG | 348 | N.D. | NT_005543.12 | 1124 | genomic |
| 322267 | TAATATTTAGGGAAGCATGA | 349 | N.D. | NT_005543.12 | 13890 | genomic |
| 322268 | GGACCCTGGGCCAGTTATTG | 350 | N.D. | NT_005543.12 | 22504 | genomic |
| 322269 | CAAACATACCTGTCACAAAT | 351 | N.D. | NT_005543.12 | 23662 | genomic |
| 322270 | GTGATATCAATTGATGGCAT | 352 | N.D. | NT_005543.12 | 29265 | genomic |
| 322271 | TGCTACATCTACTCAGTGTC | 353 | N.D. | NT_005543.12 | 31796 | genomic |
| 322272 | TGGAAACTCTTGCCTTCGGA | 354 | N.D. | NT_005543.12 | 32971 | genomic |
| 322273 | CCATCCACATTGTAGCATGT | 355 | N.D. | NT_005543.12 | 34646 | genomic |
| 322274 | TCAGGATGGTATGGCCATAC | 356 | N.D. | NT_005543.12 | 36251 | genomic |
| 322275 | TCCCATAGTGCTAGAGTCGA | 357 | N.D. | NT_005543.12 | 37218 | genomic |
| 322276 | AGGTTCTTACCAGAGAGCAG | 358 | N.D. | NT_005543.12 | 37268 | genomic |
| 322277 | CAGAGGAGCAGCACCTAAAA | 359 | N.D. | NT_005543.12 | 49133 | genomic |
| 322278 | GACCACATACCAAGCACTGA | 360 | N.D. | NT_005543.12 | 49465 | genomic |
| 322279 | ATCTTTCAGAAACCCAAGCA | 361 | N.D. | NT_005543.12 | 51347 | genomic |
| 322280 | GAGTCACCAAAGATTTACAA | 362 | N.D. | NT_005543.12 | 51542 | genomic |
| 322281 | CTGAAGTTAGCTGAAAGCAG | 363 | N.D. | NT_005543.12 | 51815 | genomic |
| 322282 | ACAGCTTTACCTATAGAGAA | 364 | N.D. | NT_005543.12 | 52118 | genomic |
| 322283 | TCCTCAAGCTCTACAAATGA | 365 | N.D. | NT_005543.12 | 54882 | genomic |
| 322284 | GACTCACTCACCACATTTAT | 366 | N.D. | NT_005543.12 | 55027 | genomic |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 322285 | AGTGATAGCAAGGCTTCTCT | 367 | N.D. | NT_005543.12 | 56816 | genomic |
| 322286 | CTTGGAGAGAATGGTTATCT | 368 | N.D. | NT_005543.12 | 61044 | genomic |
| 322287 | GAAGATGTTGATGCCTAAAT | 369 | N.D. | NT_005543.12 | 63271 | genomic |
| 322288 | GTGTTGGTTCCTGAAAGACA | 370 | N.D. | NT_005543.12 | 63665 | genomic |
| 322289 | CAGGATTTACCTTTTCTTGG | 371 | N.D. | NT_005543.12 | 63711 | genomic |
| 322290 | AGGGCAGAATAGAGGTTGCC | 372 | N.D. | NT_005543.12 | 64973 | Genomic |
| 322291 | TTTTTCTCTGGAGAAATAGA | 373 | N.D. | NT_005543.12 | 65052 | genomic |
| 323624 | GTTACTCAGTCCCATAGTGC | 374 | 59 | U04343.1 | 143 | START |
| 323625 | CAAAGAGAATGTTACTCAGT | 375 | 21 | U04343.1 | 153 | Coding |
| 323626 | CCATCACAAAGAGAATGTTA | 376 | 32 | U04343.1 | 159 | Coding |
| 323627 | GGAAGGCCATCACAAAGAGA | 377 | 54 | U04343.1 | 165 | Coding |
| 323628 | GAGCAGGAAGGCCATCACAA | 378 | 44 | U04343.1 | 170 | Coding |
| 323629 | CCAGAGAGCAGGAAGGCCAT | 379 | 36 | U04343.1 | 175 | Coding |
| 323630 | AAATAAGCTTGAATCTTCAG | 380 | 22 | U04343.1 | 205 | Coding |
| 323631 | AGTCTCATTGAAATAAGCTT | 381 | 56 | U04343.1 | 215 | Coding |
| 323632 | AGGTCTGCAGTCTCATTGAA | 382 | 41 | U04343.1 | 223 | Coding |
| 323633 | CTACTAGCTCACTCAGGCTT | 383 | 50 | U04343.1 | 273 | Coding |
| 323634 | AAATACTACTAGCTCACTCA | 384 | 30 | U04343.1 | 278 | Coding |
| 323635 | CTGCCAAAATACTACTAGCT | 385 | 24 | U04343.1 | 284 | Coding |
| 323636 | TTCAGAACCAAGTTTTCCTG | 386 | 23 | U04343.1 | 307 | Coding |
| 323637 | CCTCATTCAGAACCAAGTTT | 387 | 19 | U04343.1 | 312 | Coding |
| 323638 | GTATACCTCATTCAGAACCA | 388 | 20 | U04343.1 | 317 | Coding |
| 323639 | GCCTAAGTATACCTCATTCA | 389 | 55 | U04343.1 | 323 | Coding |
| 323640 | CTCTTTGCCTAAGTATACCT | 390 | 28 | U04343.1 | 329 | Coding |
| 323641 | CCCATATACTTGGAATGAAC | 391 | 88 | U04343.1 | 361 | Coding |
| 323642 | CTTGTGCGGCCCATATACTT | 392 | 27 | U04343.1 | 370 | Coding |
| 323643 | ATCAAAACTTGTGCGGCCCA | 393 | 80 | U04343.1 | 377 | Coding |
| 323644 | CCCTTGTCCTTGATCTGAAG | 394 | 71 | U04343.1 | 427 | Coding |
| 323645 | ACAAGCCCTTGTCCTTGATC | 395 | 56 | U04343.1 | 432 | Coding |
| 323646 | TTGATACAAGCCCTTGTCCT | 396 | 33 | U04343.1 | 437 | Coding |
| 323647 | ATACATTGATACAAGCCCTT | 397 | 41 | U04343.1 | 442 | Coding |
| 323648 | TGGATGATACATTGATACAA | 398 | 31 | U04343.1 | 448 | Coding |
| 323649 | GAATTCATCTGGTGGATGCG | 399 | 81 | U04343.1 | 493 | Coding |
| 323650 | GTTCAGAATTCATCTGGTGG | 400 | 92 | U04343.1 | 498 | Coding |
| 323651 | TGACAGTTCAGAATTCATCT | 401 | 64 | U04343.1 | 503 | Coding |
| 323652 | AGCACTGACAGTTCAGAATT | 402 | 87 | U04343.1 | 508 | Coding |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 323653 | TAGCAAGCACTGACAGTTCA | 403 | 96 | U04343.1 | 513 | Coding |
| 323654 | TGAAGTTAGCAAGCACTGAC | 404 | 87 | U04343.1 | 519 | Coding |
| 323655 | TTGACTGAAGTTAGCAAGCA | 405 | 65 | U04343.1 | 524 | Coding |
| 323656 | CTATTTCAGGTTGACTGAAG | 406 | 76 | U04343.1 | 534 | Coding |
| 323657 | TCTGTTATATTAGAAATTGG | 407 | 43 | U04343.1 | 556 | Coding |
| 323658 | GCAGGTCAAATTTATGTACA | 408 | 36 | U04343.1 | 581 | Coding |
| 323659 | GTATAGATGAGCAGGTCAAA | 409 | 56 | U04343.1 | 591 | Coding |
| 323660 | GGGTAACCGTGTATAGATGA | 410 | 71 | U04343.1 | 601 | Coding |
| 323661 | AGGTTCTGGGTAACCGTGTA | 411 | 68 | U04343.1 | 608 | Coding |
| 323662 | TAGCAAAACACTCATCTTCT | 412 | 22 | U04343.1 | 629 | Coding |
| 323663 | GTTCTTAGCAAAACACTCAT | 413 | 23 | U04343.1 | 634 | Coding |
| 323664 | ATTCTTGGTTCTTAGCAAAA | 414 | 35 | U04343.1 | 641 | Coding |
| 323665 | GATAGTTGAATTCTTGGTTC | 415 | 43 | U04343.1 | 650 | Coding |
| 323666 | ACCATCATACTCGATAGTTG | 416 | 71 | U04343.1 | 662 | Coding |
| 323667 | ATCTTGAGATTTCTGCATAA | 417 | 52 | U04343.1 | 683 | Coding |
| 323668 | ACATTATCTTGAGATTTCTG | 418 | 39 | U04343.1 | 688 | Coding |
| 323669 | CGTACAGTTCTGTGACATTA | 419 | 68 | U04343.1 | 702 | Coding |
| 323670 | AGACAAGCTGATGGAAACGT | 420 | 19 | U04343.1 | 722 | Coding |
| 323671 | GAAACAGACAAGCTGATGGA | 421 | 26 | U04343.1 | 727 | Coding |
| 323672 | GGAATGAAACAGACAAGCTG | 422 | 33 | U04343.1 | 732 | Coding |
| 323673 | CATCAGGGAATGAAACAGAC | 423 | 38 | U04343.1 | 738 | Coding |
| 323674 | CGTAACATCAGGGAATGAAA | 424 | 47 | U04343.1 | 743 | Coding |
| 323675 | AGCTCTATAGAGAAAGGTGA | 425 | 77 | U04343.1 | 817 | Coding |
| 323676 | CCTCAAGCTCTATAGAGAAA | 426 | 24 | U04343.1 | 822 | Coding |
| 323677 | GGAGGCTGAGGGTCCTCAAG | 427 | 55 | U04343.1 | 835 | Coding |
| 323678 | AGTACAGCTGTAATCCAAGG | 428 | 23 | U04343.1 | 868 | Coding |
| 323679 | TTGGAAGTACAGCTGTAATC | 429 | 60 | U04343.1 | 873 | Coding |
| 323680 | ATAATAACTGTTGGAAGTAC | 430 | 51 | U04343.1 | 883 | Coding |
| 323681 | CATCACACATATAATAACTG | 431 | 8 | U04343.1 | 893 | Coding |
| 323682 | TCCATTTCCATAGAATTAGA | 432 | 35 | U04343.1 | 921 | Coding |
| 323683 | TCTTCTTCCATTTCCATAGA | 433 | 16 | U04343.1 | 927 | Coding |
| 323684 | ATTTATAAGAGTTGCGAGGC | 434 | 32 | U04343.1 | 954 | Coding |
| 323685 | TTGGTTCCACATTTATAAGA | 435 | 18 | U04343.1 | 964 | Coding |
| 323686 | CTCTCCATTGTGTTGGTTCC | 436 | 53 | U04343.1 | 976 | Coding |
| 323687 | CTTCCCTCTCCATTGTGTTG | 437 | 19 | U04343.1 | 981 | Coding |
| 323688 | TGGTCTGTTCACTCTCTTCC | 438 | 58 | U04343.1 | 996 | Coding |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 323689 | TTCATCAGATCTTTCAGGTA | 439 | 43 | U04343.1 | 1037 | Coding |
| 323690 | ATCACTTTTGTCGCATGAAG | 440 | 82 | U04343.1 | 1088 | Coding |
| 323691 | GCTTTACTCTTTAATTAAAA | 441 | 40 | U04343.1 | 1114 | STOP |
| 323692 | GTATGGGCTTTACTCTTTAA | 442 | 57 | U04343.1 | 1120 | 3'UTR |
| 323693 | ATACTTGTATGGGCTTTACT | 443 | 62 | U04343.1 | 1126 | 3'UTR |
| 323694 | AATGAATACTTGTATGGGCT | 444 | 71 | U04343.1 | 1131 | 3'UTR |

What is claimed is:

1. A compound comprising a modified oligonucleotide consisting of 12 to 50 linked nucleosides and having a nucleobase sequence comprising a portion of at least 8 contiguous nucleobases complementary to an equal length portion of nucleobases 493 to 532 of SEQ ID NO: 295, wherein the nucleobase sequence of the modified oligonucleotide is at least 90% complementary to SEQ ID NO: 295 as measured over the entirety of said modified oligonucleotide.

2. The compound of claim 1, wherein the modified oligonucleotide is 100% complementary to an equal length portion of nucleobases 493 to 532 of SEQ ID NO: 295 as measured over the entirety of said modified oligonucleotide.

3. The compound of claim 1, wherein the modified oligonucleotide is at least 95% complementary to SEQ ID NO: 295 as measured over the entirety of said modified oligonucleotide.

4. The compound of claim 3, wherein the modified oligonucleotide is 100% complementary to SEQ ID NO: 295 as measured over the entirety of said modified oligonucleotide.

5. The compound of claim 3, wherein the modified oligonucleotide hybridizes exclusively within nucleobases 493 to 532 of SEQ ID NO: 295.

6. The compound of claim 4, wherein the modified oligonucleotide hybridizes exclusively within nucleobases 493 to 532 of SEQ ID NO: 295.

7. The compound of claim 1, consisting of a single-stranded modified oligonucleotide.

8. The compound of claim 7, comprising at least one modified internucleoside linkage.

9. The compound of claim 8, wherein each modified internucleoside linkage is a phosphorothioate internucleoside linkage.

10. The compound of claim 7, wherein at least one nucleoside comprises a modified sugar.

11. The compound of claim 10, wherein the at least one modified sugar is a bicyclic sugar.

12. The compound of claim 10, wherein the at least one modified sugar comprises a 2'-O-methoxyethyl or a 4'-$(CH_2)_n$—O-2' bridge, wherein n is 1 or 2.

13. The compound of claim 7, wherein at least one nucleoside comprises a modified nucleobase.

14. The compound of claim 13, wherein the modified nucleobase is a 5-methylcytosine.

15. The compound of claim 1, wherein the modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

16. The compound of claim 15, wherein the modified oligonucleotide comprises:
a gap segment consisting of ten linked nucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage of said modified oligonucleotide is a phosphorothioate linkage.

17. The compound of claim 7, wherein the modified oligonucleotide consists of 20 linked nucleosides.

18. A composition comprising the compound of claim 1, or a salt thereof, and a pharmaceutically acceptable carrier or diluent.

19. The composition of claim 18, wherein the modified oligonucleotide consists of 20 linked nucleosides.

20. The composition of claim 18, wherein the modified oligonucleotide is 100% complementary to an equal length portion of nucleobases 493 to 532 of SEQ ID NO: 295 as measured over the entirety of said modified oligonucleotide.

21. A method comprising administering to an individual a compound of claim 1.

22. The method of claim 21, wherein the individual is a human.

23. The method of claim 22, wherein administering the compound to the human treats a disease or condition selected from the group consisting of rheumatoid arthritis, multiple sclerosis, psoriasis, asthma, airway hyperresponsiveness, and pulmonary inflammation.

24. The method of claim 21, comprising co-administering the compound and any of the group consisting of a steroid, montelukast sodium, albuterol, beclomethasone dipropionate, triamcinolone acetonide, ipratropium bromide, flunisolide, and fluticasone propionate.

25. The method of claim 21, wherein the administering is any of the group consisting of topical, pulmonary, inhalation, insufflation, intratracheal, intranasal, epidermal, transdermal, oral, parenteral, intravenous, intraarterial, subcutaneous, intraperitoneal, intramuscular, intracranial, intrathecal, and intraventricular administration.

26. The method of claim 21, wherein the modified oligonucleotide is 100% complementary to an equal length portion of nucleobases 493 to 532 of SEQ ID NO: 295 as measured over the entirety of said modified oligonucleotide.

* * * * *